United States Patent
Dennler et al.

(10) Patent No.: US 10,675,359 B2
(45) Date of Patent: Jun. 9, 2020

(54) ENZYMATIC CONJUGATION OF ANTIBODIES

(71) Applicants: Innate Pharma, Marseilles (FR); Paul Scherrer Institut, Villigen PSI (CH)

(72) Inventors: Patrick Dennler, Wettingen (CH); Delphine Bregeon, Marseilles (FR); Laurent Gauthier, Marseilles (FR); François Romagné, Marseilles (FR); Christian Belmant, Six-Fours-les-Plages (FR); Eliane Fischer, Eglisau (CH); Roger Schibli, Baden (CH)

(73) Assignees: Innate Pharma, Marseilles (FR); Paul Scherrer Institut, Villigen (CH)

( * ) Notice: Subject to any disclaimer, the term of this patent is extended or adjusted under 35 U.S.C. 154(b) by 0 days.

(21) Appl. No.: 15/702,586

(22) Filed: Sep. 12, 2017

(65) Prior Publication Data
US 2018/0193476 A1  Jul. 12, 2018

Related U.S. Application Data

(62) Division of application No. 14/367,840, filed as application No. PCT/EP2012/076631 on Dec. 21, 2012, now Pat. No. 9,764,038.

(60) Provisional application No. 61/579,908, filed on Dec. 23, 2011, provisional application No. 61/661,569, filed on Jun. 19, 2012, provisional application No. 61/671,122, filed on Jul. 13, 2012.

(51) Int. Cl.
| | | |
|---|---|---|
| *A61K 47/68* | (2017.01) | |
| *C07K 16/00* | (2006.01) | |
| *A61K 47/60* | (2017.01) | |
| *C07C 217/08* | (2006.01) | |
| *C07C 223/02* | (2006.01) | |
| *C07C 229/26* | (2006.01) | |
| *C07C 233/62* | (2006.01) | |
| *C07C 247/04* | (2006.01) | |
| *C07C 323/12* | (2006.01) | |
| *C07C 323/60* | (2006.01) | |
| *C07D 225/08* | (2006.01) | |
| *C07D 257/08* | (2006.01) | |
| *C07D 277/06* | (2006.01) | |
| *C07F 9/50* | (2006.01) | |
| *C07K 19/00* | (2006.01) | |
| *C12N 9/10* | (2006.01) | |
| *C12P 21/00* | (2006.01) | |
| *G01N 33/68* | (2006.01) | |

(52) U.S. Cl.
CPC ......... *A61K 47/6803* (2017.08); *A61K 47/60* (2017.08); *A61K 47/68* (2017.08); *A61K 47/6807* (2017.08); *A61K 47/6813* (2017.08); *A61K 47/6817* (2017.08); *A61K 47/6865* (2017.08); *A61K 47/6871* (2017.08); *C07C 217/08* (2013.01); *C07C 223/02* (2013.01); *C07C 229/26* (2013.01); *C07C 233/62* (2013.01); *C07C 247/04* (2013.01); *C07C 323/12* (2013.01); *C07C 323/60* (2013.01); *C07D 225/08* (2013.01); *C07D 257/08* (2013.01); *C07D 277/06* (2013.01); *C07F 9/5022* (2013.01); *C07K 16/00* (2013.01); *C07K 19/00* (2013.01); *C12N 9/1044* (2013.01); *C12P 21/005* (2013.01); *G01N 33/6854* (2013.01); *C07K 2317/40* (2013.01)

(58) Field of Classification Search
CPC .... A61K 47/6803; A61K 47/60; A61K 47/68; A61K 47/6865; A61K 47/6871; A61K 47/6817; A61K 47/6813; A61K 47/6807; A61K 47/48384; A61K 47/48623; A61K 47/48646; C07K 16/00; C07K 19/00; C07K 2317/40; C07C 217/08; C07C 223/02; C07C 229/26; C07C 233/62; C07C 247/04; C07C 323/12; C07C 323/60; C07D 225/08; C07D 257/08; C07D 277/06; C07F 9/5022; C12N 9/1044; C12P 21/005

See application file for complete search history.

(56) References Cited

U.S. PATENT DOCUMENTS

| | | | |
|---|---|---|---|
| 4,741,900 A | 5/1988 | Alvarez et al. | |
| 4,816,567 A | 3/1989 | Cabilly et al. | |
| 5,156,956 A | 10/1992 | Motoki et al. | |
| 5,225,539 A | 7/1993 | Winter | |
| 5,229,275 A | 7/1993 | Goroff | |
| 5,252,469 A | 10/1993 | Andou et al. | |
| 5,530,101 A | 6/1996 | Queen et al. | |

(Continued)

FOREIGN PATENT DOCUMENTS

| | | |
|---|---|---|
| DE | 19907588 A1 | 8/2000 |
| EP | 0555649 A2 | 8/1993 |

(Continued)

OTHER PUBLICATIONS

Lloyd et al., Protein Engineering, Design & Selection 22:159-168 (Year: 2009).*

(Continued)

*Primary Examiner* — Phuong Huynh
(74) *Attorney, Agent, or Firm* — Knobbe, Martens, Olson & Bear, LLP

(57) ABSTRACT

The present application relates to methods for the functionalization of immunoglobulins, in particular with drugs. Also disclosed herein are linking reagents, functionalized antibodies, pharmaceutical compositions, and method of treating disease and/or conditions.

24 Claims, 26 Drawing Sheets
Specification includes a Sequence Listing.

(56) References Cited

U.S. PATENT DOCUMENTS

| | | |
|---|---|---|
| 5,565,332 A | 10/1996 | Hoogenboom et al. |
| 5,567,610 A | 10/1996 | Borrebaeck et al. |
| 5,573,905 A | 11/1996 | Lerner et al. |
| 5,585,089 A | 12/1996 | Queen et al. |
| 5,693,761 A | 12/1997 | Queen et al. |
| 5,693,762 A | 12/1997 | Queen et al. |
| 5,712,120 A | 1/1998 | Rodriguez et al. |
| 5,714,350 A | 2/1998 | Co et al. |
| 5,731,183 A | 3/1998 | Kobayashi et al. |
| 5,736,356 A | 4/1998 | Sano et al. |
| 5,766,886 A | 6/1998 | Studnicka et al. |
| 5,770,196 A | 6/1998 | Studnicka |
| 5,777,085 A | 7/1998 | Co et al. |
| 5,821,123 A | 10/1998 | Studnicka |
| 5,821,337 A | 10/1998 | Carter et al. |
| 5,869,619 A | 2/1999 | Studnicka |
| 5,877,293 A | 3/1999 | Adair et al. |
| 5,886,152 A | 3/1999 | Nakatani et al. |
| 5,895,205 A | 4/1999 | Werner et al. |
| 5,929,212 A | 7/1999 | Jolliffe et al. |
| 6,054,297 A | 4/2000 | Carter et al. |
| 6,162,963 A | 12/2000 | Kucherlapati et al. |
| 6,180,370 B1 | 1/2001 | Queen et al. |
| 6,204,388 B1 | 3/2001 | Danishefsky et al. |
| 6,380,394 B1 | 4/2002 | Nicolaou et al. |
| 6,387,927 B1 | 5/2002 | Altmann et al. |
| 6,407,213 B1 | 6/2002 | Carter et al. |
| 6,548,640 B1 | 4/2003 | Winter |
| 6,632,927 B2 | 10/2003 | Adair et al. |
| 6,639,055 B1 | 10/2003 | Carter et al. |
| 6,750,325 B1 | 6/2004 | Jolliffe et al. |
| 6,797,492 B2 | 9/2004 | Daugherty et al. |
| 6,881,557 B2 | 4/2005 | Foote |
| 7,087,409 B2 | 8/2006 | Barbas, III et al. |
| 7,090,843 B1 | 8/2006 | Francisco et al. |
| 7,117,096 B2 | 10/2006 | Luo et al. |
| 7,135,174 B2 | 11/2006 | Corvalan et al. |
| 7,338,933 B2 | 3/2008 | DeFrees et al. |
| 7,378,091 B2 | 5/2008 | Gudas et al. |
| 7,393,648 B2 | 7/2008 | Rother et al. |
| 7,498,298 B2 | 3/2009 | Doronina et al. |
| 7,657,380 B2 | 2/2010 | Lazar et al. |
| 7,659,241 B2 | 2/2010 | Senter et al. |
| 7,763,736 B2 | 7/2010 | Sharpless et al. |
| 7,807,619 B2 | 10/2010 | Bertozzi et al. |
| 7,981,843 B2 | 7/2011 | Flynn et al. |
| 7,989,598 B2 | 8/2011 | Steeves et al. |
| 8,133,515 B2 | 3/2012 | Boons et al. |
| 9,340,615 B2 | 5/2016 | Maeda et al. |
| 9,427,478 B2 | 8/2016 | Bregeon et al. |
| 9,676,871 B2 | 6/2017 | Strop et al. |
| 9,717,803 B2 | 8/2017 | Bregeon et al. |
| 9,764,038 B2 | 9/2017 | Dennler et al. |
| 10,036,010 B2 | 7/2018 | Fischer et al. |
| 10,071,169 B2 | 9/2018 | Bregeon |
| 10,434,180 B2 | 10/2019 | Bregeon et al. |
| 2002/0034765 A1 | 3/2002 | Daugherty et al. |
| 2002/0052028 A1 | 5/2002 | Santi et al. |
| 2002/0058286 A1 | 5/2002 | Danishefsky et al. |
| 2002/0062030 A1 | 5/2002 | White et al. |
| 2002/0102208 A1 | 8/2002 | Chinn et al. |
| 2002/0161201 A1 | 10/2002 | Filpula et al. |
| 2003/0153043 A1 | 8/2003 | Carr et al. |
| 2004/0253645 A1 | 12/2004 | Daugherty et al. |
| 2005/0026263 A1 | 2/2005 | Meares et al. |
| 2005/0238646 A1 | 10/2005 | Ledbetter et al. |
| 2005/0238649 A1 | 10/2005 | Doronina et al. |
| 2005/0256030 A1 | 11/2005 | Feng |
| 2006/0073137 A1 | 4/2006 | Adair et al. |
| 2006/0116422 A1 | 6/2006 | de Groot et al. |
| 2007/0122408 A1 | 5/2007 | Barbas, III et al. |
| 2008/0038260 A1 | 2/2008 | Ponath et al. |
| 2009/0028856 A1 | 1/2009 | Chen et al. |
| 2010/0004431 A1 | 1/2010 | Bernett et al. |
| 2011/0184147 A1 | 7/2011 | Kamiya et al. |
| 2011/0256157 A1 | 10/2011 | Howard et al. |
| 2011/0305631 A1 | 12/2011 | Govindan et al. |
| 2012/0322686 A1 | 12/2012 | Lyon et al. |
| 2013/0122020 A1 | 5/2013 | Liu et al. |
| 2013/0137763 A1 | 5/2013 | van Delft et al. |
| 2013/0189287 A1 | 7/2013 | Bregeon et al. |
| 2013/0230543 A1 | 9/2013 | Pons et al. |
| 2014/0088089 A1 | 3/2014 | Chari |
| 2015/0284713 A1 | 10/2015 | Fischer et al. |
| 2015/0346195 A1 | 12/2015 | Belmant et al. |
| 2016/0022833 A1 | 1/2016 | Bregeon et al. |
| 2016/0114056 A1 | 4/2016 | Bregeon et al. |
| 2016/0331842 A1 | 11/2016 | Bregeon et al. |
| 2017/0313787 A1 | 11/2017 | Strop et al. |
| 2018/0071402 A1 | 3/2018 | Bregeon et al. |
| 2019/0169601 A1 | 6/2019 | Fischer et al. |

FOREIGN PATENT DOCUMENTS

| | | |
|---|---|---|
| EP | 1859811 A1 | 11/2007 |
| JP | 2003199569 A | 7/2003 |
| WO | WO 1992/02190 | 1/1992 |
| WO | WO 1992/11018 | 7/1992 |
| WO | WO 1992/22583 | 12/1992 |
| WO | WO 1993/10102 | 5/1993 |
| WO | WO 1996/06931 | 3/1996 |
| WO | WO 1996/22366 | 7/1996 |
| WO | WO 1998/25929 A1 | 6/1998 |
| WO | WO 1999/02514 A2 | 1/1999 |
| WO | WO 1999/07692 A2 | 2/1999 |
| WO | WO 1999/58534 A2 | 11/1999 |
| WO | WO 1999/67252 A2 | 12/1999 |
| WO | WO 1999/67253 A2 | 12/1999 |
| WO | WO 2000/000485 A1 | 1/2000 |
| WO | WO 2000/037473 A1 | 6/2000 |
| WO | WO 2000/049019 A2 | 8/2000 |
| WO | WO 2000/049020 A2 | 8/2000 |
| WO | WO 2000/049021 A2 | 8/2000 |
| WO | WO 2000/057874 A1 | 10/2000 |
| WO | WO 2000/066589 A1 | 11/2000 |
| WO | WO 2000/071521 A1 | 11/2000 |
| WO | WO 2001/027308 A2 | 4/2001 |
| WO | WO 2001/064650 A2 | 9/2001 |
| WO | WO 2001/070716 A1 | 9/2001 |
| WO | WO 2001/073103 A2 | 10/2001 |
| WO | WO 2001/081342 A2 | 11/2001 |
| WO | WO 2001/092255 A2 | 12/2001 |
| WO | WO 2002/008440 A2 | 1/2002 |
| WO | WO 2002/014323 A2 | 2/2002 |
| WO | WO 2002/030356 A2 | 4/2002 |
| WO | WO 2002/032844 A2 | 4/2002 |
| WO | WO 2002/080846 A2 | 10/2002 |
| WO | WO 2002/083180 A1 | 10/2002 |
| WO | WO 2003/074053 A1 | 9/2003 |
| WO | WO 2004/014919 A1 | 2/2004 |
| WO | WO 2004/043493 A1 | 5/2004 |
| WO | WO 2004/043880 A2 | 5/2004 |
| WO | WO 2005/040219 A1 | 5/2005 |
| WO | WO 2005/070468 A2 | 8/2005 |
| WO | WO 2005/085251 A1 | 9/2005 |
| WO | WO 2007/008603 A1 | 1/2007 |
| WO | WO 2007/008848 A2 | 1/2007 |
| WO | WO 2007/020290 A1 | 2/2007 |
| WO | WO 2008/017122 A1 | 2/2008 |
| WO | WO 2008/102008 A1 | 8/2008 |
| WO | WO 2009/067663 A1 | 5/2009 |
| WO | WO 2009/105969 A1 | 9/2009 |
| WO | WO 2010/115630 A1 | 10/2010 |
| WO | WO 2010/136598 A1 | 12/2010 |
| WO | WO 2011/023883 A1 | 3/2011 |
| WO | WO 2011/136645 A1 | 3/2011 |
| WO | WO 2011/085523 A1 | 7/2011 |
| WO | WO 2011/120053 A1 | 9/2011 |
| WO | WO 2011/130616 A1 | 10/2011 |
| WO | WO 2012/041504 A1 | 4/2012 |
| WO | WO 2012/059882 A2 | 5/2012 |
| WO | WO 2012/112687 A1 | 8/2012 |
| WO | WO 2013/092983 A2 | 6/2013 |
| WO | WO 2013/177481 A1 | 11/2013 |

(56) References Cited

FOREIGN PATENT DOCUMENTS

| WO | WO 2014/009426 A1 | 1/2014 |
|---|---|---|
| WO | WO 2014/072482 A1 | 5/2014 |
| WO | WO 2014/140300 A1 | 9/2014 |
| WO | WO 2014/202773 A1 | 12/2014 |

OTHER PUBLICATIONS

Edwards et al., J Mol Biol. 334(1): 103-118 (Year: 2003).*
Rudikoff et al., PNAS 79: 1979-1983 (Year: 1982).*
Kussie et al., J. Immunol. 152: 146-152 (Year: 1994).*
Chen et al., EMBO J., 14: 2784-2794 (Year: 1995).*
Strop et al., Chem Biol 20: 161-167 (Year: 2013).*
Wu et al., J. Mol. Biol. 294: 151-162 (Year: 1999).*
Agard et al., "A Strain-Promoted [3+2] Azide-Alkyne Cycloaddition for Covalent Modification of Biomolecules in Living Systems", J Am Chem Soc Comm. (2004) 126:15046-15047.
Altschul et al., "Gapped BLAST and PSI-BLAST: A new generation of protein database search programs", Nucl Acids Res. (1997) 25(17): 3389-3402.
Altschul et al., "Basic Local Alignment Search Tool", J Mol Biol. (1990) 215:403-410.
Amersham Biosciences, Antibody Purification Handbook, (2002) Publication No. 18-1037-46, Edition AC, 112 pages.
Amsberry et al., "The Lactonization of 2'-Hydroxyhydrocinnamic Acid Amides: A Potential Prodrug for Amines", J. Org Chem (Apr. 1990) 55:5867-5877.
Ando et al., "Purification and Characteristics of a Novel Transglutaminase Derived from Microorganisms", Agric Biol Chem. (1989) 53(10):2613-2617.
Ausubel et al. (Eds.) Current Protocols in Molecular Biology (1993) John Wiley & Sons, Inc., Table of Contents, 15 pages.
Baeuerle et al., "Bispecific T-cell engaging antibodies for cancer therapy", Cancer Res. (2009) 69(12):4941-4944.
Bernhard et al., "Cysteine analogs of recombinant barley ribosome inactivating protein form antibody conjugates with enhanced stability and potency in vitro", Bioconjugate Chem., (1994) 5(2):126-132.
Brabez et al., "Design, synthesis and biological studies of efficient multivalent melanotropin ligands: tools towards melanoma diagnosis and treatment", J Med Chem. (2011) 54(20):7375-7384.
Carillo et al., "The Multiple Sequence Alignment Problem in Biology", Siam J. Appl Math. (1988) 48(5):1073-1082.
Carter et al., "Improved oligonucleotide site-directed mutagenesis using M13 vectors", Nucl Acids Res. (May 1985) 13(12):4431-4443.
Carter et al., "Humanization of an anti-p185HER2 antibody for human cancer therapy", Proc Natl Acad Sci. USA (1992) 89:4285-4289.
Chapman, Andrew P., "PEGylated antibodies and antibody fragments for improved therapy: a review", Advan Drug Del Rev. (Jan. 2002) 54:531-545.
Chari, Ravi V.J., "Targeted Cancer Therapy: Conferring Specificity to Cytotoxic Drugs", Acc of Chem Res. (Jan. 2008) 41(1):98-107.
Chothia et al., "Canonical Structures for the Hypervariable Regions of Immunoglobulins", J Mol Biol. (1987) 196:901-917.
Connolly et al., "In Vivo Inhibition of Fas Ligand-Mediated Killing by TR6, a Fas Ligand Decoy Receptor", J Pharmacol Exp Ther. (Jan. 2001) 298(1):25-33.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody", J Immunol. (2002) 169(6):3076-3084.
Dennler et al., Enzymatic antibody modification by bacterial transglutaminase. Bioconjugate Chemistry, (Jan. 2013) 1045:205-215.
Dennler et al., Transglutaminase-based chemo-enzymatic conjugation approach yields homogeneous antibody-drug conjugates. Bioconjugate Chemistry, (2014) 25(3):569-578.

Devereux et al., "A comprehensive set of sequence analysis programs for the VAX", Nucl Acids Res. (1984) 12(1):387-395.
Doronina et al., "Development of potent monoclonal antibody Auristatin conjugates for cancer therapy", Nat Biotech. (2003) 21(7):778-784 & Erratum Nat Biotech. (2003) 21(8):941.
Doronina et al., "Enhanced activity of monomethylauristatin F through Monoclonal Antibody Delivery", Bioconjugate Chem. (2006) 17(1):114-124.
Dosio et al., "Immunotoxins and Anticancer Drug Conjugate Assemblies: The Role of the Linkage between Components", Toxins (2011) 3:848-883.
Edelman et al., "The Covalent Structure of an Entire γG Immunoglobulin Molecule", Proc Natl Acad. USA, (1969) 63:78-85.
Folk et al., "Polyamines as Physiological Substrates for Transglutaminases", J. Biol. Chem. (Apr. 1980) 255(8):3695-3700.
Genbank Reference Sequence NM_024003.2; "Homo sapiens L1 cell adhesion molecule (L1CAM), transcript variant 2, mRNA", May 4, 2013; 8 pages.
Genbank Reference Sequence NM_024003.3; "Homo sapiens L1 cell adhesion molecule (L1CAM), transcript variant 2, mRNA", May 26, 2013; 10 pages.
Genbank Reference Sequence NM_0764493.1; "Neural cell adhesion molecule L1 isoform 2 precursor [Homo sapiens]", May 26, 2014; 6 pages.
Golay et al., "Mechanism of action of therapeutic monoclonal antibodies: Promises and pitfalls of in vitro and in vivo assays", Arch Biochem Biophys (2012) 526:146-153.
Gorman et al., "Transglutaminase Amine Substrates for Photochemical Labeling arid Cleavable Cross-linking of Proteins", J Biol Chem. (1980) 255(3):1175-1180.
Green et al., "Antigen-specific human monoclonal antibodies from mice engineered with human Ig heavy and light chain YACs", Nature Gen. (1994) 7:13-21.
Gregson et al., "Linker Length Modules DNA Cross-Linking Reactivity and Cytotoxic Potency of C8/C8' Ether-linked C2-exo-Unsaturated Pyrrolo[2,1-c][1,4]benzodiazepine (PBD) Dimers", J Med Chem (2004) 47:1161-1174.
Gribskov et al., (Eds.) Sequence Analysis Primer; Stockton Press (1991); Table of Contents, 7 pages.
Griffin et al., (Eds.) Methods in Molecular Biology-24: Computer Analysis of Sequence Data; Part I & II; Humana Press, New Jersey (1994) Tables of Contents, 8 pages.
Griffiths et al., "Human anti-self antibodies with high specificity from phage display libraries", EMBO J. (1993) 12(2):725-734.
Griffiths et al., "Isolation of high affinity human antibodies directly from large synthetic repertoires", EMBO J. (1994) 13(14):3245-3260.
Grunberg et al. 2013. Dota-functionalized polylysine: A high number of DOTA chelates positively influences the biodistribution of enzymatic conjugated anti-tumor antibody chCE7agl. PLOS ONE, 8(4):e60350.
Hamblett et al., "Effects of Drug Loading on the Antitumor Activity of a Monoclonal Antibody Drug Conjugate", Clin Cancer Res. (Oct. 2004) 10:7063-7070.
Harlow et al., (Eds.), Antibodies—A Laboratory Manual; Table of Contents, Cold Spring Harbor Laboratory Press, Cold Spring Harbor, NY (1988) TOC; 9 pages.
Hay et al., "A 2-nitroimidazole carbamate prodrug of 5-amino-1-(Chloromethyl)-3-[(5,6,7-Trimethoxyindol-2-YL)Carbonyl]-1,2-dihydro-3H-Benz[e]indole (amino-SECO-CBI-TMI) for use with ADEPT and GDEPT", Bioorg Med Chem Lttrs. (Jun. 1999) 9:2237-2242.
Hay et al., "Clinical development success rates for investigational drugs", Nat Biotech. (Jan. 2014) 32(1):40-51.
Higuchi, Russell "Recombinant PCR" Chapter 22 in Part II of PCR Protocols, a Guide to Methods and Applications [Innis et al. (Eds.)], Academic Press, (1990) pp. 177-183.
Ho et al. Site-directed Mutagenesis by Overlap Extension Using the Polymerase Chain Reaction. Gene (1989) 77(1):51-59.
Holliger et al., "Engineered antibody fragments and the rise of single domains", Nature Biotech. (2005) 23(9):1126-1136.

(56) References Cited

OTHER PUBLICATIONS

Hu et al., "Rational design of transglutaminase substrate peptides for rapid enzymatic formation of hydrogels", J Am Chem Soc. (Nov. 2003) 125(47):14298-14299.
Ill et al., "Design and construction of a hybrid immunoglobulin domain with properties of both heavy and light chain variable regions", Prot Engineer. (1997) 10(8):949-957.
Ito et al., "A General Method for Introducing a Series of Mutations into Cloned DNA Using the Polymerase Chain Reaction", Gene (Nov. 1991) 102(1):67-70.
Jackman et al., "Development of a two-part strategy to identify a therapeutic human bispecific antibody that inhibits IgE receptor signaling", J Biol Chem. (2010) 285(27):20850-20859.
Jakobovits et al., "Germ-line transmission and expression of a human-derived yeast artificial chromosome", Nature (1993) 362:255-258.
Jeffrey et al., "Development and Properties of beta-Glucuronide Linkers for Monoclonal Antibody-Drug Conjugates", Bioconj Chem. (2006) 17:831-840.
Jeger. Site-Specific Conjugation of Tumour-Targeting Antibodies Using Transglutaminase. Dissertation. ETH Zurich: University of Basel (2009) 1-135.
Jeger et al., "Site-Specific and Stoichiometric Modification of Antibodies by Bacterial Transglutaminase", Angew Chem Int Ed. (2010) 49(51):9995-9997.
Jeger et al., "Site-specific and stoichiometric modification of antibodies by bacterial transglutaminase", Supporting Information. Angewandte Chemie International Edition, Wiley VCH, (2010) 49(51): 46 pages.
Jones et al., "Replacing the complementarity-determining regions in a human antibody with those from a mouse", Nature (1986) 321:522-525.
Josten et al., "Use of microbial transglutaminase for the enzymatic biotinylation of antibodies", J Immunol Meth. (2000) 240(1-2):47-54.
Jubala et al., "CD20 Expression in Normal Canine B Cells and in Canine non-Hodgkin Lymphoma", Vet Pathol. (2005) 42:368-476.
Junutula et al., "Site-specific conjugation of a cytotoxic drug to an antibody improves the therapeutic index", Nature Biotech (2008) 26(8):925-932.
Kabat et al., (Eds.) Sequences of Proteins of Immunological Interest, 5th Edition; (1991) Table of Contents; 11 pages.
Kamal et al., "Synthesis of 1,2,3-triazole-linked pyrrolobenzodiazepine conjugates employing 'click' chemistry: DNA-binding affinity and anticancer activity", Bioorg Med Chem Lett. (Feb. 2008) 18(4):1468-1473.
Kämpfer et al., "A numerical classification of the genera Streptomyces and Streptoverticillium using miniaturized physiological tests", J Gen Microbiol. (Feb. 1991) 137:1831-1891.
Kajiwara et al., "Expression of L1 Cell Adhesion Molecule and Morphologic Features at the Invasive Front of Colorectal Cancer", Anat Pathol. (2011) 136(1):138-144.
Kamiya et al., "S-Peptide as a Potent Peptidyl Linker for Protein Cross-Linking by Microbial Transglutaminase from *Streptomyces mobaraensis*", Bioconj Chem. (2003) 14:351-357.
Kamiya et al., "Site-specific cross-linking of functional proteins by transglutamination", Enzy Micro Tech. (2003) 33:492-496.
Kingsbury et al., "A Novel Peptide Delivery System Involving Peptidase Activated Prodrugs as Antimicrobial Agents. Synthesis and Biological Activity of Peptidyl Derivatives of 5-Fluorouracil", J Med Chem. (Apr. 1984) 27:1447-1451.
Knappik et al., "Fully Synthetic Human Combinatorial Antibody Libraries (HuCAL) Based on Modular Consensus Frameworks and CDRs Randomized with Trinucleotides", J Mol Biol. (2000) 296:57-86.
Knogler et al., "Copper-67 Radioimmunotherapy and Growth Inhibition by Anti-L1-Cell Adhesion Molecule Monoclonal Antibodies in a Therapy Model of Ovarian Cancer Metastasis", Clin Cancer Res (2007) 13(2):603-611.
Kuil et al., "ITAM-derived phosphopeptide-containing dendrimers as multivalent ligands for Syk tandem SH2 domain", Org Biomol Chem. (2009) 7:4088-4094.
Kunkel, Thomas A., "Rapid and efficient site-specific mutagenesis without phenotypic selection", Proc Natl Acad Sci USA (Jan. 1985) 82:488-492.
Lesk, Arthur M. (Ed.) Computational Molecular Biology, Oxford University Press (1988); Table of Contents; 4 pages.
Lhospice et al., "Cite-specific conjugation of monomethyl auristatin E to Anti-CD30 antibodies improves their pharmacokinetics and therapeutic index in rodent models", Mol Pharmaceutics (2015) 12:1863-1871.
Lin et al., "Transglutaminase-catalyzed site-specific conjugation of small-molecule probes to proteins in vitro and on the surface of living cells", J Am Chem Soc. (2006) 128(14):4542-4543 (7pages).
Liu et al., "Identification of Active Site Residues in the "GyrA" Half of Yeast DNA Topoisomerase II", J Biol Chem. (Aug. 1998) 273(32):20252-20260.
Lonberg et al., "Antigen-specific human antibodies from mice comprising four distinct genetic modifications", Nature (1994) 368:856-859.
Lonberg, Nils, "Human antibodies from transgenic animals", Nature Biotech. (2005) 23(9):1117-1125.
Lorand et al., "Specificity of Guinea Pig Liver Transglutaminase for Amine Substrates", Biochem. (1979) 18(9):1756-1765.
Lorand et al., "Transglutaminases: Cross-linking enzymes with pleiotropic functions", Nature (Feb. 2003) 4:140-156.
Lyon et al., "Conjugation of Anticancer Drugs through Endogenous Monoclonal Antibody Cysteine Residues", Meth Enzymol. (2012) 502:123-138.
Maeda et al., "Susceptibility of human T-cell leukemia virus type I-infected cells to humanized anti-CD30 monoclonal antibodies in vitro and in vivo", Cancer Sci. (2010) 101(1):224-230.
McCafferty et al., "Phage antibodies: Filamentous phage displaying antibody variable domains", Nature (1990) 348:552-554.
Mindt et al., Modification of Different IgG1 Antibodies Glutamine and Lysine Using Bacterial and Human Tissue Transglutaminase. Bioconjug Chem. (2008) 19(1):271-278.
Morrison et al., "Chimeric human antibody molecules: Mouse antigen-binding domains with human constant region domains", Proc Natl Acad Sci. USA (1984) 81:6851-6855.
Moses et al., "The growing applications of click chemistry", Chem Soc Rev. (Aug. 2007) 36(8):1249-1262.
Murthy et al., "Residue Gln-30 of Human Erythrocyte Anion Transporter is a Prime Site for Reaction with Intrinsic Transglutaminase" J Biolog Chem. (Sep. 1994) 269(36):22907-22911.
Murthy et al., "Selectivity in the Post-Translational, Transglutaminase-dependent Acylation of Lysine Residues", Biochem. (Feb. 2009) 48:2654-2660.
Nilsson et al., A synthetic IgG-binding domain based on stapylococcal protein A. Protein Eng. (1987) 1(2):107-113.
Pearson, William R., "Rapid and Sensitive Sequence Comparison with FASTP and FASTA", Meth Enzymol. (1990) 183(5):63-98.
Pearson, William R., "Flexible sequence similarity searching with the FASTA3 program package", Methods Mol Biol. (2000) 132:185-219.
Plagmann et al., "Transglutaminase-catalyzed covalent multimerization of camelidae anti-human TNF single domain antibodies improves neutralizing activity", J Biotech. (2009) 142:170-178.
Presta, Leonard G., "Antibody engineering", Curr Opin Struct Biol. (1992) 2:593-596.
Presta et al., "Humanization of an Antibody Directed Against IgE", J Immunol. (1993) 151(5):2623-2632.
Riechmann et al., "Reshaping human antibodies for therapy", Nature (1988) 332:323-327.
Rodrigues et al., "Synthesis and β-lactamase-mediated activation of a cephalosporin-taxol prodrug", Chem Biol. (Apr. 1995) 2:223-227.
Roguska et al., "Humanization of murine monoclonal antibodies through variable domain resurfacing", Proc Natl Acad Sci. (1994) 91:969-973.
Sambrook et al., (Eds.) Molecular Cloning—A Laboratory Manual, [2nd Edition]; Cold Spring Harbor Laboratory Press, NY; (1989) Table of Contents, 30 pages.

(56) References Cited

OTHER PUBLICATIONS

Sambrook et al., (Eds.) Molecular Cloning—A Laboratory Manual, [3rd Edition]; vol. 1; Cold Spring Harbor Laboratory Press, NY; (2001); Table of Contents, 18 pages.
Sazinsky et al., "Aglycosylated immunoglobulin G1 variants productively engage activating Fc receptors", PNAS (2008) 105(51):20167-20172.
Sims et al., "A Humanized CD18 Antibody can block Function without Cell Destruction", J Immunol. (1993) 151:2296-2308.
Smith, Douglas W. (Ed.), Biocomputing—Informatics and Genome Projects, Academic Press, Inc. (1993) Table of Contents, 7 pages.
Stancovski et al., "Mechanistic aspects of the opposing effects of monoclonal antibodies to the ERBB2 receptor on tumor growth", Proc Natl Acad Sci USA. (Oct. 1991) 88(19):8691-8695.
Starling et al., "In vivo antitumor activity of a panel of four monoclonal antibody-vinca alkaloid immunoconjugates which bind to three distinct epitopes of carcinoembryonic antigen", Bioconjug Chem. (1992) 3(4):315-322.
Strop et al., "Location Matters: Site of Conjugation Modulates Stability and Pharmacokinetics of Antibody Drug Conjugates", Chem Biol. (2013) 20(2):161-167.
Sung et al., "Functional glass surface displaying a glutamyl donor substrate for transglutaminase-mediated protein immobilization", Biotech J. (2010) (5):456-462.
Suzuki et al., Glycopinion Mini-Review: N-Glycosylation/Deglycosylation as a Mechanism for the Post-Translational Modification/Remodification of Proteins. Glycoconjug J. (1995) 12:183-193.
Takazawa et al., Enzymatic Labeling of a Single Chain Variable Fragment of an Antibody With Alkaline Phosphates by Microbial Transglutaminase. Biotech Engin. (2004) 86(4):399-404.
Tan et al., "Superhumanized" Antibodies: Reduction of Immunogenic Potential by Complementarity-Determining Region Grafting with Human Germline Sequences: Application to an Anti-CD28. J Immunol. (2002) 169:1119-1125.
Tomlinson et al., the Repertoire of Human Germline VH Sequences Reveals about Fifty Groups of VH Segments with Different Hypervariable Loops. J Mol Biol. (1992) 227:776-798.
Uhlén et al., Complete Sequence of the Staphylococcal Gene Encoding Protein A—A Gene Evolved Through Multiple Duplications. J Biol Chem. (1984) 259(3):1695-1702.
Vallette et al., Construction of Mutant and Chimeric Genes Using the Polymerase Chain Reaction. Nuc Acids Res. (Jan. 1989) 17(2):723-733.
Verhoeyen et al., Reshaping Human Antibodies: Grafting an Antilysozyme Activity. Science (1988) 239:1534-1536.
Von Heinje, Gunnar [Ed.] "Sequence Analysis in Molecular Biology—Treasure Trove or Trivial Pursuit", 1987, Academic Press [TOC Only].
Wakankar et al., Analytical Methods for Physicochemical Characterization of Antibody Drug Conjugates. Landes Biosci. (Mar./Apr. 2011) 3(2):161-172.
Wängler et al., "Antibody-Dendrimer Conjugates: The Number, Not the Size of the Dendrimers, Determines the Immunoreactivity" Bioconjugate Chem. (2008) (19)4:813-820.
Ward et al., Binding Activities of a Repertoire of Single Immunoglobulin Variable Domains Secreted From *Escherichia coli*. Nature (1989) 341:544-546.
Wells et al., Cassette Mutagenesis: An Efficient Method for Generation of Multiple Mutations at Defined Sites. Gene (Jan. 1985) 34(2-3):315-323.
Xu et al., "Characterization of intact antibodydrug conjugates from plasma/serum in vivo by affinity capture capillary liquid chromatography mass spectrometry", Anal Biochem. (2011) 412(1): 56-66.
Yu et al., "Interaction between Bevacizumab and Murine VEGF-A: A Reassessment", Invest Ophtalmol Vis Sci. (Feb. 2008) 49(2):522-527.
Yurkovetskiy et al., Synthesis of a Macromolecular Camptothecin Conjugate with Dual Phase Drug Release. Mol Pharm. (Jun. 2004) 1(5):375-382.

Zoller et al., "Oligonucleotide-directed mutagenesis using M13-derived vectors: an efficient and general procedure for the production of point mutations in any fragment of DNA", Nucl Acids Res. (Aug. 1982) 10(20):6487-6500.
Zoller et al., "Oligonucleotide-directed mutagenesis of DNA fragments cloned into M13 vectors", Methods Enzymol. (1983) 100:468-500.
International Search Report dated Apr. 23, 2013 for International Application No. PCT/EP2012/076631 filed Dec. 21, 2012.
International Search Report dated Feb. 5, 2014 for International Application No. PCT/EP2012/076606 filed Dec. 21, 2012.
International Search Report and Written Opinion dated Sep. 24, 2014 for International Application No. PCT/EP2014/063064 filed Jun. 20, 2014, 16 pages.
International Search Report dated Jan. 31, 2014 for International Application No. PCT/EP2013/064605 filed Jul. 10, 2013.
International Search Report dated Apr. 15, 2014 for International Application No. PCT/EP2013/073428 filed Nov. 8, 2013.
International Search Report dated Jun. 25, 2014 for International Application No. PCT/EP2014/055140 filed Mar. 14, 2014.
International Search Report and Written Opinion of the International Searching Authority dated Aug. 20, 2014 for International Application No. PCT/EP2014/063061 filed Jun. 20, 2014.
U.S. Appl. No. 61/410,840, filed Nov. 5, 2010.
U.S. Appl. No. 61/553,917, filed Oct. 31, 2011.
U.S. Appl. No. 61/579,908, filed Dec. 23, 2011.
U.S. Appl. No. 61/661,569, filed Jun. 19, 2012.
U.S. Appl. No. 61/671,122, filed Jul. 13, 2012.
U.S. Appl. No. 61/671,128, filed Jul. 13, 2012.
U.S. Appl. No. 61/837,932, filed Jun. 21, 2013.
U.S. Office Action dated Feb. 27, 2015 in U.S. Appl. No. 13/725,382, filed Dec. 21, 2012.
U.S. Response to Office Action filed May 28, 2015 in U.S. Appl. No. 13/725,382, filed Dec. 21, 2012.
U.S. Office Action dated Aug. 13, 2015 in U.S. Appl. No. 13/725,382, filed Dec. 21, 2012.
U.S. Response to Office Action filed Dec. 11, 2015 in U.S. Appl. No. 13/725,382, filed Dec. 21, 2012.
U.S. Office Action dated Feb. 25, 2016 in U.S. Appl. No. 13/725,382, filed Dec. 21, 2012.
U.S. Response to Office Action filed May 23, 2016 in U.S. Appl. No. 13/725,382, filed Dec. 21, 2012.
U.S. Office Action dated Aug. 8, 2016 in U.S. Appl. No. 13/725,382, filed Dec. 21, 2012.
U.S. Response to Office Action filed Nov. 9, 2016 in U.S. Appl. No. 13/725,382, filed Dec. 21, 2012.
U.S. Notice of Allowance dated Mar. 28, 2017 in U.S. Appl. No. 13/725,382, filed Dec. 21, 2012.
U.S. Office Action dated Apr. 23, 2015 in U.S. Appl. No. 14/582,040, filed Dec. 23, 2014.
U.S. Response to Office Action filed May 20, 2015 in U.S. Appl. No. 14/582,040, filed Dec. 23, 2014.
U.S. Pre-Interview Communication dated Jul. 2, 2015 in U.S. Appl. No. 14/582,040, filed Dec. 23, 2014.
U.S. Response to Pre-Interview Communication filed Jul. 31, 2015 in U.S. Appl. No. 14/582,040, filed Dec. 23, 2014.
U.S. Office Action dated Oct. 8, 2015 in U.S. Appl. No. 14/582,040, filed Dec. 23, 2014.
Response to Office Action filed Dec. 8, 2015 in U.S. Appl. No. 14/582,040, filed Dec. 23, 2014.
U.S. Office Action dated Feb. 11, 2016 in U.S. Appl. No. 14/582,040, filed Dec. 23, 2014.
Response to Office Action filed Feb. 29, 2016 in U.S. Appl. No. 14/582,040, filed Dec. 23, 2014.
U.S. Notice of Allowance dated Jun. 6, 2016 in U.S. Appl. No. 14/582,040, filed Dec. 23, 2014.
U.S. Office Action dated Aug. 17, 2016 in U.S. Appl. No. 14/414,432, filed Jan. 12, 2015.
U.S. Response to Office Action filed Nov. 17, 2016 in U.S. Appl. No. 14/414,432, filed Jan. 12, 2015.
U.S. Office Action dated Mar. 31, 2017 in U.S. Appl. No. 14/414,432, filed Jan. 12, 2015.

(56) References Cited

OTHER PUBLICATIONS

U.S. Office Action dated Feb. 28, 2017 in U.S. Appl. No. 14/441,157, filed May 6, 2015.
U.S. Response to Office Action filed Apr. 26, 2017 in U.S. Appl. No. 14/441,157, filed May 6, 2015.
U.S. Response dated Feb. 14, 2018 in U.S. Appl. No. 14/441,157, filed May 6, 2015.
U.S. Notice of Allowance dated Mar. 22, 2018 in U.S. Appl. No. 14/441,157, filed May 6, 2015.
U.S. Notice of Allowability [Suppl.] dated Apr. 2, 2018 in U.S. Appl. No. 14/441,157, filed May 6, 2015.
U.S. Office Action dated Mar. 28, 2017 in U.S. Appl. No. 14/775,647, filed Sep. 11, 2015.
U.S. Preliminary Amendment dated May 3, 2013 in U.S. Appl. No. 13/883,535, filed May 3, 2013.
U.S. Office Action dated Dec. 19, 2014 in U.S. Appl. No. 13/883,535, filed May 3, 2013.
U.S. Second Preliminary Amendment dated Feb. 17, 2015 in U.S. Appl. No. 13/883,535, filed May 3, 2013.
U.S. Office Action dated Sep. 16, 2015 in U.S. Appl. No. 13/883,535, filed May 3, 2013.
U.S. Response dated Nov. 16, 2015 in U.S. Appl. No. 13/883,535, filed May 3, 2013.
U.S. Office Action dated Dec. 30, 2015 in U.S. Appl. No. 13/883,535, filed May 3, 2013.
U.S. Response dated May 2, 2016 in U.S. Appl. No. 13/883,535, filed May 3, 2013.
U.S. Office Action dated Jul. 5, 2016 in U.S. Appl. No. 13/883,535, filed May 3, 2013.
U.S. Response dated Sep. 1, 2016 in U.S. Appl. No. 13/883,535, filed May 3, 2013.
U.S. Notice of Allowance dated Feb. 8, 2017 in U.S. Appl. No. 13/883,535, filed May 3, 2013.
U.S. Rule 312 Amendment dated Apr. 3, 2017 in U.S. Appl. No. 13/883,535, filed May 3, 2013.
Alley et al., "Antibody-drug conjugates: targeted drug delivery for cancer", Curr Opin Chem Biol. (2010) 14:529-537.
Beranger S. et al., International ImMunoGeneTics Information Systems, "MCT Scientific Chart" (downloaded from the web Aug. 20, 2017) URL: http://www.imgt.org/IMGTScientificChart/Numbering/Hu_IGHGnber.html; 4 pages.
U.S. Notice of Allowability/Examiner's Amendment dated Apr. 28, 2017 in U.S. Appl. No. 13/725,382, filed Dec. 21, 2012.
U.S. Preliminary Amendment dated Jul. 19, 2017 in U.S. Appl. No. 15/654,585, filed Jul. 19, 2017.
U.S. Preliminary Amendment dated Jan. 9, 2017 in U.S. Appl. No. 15/214,331, filed Jul. 19, 2016.
U.S. Office Action dated Mar. 8, 2018 in U.S. Appl. No. 15/214,331, filed Jul. 19, 2016.
U.S. Response to Office Action filed Aug. 29, 2017 in U.S. Appl. No. 14/414,432, filed Jan. 12, 2015.
U.S. Office Action dated Nov. 17, 2017 in U.S. Appl. No. 14/414,432, filed Jan. 12, 2015.
U.S. Response to Office Action filed Apr. 4, 2018 in U.S. Appl. No. 14/414,432, filed Jan. 12, 2015.
U.S. Office Action dated Sep. 19, 2017 in U.S. Appl. No. 14/441,157, filed May 6, 2015.
U.S. Response to Office Action filed Jun. 28, 2017 in U.S. Appl. No. 14/775,647, filed Sep. 11, 2015.
U.S. Office Action dated Aug. 22, 2017 in U.S. Appl. No. 14/775,647, filed Sep. 11, 2015.
U.S. Response to Office Action filed Nov. 21, 2017 in U.S. Appl. No. 14/775,647, filed Sep. 11, 2015.
U.S. Response to Office Action filed Jun. 29, 2017 in U.S. Appl. No. 14/898,693, filed Dec. 15, 2015.
U.S. Office Action dated Oct. 19, 2017 in U.S. Appl. No. 14/898,693, filed Dec. 15, 2015.
U.S. Response to Office Action filed Jan. 19, 2018 in U.S. Appl. No. 14/898,693, filed Dec. 15, 2015.
U.S. Examiner's Amendment dated May 9, 2018 in U.S. Appl. No. 14/898,693, filed Dec. 15, 2015.
U.S. Divisional Application/Preliminary Amendment dated May 11, 2017 in U.S. Appl. No. 15/593,259, filed May 11, 2017.
U.S. Response to Pre-Exam Formalities dated Jul. 21, 2017 in U.S. Appl. No. 15/593,259, filed May 11, 2017.
Deisenhofer et al., "Crystallographic Refinement and Atomic Models of a Human Fc Fragment and Its Complex with Fragment B of Protein A from *Staphylococcus aueus* at 2.9- and 2.8-Å Resolution", Biochem. (1981) 20(9): 2361-2370.
Kelly, "An antibody-cytotoxic conjugate, BIIB015, is a new targeted therapy for Cripto positive tumours." Eur J Cancer. (2011) 47(11):1736-1746.
Lund et al., "Multiple interactions of IgG with its core oligosaccharide can modulate recognition by complement and human Fc gamma receptor I and influence the synthesis of its oligosaccharide chains". J Immunol. (1996) 157(11):4963-4969.
Praderio C., "Selma Blair says she's living with an 'aggressive form' of multiple sclerosis. Here's what to know about the incurable condition.", Business Insider (2019); accessed from businessinsider.sg on 2019-03-11; Excerpt in 1 page.
Rahman et al., "Effect of base sequence on the DNA cross-linking properties of pyrrolobenzodiazepine (PBD) dimers", Nucl Acids Res. (2011) 39(13):5800-5812.
Wright et al., "The interaction of protein A and Fc fragment of rabbit immunoglobulin G as probed by complement-fixation and nuclear-magnetic-resonance studies". Biochem J. (1977) 167(3):661-668.
U.S. Office Action dated May 31, 2018 in U.S. Appl. No. 15/593,259, filed May 11, 2017.
U.S. Response to Restriction Requirement dated Jul. 23, 2018 in U.S. Appl. No. 15/593,259, filed May 11, 2017.
U.S. Office Action dated Oct. 1, 2018 in U.S. Appl. No. 15/593,259, filed May 11, 2017.
U.S. Response to Office Action dated Mar. 29, 2019 in U.S. Appl. No. 15/593,259, filed May 11, 2017.
U.S. Office Action dated May 30, 2019 in U.S. Appl. No. 15/593,259, filed May 11, 2017.
U.S. Office Action dated Apr. 16, 2019 in U.S. Appl. No. 15/654,585, filed Jul. 19, 2017.
U.S. Response to Office Action filed Jul. 6, 2018 in U.S. Appl. No. 15/214,331, filed Jul. 19, 2016.
U.S. Office Action dated Sep. 18, 2018 in U.S. Appl. No. 15/214,331, filed Jul. 19, 2016.
U.S. Response to Office Action filed Mar. 18, 2019 in U.S. Appl. No. 15/214,331, filed Jul. 19, 2016.
U.S. Notice of Allowance dated May 31, 2019 in U.S. Appl. No. 15/214,331, filed Jul. 19, 2016.
U.S. Notice of Allowance dated Jul. 9, 2018 in U.S. Appl. No. 14/414,432, filed Jan. 12, 2015.
U.S. Preliminary Amendment filed Feb. 25, 2019 in U.S. Appl. No. 16/035,437, filed Jul. 13, 2018.
U.S. Office Action dated Feb. 14, 2018 in U.S. Appl. No. 14/775,647, filed Sep. 11, 2015.
U.S. Response to Office Action filed Aug. 8, 2018 in U.S. Appl. No. 14/775,647, filed Sep. 11, 2015.
U.S. Office Action dated Nov. 8, 2018 in U.S. Appl. No. 14/775,647, filed Sep. 11, 2015.
U.S. Response to Office Action filed Apr. 26, 2019 in U.S. Appl. No. 14/775,647, filed Sep. 11, 2015.
U.S. Notice of Allowance dated May 24, 2018 in U.S. Appl. No. 14/898,693, filed Dec. 15, 2015.
Choe et al., "Fc-Binding Ligands of Immunoglobulin G: An Overview of High Affinity Proteins and Peptides", Materials (2016) 9:994; 17 pages.
U.S. Notice of Allowance dated Nov. 11, 2019 in U.S. Appl. No. 14/775,647, filed Sep. 11, 2015.
U.S. Response to Office Action filed Sep. 30, 2019 in U.S. Appl. No. 15/593,259, filed May 11, 2017.

\* cited by examiner

Q at the H chain surface of Rituximab (VH and CH1 domains)

Accessible: Q1, Q3, Q5, Q62 and Q82
Barely exposed: Q179
Hidden: Q6 and Q39

ENZYMATIC CONJUGATION OF ANTIBODIES

CROSS-REFERENCE TO RELATED APPLICATIONS

This application is a divisional application of U.S. patent application Ser. No. 14/367,840, filed on Jun. 20, 2014, now U.S. Pat. No. 9,764,038, entitled "ENZYMATIC CONJUGATION OF ANTIBODIES," which is the U.S. National Phase of Application No. PCT/EP2012/076631 entitled "ENZYMATIC CONJUGATION OF ANTIBODIES" filed Dec. 21, 2012, which designated the United States, and which claims the benefit of U.S. Provisional Application Nos. 61/671,122, filed Jul. 13, 2012; 61/661,569, filed Jun. 19, 2012; and 61/579,908, filed Dec. 23, 2011. The disclosures of the above-referenced applications are incorporated herein by reference in their entireties, including any drawings.

REFERENCE TO SEQUENCE LISTING

The present application is being filed along with a Sequence Listing in electronic format. The Sequence Listing is provided as a file entitled Sequence Listing INNAT016D1.TXT, created Aug. 18, 2017 which is 266 KB in size. The information in the electronic format of the Sequence Listing is incorporated herein by reference in its entirety.

FIELD OF THE INVENTION

The present invention relates to a method for the functionalization of human and humanized immunoglobulins.

BACKGROUND

Therapeutic antibodies (mAbs) have important applications in medicine. However, antibodies of non-human origin such as murine antibodies have drawbacks in that humans mount an anti-mouse antibody response when administered murine antibodies. Techniques developed to overcome the risk of immunogenicity involved increasing the content of human sequences in antibodies, including grafting murine complementarity-determining regions (CDRs) onto human frameworks (FRs) to create an antibody with higher human sequence content. This process, known as CDR-grafting (Jones, et al., 1986, Nature 321:522-525), was the first described method of antibody humanization. Since then, several methods of humanization have been described including resurfacing (Roguska, et al., 1994, Proc Natl Acad Sci USA 91:969-973), specificity-determining residue (SDR) grafting (Kashmiri, et al., 2005, Methods 36:25-34), superhumanization (Hwang, et al., 2005, Methods 36:35-42), human string content optimization (Lazar, et al., 2007, Mol Immunol 44:1986-1998), and framework shuffling (Dall'Acqua, et al., 2005, Methods 36:43-60; Damschroder, et al., 2007, Mol Immunol 44:3049-3060). The underlying assumption of all these methods is that the greater global sequence identity of the humanized sequence to a natural human sequence results in a lower risk of immunogenicity. However, due to the perceived risk of losing antigen affinity, none of these methods substantially engineer the CDRs, and as such none of these humanization methods reach the global sequence identity levels of human antibodies as they still contain mostly non-human CDRs. More recently, "fully-human" mAbs generated from recombinant human antibody libraries (Griffiths, et al., 1994, Embo J 13:3245-3260; Knappik, et al., 2000, J Mol Biol 296:57-86) or transgenic mice comprising human germline configuration immunoglobulin gene sequences (Lonberg, 2005, Nat Biotechnol 23:1117-1125; Green, et al., 1994, Nat Genet 7:13-21; Lonberg, et al., 1994, Nature 368:856-859) have emerged as alternatives to murine generated and subsequently humanized mAbs. These mAbs have both high affinity as well as high human sequence content.

Linking antibodies to moieties of interest such as drugs, radioactive elements, labels or stabilizing molecules (e.g. polymers) is of high pharmaceutical interest. Current methods used for conjugation to human or humanized antibodies rely solely on direct, non-enzymatically-mediated, functionalization of certain residues with moieties of interest. Human or humanized antibodies are functionalized on cysteine residues. However a major drawback of such methods is that conjugation is not stoichiometric, with antibodies in a mixture typically having from 1 to 8 moieties (e.g. drugs) per antibody, and that conjugation can occur on unwanted cysteine residues necessitating cysteine engineering. Enzymatic methods have been shown to be capable of conjugating moieties of interest onto murine antibodies. Notably, transglutaminases (TGases) have been used to conjugate small detectable markers onto antibodies having murine variable regions (see, e.g., Josten et al. (2000) J. Immunol. Methods 240, 47-54; Mindt et al (2008) Bioconjug. Chem. 19, 271-278; Jeger et al (2010) Angew. Chem. Tnt. Ed. 49: 9995-9997); Kamiya et al (2003) Enzyme. Microb. Technol. 33, 492-496 and US patent publication no. 2011/0184147. However, the rules which govern selection by TGases of glutamine residues for modification are still largely unknown. Antibodies are estimated to have in the range of 90 lysine residues and 60 glutamine residues, including surface-exposed residues in the CDRs and FRs sequences. Current methods for producing antibody-drug conjugates are based on chemical reactions between naturally-occurring cysteines within antibodies and maleimide-reactive groups on drug-containing linkers. However such conjugation onto naturally occurring cysteine residues risks of unwanted conjugation onto different cysteines.

In view of the foregoing, there remains a need in the art for methods to conjugate moieties onto antibodies in a stoichiometric fashion and without negatively affecting the biological activity of the antibodies.

SUMMARY OF THE INVENTION

In one aspect, the present invention provides in one aspect modified (e.g. mutated, affinity optimized), human and humanized antibodies, or an antibody comprising an acceptor glutamine in a constant region, conjugated to a moiety-of-interest via a lysine-based linker (for example, any primary amine chain which is a substrate for TGase, e.g. comprising an alkylamine, oxoamine) wherein the conjugation occurs exclusively on one or more acceptor glutamine residues present in the antibody outside of the antigen combining site (e.g. outside a variable region, in a constant region). Conjugation thus does not occur on a glutamine, e.g. an at least partly surface exposed glutamine, within the variable region. The conjugate is formed by reacting the antibody and a lysine-based linker in the presence of a TGase. The lysine-based linker may comprise, for example, in addition to a primary amine, e.g. alkylamine, oxoamine, a peptide, polypeptide, any organic molecule, a drug or diagnostic moiety, or may comprise a reactive moiety that can subsequently be reacted with a compound comprising a drug or diagnostic moiety. The present approach also provides for antibody compositions that have homogenous functionalized acceptor glutamine:antibody stoichiometry.

As presented herein, the acceptor glutamine residue is part of the immunoglobulin and the lysine-based linker is part of the moiety that is conjugated to the glutamine residue on the immunoglobulin. The primary amino group is preferably separated by at least five atoms (e.g. $(CH_2)$—groups) or a spacer of equal length from the moiety-of-interest.

The antibodies of the invention are created through use of a linking reagent that can be attached, by the action of a TGase, to a polypeptide at a glutamine residue (Q) within the primary sequence of an antibody (Ab). The linking reagent (lysine based linker) comprises a lysine derivative (Lys), or a functional equivalent thereof, that is connected to at least one reactive group. In one embodiment, a moiety-of-interest (Z) can be attached to the linking reagent. In one embodiment, a plurality of reactive groups, preferably non-complementary reactive groups, can be attached to the linking reagent. The reactive group is preferably a functionality that is insensitive to water but selectively undergoes a very high conversion addition reaction with a complementary reagent. The functional equivalent of a lysine derivative comprises a 2 to 20 carbon chain, or a functional equivalent thereof, for example an aminomethylene ($H_2NCH_2$) group, a protected $H_2NCH_2$ group that can be derived from the aminomethylene, an oxoamine (($H_2NO$) group or a protected $H_2NO$ group, positioned at one or more ends of the carbon chain. The functional equivalent of the carbon chain is a chain of 3 to 20 atoms where one or more non-terminal atoms can be other than carbon, for example oxygen, sulfur, nitrogen, or other atoms. The oxygen, sulfur, or nitrogen atom can be of an ether, ester, thioether, thioester, amino, alkylamino, amido or alkylamido functionality within the carbon chain.

One exemplary functional equivalent of the carbon chain is an oligo (ethylene oxide) chain. The functionality within the carbon chain can be included to couple the reactive group to the $H_2NCH_2$ group or protected $H_2NCH_2$ group. The carbon chain, or its functional equivalent, can be substituted or unsubstituted. The substituents can be alkyl groups, aryl groups, alkyl aryl groups, carboxylic acid groups, amide groups, hydroxy groups, or any other groups that do not compete with the amino group for, or inhibit, conjugation with a glutamine residue of the protein. Typically, when a substituent is present, its presence is in a convenient starting material, such as the carboxylic acid group of lysine, from which the lysine derivative results. The aminomethylene end of a carbon chain is necessarily included in the linking reagent.

Starting materials for the functional equivalent of lysine can be an α,ω-diaminoalkane, for example, 1,2-diaminoethane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,11-diaminoundecane, or 1,12-diaminododecane. Other starting materials for the functional equivalent of a lysine derivative can be α,ω-diamino oligo (ethylene oxide), for example, $H_2N(CH_2CH_2O)_xCH_2CH_2NH_2$ where x is 1 to about 6. The α,ω-diamino oligo (ethylene oxide) can be a single oligomer or it can be a mixture of oligomers where x defines an average size. An exemplary protected $H_2NCH_2$ is the tert-butylcarbamate protected amine of tert-butyl N-(5-aminopentyl)carbamate (N-Boc-cadaverin).

In one aspect, present invention provides a multi-step (e.g. two-step) site-specific labeling and functionalization approach which involves conjugation a linking reagent with a reactive group to a human or humanized antibody, or a glutamine-engineered antibody of the invention with TGase, followed by further reaction of the reactive group. The method is particularly useful for functionalizing immunoglobulins with drugs, particularly peptides and polypeptides, relatively large chemical entities, negatively charged chemical entities and/or hydrophobic chemical entities, e.g. typical cytotoxic drugs such as duocarmycins, maytansanoids, alkylating agents, taxanes, MMAE, MMAF and the like (e.g. analogues thereof) that are derived from natural sources or analogues or derivatives thereof, typical polymers such as PEG that enhance stability of antibody fragments.

The present invention thus relates in one embodiment to a method for conjugating a moiety of interest (Z) to an antibody, comprising the steps of:

a) providing an human or humanized antibody, or an antibody comprising a glutamine in a variable region, optionally an at least partly surface exposed glutamine in a variable region, wherein the antibody comprises at least one acceptor glutamine residue in a constant region; and b) reacting said antibody with a lysine-based linker comprising a reactive group (R), preferably a protected reactive group, in the presence of a TGase, under conditions sufficient to obtain a human or humanized antibody comprising an acceptor glutamine in a constant region linked (covalently) to a moiety of interest (Z) or a reactive group (R), via a lysine-based linker.

In one embodiment, an antibody is prepared by preparing a human or humanized antibody, or an antibody comprising an acceptor glutamine in a variable region, and reacting such antibody with a compound of Formula Ia to obtain an antibody of Formula IVa. In one embodiment, an antibody is prepared by preparing a human or humanized antibody, or an antibody comprising a glutamine in a variable region, and reacting such antibody with a compound of Formula Ib to obtain an antibody of Formula II or IVb, and where applicable, optionally further reacting an antibody of Formula II with a compound of Formula III to obtain an antibody of Formula IVb.

The human or humanized antibody, or an antibody comprising a (non-functionalized) glutamine in a variable region, comprising an acceptor glutamine in a constant region linked to a reactive group (R) via a lysine-based linker can thereafter be reacted with a reaction partner comprising a moiety of interest (Z) to generate an antibody comprising an acceptor glutamine linked to a moiety of interest (Z) via a lysine-based linker. Thus, in one embodiment, the method further comprises a step (c): reacting (i) an antibody of step b) comprising an acceptor glutamine linked to a reactive group (R) via a lysine-based linker, with (ii) a compound comprising a reactive group (R') capable of reacting with reactive group R and a moiety of interest (Z), under conditions sufficient to obtain an antibody comprising an acceptor glutamine linked to a moiety of interest (Z) via a lysine-based linker.

The invention provides, inter alia, the compositions having narrow distributions of numbers of conjugates per antibody that result from the method for conjugating a moiety of interest (Z) to an antibody. Such compositions are advantageous for human therapy. In particular, in one aspect the invention provides tetrameric (e.g. full-length) human or humanized antibody compositions having a well defined distribution of number of conjugates per antibody, and in particular, a narrow Drug-Antibody Ratio (DAR) distribution. In particular, the method permits substantially complete conjugation of antibodies. In one aspect the invention provides a composition wherein a high portion of human or humanized antibodies in the composition (e.g. at least 80%, 85%, 90%, 95% of the antibodies) comprise at least one moiety of interest, wherein the composition is substantially free of antibodies comprising a number of moieties of interest that is greater than 2 times, optionally 1.5 times, the mean number of conjugates per antibody (e.g., the mean DAR). The invention provides a composition wherein a high portion of human or humanized antibodies in the composition (e.g. at least 80%, 85%, 90%, 95% of the antibodies) comprise at least one moiety of interest, wherein compositions of the invention are preferably also free of antibodies having conjugated light chains.

In one embodiment, any antibody of the invention (e.g., a human or humanized antibody or an antibody comprising an acceptor glutamine in a constant region), comprises an acceptor glutamine residue (Q), wherein the antibody is conjugated (i.e., covalently attached) via said acceptor glutamine residue (Q) to one or more moieties-of-interest (Z) through a linker that comprises a NH—(C)$_n$— moiety, optionally wherein the linker further comprises a RR' moiety, a V (or V') moiety, and/or a Y (or Y') moiety. Preferably, n is 2 to 20.

In one embodiment, any antibody or antibody fragment of the invention (e.g., a human or humanized antibody or an antibody comprising a glutamine in a variable region), may be characterized as comprising a functionalized acceptor glutamine residue (Q) having Formula IVa or Formula IVb, below,

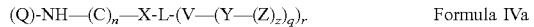    Formula IVa

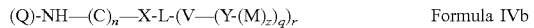    Formula IVb or a pharmaceutically acceptable salt or solvate thereof; wherein:

(C)$_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;

n is an integer from among the range of 2 to 20;

X is NH, O, S, absent, or a bond;

L is independently absent, a bond or a continuation of a bond if X is a bond, or a carbon comprising framework of 5 to 200 atoms substituted at one or more atoms;

r is an integer selected from among 1, 2, 3 or 4;

q is an integer selected from among 1, 2, 3 or 4;

z is an integer selected from among 1, 2, 3 or 4; and

V is independently absent, a bond or a continuation of a bond, a non-cleavable moiety or a conditionally-cleavable moiety;

Y is independently absent, a bond or a continuation of a bond, or a spacer system which is comprised of 1 or more spacers;

Z is a moiety that improves the pharmacokinetic properties, a therapeutic moiety or a diagnostic moiety; and M is independently: R or (RR')-L'-(V'—(Y'—(Z)$_{z'}$)$_{q'}$)$_{r'}$, wherein each of L', V', Y', z', q', and r' are as defined in Formula III for L, V, Y, z, q, and r, Z is a moiety-of-interest, optionally a moiety that improves the pharmacokinetic properties, or a therapeutic moiety or a diagnostic moiety, R is as defined in Formula Ib and wherein each (RR') is an addition product between an R of Formula Ib and its complementary R' of formula III (see, for example, FIG. 1 and FIG. 2). RR' is preferably an addition product of a: thio-maleimide (or haloacetamide) addition, for example, a N,S-disubstituted-3-thio-pyrrolidine-2,5-dione; Staudinger ligation, for example, a N,3- or N,4-substituted-5-dipenylphosphinoxide-benzoic amide; Huisgen 1,3-cycloaddition (click reaction), for example, a N,S-disubstituted-3-thio-pyrrolidine-2,5-dione, 1,4-disubstituted-1,2,3-triazole, 3,5-disubstituted-isooxazole, or 3,5-disubstituted-tetrazole; Diels-Alder cycloaddition adduct, for example the 2,4-cycloaddition product between an O or N-substituted-5-norbornene-2-carboxylic ester or amide, N-substituted-5-norbornene-2,3-dicarboxylic imide, O or N-substituted-7-oxonorbornene-5-carboxylic ester or amide, or N-substituted-7-oxonorbornene-5,6-dicarboxylic imide and a 9-substituted anthracene or 3-substituted 1,2,4,5-tetrazine; or any high yield selective amidation or imidization reaction. Some reactions and the corresponding RR' reaction products are illustrated in FIGS. 1 and 2.

Optionally, Formula IVb will comprise V or V' (but not both V and V'). Optionally, Formula IV will comprise Y or Y' (but not both Y and Y').

In one embodiment, n is an integer from among the range of 10 to 20. In one embodiment, (C)$_n$ is a heteroalkyl chain that comprises a (CH$_2$—CH$_2$—O—)$_x$ group, wherein x is an integer from among the range of 1 to 6. In one embodiment, at least one of L, V or Y are present. In one embodiment, n is an integer from among the range of 2 to 6 (i.e. 2, 3, 4, 5 or 6) and at least one of L, V or Y are present.

Optionally, in any of the linking reagents, protein-conjugated linking reagents, antibodies or antibody fragments of the invention, L comprises a linear carbon comprising framework of 5 to 30 carbon atoms optionally substituted at one or more atoms. Optionally, L comprises a CH$_2$—(CH$_2$—O—CH$_2$)$_x$—CH$_2$ or a (CH$_2$—CH$_2$—O—)$_x$ group, wherein x is an integer from among the range of 1 to 24. Optionally, the groups —(C)$_n$—X-L-collectively comprise a structure CH$_2$—(CH$_2$—O—CH$_2$)$_x$—CH$_2$ or (CH$_2$—CH$_2$—O—)$_x$, wherein x is an integer from among the range of 2 to 20, optionally wherein x is an integer from among the range of 3 to 24. Optionally, L comprises an amino acid or a di-, tri-, tetra-, or oligopeptide. In some embodiments, L is alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or citrulline. In some embodiments, L is valine or citrulline.

In one embodiment, any antibody of the invention (e.g., a human or humanized antibody or an antibody comprising a glutamine in variable region), can be characterized as comprising a functionalized acceptor glutamine residue (Q) having Formula II (e.g. an intermediate product).

It will be appreciated that Formula II, IVa and IVb can for convenience also be expressed as (Ab)-NH—(C)$_n$—X-L-(V—(Y—(R)$_z$)$_q$)$_r$, (Ab)-NH—(C)$_n$—X-L-(V—(Y—(Z)$_z$)$_q$)$_r$ and (Ab)-NH—(C)$_n$—X-L-(V—(Y-(M)$_z$)$_q$)$_r$, respectively, where (Ab) is an immunoglobulin (Ab) is conjugated via a glutamine (Q) residue to an NH of the linking reagent (e.g the compound of Formula I).

In any of Formulas herein, q, q', r and r' may optionally be specified to represent degree of branching or polymerization.

In Formula IV, the total number of R or Z moieties per antibody is preferably from about 1 to about 16. The invention includes a composition comprising a plurality of antibody compounds of Formula IV, wherein substantially each antibody of such plurality has 1, 2, 3, 4, 5, 6, 8, 10, 12, 14 or 16 moieties Z per antibody. In one embodiment, the antibody of Formula II or IV has one, two or four functionalized acceptor glutamine residue and z=1, q=1 and r=1. In one embodiment, the antibody of Formula II or IV has one, two or four functionalized acceptor glutamine residues and z=2, 3 or 4, q=1 and r=1. In one embodiment, the antibody of Formula II or IV has one, two or four functionalized acceptor glutamine residue and z=1, 2, 3 or 4, q=2 and r=1. In one embodiment, the antibody of Formula II or IV has one, two or four functionalized acceptor glutamine residue and z=1, 2, 3 or 4, q=1 and r=2. In one embodiment invention provides an antibody composition in which Z (e.g. drug) loading per antibody is homogeneous.

Preferably, in any the methods or compositions of the invention, a composition of a plurality of antibody conjugates is obtained wherein the antibodies have a homogeneous ratio of functionalized acceptor glutamines:antibody. In one embodiment the invention provides a composition comprising a plurality of antibodies of Formula II, IVa or IVb, wherein at least 70%, 80%, 85%, 90%, 95%, 98% or 99% of the antibodies in the composition have the same number of functionalized acceptor glutamine residues (Q) (e.g, a functionalized acceptor glutamine of Formula II or IV) per antibody. Preferably at least 70%, 80%, 85%, 90%, 95%, 98% or 99% of the antibodies in said first antibody composition have no more or no less than (m) functionalized acceptor glutamine residues (Q) per antibody, wherein m is an integer, e.g. m=1, 2 or 4. Optionally, at least 70%, 80%, 85%, 80%, 90%, 95%, 98% or 99% of the antibodies in the composition have the same q, r and z values. It can be specified that the antibodies will share the same —NH—(C)$_n$—X, L, V, V', Y, Y', R, RR' and/or Z moieties.

In one aspect the invention provides an antibody composition of antibodies of the invention (e.g., a human or humanized antibody or an antibody comprising an acceptor glutamine in a heavy chain constant region), optionally a plurality tetrameric or full-length antibodies, linked (covalently) to a moiety of interest (Z), preferably via a linker, wherein the composition is characterized by a mean Z:antibody ratio (e.g. mean DAR) of close to 2 (e.g, between 1.5 and 2.0, or between 1.7 and 2.0, between 1.8 and 2.0, or between 1.9 and 2.0) less than 10%, less than 5%, less than 2% or less than 1% of the antibodies in the composition comprise more than two moieties of interest (Z) per antibody. Preferably the composition is substantially free of antibodies having more than 2 moieties of interest per antibody.

In one aspect the invention provides an antibody composition of antibodies of the invention (e.g., a human or humanized antibody or an antibody comprising an acceptor glutamine in a heavy chain constant region), optionally a plurality tetrameric or full-length antibodies, linked (covalently) to a moiety of interest (Z), preferably via a linker, wherein the antibodies have a mean Z:antibody ratio (e.g. mean DAR) of at least 1.5, 1.6, 1.7 or 1.8, wherein less than 10%, less than 5%, less than 2% or less than 1% of the antibodies in the composition comprise more than two moieties of interest (Z) per antibody. Preferably, less than 25%, 20%, 15% or preferably 10% of the antibodies in the composition comprise less than two moieties of interest (Z) per antibody.

In one aspect the invention provides an antibody composition of antibodies of the invention (e.g., a human or humanized antibody or an antibody comprising an acceptor glutamine in a heavy chain constant region), optionally a plurality tetrameric or full-length antibodies, linked (covalently) to a moiety of interest (Z), preferably via a linker, wherein:
the antibodies have a mean Z:antibody ratio (e.g. mean DAR) of at least 1.5, 1.6, 1.7 or 1.8,
less than 10%, less than 5%, or less than 2% of the antibodies comprise more than two functionalized acceptor glutamines per antibody, and
less than 25%, 20%, 15% or preferably 10% of the antibodies comprise less than two moieties of interest (Z) per antibody.

Optionally, the antibodies are linked to said moiety of interest (Z) via one functionalized acceptor glutamine (e.g. a functionalized acceptor glutamine of Formula II or IV) on each heavy chain of the antibody (e.g. in a constant region). Optionally, at least 70%, 80%, 85%, 90%, 95%, 98% or 99% of the antibodies in the composition comprise one functionalized acceptor glutamine (e.g. a functionalized acceptor glutamine of Formula II or IV) on each heavy chain (e.g. in a constant region).

In one aspect the invention provides an antibody composition of antibodies of the invention (e.g., a human or humanized antibody or an antibody comprising a glutamine in a variable region), optionally a plurality tetrameric or full-length antibodies, comprising one acceptor glutamine in each heavy chain, preferably wherein said antibodies share the same primary amino acid sequence, wherein at least 70%, 80%, 85%, 90%, 95%, 98% or 99% of the antibodies in the composition comprise one functionalized acceptor glutamine (e.g. a functionalized acceptor glutamine of Formula IT or IV) on each heavy chain (e.g. in a constant region).

In one aspect the invention provides an antibody composition of antibodies of the invention (e.g., a human or humanized antibody or an antibody comprising a glutamine in a variable region), optionally a plurality tetrameric or full-length antibodies, linked (covalently) to a moiety of interest (Z), preferably via a linker, wherein the composition is characterized by a mean Z:antibody ratio (e.g. mean DAR) of close to 4 (e.g, between 3.0 and 4.0, or between 3.5 and 4.0, or between 3.6 and 4.0) wherein less than 10%, less than 5%, or less than 2% of the antibodies comprise more than four functionalized acceptor glutamines per antibody. Preferably, the composition is substantially free of antibodies having more than 4 moieties of interest (Z) per antibody.

In one aspect the invention provides an antibody composition of antibodies of the invention (e.g., a human or humanized antibody or an antibody comprising a glutamine in a variable region), optionally a plurality tetrameric or full-length antibodies, covalently linked to a moiety of interest (Z), preferably via a linker, wherein the antibodies have a mean Z:antibody ratio (e.g. mean DAR) of at least 3.2, 3.4, 3.5 or 3.6, wherein less than 10%, less than 5%, or less than 2% of the antibodies comprise more than four functionalized acceptor glutamines per antibody.

Preferably the antibodies in the compositions are linked to said moiety of interest (Z) on each of two functionalized acceptor glutamines (e.g. a functionalized acceptor glutamine of Formula II or IV) on each heavy chain of the antibody (e.g. in a constant region). Optionally, the antibodies are linked to said moiety of interest (Z) via two functionalized acceptor glutamines (e.g. a functionalized acceptor glutamine of Formula II or IV) on each heavy chain of the antibody. Optionally, at least 70%, 80%, 85%, 90% of the antibodies in the composition comprise two functionalized acceptor glutamines (e.g. a functionalized acceptor glutamine of Formula II or IV) on each heavy chain (e.g. in a constant region).

In one aspect the invention provides an antibody composition of antibodies of the invention (e.g., a human or humanized antibody or an antibody comprising an acceptor glutamine in a heavy chain constant region), optionally a plurality tetrameric or full-length antibodies, comprising one acceptor glutamine in each heavy chain, preferably wherein said antibodies share the same primary amino acid sequence, wherein at least 70%, 80%, 85%, 90% of the antibodies in the composition comprise two functionalized acceptor glutamines (e.g. a functionalized acceptor glutamine of Formula II or IV) on each heavy chain (e.g. in a constant region).

In one aspect the invention provides an antibody composition of antibodies of the invention (e.g., a human or humanized antibody or an antibody comprising a glutamine in a variable region), optionally a plurality tetrameric or full-length antibodies, comprising one acceptor glutamine on each heavy chain, wherein at least 70%, 80%, 85% or 90%, of the antibodies in the composition comprise on each heavy chain one functionalized acceptor glutamine residue (Q) having Formula IVa or IVb, below,

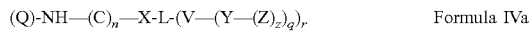  Formula IVa

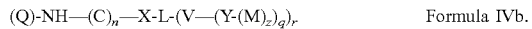  Formula IVb

Preferably the compositions are substantially free of antibodies having more than 2 moieties of interest (Z) per antibody.

In one aspect the invention provides an antibody composition of antibodies of the invention (e.g., a human or humanized antibody or an antibody comprising a glutamine in a variable region), optionally a plurality tetrameric or full-length antibodies, comprising two acceptor glutamines on each heavy chain, wherein at least 70%, 80%, 85% or 90%, of the antibodies in the composition comprise on each heavy chain (e.g. in a constant region) two functionalized acceptor glutamine residue (Q) having Formula IVb, below,

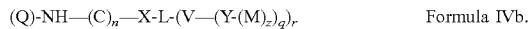  Formula IVb

Preferably the compositions are substantially free of antibodies having more than 4 moieties of interest (Z) per antibody and/or more than 4 functionalized acceptor glutamines per antibody.

In one embodiment of any of the compositions of the invention, substantially all of the antibodies in the composition share the same primary amino acid sequence. In one embodiment of any of the compositions Z is optionally a hydrophobic compound. In one embodiment of any of the compositions Z is optionally an organic compound having a molecular weight of at least 400 g/mol, 500 g/mol, 600 g/mol, 700 g/mol, 800 g/mol, 900 g/mol or 1000 g/mol. In one embodiment of any of the compositions Z is optionally a hydrophobic compound. In one embodiment of any of the compositions Z is optionally a negatively charged compound. In one embodiment of any of the compositions, the moiety of interest (Z) is optionally selected from the group consisting of taxanes, anthracyclines, camptothecins, epothilones, mytomycins, combretastatins, vinca alkaloids, nitrogen mustards, maytansinoids, calicheamycins, duocarmycins, tubulysins, amatoxins, dolastatins and auristatins, enediynes, pyrrolobenzodiazepines, and ethylenimines.

In one aspect, the antibody comprises a VH domain comprising a FR-H1 sequence, a CDR-H1 sequence, a FR-H2 sequence, a CDR-H2 sequence, a FR-H3 sequence, a CDR-H3 sequence and optionally a FR-H4 sequence, wherein one, two, three or more of (e.g. all of) said FR sequences comprise a sequence of human origin. In one embodiment, the FR and/or CDR sequences comprise one, two, three, four, five or six amino acid modifications (e.g. substitutions, deletions, insertions) in a human sequence. In one embodiment, the CDR-H1, -H2 and/or -H3 are of non-human origin. In one embodiment, the CDR-H1, -H2 and/or -H3 are of human origin. In one embodiment, a FR sequence comprises a surface-exposed glutamine residue. In one embodiment, a CDR sequence comprises a surface-exposed glutamine residue. In one embodiment, a surface-exposed glutamine residue is at position 1, and/or 16 in a heavy chain. In each case, the surface-exposed glutamine residue is not an acceptor glutamine.

In one aspect, the invention provides an antibody comprising a heavy chain framework region 1 (FR-H1) comprising a glutamine residue at position 1, 3, 5, 6, 10, 11, 12, 13 and/or 16.

In one aspect, the invention provides an antibody comprising a heavy chain framework region 2 (FR-H2) comprising a glutamine residue at position 38, 39, 43 and/or 45.

In one aspect, the invention provides an antibody comprising a heavy chain framework region 3 (FR-H3) comprising a glutamine residue at position 66, 75, 77, 81 and/or 85.

In one aspect, the invention provides an antibody comprising a heavy chain framework region 1 (CDR-H1) comprising a glutamine residue, optionally at position 26 and/or 35.

In one aspect, the invention provides an antibody comprising a heavy chain framework region 2 (CDR-H2) comprising a glutamine residue, optionally at position 50, 52, 56, 61 and/or 64. In each case, the surface-exposed glutamine residue is not an acceptor glutamine.

In one embodiment, said antibody comprises a FR-H1, FR-H2 and/or FR-H3 sequence substantially identical to or derived from a FR-H1, FR-H2 and/or FR-H3 from a V segment sequence selected from the group consisting of SEQ ID NOS 3-239.

In one aspect, the antibody comprises a VL domain comprising a FR-L sequence, a CDR-L1 sequence, a FR-L2 sequence, a CDR-L2 sequence, a FR-L3 sequence, a CDR-L3 sequence and optionally a FR-L4 sequence, wherein one, two, three or more of (e.g. all of) said FR sequences comprise a sequence of human origin. In one embodiment, the FR and/or CDR sequences comprise one, two, three, four, five or six amino acid modifications (e.g. substitutions, deletions, insertions) in a human sequence. In one embodiment, the CDR-H1, -H2 and/or -H3 are of non-human origin. In one embodiment, the CDR-L1, -L2 and/or -L3 are of human origin. In one embodiment, a FR sequence comprises a surface-exposed glutamine residue. In one embodiment, a CDR sequence comprises a surface-exposed glutamine residue. In one embodiment, a CDR-L1, -L2 and/or L3 sequence comprises a surface-exposed glutamine residue. In one embodiment, a surface-exposed glutamine residue is at position 27, 47, 55, and/or 105 in a light chain. In each case, the surface-exposed glutamine residue is not an acceptor glutamine.

In one aspect, the invention provides an antibody comprising a heavy chain framework region 1 (FR-L1) comprising a glutamine residue at position 13, 6, 11, 17 and/or 18.

In one aspect, the invention provides an antibody comprising a heavy chain framework region 2 (FR-L2) comprising a glutamine residue at position 37, 38, 42, 45 and/or 49.

In one aspect, the invention provides an antibody comprising a heavy chain framework region 3 (FR-L3) comprising a glutamine residue at position 79.

In one aspect, the invention provides an antibody comprising a heavy chain framework region 1 (CDR-L1) comprising a glutamine residue at position 27.

In one aspect, the invention provides an antibody comprising a heavy chain framework region 2 (CDR-L2), optionally comprising a glutamine residue at position 50, 53 and/or 55.

In one aspect, the invention provides an antibody comprising a heavy chain framework region 2 (CDR-L3), optionally comprising a glutamine residue at position 89, 90 and/or 93. In each case, the surface-exposed glutamine residue is not an acceptor glutamine.

In one embodiment, said antibody comprises a FR-L1, FR-L2 and/or FR-L3 sequence substantially identical to a FR-L1, FR-L2 and/or FR-L3 from a V segment sequence selected from the group consisting of SEQ ID NOS: 240-299.

In one aspect, the antibody comprises a substitution in a heavy chain variable region, wherein a non-glutamine residue at position 1, 3, 5, 6, 10, 11, 12, 13, 16, 19, 26, 35, 38, 39, 43, 35, 36, 50, 61, 64, 66, 73, 75, 77, 83, 85 and/or 94 is substituted by a glutamine residue. In one aspect, the antibody comprises a substitution in a light chain variable region, wherein a non-glutamine residue at position 3, 6, 11, 17, 18, 27, 37, 38, 42, 45, 47, 49, 50, 53, 55, 79, 89, 90, 93 and/or 105 is substituted by a glutamine residue. The glutamine residue is not an acceptor glutamine.

In one aspect, the antibody comprises a substitution in a heavy chain variable region, wherein a glutamine residue at position 1 and/or 16 is substituted by a non-glutamine residue. In one aspect, the antibody comprises a substitution in a light chain variable region, wherein a glutamine residue at position 27, 47, 55 and/or 105 is substituted by a non-glutamine residue.

In one embodiment, the antibody of the invention comprises a constant region and/or Fc region of human origin, optionally a human IgG1 isotype. In one embodiment, the antibody of the invention comprises a constant region and/or Fc region of human origin, optionally a human IgG4 isotype. In one embodiment, the antibody (i.e. the "Ab") is an antibody comprising an Fc domain or portion thereof comprising an acceptor glutamine residue. In one embodiment, the antibody is an antibody fragment comprising an acceptor glutamine residue, optionally wherein the antibody fragment comprises a peptide "tag" comprising an acceptor glutamine residue.

In one embodiment, an antibody comprises an amino acid modification that effectively eliminates antibody glycosylation (i.e., asparagine-linked glycosylation at position 297 (EU index numbering) of a heavy chain of an antibody). In one embodiment, the antibodies comprises a substitution at one or more of residues 297, 298 and/or 299 (EU index numbering) of a heavy chain. In one embodiment, an antibody additionally comprises an acceptor glutamine residue (Q) at position 297. In one embodiment, an antibody comprises a non-glutamine residue (Q) at residues 297, 298 or 299.

In one embodiment, the invention provides an antibody comprising: (i) a glutamine residue within a heavy and/or light chain variable region, optionally a surface exposed glutamine, optionally a glutamine residue within an FR or a CDR (or in an FR flanking a CDR), wherein said glutamine residue is not an acceptor glutamine, (ii) an acceptor glutamine residue in a heavy chain constant region, optionally in a CH2 domain, and, optionally (iii) an amino acid substitution in a heavy chain constant region, wherein an asparagine at position 297, a serine at position 298 and/or a threonine at position 299 of a heavy chain is replaced by a non-glutamine residue.

Also provided is a method for conjugating a moiety of interest to an antibody, comprising the steps of:
a) providing an antibody of the invention comprising: (i) a glutamine residue within a heavy and/or light chain variable region, optionally a surface exposed glutamine, optionally a glutamine residue within an FR or a CDR (or in an FR flanking a CDR), wherein said glutamine residue is not an acceptor glutamine, (ii) an acceptor glutamine residue in a heavy chain constant region, optionally in a CH2 domain, and, optionally (iii) an amino acid substitution in a heavy chain constant region, wherein an asparagine at position 297, a serine at position 298 and/or a threonine at position 299 of a heavy chain is replaced by a non-glutamine residue; and
b) reacting said antibody with a compound of Formula Ia or Formula Ib in the presence of a TGase, under conditions sufficient to obtain an antibody comprising a functionalized acceptor glutamine of Formula IVa or IVb, respectively.

Preferably, conjugation occurs solely on one or more acceptor glutamine residues within a constant region (i.e. no conjugation on glutamine residues in CDRs and/or FRs). The functionalized acceptor glutamine of Formula IV will be located outside the antigen-combining site such that no a functionalized acceptor glutamine of Formula IV is present within the antigen-combining site, or optionally more generally the variable region. Preferably, a stoichiometric composition of antibody is obtained with a homogeneous ratio of antibody:functionalized acceptor glutamine of Formula IV.

In one embodiment the antibody is a full-length antibody. In another embodiment, antibody is an antibody fragment or derivative, e.g. a Fv, Fab, Fab', F (ab')2 or a nanobody, domain antibody, single domain antibody or a "dAb". In one embodiment, the fragment or derivative (e.g. a Fab, Fab', F (ab')2 comprises a CH1 (e.g., comprising a hinge region) and/or CH2 domain or a portion thereof, wherein the CH2 comprises an acceptor glutamine residue. Optionally, said glutamine residue is at the C terminus of the heavy and/or light chain.". In one embodiment, the fragment or derivative (e.g. a Fv, Fab, Fab', F (ab')2, nanobody, domain antibody, single domain antibody or "dAb") comprises a peptide tag comprising an acceptor glutamine residue (e.g. wherein the tag is fused to a variable region of the fragment).

In one embodiment, an antibody is capable of being internalized into cells that express an antigen to which the antibody binds (e.g. a tumor or viral antigen) and/or induces internalization of the antigen on said antigen-expressing cells.

In one aspect, the invention provides a method of producing an antibody which specifically binds to an antigen suitable for TGase-mediated conjugation to a moiety-of-interest via an acceptor glutamine residue, the method comprising: providing a parent antibody, preferably of non-human origin, and preparing a variant antibody having a heavy and/or light chain comprising amino acid residues from a CDR of said parent antibody and FR amino acid residues from a human FR sequence (e.g. from a human antibody or derived from a human germline sequence), wherein the antibody comprises an acceptor glutamine present outside of the antigen-binding region (e.g. in or appended to a constant region). Optionally the antibody comprises a surface-exposed glutamine in a CDR and/or FR, wherein the surface-exposed glutamine is not an acceptor glutamine (e.g., is not functionalized with a lysine-based linker of the invention when reacted with TGase under conditions permitting a lysine-based linker of the invention to be conjugated to the acceptor glutamine within the constant region (e.g the acceptor glutamine at position 295 (EU numbering) of the heavy chain).

In one embodiment, the variant antibody has a heavy chain comprising CDR-H1, CDR-H2 and CDR-H3 of a parent antibody and/or a light chain comprising CDR-L1, CDR-L2 and CDR-L3 of a parent antibody. Optionally the variant antibody comprises a heavy chain comprising a FR-H1, FR-H2, FR-H3 and FR-H4 of human origin. Optionally the variant antibody comprises a light chain comprising a FR-L1, FR-L2, FR-L3 and FR-L4 of human origin. Optionally, any of the antibody light and/or heavy chain CDRs (e.g. CDR-H3) comprises a glutamine, optionally a surface-exposed glutamine which does not serve as an acceptor glutamine. Optionally, any of the antibody light and/or heavy chain FRs comprises a glutamine, optionally a surface-exposed glutamine. In one embodiment the method further comprises introducing an amino acid modification (e.g. 1, 2, 3, 4, 5 or more substitutions) into one of said CDR or FR residues. In one embodiment, a modification in a FR residue comprises replacing a residue of human origin by a residue of non-human origin, at a position in which the amino acids in the parent antibody variable region and human FR sequence differ. In one embodiment, a modification in a CDR residue comprises replacing a residue present in the parent antibody by a residue of human origin, at a position in which the amino acids in the parent antibody CDR and a human germline sequence differs. Optionally, in any of the modifications, the modifications optionally comprises introducing a glutamine, optionally a surface-exposed glutamine, e.g., replacing a non-glutamine residue with a glutamine. Such a glutamine will not serve as an acceptor glutamine. In one embodiment, a glutamine is present (e.g. naturally present or introduced) in a CDR-L1, -L2 or -L3.

In one aspect, the invention provides a method of producing an antibody which specifically binds to an antigen suitable for TGase-mediated conjugation to a moiety-of-interest via an acceptor glutamine residue, optionally wherein the method is a method of increasing the affinity of an antibody for a pre-determined antigen, the method comprising: providing a parent antibody having a heavy and/or light chain, introducing a glutamine residue, optionally a surface-exposed glutamine residue, into a CDR and/or into an FR of the parent antibody (e.g. CDR-H3 and/or FR-H3), wherein the glutamine residue is not an acceptor glutamine.

Reference to "Formulas I", "Formula II", "Formula III" or "Formula IV", unless the context clearly indicates otherwise, designates all compounds derived from such Formulas I to IV, including e.g., Formula I includes reference to Ia and Ib, Formula IV includes IVa and IVb.

Any of the methods of the invention can further be characterized as comprising any step described in the application, including notably in the "Detailed Description of the Invention"). The invention further relates to an antibody obtainable by any of present methods. The invention further relates to pharmaceutical or diagnostic formulations of the antibodies of the present invention. The invention further relates to methods of using an antibody of Formula IV in a method of treatment or diagnosis.

These and additional advantageous aspects and features of the invention may be further described elsewhere herein.

DETAILED DESCRIPTION OF THE INVENTION

Introduction

Figure 1:
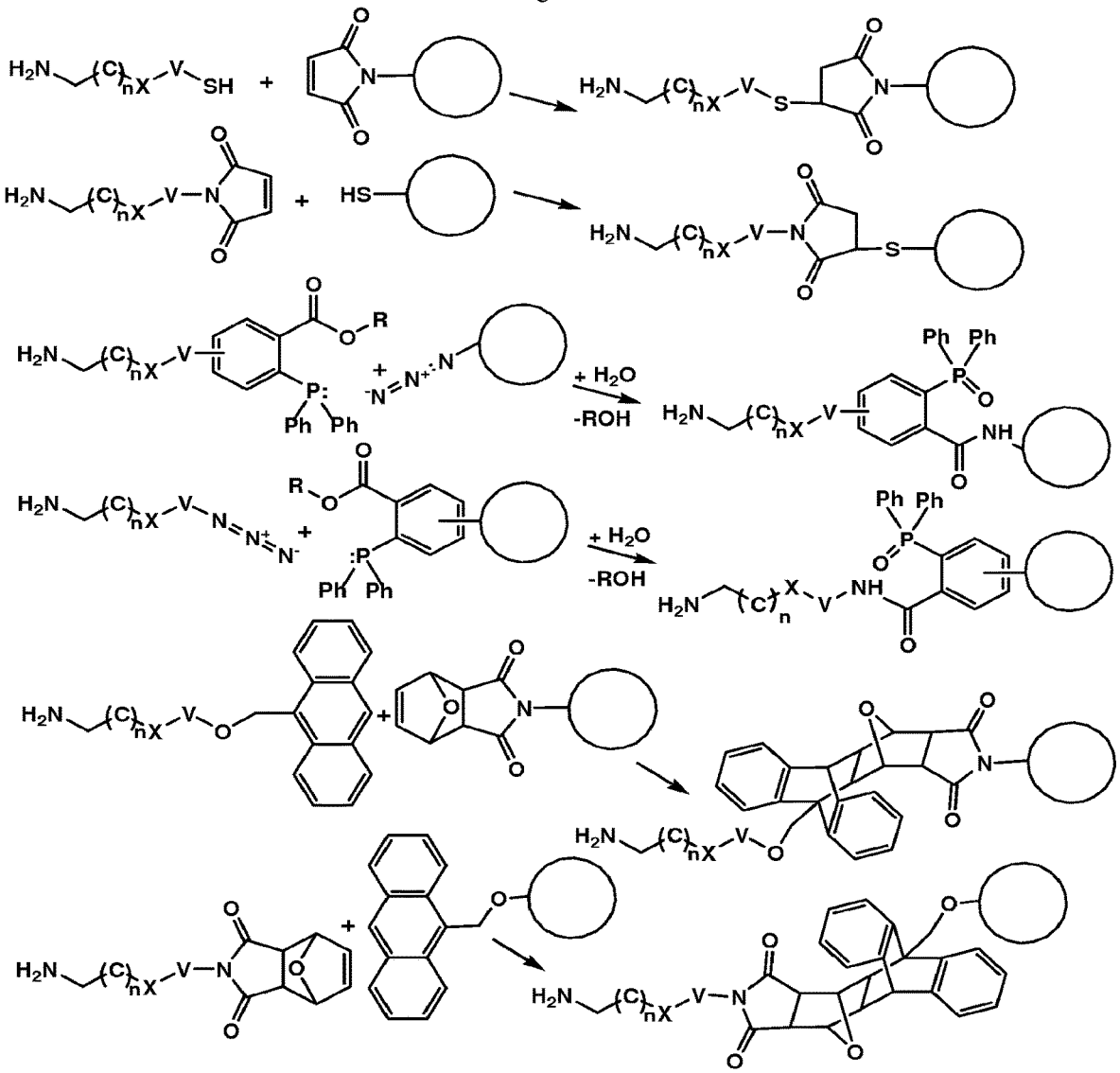
FIG. 1 shows reaction schemes for thio-maleimide additions, Staudinger ligations, and Diels-Alder cycloadditions, where reactive groups of linking reagents having a single reactive functionality combine with complementary reactive group attached to a therapeutic or diagnostic moiety.

According to the invention, the functionalization of antibodies is site-specific and occurs via, respectively between a lysine or lysine-like moiety and an acceptor glutamine residue of an antibody by transglutaminase.

The inventors now present a convenient method for the site-specific functionalization of human and humanized immunoglobulins under near physiological conditions. The enzymatic activity of the transglutaminase family catalyzes an acyl transfer reaction between the γ-carboxamide groups of peptide-bound glutamine residues and various primary amines or ε-amino groups of lysine residues, thus forming isopeptidic bonds which are stable and resistant to chemical, enzymatic, and physical degradation. The function of TGases can be described as incorporation of alkylamine derivatives into specific glutamine residues or vice versa.

Definitions

As used in the specification, "a" or "an" may mean one or more. As used in the claim(s), when used in conjunction with the word "comprising", the words "a" or "an" may mean one or more than one.

Where "comprising" is used, this can be replaced by "consisting essentially of or by "consisting of".

The term "transglutaminase", used interchangeably with "TGase" or "TG", refers to an enzyme capable of crosslinking proteins through an acyl-transfer reaction between the γ-carboxamide group of peptide-bound glutamine and the ε-amino group of a lysine or a structurally related primary amine such as amino pentyl group, e.g. a peptide-bound lysine, resulting in a ε-(γ-glutamyl)lysine isopeptide bond. TGases include, inter alia, bacterial transglutaminase (BTG) such as the enzyme having EC reference EC 2.3.2.13 (protein-glutamine-γ-glutamyltransferase).

The term "acceptor glutamine", when referring to an amino acid residue of an antibody, means a glutamine residue that, under suitable conditions, is recognized by a TGase and can be crosslinked by a TGase through a reaction between the glutamine and a lysine or a structurally related primary amine such as amino pentyl group. Optionally the acceptor glutamine is a surface-exposed glutamine.

The term "antibody" herein is used in the broadest sense and specifically includes full-length monoclonal antibodies, polyclonal antibodies, multispecific antibodies (e.g., bispecific antibodies), and antibody fragments, so long as they exhibit the desired biological activity. Various techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988).

An "antibody fragment" comprises a portion of a full-length antibody, preferably antigen-binding or variable regions thereof. Examples of antibody fragments include Fab, Fab', F(ab)$_2$, F(ab')$_2$, F(ab)$_3$, Fv (typically the VL and VH domains of a single arm of an antibody), single-chain Fv (scFv), dsFv, Fd fragments (typically the VH and CH1 domain), and dAb (typically a VH domain) fragments; VH, VL, VhH, and V-NAR domains; minibodies, diabodies, triabodies, tetrabodies, and kappa bodies (see, e.g., Ill et al., Protein Eng 1997; 10: 949-57); camel IgG; IgNAR; and multispecific antibody fragments formed from antibody fragments, and one or more isolated CDRs or a functional paratope, where isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 23, 1126-1136; WO2005040219, and published U.S. Patent Applications 20050238646 and 20020161201.

The term "antibody derivative", as used herein, comprises a full-length antibody or a fragment of an antibody, preferably comprising at least antigen-binding or variable regions thereof, wherein one or more of the amino acids are chemically modified, e.g., by alkylation, PEGylation, acylation, ester formation or amide formation or the like. This includes, but is not limited to, PEGylated antibodies, cysteine-PEGylated antibodies, and variants thereof.

A "humanized" antibody is a human/non-human chimeric antibody that contains a minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit, or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody can optionally also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992), WO 92/02190, US Patent Application 20060073137, and U.S. Pat. Nos. 6,750,325, 6,632,927, 6,639,055, 6,548,640, 6,407,213, 6,180,370, 6,054,297, 5,929,212, 5,895,205, 5,886,152, 5,877,293, 5,869,619, 5,821,337, 5,821,123, 5,770,196, 5,777,085, 5,766,886, 5,714,350, 5,693,762, 5,693,761, 5,530,101, 5,585,089, and 5,225,539.

The term "hypervariable region" when used herein refers to the amino acid residues of an antibody that are responsible for antigen binding. The hypervariable region generally comprises amino acid residues from a "complementarity-determining region" or "CDR" (e.g. residues 24-34 (L1), 50-56 (L2) and 89-97 (L3) in the light-chain variable domain and 31-35 (H1), 50-65 (H2) and 95-102 (H3) in the heavy-chain variable domain; Kabat et al. 1991) and/or those residues from a "hypervariable loop" (e.g. residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917). Typically, the numbering of amino acid residues in this region is performed by the method described in Kabat et al., supra. Phrases such as "Kabat position", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

By "framework" or "FR" residues as used herein is meant the region of an antibody variable domain exclusive of those regions defined as CDRs. Each antibody variable domain framework can be further subdivided into the contiguous regions separated by the CDRs (FR1, FR2, FR3 and FR4).

By "constant region" of an antibody as defined herein is meant the region of the antibody that is encoded by one of the light or heavy chain immunoglobulin constant region genes. By "constant light chain" or "light chain constant region" as used herein is meant the region of an antibody encoded by the kappa (Ckappa) or lambda (Clambda) light chains. The constant light chain typically comprises a single domain, and as defined herein refers to positions 108-214 of Ckappa, or Clambda, wherein numbering is according to the EU index (Kabat et al., 1991, Sequences of Proteins of Immunological Interest, 5th Ed., United States Public Health Service, National Institutes of Health, Bethesda). By "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively. For full length IgG antibodies, the constant heavy chain, as defined herein, refers to the N-terminus of the CH1 domain to the C-terminus of the CH3 domain, thus comprising positions 118-447, wherein numbering is according to the EU index. By "Fab" or "Fab region" as used herein is meant the polypeptide that comprises the VH, CH1, VL, and CL immunoglobulin domains. Fab may refer to this region in isolation, or this region in the context of a full length antibody, antibody fragment or Fab fusion protein, or any other antibody embodiments as outlined herein.

By "Fv" or "Fv fragment" or "Fv region" as used herein is meant a polypeptide that comprises the VL and VH domains of a single antibody.

By "Fc" or "Fc region", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cγ2 and Cγ3 and the hinge between Cγ1 and Cγ2. Although the boundaries of the Fc region may vary, the human IgG heavy chain Fc region is usually defined to comprise residues C226, P230 or A231 to its carboxyl-terminus, wherein the numbering is according to the EU index. Fc may refer to this region in isolation, or this region in the context of an Fc polypeptide, as described below. By "Fc polypeptide" as used herein is meant a polypeptide that comprises all or part of an Fc region. Fc polypeptides include antibodies, Fc fusions, isolated Fcs, and Fc fragments.

By "full length antibody" as used herein is meant the structure that constitutes the natural biological form of an antibody, including variable and constant regions. For example, in most mammals, including humans and mice, the full length antibody of the TgG isotype is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, and Cγ3. In some mammals, for example in camels and llamas, IgG antibodies may consist of only two heavy chains, each heavy chain comprising a variable domain attached to the Fc region.

By "variable region" as used herein is meant the region of an antibody that comprises one or more Ig domains substantially encoded by any of the VL (including Vkappa and Vlambda) and/or VH genes that make up the light chain (including kappa and lambda) and heavy chain immunoglobulin genetic loci respectively. A light or heavy chain variable region (VL and VH) consists of a "framework" or "FR" region interrupted by three hypervariable regions referred to as "complementarity determining regions" or "CDRs". The extent of the framework region and CDRs have been precisely defined, for example as in Kabat (see "Sequences of Proteins of Immunological Interest," E. Kabat et al., U.S. Department of Health and Human Services, (1983)), and as in Chothia. The framework regions of an antibody, that is the combined framework regions of the constituent light and heavy chains, serves to position and align the CDRs, which are primarily responsible for binding to an antigen.

By "amino acid modification" herein is meant an amino acid substitution, insertion, and/or deletion in a polypeptide sequence. The preferred amino acid modification herein is a substitution. By "amino acid modification" herein is meant an amino acid substitution, insertion, and/or deletion in a polypeptide sequence. By "amino acid substitution" or "substitution" herein is meant the replacement of an amino acid at a given position in a protein sequence with another amino acid. For example, the substitution Y50W refers to a variant of a parent polypeptide, in which the tyrosine at position 50 is replaced with tryptophan. A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

The term "substantially identical" in the context of two amino acid sequences means that the sequences, when optimally aligned, such as by the programs GAP or BEST-FIT using default gap weights, share at least about 50, at least about 60, at least about 70, at least about 80, at least about 90, at least about 95, at least about 98, or at least about 99 percent sequence identity. In one embodiment, residue positions that are not identical differ by conservative amino acid substitutions. Sequence identity is typically measured using sequence analysis software. Protein analysis software matches similar sequences using measures of similarity assigned to various substitutions, deletions and other modifications, including conservative amino acid substitutions. For instance, the publicly available GCG software contains programs such as "Gap" and "BestFit" which can be used with default parameters to determine sequence homology or sequence identity between closely related polypeptides, such as homologous polypeptides from different species of organisms or between a wild-type protein and a mutein thereof. See, e.g., GCG Version 6.1. Polypeptide sequences can also be compared using FASTA, applying default or recommended parameters. A program in GCG Version 6.1., FASTA (e.g., FASTA2 and FASTA3) provides alignments and percent sequence identity of the regions of the best overlap between the query and search sequences (Pearson, Methods Enzymol. 1990; 183:63-98; Pearson, Methods Mol. Biol. 2000; 132:185-219). Another preferred algorithm when comparing a sequence to a database containing a large number of sequences from various organisms is the computer program BLAST, especially blastp, using default parameters. See, e.g., Altschul et al., J. Mol. Biol. 1990; 215:403-410; Altschul et al., Nucleic Acids Res. 1997; 25:3389-402 (1997); each herein incorporated by reference. "Corresponding" amino acid positions in two substantially identical amino acid sequences are those aligned by any of the protein analysis software mentioned herein, typically using default parameters.

An antibody having a "biological characteristic" of a reference antibody, is one that possesses one or more of the biological characteristics of that antibody that distinguish it from other antibodies that bind to the same antigen.

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of an antibody molecule will exhibit 98%, 98%, or 99% homogeneity for antibody molecules in the context of all present peptide species in the composition or at least with respect to substantially active peptide species in the context of proposed use.

In the context of the present invention, "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

The term "reactive moiety" herein refers to a moiety that can be coupled with another moiety without prior activation or transformation.

The term "protecting group" refers to a group that temporarily protects or blocks, i e., intended to prevent from reacting, a functional group, e.g, an amino group, a hydroxyl group, or a carboxyl group, during the transformation of a first molecule to a second molecule.

The phrase "moiety that improves the pharmacokinetic properties", when referring to a compound (e.g. an antibody) refers to a moiety that changes the pharmacokinetic properties of the one or more moieties Z in such a way that a better therapeutic or diagnostic effect can be obtained. The moiety can for example increase the water solubility, increase the circulation time, or reduce immunogenicity.

The phrase "linking group" refers to a structural element of a compound that links one structural element of said compound to one or more other structural elements of said same compound.

The phrase "a number representing degree of branching" is used to denote that the subscript number next to a closing bracket represents how many units of the moiety within the brackets are attached to the moiety directly to the left of the corresponding opening bracket For example, A-(B)$_b$ with b being a number representing a degree of branching means that b units B are all directly attached to A This means that when b is 2, the formula reduces to B-A-B.

The phrase "a number representing degree of polymerization" is used to denote that the subscript number next to a closing bracket represents how many units of the moiety within the brackets are connected to each other. For example, A-(B)$_1$, with b being a number representing a degree of polymerization means that when b is 2, the formula reduces to A-B-B.

As used herein, "alkyl" refers to a straight or branched hydrocarbon chain that comprises a fully saturated (no double or triple bonds) hydrocarbon group. The alkyl group may have, for example, 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, the term "heteroalkyl" refers to a straight or branched alkyl group that contains one or more heteroatoms, that is, an element other than carbon (including but not limited to oxygen, sulfur, nitrogen, phosphorus) in place of one or more carbon atoms.

Whenever a group is described as being "substituted" that group substituted with one or more of the indicated substituents. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, heteroalkyl, aryl, heteroaryl, heteroalicyclyl, aralkyl, heteroaralkyl, (heteroalicyclyl)alkyl, hydroxy, alkoxy, aryloxy, acyl, mercapto, alkylthio, arylthio, cyano, halogen, thiocarbonyl, carbamyl, thiocarbamyl, amido, sulfonamido, sulfonamido, carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

Where the number of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Producing Antibodies

Antibodies may be produced by a variety of techniques known in the art. Typically, they are produced by immunization of a non-human animal, preferably a mouse, with an immunogen comprising a polypeptide, or a fragment or derivative thereof, typically an immunogenic fragment, for which it is desired to obtain antibodies (e.g. a human polypeptide). The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, N.Y. (1988), the entire disclosure of which is herein incorporated by reference). Other protocols may also be used as long as they result in the production of B cells expressing an antibody directed to the antigen used in immunization. Lymphocytes from a non-immunized non-human mammal may also be isolated, grown in vitro, and then exposed to the immunogen in cell culture. The lymphocytes are then harvested and the fusion step described below is carried out. For preferred monoclonal antibodies, the next step is the isolation of splenocytes from the immunized non-human mammal and the subsequent fusion of those splenocytes with an immortalized cell in order to form an antibody-producing hybridoma. The hybridoma colonies are then assayed for the production of antibodies that specifically bind to the polypeptide against which antibodies are desired. The assay is typically a colorimetric ELISA-type assay, although any assay may be employed that can be adapted to the wells that the hybridomas are grown in. Other assays include radioimmunoassays or fluorescence activated cell sorting. The wells positive for the desired antibody production are examined to determine if one or more distinct colonies are present. If more than one colony is present, the cells may be re-cloned and grown to ensure that only a single cell has given rise to the colony producing the desired antibody. After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference).

Antibodies may also be produced by selection of combinatorial libraries of immunoglobulins, as disclosed for instance in (Ward et al. Nature, 341 (1989) p. 544, the entire disclosure of which is herein incorporated by reference). Phage display technology (McCafferty et al (1990) Nature 348:552-553) can be used to produce antibodies from immunoglobulin variable (V) domain gene repertoires from unimmunized donors. See, e.g., Griffith et al (1993) EMBO J. 12:725-734; U.S. Pat. Nos. 5,565,332; 5,573,905; 5,567,610; 5,229,275). When combinatorial libraries comprise variable (V) domain gene repertoires of human origin, selection from combinatorial libraries will yield human antibodies.

Additionally, a wide range of antibodies are available in the scientific and patent literature, including DNA and/or amino acid sequences, or from commercial suppliers. Examples of antibodies include antibodies that recognize an antigen expressed by a target cell that is to be eliminated, for example a proliferating cell or a cell contributing to a pathology. Examples include antibodies that recognize tumor antigens, microbial (e.g. bacterial) antigens or viral antigens. Other examples include antigens present on immune cells that are contributing to inflammatory or autoimmune disease, including rejection of transplanted tissue (e.g. antigens present on T cells (CD4 or CD8 T cells).

Antibodies will typically be directed to a pre-determined antigen. As used herein, the term "bacterial antigen" includes, but is not limited to, intact, attenuated or killed bacteria, any structural or functional bacterial protein or carbohydrate, or any peptide portion of a bacterial protein of sufficient length (typically about 8 amino acids or longer) to be antigenic. Examples include gram-positive bacterial antigens and gram-negative bacterial antigens. In preferred embodiments of the present invention the bacterial antigen is derived from a bacterium selected from the group consisting of *Helicobacter* species, in particular *Helicobacter pyloris*; *Borelia* species, in particular *Borelia burgdorferi*; *Legionella* species, in particular *Legionella pneumophilia*; *Mycobacteria* s species, in particular *M. tuberculosis, M. avium, M. intracellulare, M. kansasii, M. gordonae*; *Staphylococcus* species, in particular *Staphylococcus aureus*; *Neisseria* species, in particular *N. gonorrhoeae, N. meningitidis*; *Listeria* species, in particular *Listeria monocytogenes*; *Streptococcus* species, in particular *S. pyogenes, S. agalactiae; S. faecalis; S. bovis, S. pneumnonias*; anaerobic *Streptococcus* species; pathogenic *Campylobacter* species; *Enterococcus* species; *Haemophilus* species, in particular *Haemophilus* influenzue; *Bacillus* species, in particular *Bacillus anthracis*; *Corynebacterium* species, in particular *Corynebacterium diphtheriae*; *Erysipelothrix* species, in particular *Erysipelothrix rhusiopathiae*; *Clostridium* species, in particular *C. perfringens, C. tetani*; *Enterobacter* species, in particular *Enterobacter aerogenes, Klebsiella* species, in particular *Klebsiella* 1S *pneumoniae, Pasteurella* species, in particular *Pasteurella multocida, Bacteroides* species; *Fusobacterium* species, in particular *Fusobacterium nucleatum*; *Streptobacillus* species, in particular *Streptobacillus moniliformis*; *Treponema* species, in particular *Treponema pertenue*; *Leptospira*; pathogenic *Escherichia* species; and *Actinomyces* species, in particular *Actinomyces israelli*.

As used herein, the term "viral antigen" includes, but is not limited to, intact, attenuated or killed whole virus, any structural or functional viral protein, or any peptide portion of a viral protein of sufficient length (typically about 8 amino acids or longer) to be antigenic. Sources of a viral antigen include, but are not limited to viruses from the families: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arenaviridae (hemorrhagic fever viruses); Reoviridae (e.g., reoviruses, orbiviruses and rotaviruses); Bornaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g., African swine fever virus); and unclassified viruses (e.g., the agent of delta hepatitis (thought to be a defective satellite of hepatitis B virus), Hepatitis C; Norwalk and related viruses, and astroviruses). Alternatively, a viral antigen may be produced recombinantly.

As used herein, the terms "cancer antigen" and "tumor antigen" are used interchangeably and refer to antigens that are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

The cancer antigens are usually normal cell surface antigens which are either over-expressed or expressed at abnormal times. Ideally the target antigen is expressed only on proliferative cells (preferably tumour cells), however this is rarely observed in practice. As a result, target antigens are usually selected on the basis of differential expression between proliferative and healthy tissue. Antibodies have been raised to target specific tumour related antigens including: Cripto, CD4, CD20, CD30, CD19, CD33, Glycoprotein NMB, CanAg, Her2 (ErbB2/Neu), CD56 (NCAM), CD22 (Siglec2), CD33 (Siglec3), CD79, CD138, CD171, PSCA, PSMA (prostate specific membrane antigen), BCMA, CD52, CD56, CD80, CD70, E-selectin, EphB2, Melanotransferin, Mud 6 and TMEFF2. Examples of cancer antigens also include B7-H3, B7-H4, B7-H6, PD-L1, MAGE, MART-1/Melan-A, gp100, adenosine deaminase-binding protein (ADAbp), cyclophilin b, colorectal associated antigen (CRC)-C017-1A/GA733, carcinoembryonic antigen (CEA) and its immunogenic epitopes CAP-1 and CAP-2, etv6, aml1, prostate specific antigen (PSA), T-cell receptor/CD3-zeta chain, MAGE-family of tumor antigens, GAGE-family of tumor antigens, BAGE, RAGE, LAGE-1, NAG, GnT-V, MUM-1, CDK4, MUC family, VEGF, VEGF receptors, PDGF, TGF-alpha, EGF, EGF receptor, a member of the human EGF-like receptor family such as HER-2/neu, HER-3, HER-4 or a heterodimeric receptor comprised of at least one HER subunit, gastrin releasing peptide receptor antigen, Muc-1, CA125, $\Delta v\beta 3$ integrins, $\alpha 5\beta 1$ integrins, $\alpha IIb\beta 3$-integrins, PDGF beta receptor, SVE-cadherin, IL-8, hCG, IL-6, IL-6 receptor, IL-15, $\alpha$-fetoprotein, E-cadherin, $\alpha$-catenin, $\beta$-catenin and $\gamma$-catenin, p120ctn, PRAME, NY-ESO-1, cdc27, adenomatous polyposis *coli* protein (APC), fodrin, Connexin 37, Ig-idiotype, p15, gp75, GM2 and GD2 gangliosides, viral products such as human papillomavirus proteins, imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2, although this is not intended to be exhaustive.

DNA encoding an antibody of interest can be placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

In certain embodiments, the DNA of a hybridoma or other cell producing an antibody can be modified prior to insertion into an expression vector, for example, by substituting the coding sequence for human heavy- and light-chain constant domains in place of the homologous non-human sequences (e.g., Morrison et al., PNAS pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody of the invention.

Human antibodies may also be produced by using, for immunization, transgenic animals that have been engineered to express a human antibody repertoire (Jakobovitz et Nature 362 (1993) 255), or by selection of antibody repertoires using phage display methods. For example, a Xeno-Mouse (Abgenix, Fremont, Calif.) can be used for immunization. A XenoMouse is a murine host according to this invention that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

Humanized antibodies are typically specific chimeric immunoglobulins, immunoglobulin chains or fragments thereof (such as Fv, Fab, Fab', F (ab') 2, "dab", or other antigen-binding subsequences of antibodies) which contain minimal sequence derived from the murine immunoglobulin.

For the most part, humanized antibodies are human immunoglobulins (recipient antibody) in which residues from a complementary-determining region (CDR) of the recipient are replaced by residues from a CDR of the original antibody (the parent or donor antibody) while maintaining the desired specificity, affinity, and capacity of the original antibody. The CDRs of the parent antibody, some or all of which are encoded by nucleic acids originating in a non-human organism, are grafted in whole or in part into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536.

Generally, in a humanization process, nucleotides encoding the interaction-regions of a murine antibody can be cloned into a cDNA-vector encoding human IgG, which can be done such that a chimeric antibody is generated consisting of a human IgG backbone harboring the murine complementarity-determining regions (CDRs). However, such chimeric antibodies may exhibit a lower affinity, lower stability, or other undesired features in comparison with the original murine antibody, and may also be immunogenic. Therefore, individual amino acids in the chimeric Ab may need to be optimized to obtain a functional mAb of high quality for therapeutic applications in humans. "Backmutation" of selected acceptor framework residues to the corresponding donor residues is often required to regain affinity that is lost in the initial grafted construct (U.S. Pat. No. 5,693,762, incorporated entirely by reference). A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein). Humanization or other methods of reducing the immunogenicity of nonhuman antibody variable regions may include resurfacing methods, as described for example in Roguska et al., 1994, Proc. Natl. Acad. Sci. USA 91:969-973.

In one embodiment, the parent antibody has been affinity matured, as is known in the art. Structure-based methods may be employed for humanization and affinity maturation, for example as described in U.S. Pat. No. 7,657,380. Selection based methods may be employed to humanize and/or affinity mature antibody variable regions, that is, to increase the affinity of the variable region for its target antigen. Other humanization methods may involve the grafting of only parts of the CDRs, including but not limited to methods described in U.S. Pat. No. 7,981,843 directed to minimal CDR3 fragments, or U.S. Pat. No. 6,797,492; Tan et al., 2002, J. Immunol. 169:1119-1125; De Pascalis et al., 2002, J. Immunol. 169:3076-3084. Other humanization methods may involve grafting less than all the CDRs, e.g. U.S. Pat. No. 7,087,409 describes retaining CDR3 followed by the separate and sequential replacement of frameworks, CDR1 and CDR2. Structure-based methods may be employed for humanization and affinity maturation, or to reduce immunogenicity of the antibody for example as described in U.S. Pat. No. 7,117,096.

In general, the humanized antibody will comprise substantially all of at least one, and typically two, variable domains, in which all or substantially all of the CDR regions correspond substantially to those of the parent antibody and all or substantially all of the FR regions are those of a human (or primate) immunoglobulin consensus sequence.

Typically, a humanized antibody has one or more amino acid residues introduced into it from a source that is non-human (e.g., the parent antibody). These non-human amino acid residues are often referred to as "import" residues, which are typically taken from an "import" variable domain. Humanization can be essentially performed following the method of Winter and co-workers (Jones et al, Nature, 321: 522-525 (1986); Riechmann et al., Nature, 332: 323-327 (1988); Verhoeyen et al., Science, 239: 1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species.

The import residues can be selected to comprise a glutamine residue; the residue will not be an acceptor glutamine. For example, the glutamine may be present in any of CDR-H1, CDR-H2 and/or CDR-H3, in a heavy chain, and/or in any of CDR-L1, CDR-L2 and/or CDR-L3 of a light chain.

The choice of human variable domains, both light and heavy, to be used in making the humanized antibodies is very important to reduce antigenicity. According to the so-called "best-fit" method, the sequence of the variable domain of an antibody of this invention is screened against a library of known human variable-domain sequences. The human sequence which is closest to that of the mouse is then accepted as the human framework (FR) for the humanized antibody (Sims et al., J. Immunol. 151, pp. 2296 (1993); Chothia and Lesk, J. Mol. 196, pp. 901). Another method uses a particular framework from the consensus sequence of all human antibodies of a particular subgroup of light or heavy chains. The same framework can be used for several different humanized antibodies (Carter et al., PNAS 89, pp. 4285 (1992); Presta et J. Immunol., 51, p. 1993)). Other methods designed to reduce the immunogenicity of the antibody molecule in a human patient include veneered antibodies (see, e.g., U.S. Pat. No. 6,797,492 and U.S. patent application publications 20020034765 and 20040253645) and antibodies that have been modified by T-cell epitope analysis and removal (see, e.g., U.S. patent application publications 20030153043 and U.S. Pat. No. 5,712,120).

It is further important that antibodies be humanized with retention of high affinity for the target antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen (s), is achieved. In general, the CDR residues are directly and most substantially involved in influencing antigen binding.

As mentioned, mutation of selected acceptor framework residues to the corresponding donor residues is often required. Thus, in some instances, framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In practice, humanized antibodies are typically human antibodies in which some hypervariable region residues and possibly some FR residues are substituted by residues from analogous sites in rodent antibodies.

In one example, a parent antibody variable region amino acid sequence (e.g. one or a plurality of FRs or an entire variable region or portion thereof) is compared against a collection of human amino acid sequences (e.g. human germline amino acid sequences) and a variant immunoglobulin(s) (e.g. a heavy and/or light chain) is constructed that comprises a parent antibody CDR amino acid sequence(s) (i.e. sequences from one, two or three parent CDRs for each of the heavy and/or light chain of an antibody) and an amino acid sequence from one or more FRs taken from the human amino acid sequence(s), wherein the FR comprises a glutamine residue (such residue will not be an acceptor glutamine). Each of the CDR sequences from a parent antibody may be an entire CDR according to Kabat or other numbering systems, or a portion thereof sufficient to confer antigen specificity.

In one embodiment the antibody is constructed such that all the FRs in the heavy and/or light chain are amino acid sequence(s) of human origin, i.e. the 4 FRs of the heavy chain are of human origin and/or the 4 FRs of the heavy chain are of human origin. In one embodiment, all FR of a particular heavy and/or light chain are from a single human antibody or single human consensus sequence. In one embodiment, the FRs of a particular heavy and/or light chain are independently from two or more different human antibody or human consensus sequences.

It will be appreciated that FR sequences in a humanized antibody can be constructed by modifying those positions in a parent antibody in which the amino acids in the parent antibody variable region and human sequence differ. In one embodiment, a non-glutamine residue in a FR region is substituted by a glutamine (such residue will not be an acceptor glutamine). In one example, a parent antibody FR sequence (e.g. a FR sequence or a sequence that comprises it such as a variable region) is compared against a collection of human amino acid sequences (e.g. human germline amino acid sequences) and a variant immunoglobulin(s) is constructed that comprises the parent antibody CDR amino acid sequence(s) (i.e. sequences from one, two or three parent CDRs for each of the heavy and/or light chain of an antibody) and an amino acid substitution is made in one or more FRs taken from the human amino acid sequence(s) at a position in which the amino acids in the parent antibody variable region and human sequence differ, wherein the substitution comprises replacing a non-glutamine residue by a glutamine residue.

An antibody comprising a modification in it CDR or FR domains will typically retain a biological characteristics of interest of the parent antibody.

In any of the antibodies or methods of the invention, a sequence (e.g. a CDR or FR sequence) of human origin may be characterized as comprising a sequence of at least 5, 10, 15, 20 or 25 contiguous amino acids of a human sequence and/or as being substantially identical to a human sequence.

A VL sequence may optionally comprise mutations (e.g. a back-mutation) in one or more Vernier zone residues 24, 35, 36, 46, 47, 48, 49, 64, 66, 68-69, 71 and/or 99, and/or in one or more VH-VL interface residues 34, 36, 38, 44, 46, 87, 89, 91, 96 and/or 98, and a VH sequence may optionally comprise mutations in one or more Vernier zone residues 2, 27, 28, 29, 30, 47, 48, 49, 67, 69, 71, 73, 78, 93, 94 and/or 103, and/or in one or more VH-VL interface residues 34, 36, 38, 44, 47, 91, 93, 95, 100 and/or 103, with amino acid numbering according to Kabat.

The humanized antibody herein comprises non-human hypervariable region or CDR residues incorporated into a human VH domain. In one embodiment, the humanized antibody comprises no surface-exposed glutamine in the VH domain. In one embodiment, the humanized antibody comprises one, two, three or more glutamines in the VH domain, wherein the glutamine is not an acceptor glutamine, optionally in a CDR-H1, -2 and/or -3, and/or in a FR-H1, -H2 and/or -H3, optionally wherein the antibody has a FR sequence of human origin. In one embodiment, a glutamine is present at position 1, 3, 5, 6, 10, 11, 12, 13, 16, 19, 38, 39, 43, 35, 36, 66, 73, 75, 77, 83, 85 and/or 94 in a VH FR domain. In one embodiment, a glutamine is present at position 26, 35, 50, 61 and/or 64 in a VH CDR. In one embodiment, the humanized antibody comprises no FR substitution in the VH domain. In another embodiment, the humanized antibody comprises a VH domain FR substitution at one, two, three, four or more positions, optionally a position selected from 2, 27, 28, 29, 30, 34, 36, 38, 44, 47, 48, 49, 67, 69, 71, 73, 78, 91, 93, 94, 95, 100 and/or 103, utilizing the variable domain numbering system according to Kabat. In one embodiment, the substitution comprises a glutamine, i.e. replacing a non-glutamine residue by a glutamine residue. Fewer rather than more framework substitutions can minimize immunogenicity, but binding efficacy is also an important consideration. Thus, preferred substitutions are back-mutations, i.e., mutations which replace an amino acid at a certain position in the human FR with the amino acid at the corresponding position in a non-human donor FR.

The humanized antibody herein also comprises non-human hypervariable region or CDR residues incorporated into a human VL domain. In one embodiment, the humanized antibody comprises no surface-exposed glutamine in the VL domain, preferably no acceptor glutamine. In one embodiment, the humanized antibody comprises one, two, three or more glutamines in the VL domain, optionally in a CDR-L1, -2 and/or -3, and/or in a FR-L1, -L2 and/or -L3, optionally wherein the antibody has a FR sequence of human origin. In one embodiment, a glutamine is present at position 3, 6, 11, 17, 18, 37, 38, 42, 45, 47, 49, 79 and/or 105 in a VL FR domain. In one embodiment, a glutamine is present at position 27, 50, 53, 55, 89, 90 and/or 93 in a VL CDR. In one embodiment, the humanized antibody comprises no FR substitution in the VL domain. In another embodiment, the humanized antibody comprises a VL domain FR substitution at one, two, three, four or more positions, optionally a position selected from 24, 34, 35, 36, 38, 44, 46, 47, 48, 49, 64, 66, 68-69, 71, 87, 89, 91, 96 and/or 99, utilizing the variable domain numbering system according to Kabat. In one embodiment, the substitution comprises a glutamine, i.e. replacing a non-glutmine residue by a glutamine residue. Fewer rather than more framework substitutions can minimize immunogenicity, but binding efficacy is also an important consideration. Thus, preferred substitutions are back-mutations, i.e., mutations which replace an amino acid at a certain position in the human FR with the amino acid at the corresponding position in a non-human donor FR.

In one example, the antibody of the invention specifically binds to cancer antigen human L1-CAM (CD171; L1 cell adhesion molecule) which has been found to be expressed in a variety of cancers (see, e.g., Kajiwara et al, (2011) Am. J. Clin. Pathol. 136 (1), 138-144). The L1-CAM nucleotide and amino acid sequences are disclosed in Genbank accession numbers NM_024003.2 and NP_076493.1, respectively, the disclosures of which are incorporated by reference. An example of an anti-L1-CAM antibody suitable for use in accordance with the invention is a chCE7-(or CE7-) derived antibody, e.g, having a heavy chain comprising CDRs (e.g., CDR-H1, -H2 and -H3) from chCE7 heavy chain shown in SEQ ID NO 1 and a light chain comprising CDRs (e.g., CDR-L1, -L2 and -L3) from chCE7 heavy chain shown in SEQ ID NO 2, optionally wherein any of said CDRs further comprises one, two, three, four or five amino acid modifications so long as the antibody retains specific binding to L1-CAM. ChCE7 shown in SEQ ID NOS 1 and 2 is respectively composed of murine VH and murine VL fused to the Fc part of human IgG1 (see, e.g., Jeger et al., (2010) Angew. Chem. Int., 49, 9995-9997). chCE7 optionally comprises specific mutations were introduced in the CH2 domain of the chCE7 heavy chain using overlapping polymerase chain reaction (PCR) and standard molecular biology techniques (Q295N and N297Q variants), including chCE7 N297Q variants with an acceptor glutamine at position 295 and 297, and chCE7aglQ295N, N297Q variants with an acceptor glutamine at position 297.

An exemplary humanized CE7 antibody comprises a VH domain comprising a CDR-H1 sequence corresponding to residues 31-35 of SEQ ID NO:1, a CDR-H2 sequence corresponding to residues 50-66 of SEQ ID NO: 1, and a CDR-H3 sequence corresponding to residues 99-109 of SEQ ID NO:1, wherein any CDR may optionally comprise one, two, three, four or more amino acid substitutions. The humanized antibody may further comprise a glutamine in a VH FR domain at one, two, three, four or more of Kabat positions 1, 3, 5, 6, 10, 11, 12, 13, 16, 19, 38, 39, 43, 35, 36, 66, 73, 75, 77, 83, 85 and/or 94. In one embodiment, the VH domain comprises a framework region substitution in at least one Kabat position selected from the group consisting of from 2, 27, 28, 29, 30, 34, 36, 38, 44, 47, 48, 49, 67, 69, 71, 73, 78, 91, 93, 94, 95, 100 and 103.

An exemplary humanized CE7 antibody may also or alternatively comprise a VL domain comprising a CDR-L1 sequence corresponding to residues 24-34 of SEQ ID NO:2, a CDR-L2 sequence corresponding to residues 50-56 of SEQ ID NO:2, and an CDR-L3 sequence corresponding to residues 89-95 (or 89-97) of SEQ ID NO:2, wherein any CDR may optionally comprise one, two, three, four or more amino acid substitutions. The humanized antibody may further comprise a glutamine in a VL FR domain at one, two, three, four or more of Kabat positions 3, 6, 11, 17, 18, 37, 38, 42, 45, 47, 49, 79 and/or 105. In one embodiment, the VL domain comprises a framework region substitution in at least one Kabat position selected from the group consisting of from 24, 34, 35, 36, 38, 44, 46, 47, 48, 49, 64, 66, 68-69, 71, 87, 89, 91, 96 and 99.

Optionally, in a particular aspect, the VH domain of any antibody of the invention comprises amino acid modifications of one or more CDR residues, e.g. where the modifications essentially maintain or improve affinity of the antibody. For example, the antibody variant may have one, two, three, or from one to about seven amino acid substitutions in the above VH CDR sequences. Such antibody variants may be prepared by affinity maturation, e.g., as described below.

Substitutions can also be made within CDR, e.g. the CDR residues imported from the parent antibody, including but not limited to methods described in SDR-grafting (Kashmiri, et al., 2005, Methods 36:25-34; Gonzales, et al., 2004, Mol Immunol 41:863-872) or making substitutions within CDRs so as to obtain sequences having maximal identity to human V-J segments as described, e.g., in US patent publication number US 2010/004431.

In one embodiment, a non-glutamine residue in a non-human hypervariable region or CDR is substituted by a glutamine. In one example, a parent antibody hypervariable region sequence (e.g. a CDR) is compared against a collection of human amino acid sequences (e.g. human germline V- and J-segment amino acid sequences) and a variant immunoglobulin(s) is constructed that comprises the parent antibody variable region amino acid sequence and an amino acid substitution taken from the human germline V- and J-segment at a position in which the amino acids in the parent antibody variable region and human sequence (e.g. germline V- and J-segment) differ.

In another embodiment, a glutamine residue is present in a CDR (e.g., from a parent antibody variable region) and the glutamine is maintained (i.e. not substituted) in a humanized antibody.

For example, the glutamine may be present in any of CDR-H1, CDR-H2 and/or CDR-H3, optionally at position 26, 35, 50, 61 and/or 64 in a heavy Ig chain, and/or in any of CDR-L1, CDR-L2 and/or CDR-L3, optionally at position 27, 50, 53, 55, 89, 90 and/or 93 of a light Ig chain.

The humanized antibody may or may not further comprise at least a portion of an immunoglobulin constant region (Fc), typically that of a human immunoglobulin. For further details see Jones et al., Nature, 321, pp. 522 (1986); Reichmann et al, Nature, 332, pp. 323 (1988); Presta, Curr. Op. Struct. Biol., 2, pp. 593 (1992); Verhoeyen et Science, 239, pp. 1534; and U.S. Pat. No. 4,816,567, the entire disclosures of which are herein incorporated by reference.

Wild-type full-length IgG antibodies of human isotype will possess a conserved acceptor glutamine at residue 295 of the heavy chain which when in non-glycosylated form will be accessible to a TGase and therefore reactive with a compound of Formula I in the presence of a TGase, under suitable conditions, to form a conjugate from the antibody and the compound of Formula II or IV. The antibody will lack glycosylation at the asparagine at residue 297 of the heavy chain.

Additional or alternative sites reactive with a compound of Formula I in the presence of a TGase can be created by engineering the antibodies. The compounds of the invention include glutamine engineered antibodies where one or more amino acids of a wild-type or parent antibody are replaced with (substituted by) a glutamine amino acid, or where a glutamine residue, optionally together with other amino acid residues, is introduced or added to a wild-type or parent antibody (e.g. wherein the glutamine residue is added to an antibody fragment).

It should be noted that a single site mutation that provides a glutamine that is accessible to a TGase may yield more than one engineered glutamine residue that can be conjugated if the antibody comprises more than one engineered chain. For example, a single site mutation will yield two engineered glutamine residues in a tetrameric IgG due to the dimeric nature of the IgG antibody. The engineered glutamine residues will be in addition to any acceptor glutamine already present in an antibody, if any. The glutamine amino acid residues that are reactive, in the presence of a TGase under suitable conditions, with a compound of Formula I may be located in the heavy chain, typically in the constant domain.

In another embodiment, a strategy for making amino acid modifications in antibodies can be used which result in compositions of antibodies (e.g. antibodies having functionalized acceptor glutamine of Formula II or IV) with greater homogeneity of resulting stoichiometry (in particular the functionalized acceptor glutamine:antibody ratio). For example, by introducing an amino acid modification at residue 297 and/or 299, antibodies can be obtained that are devoid of natural asparagine-liked glycolsylation at position 297. In one embodiment, an asparagine at amino acid position 297 is substituted with a glutamine residue. The antibody will have a constant region with a N297Q substitution (a N297Q variant antibody). In one embodiment, an asparagine at amino acid position 297 is substituted with a non-glutamine residue. The antibody will have a constant region with a N297X substitution (a N297X variant antibody), wherein X is an amino acid other than glutamine. Optionally, X is an amino acid other than glutamine and other than aspartic acid. Optionally, X is an amino acid other than glutamine and other than an electrically negatively charged amino acid. Other substitutions leading to elimination of asparagine-linked glycosylation at N297 include modifications at residues T299 (or S298 together with T299), see, e.g., any of the mutations and combinations of mutations disclosed in Sazinsky et al. 2008 Proc. Nat. Acad. Sci. U.S.A. 105(51):20167-20172, the disclosure of which is incorporated by reference. An antibody having a N297Q substitution and a glutamine at residue 295 will therefore have two conjugation sites per heavy chain. In tetravalent form will therefore have four conjugates per antibody.

In one embodiment, the residue at amino acid position 297, 298 and/or 299 is substituted with a non-glutamine residue (e.g. the antibody will have a constant region with a N297X (a N297X variant antibody), S298X and/or T299X substitution, wherein X is any amino acid. Such an antibody, when comprising a glutamine at position 295 (a glutamine is naturally present in human constant regions at position 295) but no other acceptor glutamine residues will have two conjugates per antibody when the antibody comprises two heavy chains.

Engineered antibodies can be prepared by a variety of methods which include, but are not limited to, isolation from a natural source (in the case of naturally occurring amino acid sequence variants), preparation by site-directed (or oligonucleotide-mediated) mutagenesis (Carter (1985) et al Nucleic Acids Res. 13:4431-4443; Kunkel et al (1987) Proc. Natl. Acad. Sci. USA 82:488; Liu et al (1998) J. Biol. Chem. 273:20252-20260), PCR mutagenesis (Ito et al (1991) Gene 102:67-70; and Vallette et al (1989) Nuc. Acids Res. 17:723-733) and cassette mutagenesis (Wells et al (1985) Gene 34:315-323) of an earlier prepared DNA encoding the polypeptide. Mutagenesis protocols, kits, and reagents are commercially available, e.g. QuikChange® Multi Site-Direct Mutagenesis Kit (Stratagene, La Jolla, Calif.). Single mutations are also generated by oligonucleotide directed mutagenesis using double stranded plasmid DNA as template by PCR based mutagenesis (Sambrook and Russel, (2001) Molecular Cloning: A Laboratory Manual, 3rd edition). Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies (Sambrook et al Molecular Cloning, A Laboratory Manual. Cold Spring Harbor Laboratory Press, Cold Spring Harbor, N.Y., 1989; and Ausubel et al Current Protocols in Molecular Biology, Greene Publishing and Wiley-Interscience, New York. N.Y., 1993).

Preparing an engineered antibody may comprise:
(i) mutagenizing a nucleic acid sequence encoding the engineered antibody;
(ii) expressing the engineered antibody; and
(iii) isolating and purifying the engineered antibody.

Fragments and derivatives of antibodies of this invention (which are encompassed by the term "antibody" or "antibodies" as used in this application, unless otherwise stated or clearly contradicted by context), can be produced by techniques that are known in the art. "Fragments" comprise a portion of the intact antibody, generally the antigen binding site or variable region. Examples of antibody fragments include Fab, Fab', Fab'-SH, F(ab')2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments. Included, inter alia, are a nanobody, domain antibody, single domain antibody or a "dAb".

The DNA of a hybridoma producing an antibody of the invention may be modified so as to encode a fragment of the invention. The modified DNA is then inserted into an expression vector and used to transform or transfect an appropriate cell, which then expresses the desired fragment.

The fragment will comprise a variable region domain that will generally be covalently attached to at least one, two or more glutamine residue covalently linked through a —NH—$(C)_n$—X-L moiety (and optionally further a V and/or Y moiety, optionally further an R or RR' moiety, to a moiety-of-interest Z, e.g. a polymer molecule, a drug, a radioactive moiety. The variable region will comprise hypervariable region or CDR sequences, and FR sequences.

The location of the glutamine residue may be varied according to the size and nature of the antibody fragment required. Thus, in one extreme example an acceptor glutamine residue to be conjugated to a lysine-based linker of Formula I may be attached directly to a C-terminal amino acid of the variable region domain. This may be for example the C-terminus of a VH or VL chain as described above. If desired, in this example, further amino acids, including further acceptor glutamine residues, may be covalently linked to the C-terminus of the first glutamine residue. In one example, a peptide "tag" comprising one or more non-glutamine residues followed by an acceptor glutamine residue (the acceptor glutamine residue is C-terminal to the non-glutamine residue in the tag) is attached directly to a C-terminal amino acid of the variable region domain. In one example, a peptide "tag" comprising one or more glutamine residues followed by one or more non-glutamine residues (the non-glutamine residues are C-terminal to the glutamine residue in the tag) is attached directly to a C-terminal amino acid of the variable region domain. A peptide tag can be of any suitable length, e.g a tag may comprise between 2 and 50, preferably 2 and 20 or 2 and 10 amino acid residues.

In practice however, it is generally preferable that the variable region domain is covalently attached at a C-terminal amino acid to at least one other antibody domain or a fragment thereof which contains, or is attached to one or more acceptor glutamine residues. Thus, for example where a VH domain is present in the variable region domain this may be linked to an immunoglobulin CH1 domain or a fragment thereof. Similarly a VL domain may be linked to a CK domain or a fragment thereof. In this way for example the fragment according to the invention may be a Fab fragment wherein the antigen binding domain contains associated VH and VL domains covalently linked at their C-termini to a CH1 and CK domain respectively. The CH1 domain may be extended with further amino acids, for example to provide a hinge region domain as found in a Fab' fragment, or to provide further domains, such as antibody CH2 and CH3 domains. In one example, a polypeptide "tag" comprising one or a plurality (e.g. 2, 3, 4, 5, 6) non-glutamine residues followed by a glutamine residue (the glutamine residue is C-terminal to the non-glutamine residue in the tag) is attached directly to a C-terminal amino acid of a full or truncated CH1, CH2 or CH3 domain, or to a C-terminal amino acid of a full or truncated CK domain. In one example, a polypeptide "tag" comprising one or more glutamine residues followed by one or more non-glutamine residues (the non-glutamine residues are C-terminal to the glutamine residue in the tag) is attached directly to a C-terminal amino acid of a full or truncated CH1, CH2 or CH3 domain, or to a C-terminal amino acid of a full or truncated CK domain.

The present invention provides an antibody fragment in which the variable region domain is monomeric and comprises an immunoglobulin heavy (VH) or light (VL) chain variable domain, or is dimeric and contains VH-VH, VH-VL or VL-VL dimers in which the VH and VL chains are non-covalently associated or covalently coupled, wherein the fragment (i.e. the VL and/or VH) is covalently linked through a —NH—$(C)_n$—X-L moiety (and optionally further a V and/or Y moiety, optionally further L', V', Y', and (RR')moieties, to a moiety-of-interest Z, e.g. a polymer molecule, a drug, a radioactive moiety. Preferably each VH and/or VL domain is covalently attached at a C-terminal amino acid to at least one other antibody domain or a fragment thereof.

In one embodiment, the invention provides a monovalent antibody fragment comprising a heavy chain and a light chain, wherein: said heavy chain consists of a VH domain covalently linked at its C-terminus to a CH1 domain; said light chain consists of a VL domain, which is complementary to the VH domain, covalently linked at its C-terminus to a CL domain; said CH1 domain comprises (e.g., the CH1 is extended) to provide a hinge domain which comprises a glutamine residue; and the glutamine residue in the hinge domain is covalently linked through a —NH—$(C)_n$—X-L moiety. In another embodiment, the invention provides a monovalent antibody fragment comprising a heavy chain and a light chain, wherein: said heavy chain consists of a VH domain covalently linked at its C-terminus to a CH1 domain; said light chain consists of a VL domain, which is complementary to the VH domain, covalently linked at its C-terminus to a CL domain; said CL domain comprises (e.g., the CL is extended) to provide a hinge domain which comprises a glutamine residue; and the glutamine residue in the hinge domain is covalently linked through a —NH—$(C)_n$—X-L moiety.

The invention has the advantage over cysteine-based conjugation methods of not requiring cysteine-engineering to remove cysteine residues that could react with the moiety of interest. Thus, in one embodiment, the antibody fragment of the invention contains cysteine residues in the VH, CH1, VL and CL domains that are in disulphide linkage to each other; preferably the antibody fragment comprises some or all cysteines capable of forming interchain disulfide bonds in naturally present in VH, CH1, VL and CL domains. In one embodiment, the antibody comprises a light chain comprising a cysteine at position 214 and/or a heavy chain comprising a cysteine at position 127, 128, 233 and/or 235.

In one embodiment, the antibody fragment is linked through a —NH—$(C)_n$—X-L moiety to a polymer (e.g. a PEG-comprising molecule).

Lysine-based Linkers

The antibodies of the invention will be conjugated to a moiety-of-interest via a linking reagent that can be attached, by the action of a TGase, at a glutamine residue (Q) within the sequence of the antibody (Ab). The linking reagent comprises a lysine derivative (Lys), or a functional equivalent thereof, that is connected to at least one moiety of interest (Z) or a reactive group (R). In one embodiment, a plurality of reactive groups, preferably non-complementary reactive groups, can be attached to the linking reagent. The reactive group is preferably a functionality that is insensitive to water but selectively undergoes a very high conversion addition reaction with a complementary reagent.

The lysine derivative can be a 2 to 20 alkyl or heteroalkyl chain, or a functional equivalent thereof, with an $H_2N$, $H_2NOCH_2$, $H_2NCH_2$ (aminomethylene) group or a protected $H_2N$, $H_2NOCH_2$, $H_2NCH_2$ group positioned at one or more ends of the alkyl or heteroalkyl chain. The heteroalkyl chain can be a chain of 3 to 20 atoms where one or more non-terminal atoms can be other than carbon, for example oxygen, sulfur, nitrogen, or other atoms. The oxygen, sulfur, or nitrogen atom can be of an ether, ester, thioether, thioester, amino, alkylamino, amido or alkylamido functionality within the carbon chain.

The heteroalkyl chain can be an oligo (ethylene oxide) chain. The functionality within the alkyl or heteroalkyl chain can be included to couple the reactive group to the $H_2N$, $H_2NOCH_2$, $H_2NCH_2$ group or protected $H_2N$, $H_2NOCH_2$, $H_2NCH_2$ group. The alkyl or heteroalkyl chain can be substituted or unsubstituted. The substituents can be alkyl groups, aryl groups, alkyl aryl groups, carboxylic acid groups, amide groups, hydroxy groups, or any other groups that do not compete with the amino group for, or inhibit, conjugation with a glutamine residue of the protein. Typically, when a substituent is present, its presence is in a convenient starting material, such as the carboxylic acid group of lysine, from which the lysine derivative results. The $H_2N$, $H_2NOCH_2$, $H_2NCH_2$ end of a alkyl or heteroalkyl chain is necessarily included in the linking reagent.

Exemplary starting materials for the functional equivalent of lysine can be an α,ω-diaminoalkane, for example, 1,2-diaminoethane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,11-diaminoundecane, or 1,12-diaminododecane. Other starting materials for the functional equivalent of a lysine derivative can be α,ω-diamino oligo (ethylene oxide), for example, $H_2N(CH_2CH_2O)_xCH_2CH_2NH_2$ where x is 1 to about 6. The α,ω-diamino oligo (ethylene oxide) can be a single oligomer or it can be a mixture of oligomers where x defines an average size. An exemplary protected $H_2NCH_2$ is the tert-butylcarbamate protected amine of tert-butyl N-(5-aminopentyl)carbamate (N-Boc-cadaverin).

The linking reagent, a pharmaceutically acceptable salt or solvate thereof, or a protein conjugated linking reagent may comprise the general Formula Ia or Ib. Formulae Ia (having an Z group) and Ib (having a R group) are shown as follows:

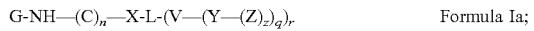

G-NH—$(C)_n$—X-L-(V—$(Y—(Z)_z)_q)_r$  Formula Ia;

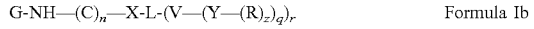

G-NH—$(C)_n$—X-L-(V—$(Y—(R)_z)_q)_r$  Formula Ib or a pharmaceutically acceptable salt or solvate thereof wherein:

G is an H, amine protecting group, or an immunoglobulin (Ab) or other protein attached via an amide bond;

$(C)_n$ is a substituted or unsubstituted alkyl or heteroalkyl chain, optionally where the carbon adjacent to the nitrogen is unsubstituted, optionally wherein any carbon of the chain is substituted alkoxy, hydroxyl, alkylcarbonyloxy, alkyl-S—, thiol, alkyl-C(O)S—, amine, alkylamine, amide, or alkylamide (e.g. with a O, N or S atom of an ether, ester, thioether, thioester, amine, alkylamine, amide, or alkylamide);

n is an integer selected from among the range of 2 to 20, preferably 3 to 6;

X is NH, O, S, or absent;

L is a bond or a carbon comprising framework of 1 to 200 atoms substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), an amino acid, a di-, tri-, tetra-, or oligopeptide, other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 4;
q is an integer selected from among 1, 2, 3 or 4; and
z is an integer selected from among 1, 2, 3 or 4;

V is independently absent, a bond or a continuation of a bond if L is a bond, a non-cleavable moiety or a conditionally-cleavable moiety, optionally following prior conditional transformation, which can be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";

Y is independently absent, a bond or a continuation of a bond if V is a bond or continuation of a bond, or a spacer system (e.g., a self-eliminating spacer system or a non-self-elimination spacer system) which is comprised of 1 or more spacers;

Z is a moiety that improves the pharmacokinetic properties, a therapeutic moiety or a diagnostic moiety; and R is a reactive moiety, preferably a moiety comprising an unprotected or protected thiol, maleimide, haloacetamide, o-phoshenearomatic ester, azide, fulminate, alkyne, cyanide, anthracene, 1,2,4,5-tetrazine, norbornene, other stained or otherwise electronically activated alkene or, optionally, a protected or unprotected amine when X is absent and L, V, or Y is other than a bond or a continuation of a bond. In an alternative embodiment R is a reactive moiety, preferably a moiety comprising an unprotected or protected thiol, an unprotected or protected amine, maleimide, haloacetamide, o-phoshenearomatic ester, azide, fulminate, alkyne, cyanide, anthracene, 1,2,4,5-tetrazine, norbornene, other stained or otherwise electronically activated alkene, provided that R is not an amine when n=5 and X, L, V and Y are absent. Optionally, R is not an amine when n=4 and X, L, V and Y are absent. When more than one R group is present in a compound of the formula Ib, the R groups will preferably be compatible such that no R group is a complementary reagent to any other R group.

The $(C)_n$ group may for example be a straight, branched and/or cyclic $C_{2-30}$ alkyl, $C_{2-30}$ alkenyl, $C_{2-30}$ alkynyl, $C_{2-30}$ heteroalkyl, $C_{2-30}$ heteroalkenyl, $C_{2-30}$ heteroalkynyl, optionally wherein one or more homocyclic aromatic compound radical or heterocyclic compound radical may be inserted; notably, any straight or branched $C_{2-5}$ alkyl, $C_{5-10}$ alkyl, $C_{11-20}$ alkyl, —O—$C_{1-5}$ alkyl, —O—$C_{5-10}$ alkyl, —O—$C_{11-20}$ alkyl, $CH_2$—$(CH_2$—O—$CH_2)_{1-12}$—$CH_2$ or $(CH_2$—$CH_2$—O—$)_{1-12}$, an amino acid, an oligopeptide, glycan, sulfate, phosphate or carboxylate.

In one example the $(C)_n$ group is a carbon comprising framework substituted with one or more O atoms. In one embodiment, the carbon adjacent to the nitrogen is substituted with an O atom. In one embodiment, the carbon adjacent to the nitrogen is unsubstituted. In one embodiment, the $(C)_n$ group is or comprises an ethylene oxide group, e.g. a $CH_2$—$(CH_2$—O—$CH_2)_n$—$CH_2$ group or an $(CH_2$—$CH_2$—O—$)_n$, where n is an integer from 1 to 10.

The L group can be a carbon comprising framework, where L is a linear hydrocarbon, a symmetrically or asymmetrically branched hydrocarbon, monosaccharide, disaccharide, linear or branched oligosaccharide (asymmetrically branched or symmetrically branched), an amino acid, a di-, tri-, tetra-, or oligopeptide, other natural oligomer, dimer, trimer, or higher oligomer (linear asymmetrically branched or symmetrically branched) resulting from any chain-growth or step-growth polymerization process. For example, L may comprise or be a straight, branched and/or cyclic $C_{2-30}$ alkyl, $C_{2-30}$ alkenyl, $C_{2-30}$ alkynyl, $C_{2-30}$ heteroalkyl, $C_{2-30}$ heteroalkenyl, $C_{2-30}$ heteroalkynyl, optionally wherein one or more homocyclic aromatic compound radical or heterocyclic compound radical may be inserted; notably, any straight or branched $C_{2-5}$ alkyl, $C_{5-10}$ alkyl, $C_{11-20}$ alkyl, —O—$C_{1-5}$ alkyl, —O—$C_{5-10}$ alkyl, —O—$C_{11-20}$ alkyl, $CH_2$—$(CH_2$—O—$CH_2)_{1-30}$—$CH_2$ or $(CH_2$—$CH_2$—O—$)_{1-30}$, e.g., $(CH_2$—$CH_2$—O—$)_{12}$, $(CH_2$—$CH_2$—O—$)_{1-24}$, an amino acid, an oligopeptide, glycan, sulfate, phosphate, carboxylate. Optionally, L is absent.

L, V and/or Y have r, q, and/or z sites of attachment for the respective V, Y, and Z or R groups, where r and q represent the degree of branching or polymerization. The sites of attachment can comprise a bond or comprise a functional group selected from an alkene, alkyne, ether, thioether, ester, thioester, amine, amide, alkylamide, or other functional group readily generated by a condensation or addition reaction.

In one example the carbon comprising framework of the L group is optionally substituted with one or more O atoms. In one embodiment, the L group comprises one or more ethylene oxide groups ($CH_2$—O—$CH_2$). Optionally, the L group comprises a carbon framework comprising a ($CH_2$—$CH_2$—O—$)_n$ group, wherein n is an integer selected among the range of 1 to 10 (e.g., 1, 2, 3, 4, 5, 6, 7, 8, 9 or 10).

In Formulae Ia, Ib, II, IVa and IVb, the linking group L links the aminopeptidyl moiety —NH—$(C)_n$—X to the reactive group R or Z, optionally through one or more V and/or Y moieties where present. L may be a bond connecting V, Y, R or Z directly to the aminopeptidyl moiety. In another aspect, however, L is a linking group that functionally links or spaces the one or more moieties V and/or Y reactive moiety R or moiety of interest (Z). In Formulae Ib, II and IVb, spacing improves efficiency and completion of BTGase coupling, make additionally the reactive moiety R more accessible to the reaction partner, for example when the reactive moiety is present on a lysine-based linker and coupled to the antibody and then brought into contact with a reaction partner. In Formulae Ia and IVa, the linking group L links the aminopeptidyl moiety —NH—$(C)_n$—X to the moiety-of-interest (Z), optionally through one or more V and/or Y moieties where present. L may be a bond connecting V, Y or Z directly to the aminopeptidyl moiety. In another aspect, however, L is a linking group that functionally links or spaces the one or more moieties V and/or Y reactive moiety Z. In Formulae Ia and IVa, spacing improves efficiency and completion of BTGase coupling, providing for highly homogenous compounds. In antibodies comprising a functionalized acceptor glutamine of Formula IVa or IVb spacing may also provide for a better accessibility of V, which in the case of enzymatic cleavage or transformation of V, may improve the rate at which V is transformed and/or cleaved.

L and $(C)_n$ groups can be configured based on the overall structure of the linker that is to be used. Particularly when a multi-step method of the invention is used and the linker (e.g. the linker of Formula Ia or Ib is free of or does not comprise a large, charged or hydrophobic moiety (e.g. a cyclic, polycyclic or macrocyclic moiety), the L group may be a bond or a shorter carbon framework. For example, L may represent or comprise a carbon framework of 1, 2, 3, 4, 5, or 6 linear carbon atoms, unsubstituted or optionally substituted at one or more atoms. Preferably, where L additionally comprises other groups, the 5-20 linear carbon atoms will be adjacent to the $(C)_n$ group, or where present, the X group.

When a linker (e.g. the linker of Formula Ia or Ib or an antibody of Formula II, IVa or IVb) comprises a large, charged or hydrophobic moiety (e.g. a cyclic, polycyclic or macrocyclic moiety), for example, wherein V, Y and/or Z comprises a large, charged or hydrophobic moiety (e.g. a cyclic, polycyclic or macrocyclic moiety), the L group may be longer carbon framework. For example, L may represent or comprise a carbon framework of:

a) 2-30 linear carbon atoms optionally substituted at one or more atoms;

b) 2-15 linear carbon atoms optionally substituted at one or more atoms;

c) 5-20 linear carbon atoms optionally substituted at one or more atoms;

d) 5-30 linear carbon atoms optionally substituted at one or more atoms;

e) 5-15 linear carbon atoms optionally substituted at one or more atoms; or f) 4, 5 or 6 linear carbon atoms optionally substituted at one or more atoms.

Preferably, the 5-20 linear carbon atoms will be adjacent to (the continuation of) the $(C)_n$ group, or where present, the X group.

In some embodiments, L is a —(C═O)—$C_{1-6}$ alkyl group. In some embodiments, L is a $C_{1-6}$ alkoxy-$C_{1-6}$ alkyl group. In some embodiments, L is a —(C═O)—$C_{1-6}$ alkoxy-$C_{1-6}$ alkyl group. In some embodiments, L is a —(C═O)—$C_{10-20}$ alkyl group. In some embodiments, L is a $C_{1-6}$ alkyl group. In some embodiments, L is a $C_{10-20}$ alkyl group. In some embodiments, L is a —(C═O)—O—$C_{1-6}$ alkyl group. In some embodiments, L is a —(C═O)—O—$C_{2-20}$ alkyl group. In some embodiments, L is a —(C═O)— group. In some embodiments, L is selected from among

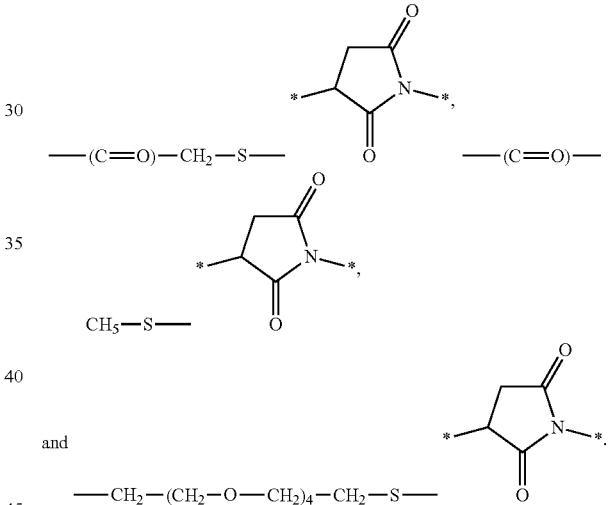

In some embodiments, L is or comprises an amino acid or a di-, tri- tetra- or oligopeptide. In some embodiments, L is selected from among alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and citrulline.

In any of the compounds of the invention (e.g. in any of Formula I, II and/or IV), linking element (L) can optionally be characterized as having a chain length of at least 2.8 Angstroms, 3, Angstroms, 4 Angstroms, 5 Angstroms, 10 Angstroms, 15 Angstroms, 18 Angstroms, 30 Angstroms, 40 Angstroms or 60 Angstroms. Optionally L has a length of no more than 100 Angstroms, optionally no more than 60 Angstroms Optionally, L is characterized as having a length of between 2.8, 3, 4, 5, 10, 20 or 30 Angstroms and 60 Angstroms. Optionally, L is characterized as having a length of between 2.8 and 19 Angstroms, or between 4 and 19 Angstroms.

Examples of compounds of Formula Ia include but are not limited to compound having the $(C)_n$, X, L, V, Y and Z groups shows in Table 2 herein. Examples of compounds of Formula Ib include but are not limited to compound having the (C)$_n$, X, L, V, Y and R groups shows in Table 3 herein. R groups in Table 3 indicated as (S) can also be S(C=O)CH$_3$ when present as a protected reactive group. The symbol (-) in the tables indicates that the particular X, L, V or Y moiety is absent. V and Y groups, for example, can comprise any structural features in the sections titled "The V Moiety" and "The Y Moiety" herein. The L, V and/or Y groups of Formulae Ia and Ib represented in each of Tables 2 and 3 can have r, q, and/or z sites of attachment for the respective V, Y, and R or Z groups, where r and q represent the degree of branching or polymerization; r, q, and/or z can be selected from 1, 2, 3 or 4.

A compound of this invention may contain more than one L moiety. Any L' moiety can be defined in the same way as a L moiety. The L moieties may or may not be the same. The linking group L may be a water-soluble moiety or contain one or more water-soluble moieties, such that L contributes to the water solubility of a compound of Formula (I)-(VI). An L may also be a moiety or contain one or more moieties that reduce(s) aggregation, which may or may not be a moiety/moieties that also increase(s) the water solubility.

L may be for example a linear linker or a branched linker. In one aspect, the L moiety is branched, optionally further a dendritic structure, so that it can be connected to at least two, three, four or more V, Y or R moieties (or Z where applicable). Each V-Y moiety is however only attached once to an L moiety. Branching can occur at one or more branching atoms that may for example be carbon, nitrogen, silicon, or phosphorus.

When the lysine-based linker comprises branching in L, the number of branches in L that are connected to V and/or Y will generally be prepared so as to equal the total number of branches available for reaction. That is, in preparing the lysine-based linker, chemical conversion will preferably be carried to completion, thereby maintain the controlled stoichiometry offered by the site-specific TGase-mediated conjugation approach. Thus, preferably, when L is branched, compounds of this invention will be functionalized such that each L, V or Y is connected to a R or Z moiety, such that the components of the mixture of antibodies (or the lysine-based linker during preparation) substantially all have the same r value. For example, it can be specified that 90%, 95%, 98% of the antibodies or the lysine-based linker have the same r value. In one embodiment, L is a linear linker. In another embodiment, L is a branched linker.

Any one of the L moieties disclosed herein can be utilized in Formula Ia, Ib, II, IVa, and IVb. Any one of the L moieties described herein can be used in combination with any of the (C)$_n$, X, V, Y, Z, R, M, z, q, and r groups described herein. Any one of the L' moieties disclosed herein can be utilized in Formula III. Any one of the L' moieties described herein can be used in combination with any of the R', V', Y', Z, z', q', and r' groups described herein.

Exemplary linkers of Formula Ia include but are not limited to:

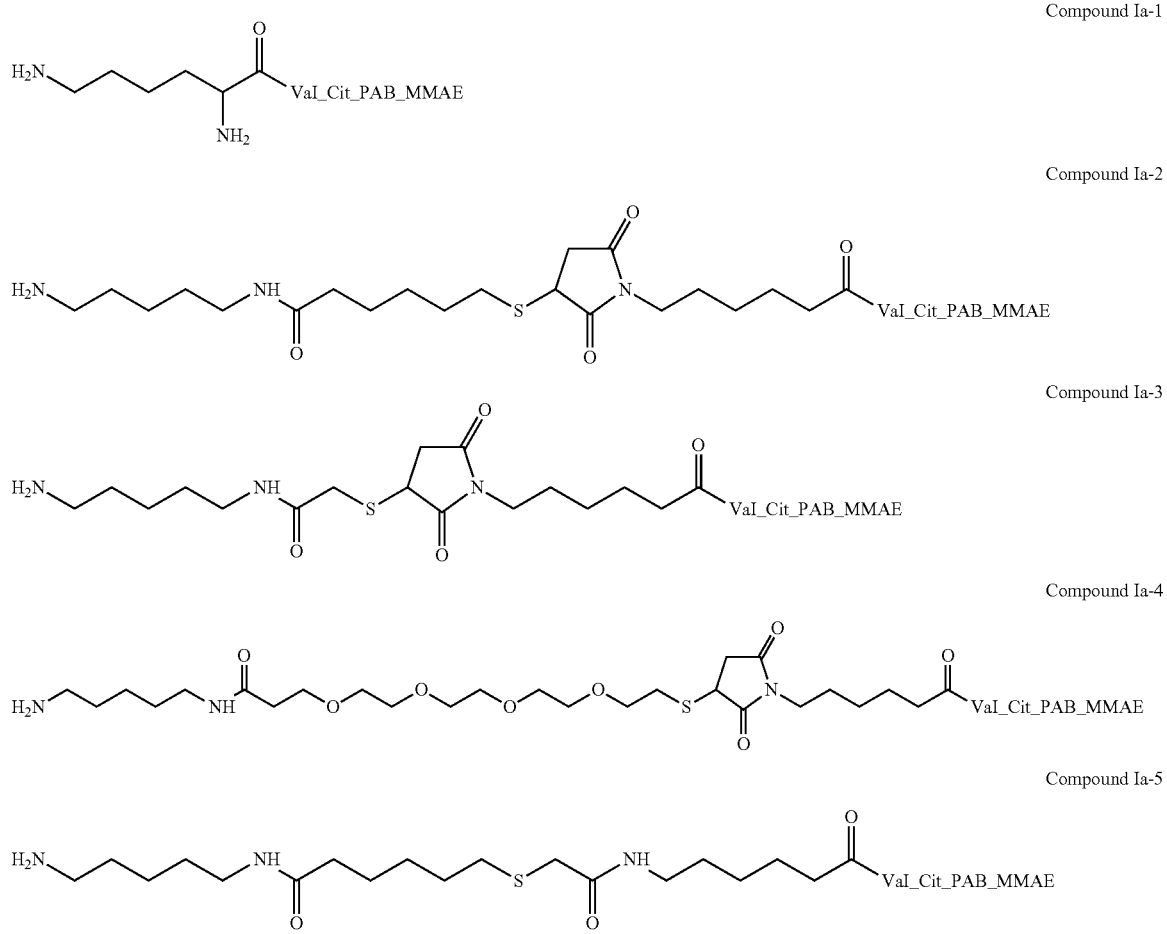

Compound Ia-1

Compound Ia-2

Compound Ia-3

Compound Ia-4

Compound Ia-5

-continued
Compound Ia-6
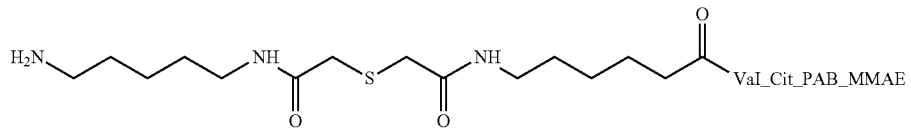
Compound Ia-7
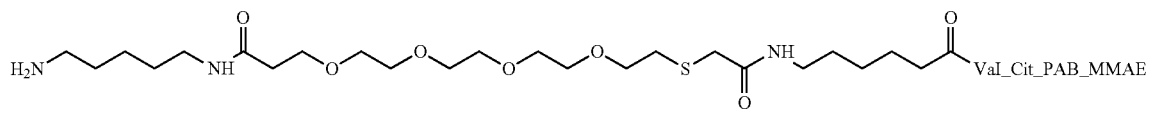
Compound Ia-8
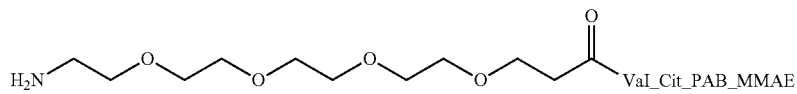
Compound Ia-9
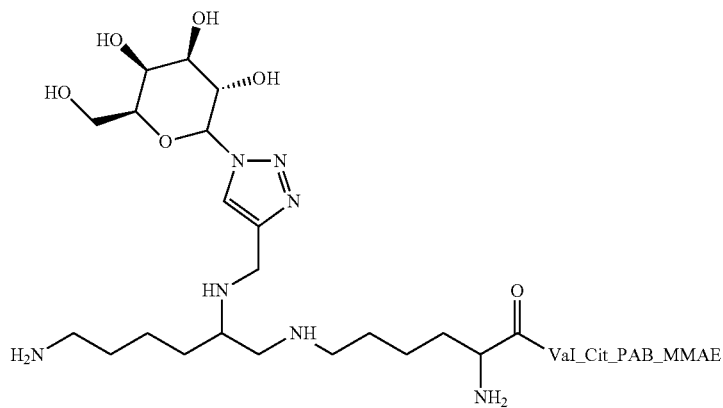
Compound Ia-10
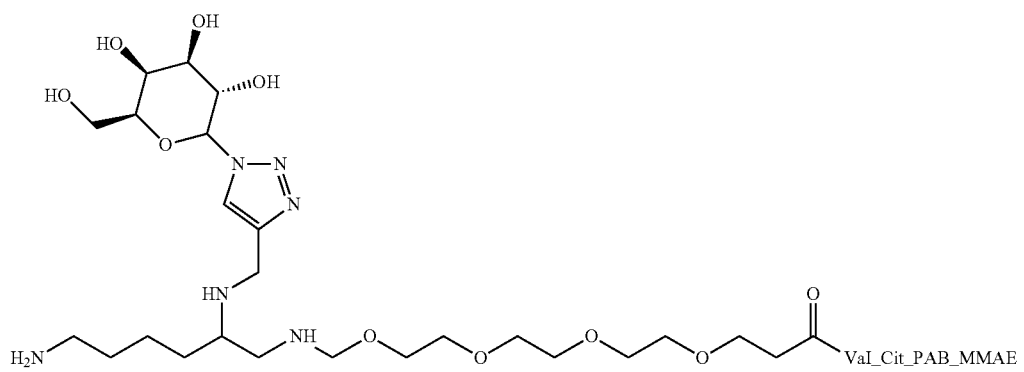
Compound Ia-11
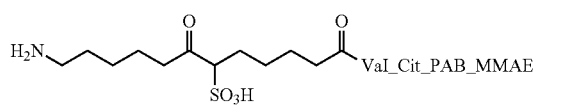
Compound Ia-12
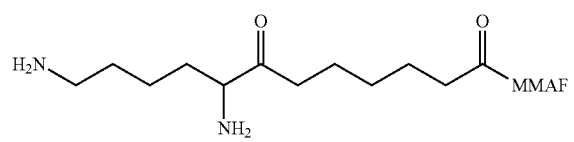
Compound Ia-13
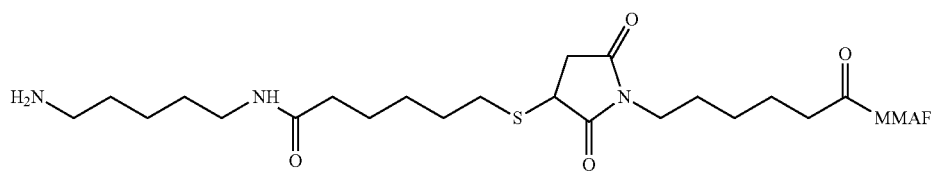

-continued
Compound Ia-14
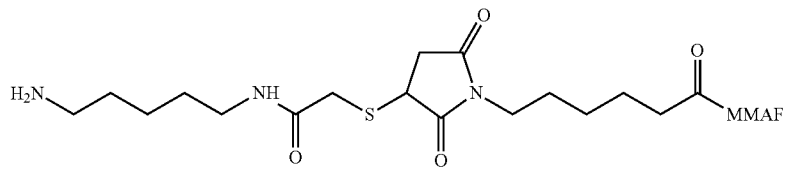
Compound Ia-15
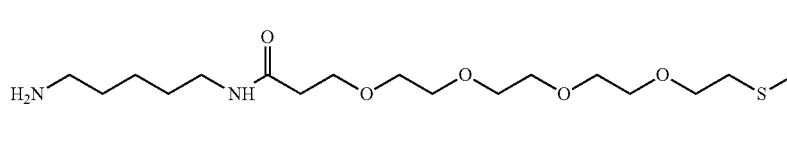
Compound Ia-16
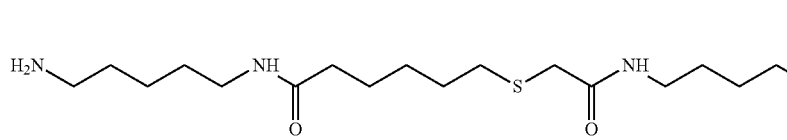
Compound Ia-17
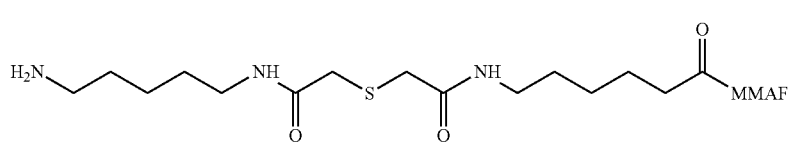
Compound Ia-18
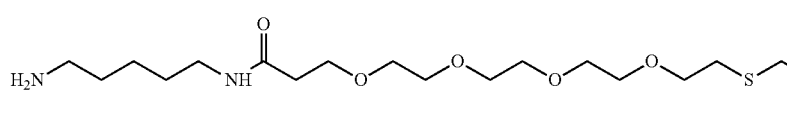
Compound Ia-19
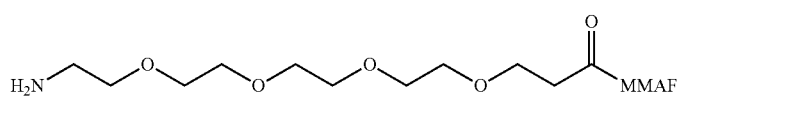
Compound Ia-20
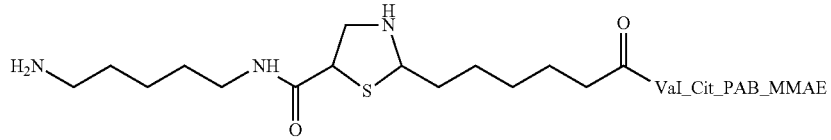
Compound Ia-21
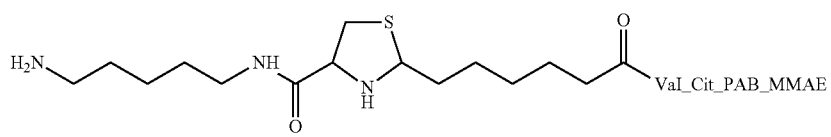
Compound Ia-22
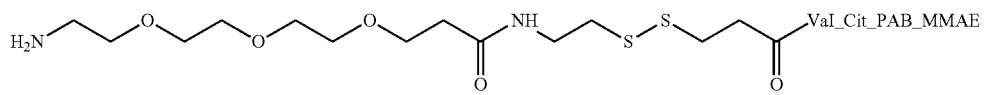
Compound Ia-23
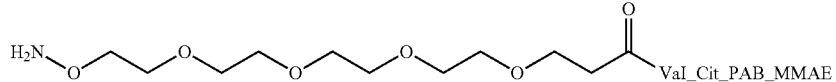

Exemplary linkers of Formula Ib include but are not limited to:
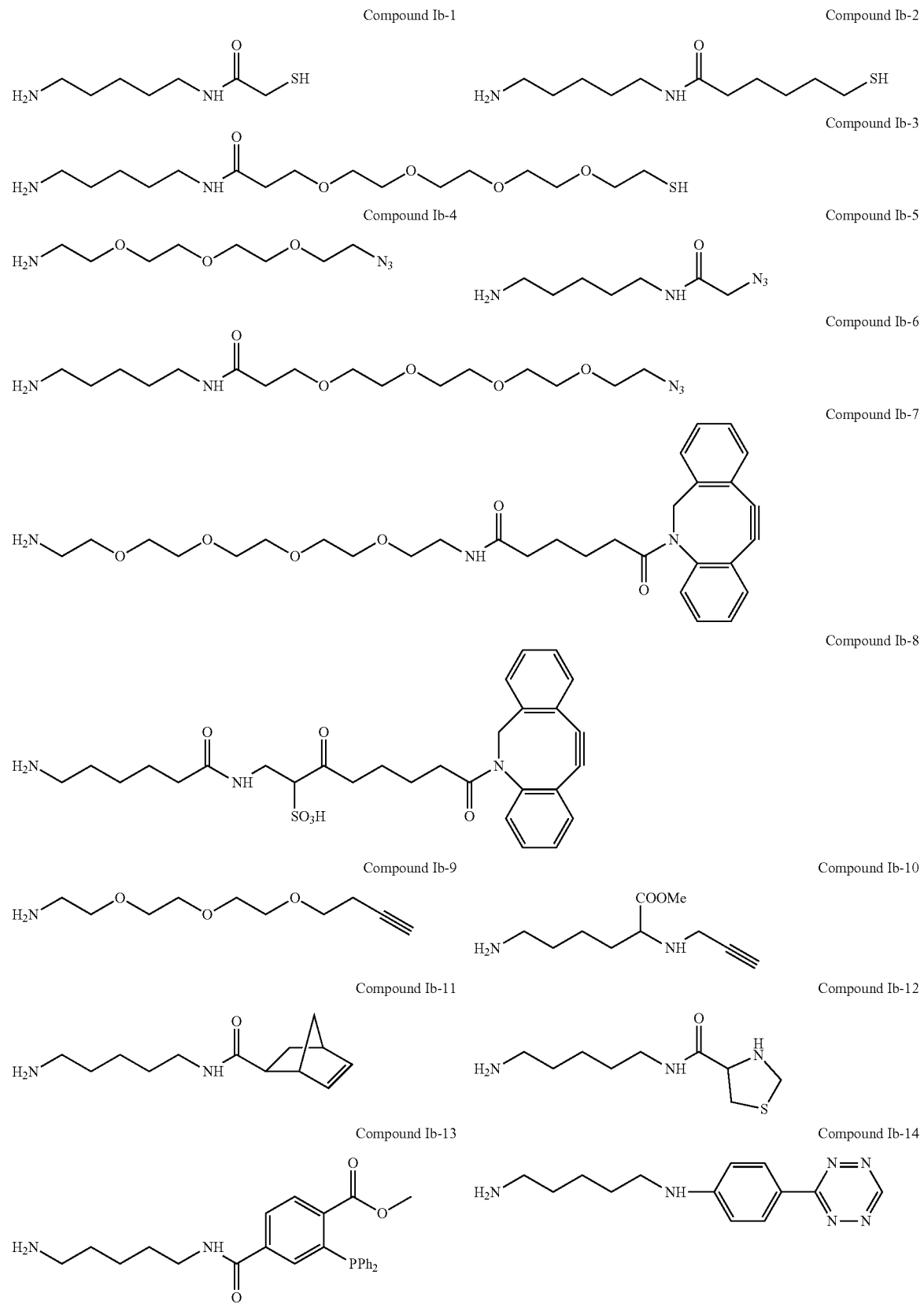

-continued

Compound Ib-15

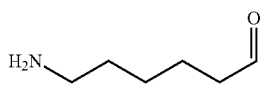

The Reactive Moiety R

R is a reactive moiety, for example a moiety comprising an unprotected or protected bioorthogonal-reaction compatible reactive group, for example an unprotected or protected thiol, epoxide, maleimide, haloacetamide, o-phoshenearomatic ester, azide, fulminate, sulfonate ester, alkyne, cyanide, amino-thiol, carbonyl, aldehyde, generally any group capable of oxime and hydrazine formation, 1,2,4,5-tetrazine, norbornene, other stained or otherwise electronically activated alkene, a substituted or unsubstituted cycloalkyne, generally any reactive groups which form via bioorthogonal cycloaddition reaction a 1,3- or 1,5-disubstituted triazole, any diene or strained alkene dienophile that can react via inverse electron demand Diels-Alder reaction, a protected or unprotected amine, a carboxylic acid, an aldehyde, or an oxyamine.

When more than one R group is present in a compound of the formula, the R groups will preferably be compatible such that no R group is a complementary reagent to any other R group. The L, V and/or Y groups of formulae I-IV can have r, q, and/or z sites of attachment for the respective V, Y, and R groups, where r and q represent the degree of branching or polymerization. The sites of attachment can comprise a bond or comprise a functional group selected from an alkene, alkyne, ether, thioether, ester, thioester, amine, amide, alkylamine, or other functional group readily generated by a condensation or addition reaction.

The reactive group of the linking reagent can for example chosen to undergo thio-maleimide (or haloacetamide) addition, Staudinger ligation, Huisgen 1,3-cycloaddition (click reaction), or Diels-Alder cycloaddition with a complementary reactive group attached to an agent comprising a therapeutic moiety, a diagnostic moiety, or any other moiety for a desired function.

Optionally, two or more compatible reactive groups can be attached to the linking reagent.

In one embodiment, the reactive group is a haloacetamide, (e.g. bromo-acetamide, iodo-acetamide, cloro-acetamide). Such reactive groups will be more stable in vivo (and in serum) compared with maleimide groups.

In one embodiment, the reactive group is a reagent capable of undergoing a "click" reaction. For example a 1,3-dipole-functional compound can react with an alkyne in a cyclization reaction to form a heterocyclic compound, preferably in the substantial absence of added catalyst (e.g., Cu(I)). A variety compounds having at least one 1,3-dipole group attached thereto (having a three-atom pi-electron system containing 4 electrons delocalized over the three atoms) can be used to react with the alkynes disclosed herein. Exemplary 1,3-dipole groups include, but are not limited to, azides, nitrile oxides, nitrones, azoxy groups, and acyl diazo groups.

Examples include o-phosphenearomatic ester, an azide, a fulminate, an alkyne (including any strained cycloalkyne), a cyanide, an anthracene, a 1,2,4,5-tetrazine, or a norbornene (or other strained cycloalkene).

In one embodiment, R is a moiety having a terminal alkyne or azide; such moieties are described for example in U.S. Pat. No. 7,763,736, the disclosure of which is incorporated herein by reference. Suitable reaction conditions for use of copper (and other metal salt) as catalysts of click-reactions between terminal alkynes and azides are provided in U.S. Pat. No. 7,763,736.

In one embodiment, R is a substituted or unsubstituted cycloalkyne. Cycloalkynes, including heterocyclic compounds, will preferably be used in linking reagents of the invention in which an L group is present, preferably wherein L is an alkyl or heteroalkyl chain of 3-30, optionally 5-30 or 5-15 linear carbon atoms, optionally substituted at one or more atoms. Optionally, L is a $(CH_2-CH_2-O)_{1-24}$ group or a $(CH_2)_{x1}-(CH_2-O-CH_2)_{1-24}-(CH_2)_{x2}-$, wherein x1 and x2 are independently an integer selected among the range of 0 to 20. As shown herein, presence of an L group enables high TGase-mediated coupling when cycloalkynes are used.

Cycloalkynes, including specific compounds, are described for example in U.S. Pat. No. 7,807,619, the disclosure of which is incorporated herein by reference.

In some embodiments, a cycloalkyne may be a compound of Formula A:

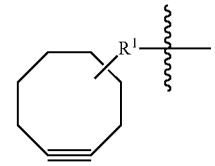

Formula A where:

$R^1$ is selected from a carbonyl, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, and a halosulfonyl;

$R^1$ can be at any position on the cyclooctyne group other than at the two carbons joined by the triple bond.

In some embodiments, the modified cycloalkyne is of Formula A, wherein one or more of the carbon atoms in the cyclooctyne ring, other than the two carbon atoms joined by a triple bond, is substituted with one or more electron-withdrawing groups, e.g., a halo (bromo, chloro, fluoro, iodo), a nitro group, a cyano group, a sulfone group, or a sulfonic acid group. Thus, e.g., in some embodiments, a subject modified cycloalkyne is of Formula B:

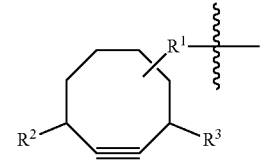

Formula B where:

each of $R^2$ and $R^3$ is independently: (a) H; (b) a halogen atom (e.g., bromo, chloro, fluoro, iodo); (c) —W—$(CH_2)_n$—Z (where: n is an integer from 1-4 (e.g., n=1, 2, 3, or 4); W, if present, is O, N, or S; and Z is nitro, cyano, sulfonic acid, or a halogen); (d) —$(CH_2)_n$—W—$(CH_2)_m$—$R^4$ (where: n and m are each independently 1 or 2; W is O, N, S, or sulfonyl; if W is O, N, or S, then $R^4$ is nitro, cyano, or halogen; and if W is sulfonyl, then $R^4$ is H); or (e) —$(CH_2)_n$—$R^4$ (where: n is an integer from 1-4 (e.g., n=1, 2, 3, or 4); and $R^4$ is nitro, cyano, sulfonic acid, or a halogen); and $R^1$ is selected from a carbonyl, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone and a halosulfonyl. $R^1$ can be at any position on the cyclooctyne group other than at the two carbons linked by the triple bond.

In one embodiment, R is a substituted or unsubstituted heterocyclic strained alkyne. Cycloalkynes, including specific compounds, are described for example in U.S. Pat. No. 8,133,515, the disclosure of which is incorporated herein by reference. In one embodiment, the alkyne is of the Formula C:

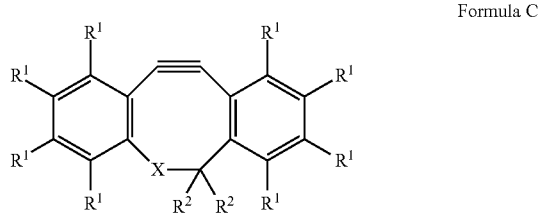

Formula C wherein:

each $R^1$ is independently selected from the group consisting of hydrogen, halogen, hydroxy, alkoxy, nitrate, nitrite, sulfate, and a $C_1$-$C_{10}$ alkyl or heteroalkyl;

each $R^2$ is independently selected from the group consisting of hydrogen, halogen, hydroxy, alkoxy, nitrate, nitrite, sulfate, and a $C_1$-$C_{10}$ organic group; X represents CH—N—$OR^4$, C—N—$NR^3R^4$, $CHOR_4$, or $CHNHR_4$; and each $R^3$ represents hydrogen or an organic group and $R^4$ represents $(C)_n$, or when present, X, L, V, Y or L', V', Y' or Z of a linker of the invention.

Alkynes such as those described herein above can be reacted with at least one 1,3-dipole-functional compound (e.g., embodied as an R' moiety in a compound of Formula III) in a cyclization reaction to form a heterocyclic compound, preferably in the substantial absence of added catalyst (e.g., Cu(I)). A wide variety compounds having at least one 1,3-dipole group attached thereto (having a three-atom pi-electron system containing 4 electrons delocalized over the three atoms) can be used to react with the alkynes disclosed herein. Exemplary 1,3-dipole groups include, but are not limited to, azides, nitrile oxides, nitrones, azoxy groups, and acyl diazo groups.

The reactive moiety R is connected to L, or when present, V or Y, and is able to react with a suitable functional group (R') on a reaction partner, e.g. a complementary reagent of Formula III which undergoes a high conversion addition reaction when brought into contact with a reactive moiety R. When reactive moiety R is present in an antibody of Formula II, the reaction results in formation of an antibody of Formula IV. In this reaction, the moieties R and R' are transformed into the moiety (RR'). Any R' moiety can be defined in the same way as a R moiety, so long as R and R' are complementary when used in moieties that are to be reacted together.

A compound of this invention may contain more than one reactive moiety R. The R moieties may or may not be the same. Any one of the R moieties disclosed herein can be utilized in Formula Ib and II. Any one of the R moieties described herein can be used in combination with any of the $(C)_n$, X, L, V, Y, z, q, and r groups described herein. Any one of the R' moieties disclosed herein can be utilized in Formula III. Any one of the R' moieties described herein can be used in combination with any of the L', V', Y', Z, z', q', and r' groups described herein.

FIG. 1 shows reaction schemes for thio-maleimide additions, Staudinger ligations, and Diels-Alder cycloadditions, where reactive groups of linking reagents having a single reactive functionality combine with complementary reactive group attached to a therapeutic or diagnostic moiety.

Figure 2:
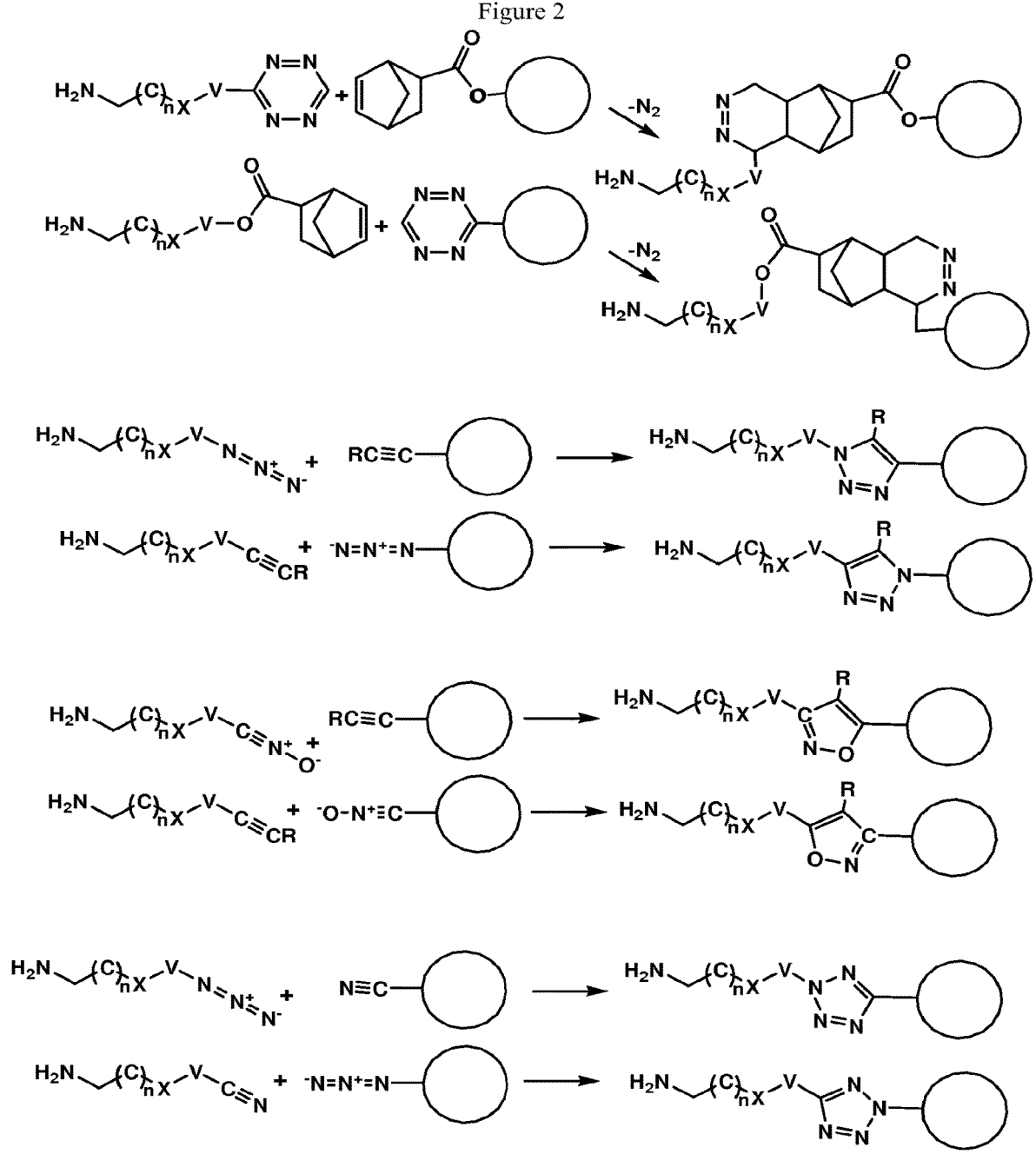
FIG. 2 shows reaction schemes for Diels-Alder cycloadditions and click reactions where the reactive groups of linking reagents combine with complementary reactive group attached to an agent including a therapeutic, diagnostic, or other moiety.

FIG. 2 shows reaction schemes for Diels-Alder cycloadditions and click reactions where the reactive groups of linking reagents combine with complementary reactive group attached to an agent including a therapeutic, diagnostic, or other moiety.

It should be understood that, although not illustrated in FIGS. 1 and 2, the $H_2NCH_2$ group of the linking reagent may have undergone reaction with the glutamine residue of a protein (e.g. antibody) prior to the high conversion addition reaction or that the aminomethylene may be in a protected state. Alternatively, in other embodiments, the $H_2NCH_2$ group of the linking reagent will not have undergone reaction with the glutamine residue of a protein (e.g. antibody) prior to the high conversion addition reaction or that the aminomethylene may be in a protected state; in this case the linking reagent and reaction partner can be used to conveniently form various combinations of linkers having different V, Y, and/or Z moieties that are ready to conjugate to an antibody.

Figure 3:
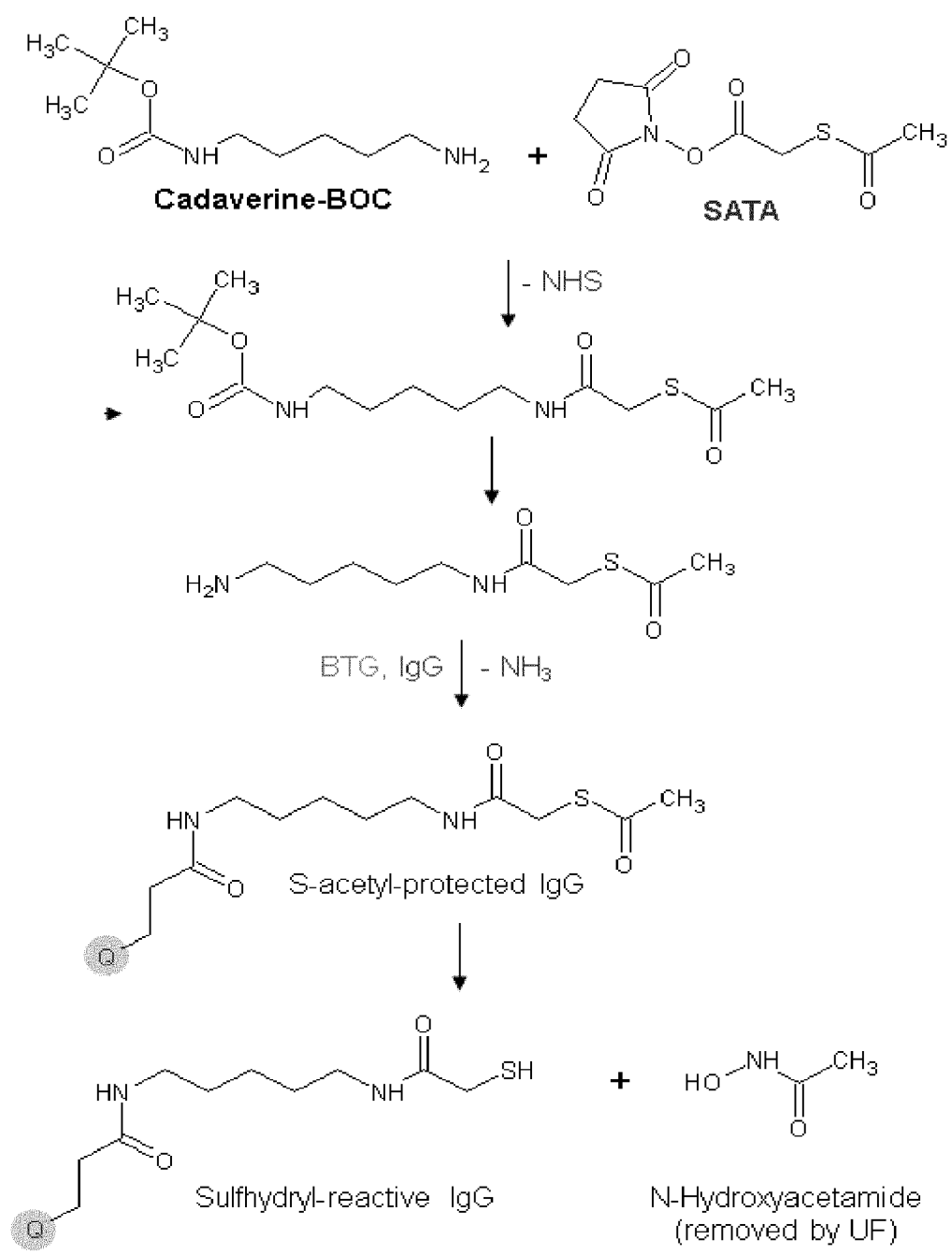
FIG. 3 shows the preparation of an exemplary linking reagent, according to an embodiment of the invention, and its conjugation with a protein, where: V and Y are absent, R is a thiol (sulfhydryl) reactive group that is ultimately generated from the S-acetyl protected thiol, $SC(O)CH_3$; r is 0; q is 0; z is 1; L is the two carbon comprising framework $C(O)CH_2$; X is NH; $(C)_n$ is $(CH_2)_5$; and G is transformed from the $(H_3C)_3COC(O)$ protecting group to H and ultimately to the amide upon conjugation of a glutamine residue of a protein.
Figure 4:
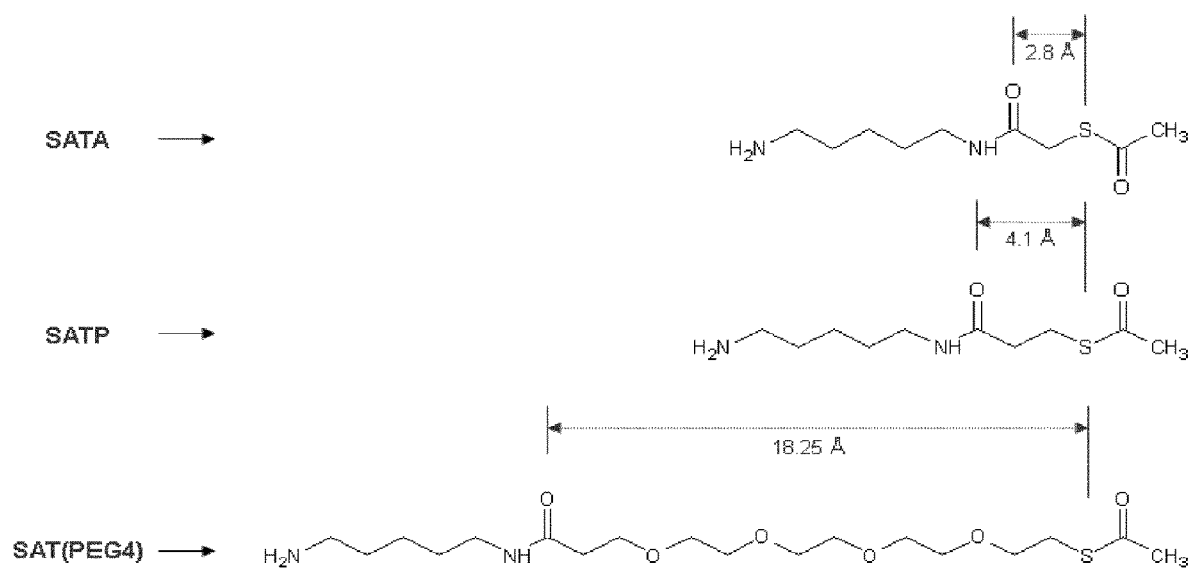
FIG. 4 illustrates the preparation of various exemplary linking reagents, according to various embodiments of the invention, with a single S-acetyl protected thiol reactive group that can be prepared from an N-succinimidyl-S-acetylthioester reagent.

The preparation of an exemplary linking reagent, according to an embodiment of the invention, and its conjugation with a protein is illustrated in FIG. 3, where: V and Y are absent, R is a thiol (sulfhydryl) reactive group that is ultimately generated from the S-acetyl protected thiol, $SC(O)CH_3$; r is 1; q is 1; z is 1; L is the two carbon comprising framework $C(O)CH_2$; X is NH; $(C)_n$ is $(CH_2)_5$; and G is transformed from the $(H_3C)_3COC(O)$ protecting group to H and ultimately to the amide upon conjugation of a glutamine residue of a protein. FIG. 4 illustrates the preparation of various exemplary linking reagents, according to various embodiments of the invention, with a single S-acetyl protected thiol reactive group that can be prepared from an N-succinimidyl-S-acetylthioester reagent. In addition to S-acetyl, other S-protecting groups can be employed, including p-hydroxyphenylacyl, 2-quinoline, or Hqm and Hgm groups that can be deprotected by the addition of hydrazine.

Figure 5:
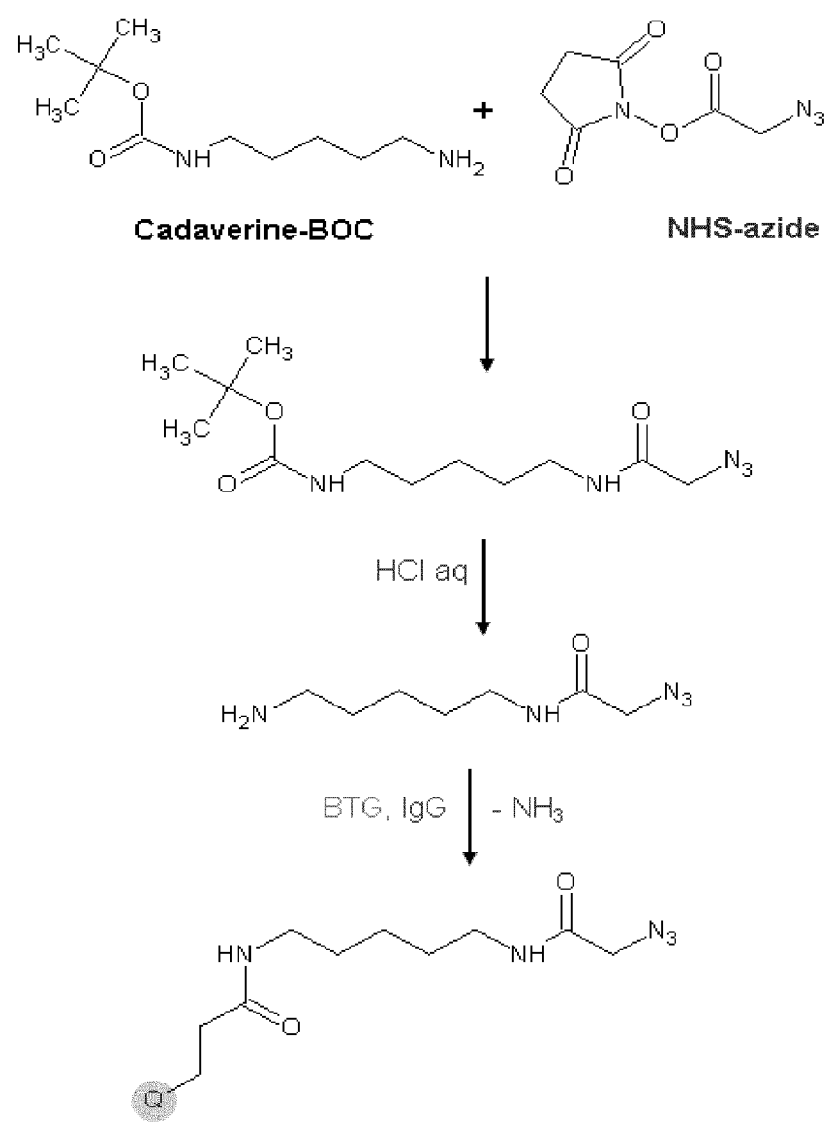
FIG. 5 illustrates the preparation of an exemplary linking reagent, according to an embodiment of the invention, and its conjugation with a protein, where: V and Y are absent, R is an azide reactive group; r is 0; q is 0; z is 1; L is the two carbon comprising framework $C(O)CH_2$; X is NH; $(C)_n$ is $(CH_2)_5$; and G is transformed from the $(H_3C)_3COC(O)$ protecting group to H and ultimately to the amide upon conjugation of a glutamine residue of a protein.
Figure 6:
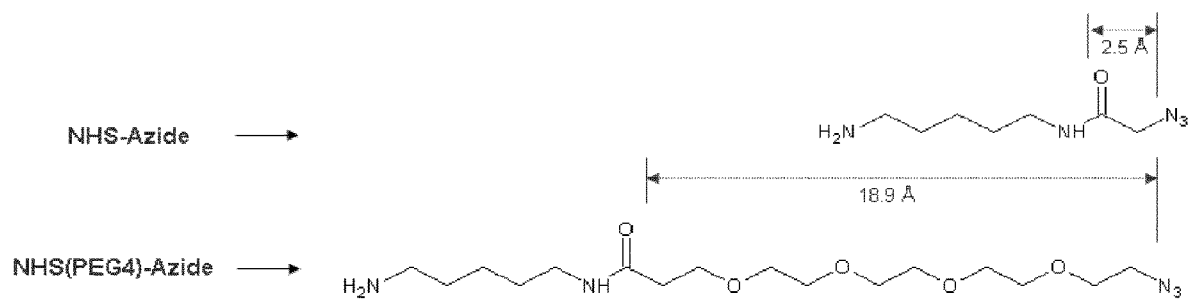
FIG. 6 illustrates the preparation of various exemplary linking reagents, according to embodiments of the invention, with a single azide reactive group that can be prepared from an N-succinimidyl-azide reagent.

FIG. 5 illustrates the preparation of an exemplary linking reagent, according to an embodiment of the invention, and its conjugation with a protein, where: V and Y are absent, R is an azide reactive group; r is 1; q is 1; z is 1; L is the two carbon comprising framework $C(O)CH_2$; X is NH; $(C)_n$ is $(CH_2)_5$; and G is transformed from the $(H_3C)_3COC(O)$ protecting group to H and ultimately to the amide upon conjugation of a glutamine residue of a protein. FIG. 6 illustrates the preparation of various exemplary linking reagents, according to embodiments of the invention, with a single azide reactive group that can be prepared from an N-succinimidyl-azide reagent.

Figure 7:
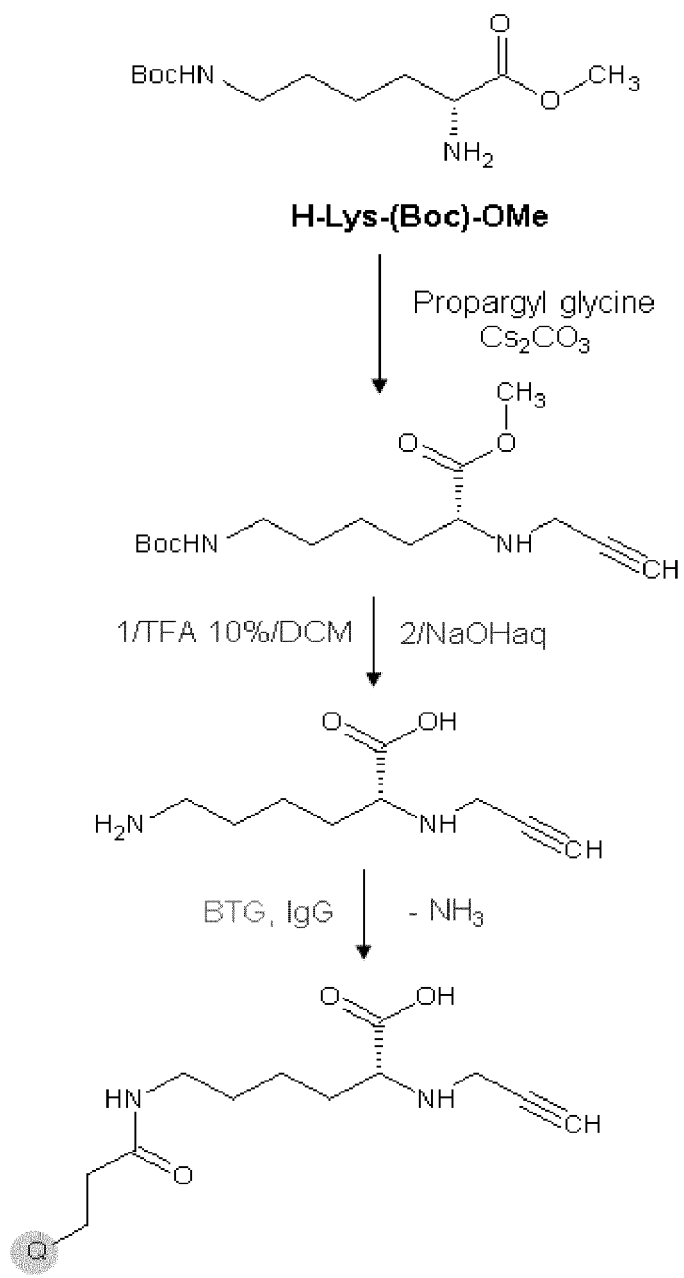
FIG. 7 depicts the preparation of an exemplary linking reagent, according to an embodiment of the invention, and its conjugation with a protein, where: V and Y are absent, R is an alkyne reactive group; r is 0; q is 0; z is 1; L is a one carbon comprising framework $CH_2$; X is NH; $(C)_n$ is $(CH_2)_4CH(CO_2H)$; and G is transformed from the $(H_3C)_3COC(O)$ protecting group to H and ultimately to the amide upon conjugation of a glutamine residue of a protein.
Figure 8:
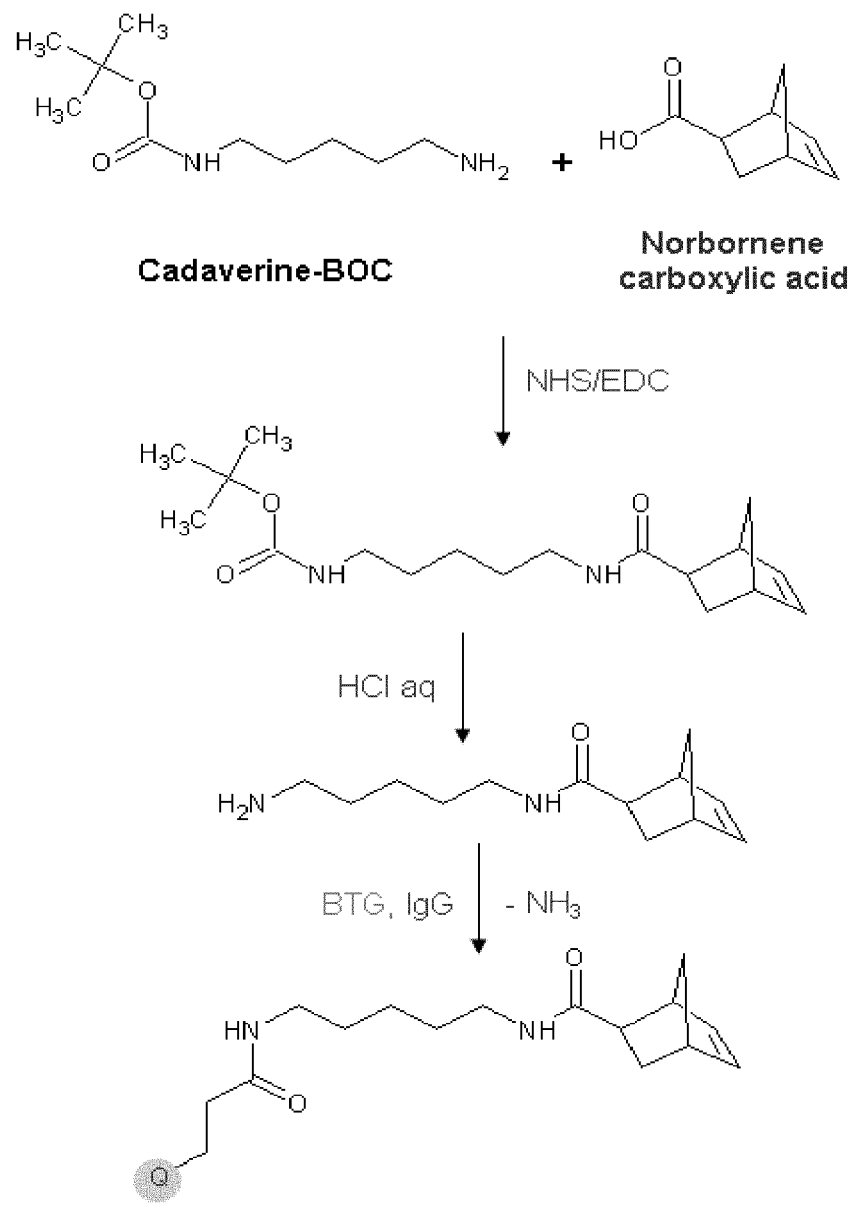
FIG. 8 shows the preparation of an exemplary linking reagent, according to an embodiment of the invention, and its conjugation with a protein, where: R is a norbornene reactive group; r is 0; q is 0; z is 1; L is the one carbon comprising framework $C(O)$; X is NH; $(C)_n$ is $(CH_2)_4CH(CO_2H)$; and G is transformed from the $(H_3C)_3COC(O)$ protecting group to H and ultimately to the amide upon conjugation of a glutamine residue of a protein.
Figure 9:
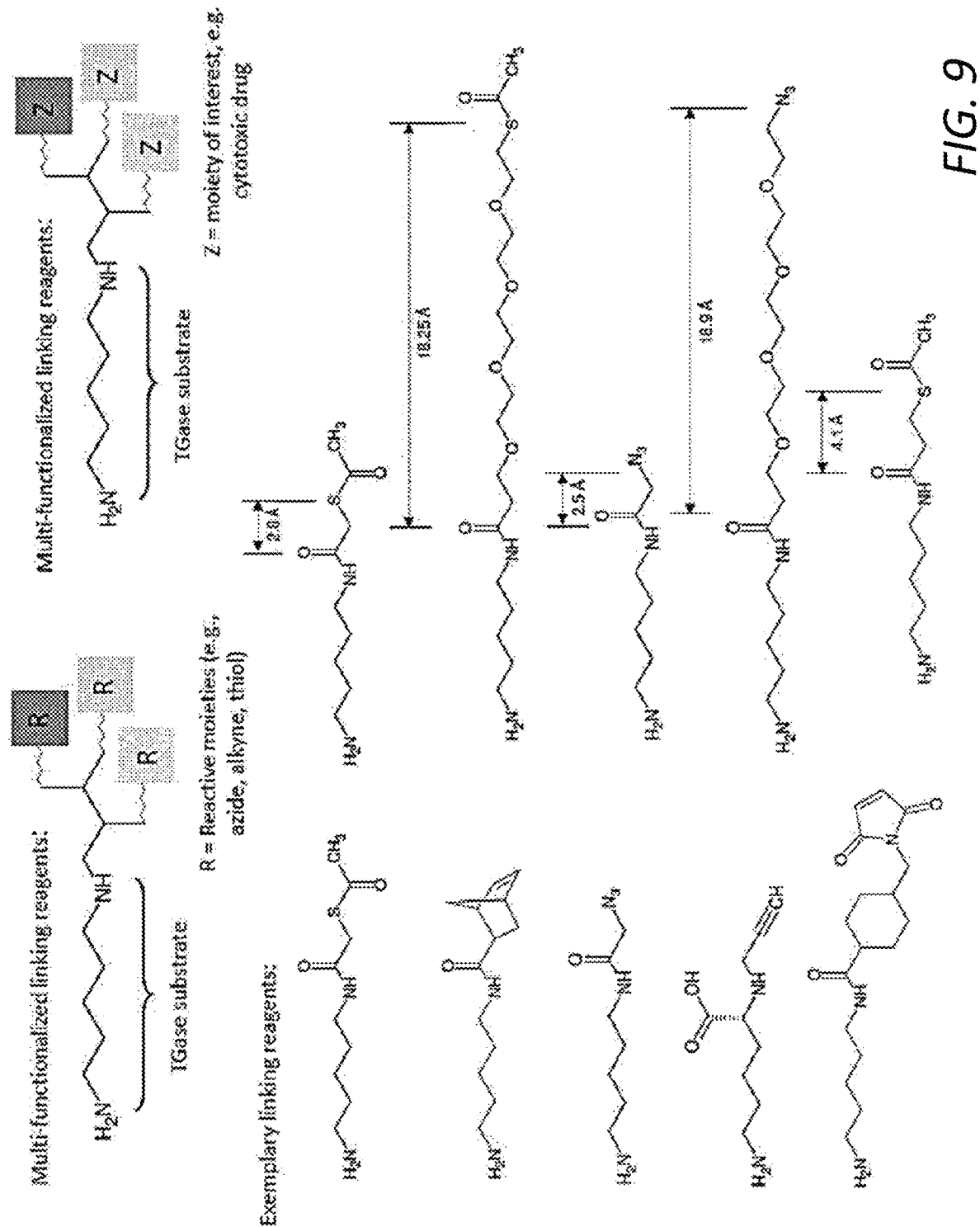
FIG. 9 shows various examples of linking reagents according to the invention.
Figure 10A:
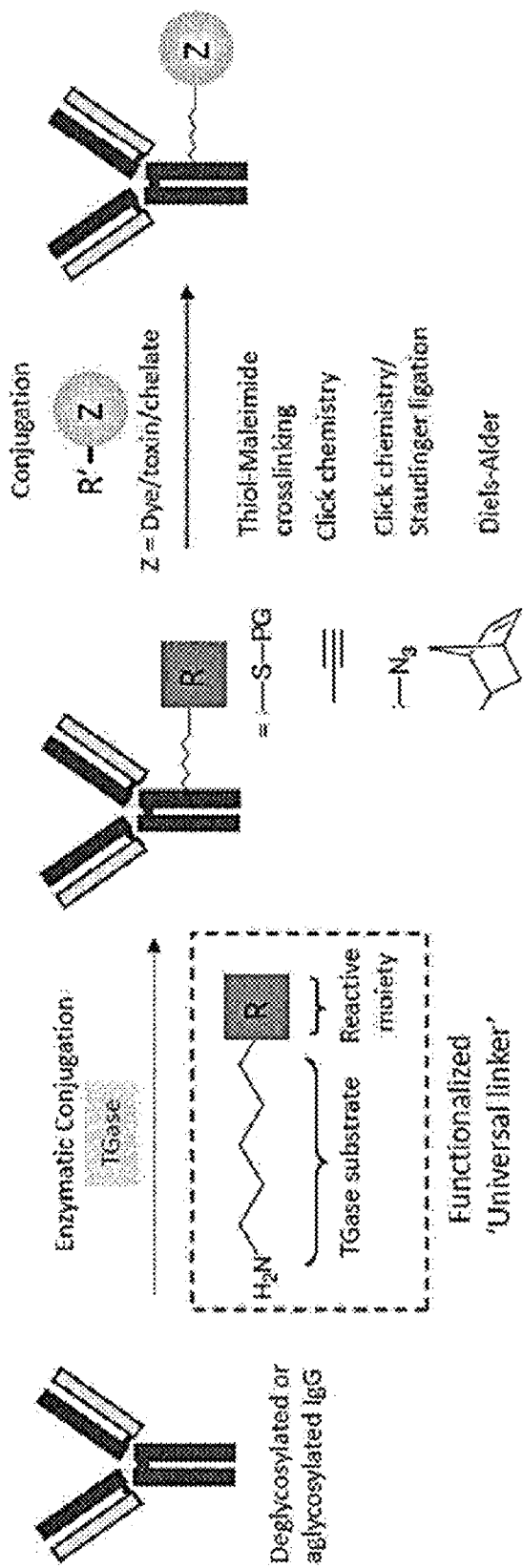
FIGS. 10A and 10B show a general scheme for preparing conjugated antibodies.
Figure 10B:
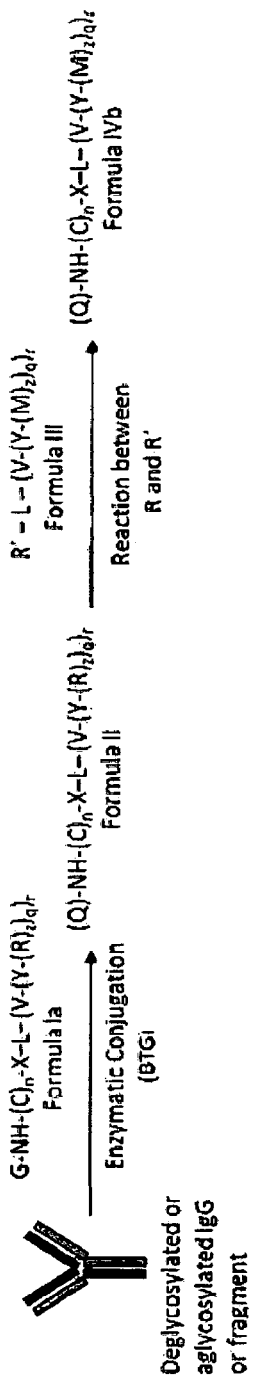
Figure 10B:
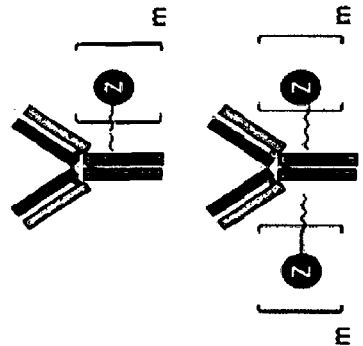
Figure 10B:
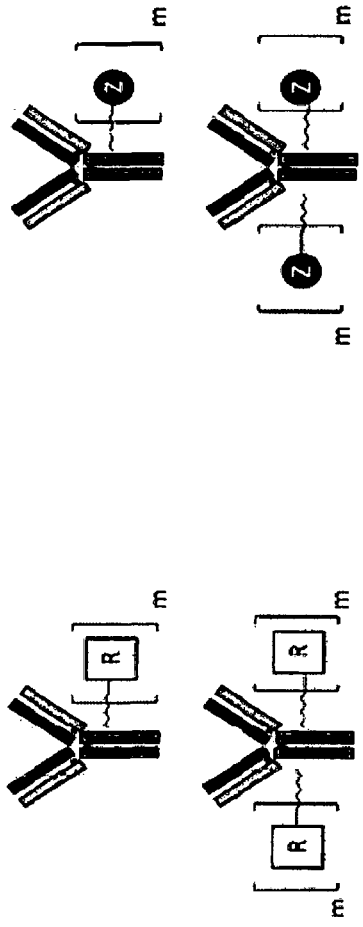

FIG. 7 depicts the preparation of an exemplary linking reagent, according to an embodiment of the invention, and its conjugation with a protein, where: V and Y are absent, R is an alkyne reactive group; r is 1; q is 1; z is 1; L is a one carbon comprising framework $CH_2$; X is NH; $(C)_n$ is $(CH_2)_4CH(CO_2H)$; and G is transformed from the $(H_3C)_3COC(O)$ protecting group to H and ultimately to the amide upon conjugation of a glutamine residue of a protein. FIG. 8 shows the preparation of an exemplary linking reagent, according to an embodiment of the invention, and its conjugation with a protein, where: R is a norbornene reactive group; r is 1; q is 1; z is 1; L is the one carbon comprising framework C(O); X is NH; $(C)_n$ is $(CH_2)_4CH(CO_2H)$; and G is transformed from the $(H_3C)_3COC(O)$ protecting group to H and ultimately to the amide upon conjugation of a glutamine residue of a protein.

The selective and very high conversion addition reaction that can be carried out with the linking reagents, according to this aspect of the invention, can be uncatalyzed or catalyzed reactions. For example, the 2+4 Diels-Alder cycloadditions, thio-maleimide (or haloacetamide) additions, and Staudinger ligations can be carried out without a catalyst. Other very high conversion addition reactions, for example any of the click reactions, can be catalyzed with metal salts, such as Cu, Ru, Ni, Pd, and Pt salts.

The linking group (RR') in M of compounds of Formula IV represents the remainder of R when the reactive moiety R of Formula IT has reacted with a reactive moiety R' in a compound of Formula III. This group (RR') then links the moiety Z (e.g. comprised in the compound of formula IV) with L, V or Y. The group that remains may be a bond.

The V Moiety

The V moiety may be incorporated in the lysine-based linker (e.g. connected to L, optionally through Y). However, the V moiety may instead or in addition be incorporated in a compound comprising a moiety-of-interest Z (e.g. a compound R'-V-Y-Z of formula III) that will be reacted with an antibody conjugated with a lysine-based linker to form an antibody conjugated to the moiety-of-interest Z. Any V' moiety can be defined in the same way as a V moiety.

In the compounds of the invention, the V moiety is a group that is either non-cleavable or conditionally cleavable, optionally after prior conditional transformation. In the latter case, it is designed to be transformed and/or cleaved from Y, or Z when Y is absent, by a chemical, photochemical, physical, biological, or enzymatic process, e.g. in certain conditions. This condition may for example comprise bringing a compound of the invention in an aqueous environment, which leads to hydrolysis of V, or bringing a compound of the invention in an environment that contains an enzyme that recognizes and cleaves V, or bringing a compound of the invention under reducing conditions, which leads to reduction of V, or bringing a compound of the invention in contact with radiation, e g, UV light, which leads to transformation and/or cleavage, or bringing a compound of the invention in contact with heat, which leads to transformation and/or cleavage, or bringing a compound of the invention under reduced pressure or bringing a compound of the invention under elevated or high pressure, which leads to transformation and/or cleavage. This condition may further be met after administrating a compound of this invention to an animal, e.g., a mammal: the condition may be met when the compound localizes to for example a specific organ, tissue, cell, subcellular target, or microbial target, for example by the presence of internal factors (e.g., target-specific enzymes or hypoxia) or application of external factors (e g., radiation, magnetic fields) or the condition may already be met directly upon administration (e.g., enzymes). In general, transformation of V will directly or indirectly lead to cleavage of V from Y, or Z when Y is absent. It may occur that two or more separate transformations and/or cleavages, requiring the same or different conditions, are required in order to cleave V completely from Y or Z. In this way, increased selectivity may be obtained. A compound of this invention may contain more than one V moiety. These V moieties may or may not be the same and may or may not require the same conditions for transformation and/or cleavage.

V may comprise for example a carbon comprising framework of 1 to 200 atoms, optionally a carbon comprising framework of at least 10 atoms, e.g. 10 to 100 atoms or 20 to 100 atoms, substituted at one or more atoms, optionally wherein the carbon comprising framework is a linear hydrocarbon or comprises a cyclic group, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), an amino acid, a di-, tri-, tetra-, or oligopeptide, or more generally any dimer, trimer, or higher oligomer (linear, asymmetrically branched or symmetrically branched) resulting from any chain-growth or step-growth polymerization process.

Generally, V may be any straight, branched and/or cyclic $C_{2-30}$ alkyl, $C_{2-30}$ alkenyl, $C_{2-30}$ alkynyl, $C_{2-30}$ heteroalkyl, $C_{2-30}$ heteroalkenyl, $C_{2-30}$ heteroalkynyl, optionally wherein one or more homocyclic aromatic compound radical or heterocyclic compound radical may be inserted; notably, any straight or branched $C_{2-5}$ alkyl, $C_{5-10}$ alkyl, $C_{11-20}$ alkyl, $-O-C_{1-5}$ alkyl, $-O-C_{5-10}$ alkyl, $-O-C_{11-20}$ alkyl, or $(CH_2-CH_2-O-)_{1-24}$ or $(CH_2)_{x1}-(CH_2-O-CH_2)_{1-24}-(CH_2)_{x2}$-group, wherein x1 and x2 are independently an integer selected among the range of 0 to 20, an amino acid, an oligopeptide, glycan, sulfate, phosphate, or carboxylate. Optionally, V may be or absent. In some embodiments, V is a $C_{2-6}$ alkyl group.

In one aspect of this invention, a compound of the invention is used to target one or more therapeutic and/or diagnostic moieties Z to target cells. In this instance, V may for example contain a substrate molecule that is cleaved by an enzyme present in the vicinity of the target cells or inside the target cells, for example tumor cells. V can for example contain a substrate that is cleaved by an enzyme present at elevated levels in the vicinity of or inside the target cells as compared to other parts of the body, or by an enzyme that is present only in the vicinity of or inside the target cells.

If target cell specificity is achieved solely based upon the selective transformation and/or cleavage of V at the target site, the condition (eventually) causing the cleavage should preferably, at least to a certain degree, be target cell-specific, whereas the presence of another target-specific moiety in the compound of the invention, for instance when the antibody recognizes an antigen present on a target cell with a degree of specificity, reduces or takes away this requirement. For example, when an antibody causes specific internalization into a target cell, an enzyme also present in other cells may transform and/or cleave V. In one embodiment, transformation and/or cleavage of V occurs intracellularly. In another embodiment, transformation and/or cleavage of V occurs extracellularly.

In one embodiment, the V moiety is a conditionally cleavable moiety.

In one embodiment, V contains a di-, tri-, tetra-, or oligopeptide which consists of an amino acid sequence recognized by a protease, for example plasmin, a cathepsin, cathepsin B, prostate-specific antigen (PSA), urokinase-type plasminogen activator (u-PA), or a member of the family of matrix metalloproteinases, present in the vicinity of or inside the target cells, for example tumor cells. In one embodiment the invention relates to a conjugate wherein V is a dipeptide, tripeptide, tetrapeptide, or oligopeptide moiety comprised of natural L amino acids, unnatural D amino acids, or synthetic amino acids, or a peptidomimetic, or any combination thereof. In one embodiment, V is a peptide. In another embodiment, V is a dipeptide. In another embodiment, V is a tripeptide. In another embodiment, V is a tetrapeptide. In yet another embodiment, V is a peptidomimetic.

In one embodiment, V contains a substrate for an enzyme.

In another embodiment, V contains a beta-glucuronide that is recognized by beta-glucuronidase present in the vicinity of or inside tumor cells.

In one embodiment, V contains a substrate for an extracellular enzyme. In another embodiment, V contains a substrate for an intracellular enzyme.

In yet another embodiment, V contains a substrate for a lysosomal enzyme.

In yet another embodiment, V contains a substrate for the serine protease plasmin.

In yet another embodiment, V contains a substrate for one or more of the cathepsins, for example cathepsin B. When V is cleaved extracellularly, the one or more Z moieties may be released extracellularly. This may provide the advantage that these Z moieties are not only able to affect or detect the cell(s) directly surrounding the site of activation, but also cells somewhat further away from the site of activation due to diffusion (bystander effect).

In one embodiment the invention relates to a compound wherein V comprises a tripeptide. The tripeptide may be linked via its C-terminus to Y. In one embodiment, the C-terminal amino acid residue of the tripeptide is selected from arginine, citrulline, and lysine, the middle amino acid residue of the tripeptide is selected from alanine, valine, leucine, isoleucine, methionine, phenylalanine, cyclohexylglycine, tryptophan and proline, and the N-terminal amino acid residue of the tripeptide is selected from any natural or unnatural amino acid.

In another embodiment the invention relates to a compound wherein V comprises a dipeptide. The dipeptide may be linked via its C-terminus to Y. In one embodiment, the C-terminal amino acid residue of the dipeptide is selected from alanine, arginine, citrulline, and lysine, and the N-terminal amino acid residue of the dipeptide is selected from any natural or unnatural amino acid. In one embodiment, V is selected from phenylalanine-lysine and valine-citrulline.

An example of a linker of the invention comprising a lysine residue as $(C)_n$ moiety and a valine-citrulline as the (V) moiety is shown below:

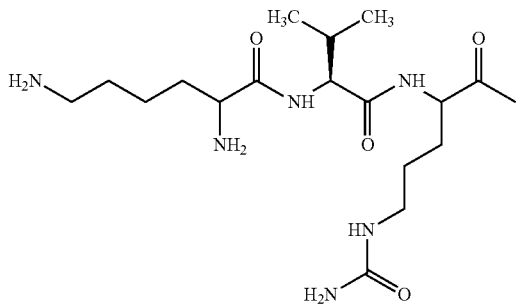 [SMILES: CC(=O)C(CCCNC(N)=O)NC(=O)[C@@H](NC(=O)C(N)CCCCN)C(C)C]

Optionally, the di-, tri-, tetra, or oligopeptide(s) comprise or consist or amino acids with non-negatively charged side chains (amino acids other than aspartic acid or glutamic acid). Optionally, the di-, tri-, tetra, or oligopeptide(s) comprise or consist or amino acids selected from: amino acids with positively charged side chains, amino acids with polar uncharged side chains, and amino acids with hydrophobic side chains.

In another aspect of this invention, a compound of this invention is used to improve the pharmacokinetic properties of Z. V may in this case for example be or contain a group that is cleaved by ubiquitous enzymes, e.g., esterases that are present in the circulation, by pH-controlled intramolecular cyclization, or by acid-catalyzed, base-catalyzed, or non-catalyzed hydrolysis, or V may for example be or contain a disulfide. V may therefore, optionally together with the connecting atom of L and/or Y (or Z if Y is absent), for example form a carbonate, carbamate, urea, ester, amide, imine, hydrazone, oxime, disulfide, acetal, or ketal group. It is understood that V can also be or contain such a moiety and/or be transformed and/or cleaved in the same or a similar way when a compound of this invention is used for other purposes than solely improving the pharmacokinetic properties of Z.

When the compounds of the invention are used for other purposes, e.g., an ex vivo diagnostic assay, V may be or contain any of the moieties mentioned above and transformation and/or cleavage of V may occur by any one of the processes mentioned above or by any other functional transformation or cleavage process known to a person skilled in the art. For example, in a diagnostic assay, V may be cleaved or transformed by an enzyme, by reduction, or below, above, or at a certain pH.

When V is conditionally cleavable, the compounds of this invention are designed to eventually release at least one Z after cleavage and optional prior transformation of V. Release of Z from a compound of this invention via another mechanism is however not excluded from this invention.

In any embodiment, V may contain a blocking group to prevent premature transformation and/or cleavage of V before the condition is met under which V is designed to be transformed and/or cleaved.

In another aspect of this invention, V is a moiety that is non-cleavable. This means that V cannot be cleaved from Y, or Z when Y is absent, under the conditions the compound containing such a V moiety is designed to be applied, meaning that Z cannot be released in this way. Release of Z from a compound of this invention via another mechanism is however not excluded. When V is a non-cleavable moiety, Y may optionally be absent. A non-cleavable V moiety may be any moiety that cannot be cleaved, or that can be cleaved only very slowly, under the conditions the compound containing such a V moiety is designed to be applied, e.g. in vivo or in vitro. For example, when applied in vivo, V will not or only very slowly be cleaved by enzymes present in the in vivo model used or by hydrolysis or as a consequence of other biological processes that may occur in said model. Such V may therefore, optionally together with the connecting atom of L and/or Z, for example, be a carbonyl group, an amide group, an urea group, an ester group, a carbonate group, a carbamate group, or an optionally substituted methyleneoxy or methyleneamino group V may be preferred to be non-cleavable when it is not required that the one or more moieties Z are released. This may for example be the case when Z does not require to become released before it can exert its therapeutic or diagnostic properties.

In one embodiment V is connected to L via a functional group in the side chain of one of the natural or unnatural amino acids. In another embodiment, the N-terminal amino acid of V is connected via its alpha amino group to L.

Any one of the V moieties disclosed herein can be utilized in Formula Ia, Ib, II, IVa and IVb. Any one of the V moieties described herein can be used in combination with any of the $(C)_n$, X, L, R, Y, Z, M, z, q, and r groups described herein. Any one of the V' moieties disclosed herein can be utilized in Formula III. Any one of the V' moieties described herein can be used in combination with any of the R', V', Y', Z, z', q', and r' groups described herein.

The Spacer System Y

The spacer system Y, when present, links V and optionally L to one or more moieties R, and following reaction with a compound of Formula III, a moiety-of-interest Z. In one embodiment, Y is absent. In another embodiment, Y is a self-elimination spacer system. A spacer system Y may be incorporated in a compound of this invention to for example improve the properties of Z or the compound in general, to provide suitable coupling chemistries, or to create space between V and Z. Any Y' moiety can be defined in the same way as a Y moiety.

Spacer system Y may comprise for example a carbon comprising framework of 1 to 200 atoms, optionally a carbon comprising framework of at least 10 atoms, e.g. 10 to 100 atoms or 20 to 100 atoms, substituted at one or more atoms, optionally wherein the carbon comprising framework is a linear hydrocarbon or comprises a cyclic group, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), an amino acid, a di-, tri-, tetra-, or oligopeptide, or more generally any dimer, trimer, or higher oligomer (linear, asymmetrically branched or symmetrically branched) resulting from any chain-growth or step-growth polymerization process.

Y may be any straight, branched and/or cyclic $C_{2-30}$ alkyl, $C_{2-30}$ alkenyl, $C_{2-30}$ alkynyl, $C_{2-30}$ heteroalkyl, $C_{2-30}$ heteroalkenyl, $C_{2-30}$ heteroalkynyl, optionally wherein one or more homocyclic aromatic compound radical or heterocyclic compound radical may be inserted; notably, any straight or branched $C_{2-5}$ alkyl, $C_{5-10}$ alkyl, $C_{11-20}$ alkyl, —O—$C_{1-5}$ alkyl, —O—$C_{5-10}$ alkyl, —O—$C_{11-20}$ alkyl, or $(CH_2-CH_2-O-)_{1-24}$ or $(CH_2)_{x1}-(CH_2-O-CH_2)_{1-24}-(CH_2)_{x2}$-group, wherein x1 and x2 are independently an integer selected among the range of 0 to 20, an amino acid, an oligopeptide, glycan, sulfate, phosphate, or carboxylate. Optionally, Y is absent. In some embodiments, Y is a $C_{2-6}$ alkyl group.

A compound of this invention may contain more than one spacer system Y. These moieties Y may or may not be the same. In some embodiments the spacer system Y is a self-elimination spacer that is connected to one or more other self-elimination spacers via a direct bond. Herein, a single self-elimination spacer may also be referred to as a spacer system. A spacer system may be branched or unbranched and contain one or more attachment sites for Z as well as V. According to the invention, self-elimination spacers that are able to release only a single moiety are called 'single release spacers'. Self-elimination spacers that are able to release two or more moieties are called 'multiple release spacers'. Spacers, may be either branched or unbranched and self-eliminating through a 1,2+2n-elimination (n>/=1), referred to as "electronic cascade spacers". Spacers may eliminate through a cyclization process under formation of a cyclic urea derivative, referred to as "ω-amino aminocarbonyl cyclization spacers".

The spacer system Y may self-eliminating or non-self-eliminating. A "self-eliminating" spacer unit allows for release of the drug moiety without a separate hydrolysis step. When a self-eliminating spacer is used, after cleavage or transformation of V, the side of Y linked to V becomes unblocked, which results in eventual release of one or more moieties Z. The self-elimination spacer systems may for example be those described in WO 02/083180 and WO 2004/043493, which are incorporated herein by reference in their entirety, as well as other self-elimination spacers known to a person skilled in the art. In certain embodiments, a spacer unit of a linker comprises a p-aminobenzyl unit. In one such embodiment, a p-aminobenzyl alcohol is attached to an amino acid unit via an amide bond, and a carbamate, methylcarbamate, or carbonate is made between the benzyl alcohol and a cytotoxic agent. In one embodiment, the spacer unit is p-aminobenzyloxycarbonyl (PAB). Examples of self-eliminating spacer units further include, but are not limited to, aromatic compounds that are electronically similar to p-aminobenzyl alcohol (see, e.g. US 2005/0256030 A1), such as 2-aminoimidazol-5-methanol derivatives (Hay et al. (1999) Bioorg. Med. Chem. Lett. 9:2237) and ortho- or para-aminobenzylacetals. Spacers can be used mat undergo cyclization upon amide bond hydrolysis, such as substituted and unsubstituted 4-aminobutyric acid amides (Rodrigues et al. Chemistry Biology, 1995, 2, 223) and 2-aminophenyl-propionic acid amides (Amsberry, et al., J. Org. Chem., 1990, 55. 5867). Elimination of amine-containing drugs that are substituted at the a-position of glycine (Kingsbury, et al., J. Med. Chem., 1984, 27, 1447) are also examples of self-immolative spacers.

A "non-self-eliminating" spacer unit is one in which part or all of the spacer unit remains bound to the moiety Z upon enzymatic (e.g., proteolytic) cleavage of the antibody-moiety-of-interest conjugate. Examples of non-self-eliminating spacer units include, but are not limited to, a glycine spacer unit and a glycine-glycine spacer unit. Other combinations of peptidic spacers susceptible to sequence-specific enzymatic cleavage are also contemplated. For example, enzymatic cleavage of an antibody-moiety-of-interest conjugate containing a glycine-glycine spacer unit by a tumor-cell associated protease would result in release of a glycine-glycine-drug moiety from the remainder of the antibody-moiety-of-interest conjugate. In one such embodiment, the glycine-glycine-drug moiety is then subjected to a separate hydrolysis step in the tumor cell, thus cleaving the glycine-glycine spacer unit from the drug moiety.

In a compound of this invention, a spacer system Y may be connected to more than one V moiety. In this case, transformation and/or cleavage of one of these V moieties may trigger the release of one or more Z moieties. When V moieties that are transformed or cleaved under different conditions are connected to the same Y, release of one or more Z moieties may occur when a compound of this invention is brought under one of several different conditions.

Any one of the Y moieties disclosed herein can be utilized in Formula Ia, Ib, II, IVa and IVb. Any one of the Y moieties described herein can be used in combination with any of the $(C)_n$, X, L, V, Y, R, Z, M, z, q, and r groups described herein. Any one of the Y' moieties disclosed herein can be utilized in Formula III. Any one of the Y' moieties described herein can be used in combination with any of the R', L', V', Z, z', q', and r' groups described herein.

Conjugation of Lysine-based Linkers to an Antibody

TGases' transamidating activity was first observed in guinea-pig liver, and later in microorganisms, plants, invertebrates, fish, amphibians, and mammals. All TGs, except plant and bacterial TGs (referred to as BTG), require Ca2+ for activation. The Ca2+ concentrations required by mammalian TGases are normally in the supraphysiological range associated with most intracellular processes and Ca2+ activation is also modulated by further regulatory processes, such that TGases are inactive under normal conditions and only activated following major disruptions in physiological homoeostatic mechanisms. Transglutaminases play an important role in biological processes which are dependent on the rapid covalent crosslinking of proteins, e.g. blood coagulation, skin-barrier formation and extracellular-matrix assembly. TGase-mediated reactions result in supramolecular protein structures with high rigidity and stability.

Enzymes of the TG-family catalyze covalent protein crosslinking by forming proteinase resistant isopeptide bonds between a lysine donor residue of one protein and an acceptor glutamine residue of another protein, and is accompanied by the release of ammonia. The catalytic mechanism of transglutaminases has been proposed as follows. After the Glycine-containing first substrate (acceptor or Q-substrate) binds to the enzyme, it forms a γ-glutamylthioester with the cysteine residue in the active center of TGase, known as the acylenzyme intermediate, accompanied by the release of ammonia. The second substrate (donor or K-substrate) then binds to the acylenzyme intermediate and attacks the thioester bond. The product (two proteins crosslinked by an Nε(γ-glutamyl)lysine isopetide bridge) is formed and released. This re-establishes the active-centre Cys residue of the enzyme in its original form and allows it to participate in another cycle of catalysis. The formation of the covalent acylenzyme intermediate is thought to be the rate-limiting step in these reactions. The catalytic triad of many transglutaminases is papain-like, containing Cys-His-Asp (where His is histidine and Asp is aspartic acid) and, crucially, a tryptophan (Trp) residue located 36 residues away from the active-centre Cys. In contrast, bacterial TG isolated from *Streptoverticillium* sp (vide supra) has an atypical catalytic triad and shows no sequence homology with the papain-like catalytic triad of other TGases.

TGases display strict specificity in recognition of glutamine protein substrates. However, TGases display broad specificity for recognition of the acyl-acceptor amine group, which can either be the ε-amino group of peptidyl lysine or a low-molecular mass primary amine (frequently a polyamine) (see, e.g. Folk, et al. (1980) J. Biol. Chem. 255, 3695-3700. For example, in addition to lysine, the small lysine-mimicking primary amine 5-pentylamine (cadaverin) and variants or fragments thereof can efficiently bind to the acylenzyme intermediate, and a pseudo-isopeptide bond with the glutamine-containing protein is formed. See, e.g., Lorand, L. et al. (1979) Biochemistry 18, 1756-1765 (1979); Murthy, S. N. et al. (1994). J. Biol. Chem. 269, 22907-22911 (1994); Murthy, P. et al. (2009) Biochemistry (2009).

Bacterial, archaeal and eukaryotic TGases have been characterized and differ in several ways from mammalian TGases (Lorand, L. & Graham, R. M. (2003) Nat. Rev. Mol. Cell Biol. 4, 140-156). BTG and more generally microbial TGases (EC 2.3.2.13, protein-glutamine-γ-glutamyltransferase) such as *Streptomyces mobaraensis* are calcium-independent and have an amino acid sequence of) very different from those of mammalian TGs (Ando et al. (1989) Agric. Biol. Chem. 53, 2613-2617). BTG is furthermore much smaller (37.8 kDa versus 76.6 kDa for guinea pig liver TG). Additionally, BTG shows broader substrate specificity for the amine acceptor glutamine substrates in proteins than do mammalian TGases. These characteristics, together with a higher reaction rate, low cost of production, and a decreased tendency to catalyze deamidation make BTG a preferred enzyme for use in industrial applications such as those of the present invention.

The antibodies that are to be conjugated to the lysine-based linker will preferably be free of N-linked glycosylation (e.g. an antibody which does not comprises glycosylation sites or a modified full-length antibody). Full-length wild-type IgG antibodies naturally comprise N-linked glycosylation at residue 297 of the heavy chain which interferes and prevents with TGase-mediated conjugation onto glutamine residues in the CH2 domain. Consequently, antibodies may be deglycosylated. Deglycosylation can be carried out as described herein or according to any suitable method. For example, antibody (1 mg) in PBS buffer (0.1 mol/L NaCl and 0.05 mol/L sodium phosphate buffer, pH 7.4) are incubated with 100 units (0.2 µL) of N-glycosidase F (PNGase F) from *Flavobacterium meningosepticum* (New England BioLabs, Ipswich, UK) at 37° C. overnight. The enzyme is then removed by centrifugation-dialysis (Vivaspin MWCO 50 kDa, Vivascience, Winkel, Switzerland). The product can be analyzed by LC/MS.

In one embodiment, the product is analyzed for drug loading (e.g. number of conjugates per antibody. Such methods can be used to determine the mean number of conjugates per antibody (e.g., the mean DAR) as well as the distribution of number of conjugates per antibody in a composition, i.e. the percentage of total antibody with any given level of drug loading or DAR. The portion of antibodies having a number (n) of conjugated acceptor glutamines (e.g. n=1, 2, 3, 4, 5, 6, etc.) can be determined. One technique adapted to such determination and more generally drug loading is hydrophobic interaction chromatography (HIC), HIC can be carried out as described for example in Hamblett et al. (2004) Cancer Res. 10: 7063-7070; Wakankar et al. (2011) mAbs 3(2): 161-172; and Lyon et al (2012) Methods in Enzymology, Vol. 502: 123-138, the disclosure of which are incorporated herein by reference.

The method allows the application of any suitable type of transglutaminase (TGase) for this purpose. Several types of transglutaminases have been reported in various living organisms including microbials. Examples are TGase from guinea pig liver (GTGase), fish liver (FTGase) and microorganisms (MTGase) and any recombinant TGase (rTGase). Other TGases than the ones listed here can also be used according to the invention. Examples of useful TGases include microbial transglutaminases, such as e.g. from *Streptomyces mobaraense*, *Streptomyces cinnamoneum* and *Streptomyces griseocarneum* fall disclosed in U.S. Pat. No. 5,156,956, which is incorporated herein by reference), and *Streptomyces lavendulae* (disclosed in U.S. Pat. No. 5,252, 469, which is incorporated herein by reference) and *Streptomyces ladakanum* (JP2003199569, which is incorporated herein by reference). It should be noted that members of the former genus *Streptoverticillium* are now included in the genus *Streptomyces* (Kaempfer, J Gen Microbiol, 137, 1831-1892, 1991). Other useful microbial transglutaminases have been isolated from *Bacillus subtilis* (disclosed in U.S. Pat. No. 5,731,183, which is incorporated herein by reference) and from various Myxomycetes. Other examples of useful microbial transglutaminases are those disclosed in WO 96/06931 (e.g. transglutaminase from *Bacillus lydicus*) and WO 96/22366, both of which are incorporated herein by reference. Useful non-microbial transglutaminases include guinea-pig liver transglutaminase, and transglutaminases from various marine sources like the flat fish Pagrus major (disclosed in EP-0555649, which is incorporated herein by reference), and the Japanese oyster *Crassostrea gigas* (disclosed in U.S. Pat. No. 5,736,356, which is incorporated herein by reference). A preferred TGase is bacterial transglutaminase (BTG) (see, e.g. EC 2.3.2.13, protein-glutamine-γ-glutamyltransferase). In a more preferred embodiment, the TGase is from *S. mobaraense*. In another embodiment, the TGase is a mutant TGase having at least 80% sequence homology with native TGase. A preferred example is recombinant bacterial transglutaminase derived from *streptomyces mobaraensis* (available from Zedira, Darmstadt, Germany).

The TGase-catalyzed reaction can be carried out under mild conditions, from several hours to a day (e.g. overnight). Recombinant BTG (EC 2.3.2.13) from *streptomyces mobaraensis* (Zedira, Darmstadt, Germany) can be used at a concentration of between 1 and 20 U/mL, preferably between 6 U/mL and 20 U/mL. The lysine-based linker substrates are reacted with antibody (1 mg/mL) at ligand concentrations between 400 and 600 mol/L, providing a 60 to 90-fold excess of the substrates over the antibody, or optionally at lower excess of substrates, e.g. 1- to 20-fold, or 10-20 fold. The reactions are performed in potassium-free phosphate buffered saline (PBS; pH 8) at 37° C. After 4 h to several days (depending on the antibody and the ligand), steady-state conditions are achieved. Excess ligand and enzyme are then removed using centrifugation-dialysis (Vivaspin MWCO 50 kDa, Vivascience, Winkel, Switzerland). Reactions are monitored by LC/MS. Higher amounts of TGase can be used as a function of different lysine-derivatives and substrates.

An acceptor glutamine present on an antibody (e.g. part of the antibody's primary structure, including for example an antibody fragment with a peptide tag) will, under suitable conditions, be recognized by a TGase and covalently bound to a lysine-based linker (e.g., compound of Formula I). The results is an antibody of Formula II (the acceptor glutamine is functionalized with the compound of Formula I). Resulting antibody conjugates can be analyzed using any suitable method. Preferably, the stoichiometry of the conjugated antibodies can be characterized by liquid chromatography mass spectrometry (LC/MS) using a top-down approach in order to assess the number of lysine-based linker and/or where applicable moieties-of-interest conjugated to antibodies, and in particular the homogeneity of the composition. Conjugates can be reduced before LC/MS analysis and light chains and heavy chains are measured separately.

Reaction Partners Comprising a Moiety-of-interest Z and Reactive Group R'

Once a lysine-based linker (e.g., compound of Formula I) comprising a reactive moiety R is conjugated to an antibody (e.g., resulting in an antibody of Formula II) the antibody can be reacted with a compound comprising a moiety Z and a reactive group R', thereby forming an antibody-moiety-of-interest conjugate. Typically, the conjugated antibody (e.g. the antibody of Formula II) is subjected to a deprotection step to provide an unprotected reactive group (R) and the antibody is then reacted with a compound comprising a reaction partner R'.

R' is a reactive moiety and can be defined in the same way as reactive group (R), so long as R' is complementary (reactive with) reactive group R. R' may be, for example, a moiety comprising an unprotected or protected bioorthogonal-reaction compatible reactive group, for example an unprotected or protected thiol, epoxide, maleimide, haloacetamide, o-phoshenearomatic ester, azide, fulminate, sulfonate ester, alkyne, cyanide, amino-thiol, carbonyl, aldehyde, generally any group capable of oxime and hydrazine formation, 1,2,4,5-tetrazine, norbornene, other stained or otherwise electronically activated alkene, a substituted or unsubstituted cycloalkyne, generally any reactive groups which form via bioorthogonal cycloaddition reaction a 1,3- or 1,5-disubstituted triazole, any diene or strained alkene dienophile that can react via inverse electron demand Diels-Alder reaction, a protected or unprotected amine, a carboxylic acid, an aldehyde, an oxyamine, so long as such group when unprotected is reactive with R (when R' is unprotected).

When more than one R' group is present in a compound of the formula, the R' groups will preferably be compatible such that no R' group is a complementary reagent to any other R' group. The L', V' and/or Y' groups of formulae I-IV can have r, q, and/or z sites of attachment for the respective V', Y', and R' groups, where r and q represent the degree of branching or polymerization. The sites of attachment can comprise a bond or comprise a functional group selected from an alkene, alkyne, ether, thioether, ester, thioester, amine, amide, alkylamide, or other functional group readily generated by a condensation or addition reaction.

In one embodiment, R' is a moiety having a terminal alkyne or azide, a substituted or unsubstituted cycloalkyne, for example a compound of Formula A (above), a modified cycloalkyne is of Formula B (above), or a substituted or unsubstituted heterocyclic strained alkyne of Formula C (above).

Any one of the R' moieties disclosed herein can be utilized in Formula III. Any one of the R' moieties described herein can be used in combination with any of the L', V', Y', Z, z', q', and r' groups described herein.

The compounds of (e.g. Formula III) to be used in reaction with an antibody can be reacted with antibody (e.g., 1 mg/mL) at ligand concentrations between 2 and 20 (or between 4 and 20) molar equivalents to the antibody, optionally between 2 and 10 (or between 4 and 10) molar equivalents to the antibody, optionally at a less than, or about, 20, 10, 5, 4 or 2 molar equivalents to the antibody. However it will be appreciated that higher excesses (equivalents of reaction partner (e.g. Formula ITT) to antibody (40 to 80 fold, 60 to 90-fold) can also be used.

The compounds of Formula III to be used in reaction with an antibody conjugated to a lysine-based linker (but without a moiety-of-interest), e.g., an antibody of Formula II, as well as the resulting antibody conjugates therefore comprise one or more moieties-of-interest Z. The compounds of Formula III may additionally comprise a moiety V and/or Y, typically depending on which elements are included in the lysine-based linker.

The compounds of Formula III to be used in reaction with an antibody conjugated to a lysine-based linker (e.g. an antibody of Formula II) will comprise moieties Z connected to linker L' when Y' and V' are absent, connected to the spacer system Y' or, when Y' is absent, connected to V'. Consequently, a compound of Formula III may comprise a moiety Z connected to or comprising a reactive group R', optionally the moiety Z connected to a reactive group R' via a spacer system Y' or, when Y' is absent, to a reactive group R' via V', or to a reactive group R' via a V'—Y', wherein Z is preferably connected to Y' and V' is connected to R' and Y'.

A compound of Formula III may contain one, two or more Z moieties that are the same or that differ from one another, e.g. different therapeutic moieties, and/or diagnostic moieties.

In one embodiment, the antibody of Formula II is reacted with a compound of Formula III comprising a moiety of interest Z comprising and a reactive group R' capable of forming a bond with reactive group R of Formula Ib or II, optionally wherein the compound further comprises a V' and/or Y' group. The compound comprising a moiety of interest Z comprising and a reactive group R' preferably comprises a structure of Formula III, below,

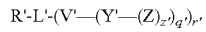

Formula III where:

R' is a reactive group, e.g. a reactive group complementary for forming at least one bond with reactive group R of Formula Ib or II;

L' is a bond or a carbon comprising framework of 1 to 200 atoms substituted at one or more atoms, optionally wherein the carbon comprising framework is a linear hydrocarbon, a symmetrically or asymmetrically branched hydrocarbon monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

V' is independently absent, a non-cleavable moiety or a conditionally-cleavable moiety that can optionally be cleaved or transformed by a chemical, photochemical, physical, biological, or enzymatic process, cleavage of V ultimately leading to release of one or more Z moieties. In some embodiments, V is, preferably, a di-, tri-, tetra-, or oligopeptide as described below in the section entitled "The V Moiety", Y' is independently absent or a spacer system (e.g., a self-eliminating spacer system or a non-self-elimination spacer system) which is comprised of 1 or more spacers, Z is independently a reactive group (optionally protected) other than a complementary reactive group for reaction with R', a moiety that improves the pharmacokinetic properties, a therapeutic moiety, or diagnostic moiety;

q' and r' are an integer selected among 1, 2, 3 or 4, representing degree of branching; and z' is an integer selected among 1, 2, 3 or 4.

Where Z is a reactive group, it can be a moiety comprising an unprotected or protected thiol, maleimide, haloacetamide, o-phoshenearomatic ester, azide, fulminate, alkyne, cyanide, anthracene, 1,2,4,5-tetrazine, norbornene, other stained or otherwise electronically activated alkene or, optionally, a protected or unprotected amine when X is absent and L, V, or Y is other than a bond or a continuation of a bond. In an alternative embodiment Z can be a reactive moiety, preferably a moiety comprising an unprotected or protected thiol, an unprotected or protected amine, maleimide, haloacetamide, o-phoshenearomatic ester, azide, fulminate, alkyne, cyanide, anthracene, 1,2,4,5-tetrazine, norbornene, other stained or otherwise electronically activated alkene. Preferably R is not an amine when n=5 and X, L, V and Y are absent. Preferably R is not an amine when n=4 and X, L, V and Y are absent.

The moiety R' is connected to Z, or optionally to Z via V' and/or Y' and is able to react with a suitable functional group R on a reaction partner, e.g. group R on the lysine-based linker of formula Ib or II. As discussed above, when the reactive moiety R' is designed to react with a reactive group R, a compound of Formula or IVb is formed.

The L' group can be a carbon comprising framework, where L is a symmetrically or asymmetrically branched hydrocarbon, monosaccharide, disaccharide, oligosaccharide, other natural oligomer, dimer, trimer, or higher oligomer resulting from any chain-growth or step-growth polymerization process, wherein L' has r', q', and/or z' sites of attachment for the respective V', Y', and R' groups, where r' and q' represent the degree of branching or polymerization. The sites of attachment can comprise a bond or comprise a functional group selected from an alkene, alkyne, ether, thioether, ester, thioester, amine, amide, alkylamide, or other functional group readily generated by a condensation or addition reaction.

The linking group (RR') in M of compounds of Formula IVb represents the R' addition product of a reactive moiety R' and a reactive moiety R. This group then links the moiety Z with L, V or Y, preferably via (RR') of M is L', V', and/or Y'. The group that remains may be a bond. Typically, however, L', V', and/or Y' is a linking group. RR' can be an addition product of a: thio-maleimide (or haloacetamide) addition, for example, a N,S-disubstituted-3-thio-pyrrolidine-2,5-dione; Staudinger ligation, for example, a N,3- or N,4-substituted-5-dipenylphosphinoxide-benzoic amide; Huisgen 1,3-cycloaddition (click reaction), for example, a N,S-disubstituted-3-thio-pyrrolidine-2,5-dione, 1,4-disubstituted-1,2,3-triazole, 3,5-disubstituted-isooxazole, or 3,5-disubstituted-tetrazole; Diels-Alder cycloaddition adduct, for example the 2,4-cycloaddition product between an O or N-substituted-5-norbornene-2-carboxylic ester or amide, N-substituted-5-norbornene-2,3-dicarboxylic imide, O or N-substituted-7-oxonorbornene-5-carboxylic ester or amide, or N-substituted-7-oxonorbornene-5,6-dicarboxylic imide and a 9-substituted anthracene or 3-substituted 1,2,4, 5-tetrazine; or any high yield selective amidation or imidization reaction. Some reactions and the RR' reaction products are illustrated in FIGS. 1 and 2.

Examples of compounds of Formula III include but are not limited to compound having the R', L', V', Y' and Z groups shows in Table 4 herein. Examples of compounds of Formula III include but are not limited to compound having the R', L', V', Y' and Z groups shows in Table 3 herein. The symbol (-) in the tables indicates that the particular R', L', V', Y' or Z is absent. V and Y groups, for example, can comprise any structural features in the sections titled "The V Moiety" and "The Y Moiety" herein. The L, V and/or Y groups of Formula III represented in Table 4 can have r', q', and/or z' sites of attachment for the respective V, Y, and R or Z groups, where r and q represent the degree of branching or polymerization; r', q', and/or z' can be selected from 1, 2, 3 or 4.

The Moiety Z

The moieties Z can be connected to Y or Y' or, when absent, to V or V', or, when absent, to L or, when absent to X, or to L' or, when absent to R', (RR'), or to $(C)_n$. Connections to Y, V or L may optionally be via R or RR'. Connection may be via any suitable atoms. In one embodiment, Z is coupled via oxygen (from for example a hydroxyl group or carboxyl group), carbon (from for example a carbonyl group), nitrogen (from for example a primary or secondary amino group), or sulfur (from for example a sulfhydryl group). In one embodiment, Z is coupled in the compounds of this invention via a group such that its therapeutic abilities or diagnostic characteristics are, at least partly, blocked or masked. In case a compound of the invention is to be used for treating or preventing disease in an animal, e.g., a mammal, the Z moieties are generally therapeutic moieties. In case a compound of the invention is used to make a diagnosis or used in an ex vivo or in vivo diagnostic assay, the Z moieties are generally diagnostic moieties, for example chromogenic, fluorogenic, phosphorogenic, chemiluminescent, or bio luminescent compounds.

In one embodiment, the Z moiety is compound, preferably an organic compound, having a molecular weight of at least 300 g/mol, 400 g/mol, 500 g/mol, 600 g/mol, 700 g/mol, 800 g/mol, 900 g/mol, 1000-g/mol or 2000 g/mol.

In one embodiment, the Z moiety is a chemical compound displaying hydrophobic properties, optionally additionally having a molecular weight of at least 300 g/mol, 400 g/mol, 500 g/mol, 600 g/mol, 700 g/mol, 800 g/mol, 900 g/mol. 1000-g/mol or 2000 g/mol. Hydrophobic character may be determined, for example, by decreased water solubility, decreased polarity, decreased potential for hydrogen bonding, and/or an increased oil/water partition coefficient. The presently disclosed methods can be used to produce antibody conjugates where moiety of interest (Z) comprises a hydrophobic drug. As used herein, the term "hydrophobic" is a physical property of a molecule that is repelled from a mass of water. Hydrophobic compounds can be solubilized in nonpolar solvents, including but not limited to, organic solvents. Hydrophobicity can be conferred by the inclusion of apolar or nonpolar chemical groups that include, but are not limited to, saturated and unsaturated aliphatic hydrocarbon groups and such groups substituted by one or more aromatic, cycloaliphatic or heterocyclic group(s). Conversely, "hydrophilic" molecules are capable of hydrogen bonding with a water molecule and are therefore soluble in water and other polar solvents. The terms "hydrophilic" and "polar" can be used interchangeably. Hydrophilic characteristics derive from the presence of polar or charged groups, such as carbohydrates, phosphate, carboxylic, sulfato, amino, sulfhydryl, nitro, hydroxy and other like groups.

Hydrophobic molecules are poorly water soluble, for example, having a solubility of less than about 10 mg/ml. In some embodiments, the hydrophobic compound can have a solubility of less than about 1 mg/ml in water. In other embodiments, the hydrophobic compound has a solubility in water of less than about 50, μg/ml, 10 μg/ml, and in particular embodiments, about 1 μg/ml or 2.5 μg/ml. In other embodiments, the hydrophobic compound can have a solubility of about 0.001 μg/ml to about 10 mg/ml, including but not limited to 0.001 μg/ml, 0.01 μg/ml, 0.1 μg/ml, 1 μg/ml, 2 μg/ml, 5 μg/ml, 10 μg/ml, 50 μg/ml, 100 μg/ml, 500 μg/ml, 1 mg/ml, 5 mg/ml, and 10 mg/ml, and any other concentration between 0.001 μg/ml and 10 mg/ml.

Representative, non-limiting examples of hydrophobic drugs that can be formulated using the presently disclosed methods include taxanes, e.g. paclitaxel (PTX), and camptothecin (CPT), maytansanoids, duocarmycins, dolastatins and auristatins. Such drugs are poorly soluble in water, e.g. PTX has a solubility in water of less than about 1 μg/ml, CPT has a water solubility of about 2.5 μg/ml. Linkers and modified antibodies of the invention can advantageously link hydrophobic drugs to antibodies.

In other embodiments, in view of hydrophobic drugs being poor substrates for TGase (in the absence of improved linkers or modified antibodies of the invention), the Z moiety may advantageously be a hydrophilic drug. Examples of hydrophilic drugs include amatoxins. Amatoxins are cyclic peptides composed of 8 amino acids as isolated from the genus *Amanita*. Amatoxins also include a range of chemical derivatives, semisynthetic analogs and synthetic analogs built from building blocks according to the master structure of the −5 natural compounds (cyclic, 8 aminoacids), synthetic or semisynthetic analogs containing non-hydroxylated amino acids instead of the hydroxylated amino acids, synthetic or semisynthetic analogs, in which the thioether sulfoxide moiety is replaced by a sulfide, sulfone, or by atoms different from sulfur, e.g. a carbon atom as in a carbaanalog of amanitin. Functionally, amatoxins are defined as peptides or depsipeptides that inhibit mammalian RNA polymerase IT. Preferred amatoxins are those with a functional group (e.g. a carboxylic group, an amino group, a hydroxy group, a thiol or a thiol-capturing group) that can be reacted with linker molecules or proteins. Amatoxins are described for example in European Patent publication no. 1859811, PCT publication nos. WO2010/115630 and WO2012/041504).

In one embodiment, the Z moiety is a large compound (e.g., molecular weight of at least 300 g/mol, 400 g/mol, 500 g/mol, 600 g/mol or 700 g/mol) comprising a polycyclic group, tricycle or one or more macrocycles. Such groups are often typical of hydrophobic and/or rigid structures. Examples of cytotoxic drugs that comprise a macrocycle (e.g. a ring of nine or more atoms) include maytansinoids, amatoxins, epothilones and taxanes. In one embodiment, the Z moiety comprises a ring of 9, 10, 11, 12, 13, 14, 15, 16, 17 or 18 atoms, or between 9 and 200 atoms. In one embodiment, the Z moiety is a chemical compound having a negative charge, optionally additionally displaying hydrophobic properties and/or having a molecular weight of at least 300 g/mol, 400 g/mol, 500 g/mol, 600 g/mol, 700 g/mol, 800 g/mol, 900 g/mol, 1000 g/mol or 2000 g/mol.

When more than one Z moiety is connected to a self-elimination spacer system Y or Y', at least one Z should be released upon self-elimination of Y or Y'. The moiety Z initially released may be a moiety that is not a fully active moiety itself. In other words, Z may be a moiety that has limited diagnostic or therapeutic abilities, e.g. a moiety that acts as a prodrug. Such a Z moiety may require further processing or metabolism, e.g., hydrolysis, enzymatic cleavage, or enzymatic modification (for example phosphorylation, reduction, or oxidation) in order to become fully active. In one embodiment, such further processing is intentionally designed for Z to for example allow Z to reach its final target or cross a biological barrier, e.g., a cell membrane or a nuclear membrane, before it is fully activated. Z may for example contain a hydrophobic moiety that enables Z to cross a cell membrane. This hydrophobic moiety may then be hydrolyzed or removed in any other way intracellularly.

In one aspect of the invention, a Z moiety may be a backbone (e.g. polymer) to which a plurality of drugs or diagnostic moieties are linked. For example, Z may be a polyacetal- or polyacetal derivative-based polymer comprising a plurality of drug molecules, see, e.g., Yurkovetskiy et al. (2004) Mol. Pharm. 1(5): 375-382 and WO 2011/120053, the disclosures of which are incorporated herein by reference; for example Z may be a polymer compound of Formula I of WO 2011/120053 comprising a plurality of cytotoxic anti-cancer agents.

In one aspect of this invention, one or more moieties Z are each selected from a therapeutic or diagnostic agent.

In another embodiment of this invention, one or more moieties Z are each a therapeutic agent. In another embodiment of this invention, all moieties Z are each a therapeutic agent In yet another embodiment, the moieties Z each are the same therapeutic moiety.

In yet another embodiment, the moieties Z comprise at least two different therapeutic moieties.

The moiety Z includes, for example, antineoplastic agents, drugs, toxins (such as enzymatically active toxins of bacterial or plant origin and fragments thereof e.g. ricin and fragments thereof) biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

In one embodiment, the one or more moieties Z are each independently chosen from an antibiotic, an anti-bacterial agent, an antimicrobial agent, an anti-inflammatory agent, an anti-infectious disease agent, an anti-autoimmune disease agent, an anti-viral agent, or an anticancer agent, preferably a cytotoxic anti-cancer agent.

In another embodiment, the one or more moieties Z are each an anticancer agent. In a further embodiment, the one or more moieties Z are each a hydroxyl-containing anticancer agent.

In one embodiment, Z is an alkylating agent, preferably a DNA alkylating agent. An alkylation agent is a compound that can replace a hydrogen atom with an alkyl group under physiological conditions (e.g. pH 7.4, 37 C, aqueous solution). Alkylation reactions are typically described in terms of substitution reactions by N, O and S heteroatomic nucleophiles with the electrophilic alkylating agent, although Michael addition reactions are also important. Examples of alkylating agents include nitrogen and sulfur mustards, ethylenimines, methanosulfonates, CC-1065 and duocarmycins, nitrosoureas, platinum-containing agents, agents that effectuate Topoisomerase II-mediated site dependent alkylation of DNA (e.g. psorospermin and related bisfuranoxanthones), ecteinascidin and other or related DNA minor groove alkylation agents.

In one embodiment, Z is a DNA minor groove binding and/or alkylating agent, e.g, a pyrrolobenzodiazepine, a duocarmycin, or derivatives thereof.

In a further embodiment, the one or more moieties Z are each independently selected from the group consisting of taxanes, anthracyclines, camptothecins, epothilones, mytomycins, combretastatins, vinca alkaloids, nitrogen mustards, maytansinoids, calicheamycins, duocarmycins, tubulysins, dolastatins and auristatins, enediynes, amatoxins, pyrrolobenzodiazepines, ethylenimines, radioisotopes, therapeutic proteins and peptides, and toxins or fragments thereof.

In a further embodiment, the one or more moieties Z are each independently selected from cyclophosphamide, ifosfamide, chlorambucil, 4-(bis(2-chloroethyl)amino)phenol, 4-(bis(2-fluoroethyl)ammo)phenol, N,N-bis(2-chloroethyl)-p-phenylenediamine, N,N-bis(2-fluoro-ethyl)-p-phenylenediamine, carmustine, lomustine, treosulfan, dacarbazine, cisplatin, carboplatin, vincristine, vinblastine, vindesine, vinorelbine, paclitaxel, docetaxel, etoposide, teniposide, topotecan, inirotecan, 9-aminocamptothecin, 9-nitrocamptothecin, 10-hydroxycamptothecin, lurtotecan, camptothecin, crisnatol, mitomycin C, mitomycin A, methotrexate, trimetrexate, mycophenolic acid, tiazofurin, ribavirin, hydroxyurea, deferoxamine, 5-fluorouracil, floxuridine, doxifluridine, raltitrexed, cytarabine, cytosine arabinoside, fludarabine, 6-mercaptopurine, thioguanine, raloxifen, megestrol, goserelin, leuprolide acetate, flutamide, bicalutamide, vertoporfin, phthalocyanine, photosensitizer Pc4, demethoxy-hypocrellin A, interferon-alpha, interferon-gamma, tumor necrosis factor, lovastatin, staurosporine, actinomycin D, bleomycin A2, bleomycin B2, peplomycin, daunorubicin, doxorubicin, N-(5,5-diacetoxypentyl)doxorubicin, morpholino doxorubicin, idarubicin, epirubicin, pirarubicin, zorubicin, mitoxantrone, thapsigargin, $N^8$-acetylspermidine, tallysomycin, esperamycin, butyric acid, retinoic acid, 1,8-dihydroxybicyclo[7.3.1]trideca-4-ene-2,6-diyne-13-one, anguidine, podophyllotoxin, combretastatin A-4, pancratistatin, tubulysin A, tubulysin D, carminomycin, streptonigrin, elliptmium acetate, maytansine, maytansinol, calicheamycin, mertansine (DM1), N-acetyl-$\gamma_1^I$-calicheamycin, calicheamycin-$\gamma_1^I$, calicheamycin-$\alpha_2^I$, calicheamycin-$\alpha_3^I$, duocarmycin SA, duocarmycin A, CC-1065, CBI-TMI, duocarmycin C2, duocarmycin B2, centanamycin, dolastatin, auristatin E, monomethylauristatin E (MMAE), monomethylauristatin F (MMAF), α-amanitin, β-amanitin, γ-amanitin, ε-amanitin, amanin, amaninamide, amanullin, and amanullinic acid and derivatives thereof.

Exemplary auristatin embodiments include the N-terminus linked monomethylauristatin drug moieties comprising a structure of any of Formulas V and VI below:

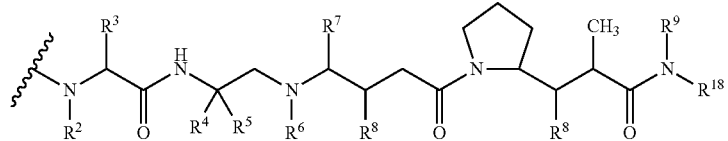

Formula V

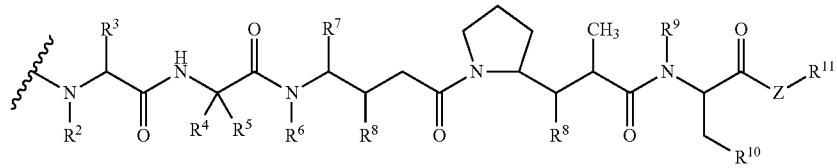

Formula VI wherein the wavy line of V and VI indicates the covalent attachment site to a L, L', V, V', Y, Y', (RR'), R' or $(C)_n$ group of a compound of the invention (e.g. a compound of Formula I, II or IV), and independently at each location:

$R^2$ is selected from H and $C_1$-$C_8$ alkyl;

$R^3$ is selected from H, $C_1$-$C_8$ alkyl, $C_1$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$ wherein $R^{12}$ is $C_1$-$C_8$ alkyl;

$R^{11}$ is selected from H, $C_1$-$C_{20}$ alkyl, aryl, C3-C8 heterocycle, —$(R^{13}O)_m$—$R^{14}$, or —$(R^{13}O)_m$—$CH(R^{15})_2$; m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —$(CH_2)_n$—$N(R^{16})_2$, —$(CH_2)_n$—$SO_3$—$C_1$-$C_8$ alkyl;

each occurrence of $R^{16}$ is independently H, $C_1$-$C_8$ alkyl, or —$(CH_2)_n$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

In one embodiment, $R^3$, $R^4$ and $R^7$ are independently isopropyl or sec-butyl and $R^5$ is —H or methyl. In an exemplary embodiment. $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is —$OCH_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —$OCH_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is —$CH(R^{15})_2$, wherein $R^{15}$ is —$(CH_2)_n$—$N(R^{16})_2$, and $R^{16}$ is —$C_1$-$C_8$ alkyl or —$(CH_2)_n$—COOH.

In another embodiment, when Z is —NH, $R^{11}$ is —$CH(R^{15})_2$, wherein $R^{15}$ is —$(CH_2)_n$—$SO_3H$.

One exemplary auristatin embodiment of formula V is MMAE, wherein the wavy line indicates the covalent attachment to a L, L', V, V', Y, Y', (RR'), R' or $(C)_n$, group of a compound of the invention (e.g. a compound of Formula I, II or IV):

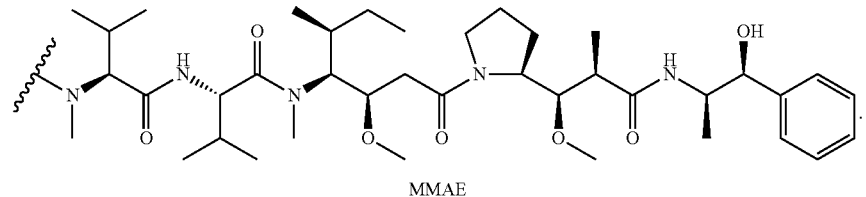 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE

An exemplary auristatin embodiment of formula VI is MMAF, wherein the wavy line indicates the covalent attachment to a linker (L) of an antibody-drug conjugate (see US 2005/0238649 and Doronina et al. (2006) Bioconjugate Cfiem. 17: 1 14-124):

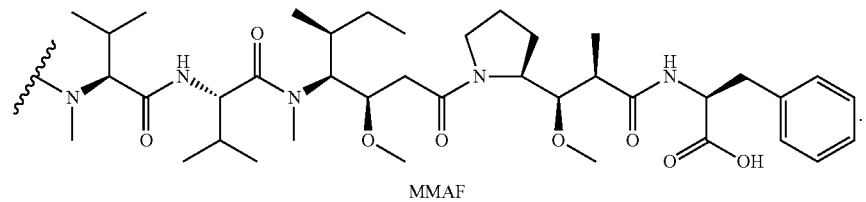

MMAF

Other exemplary Z embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Other drug moieties include the following MMAF derivatives, wherein the wavy line indicates the covalent attachment to a L, L', V, V', Y, Y', (RR'), R' or (C)$_n$ group of a compound of the invention (e.g. a compound of Formula I, II or IV):
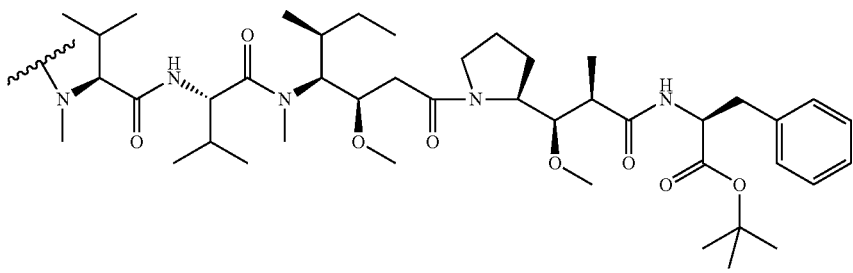
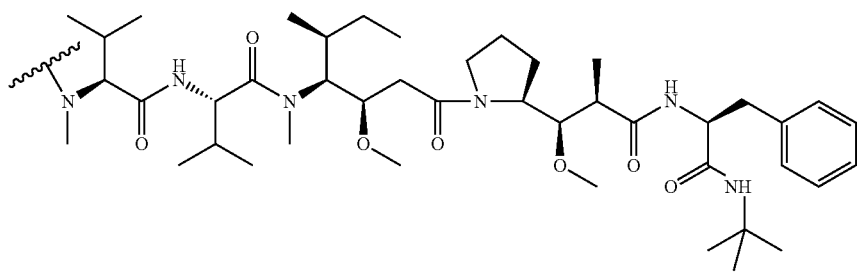
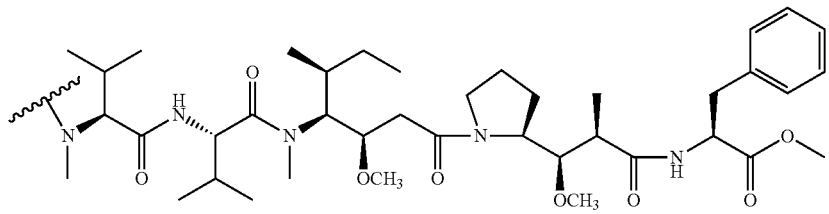
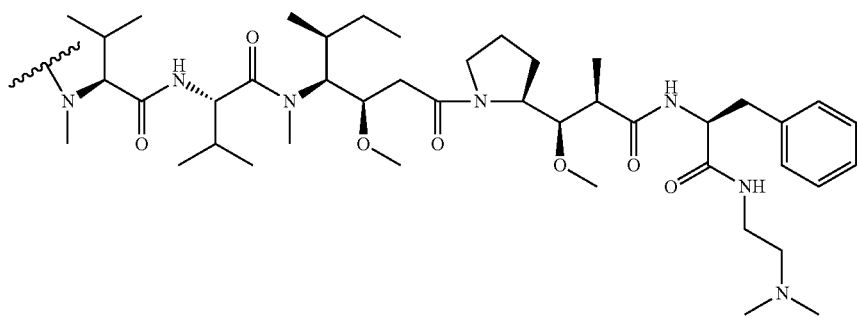
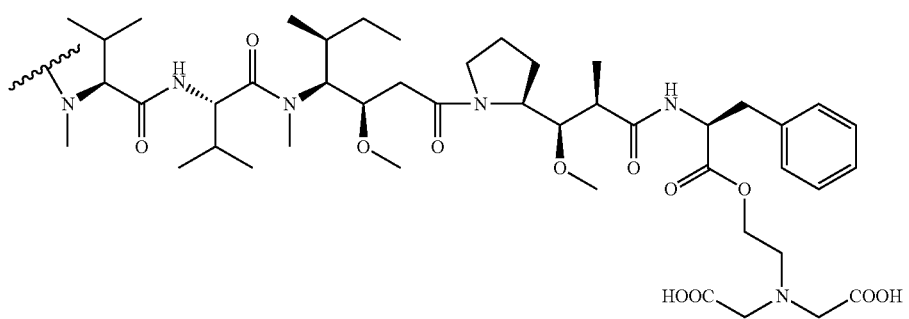

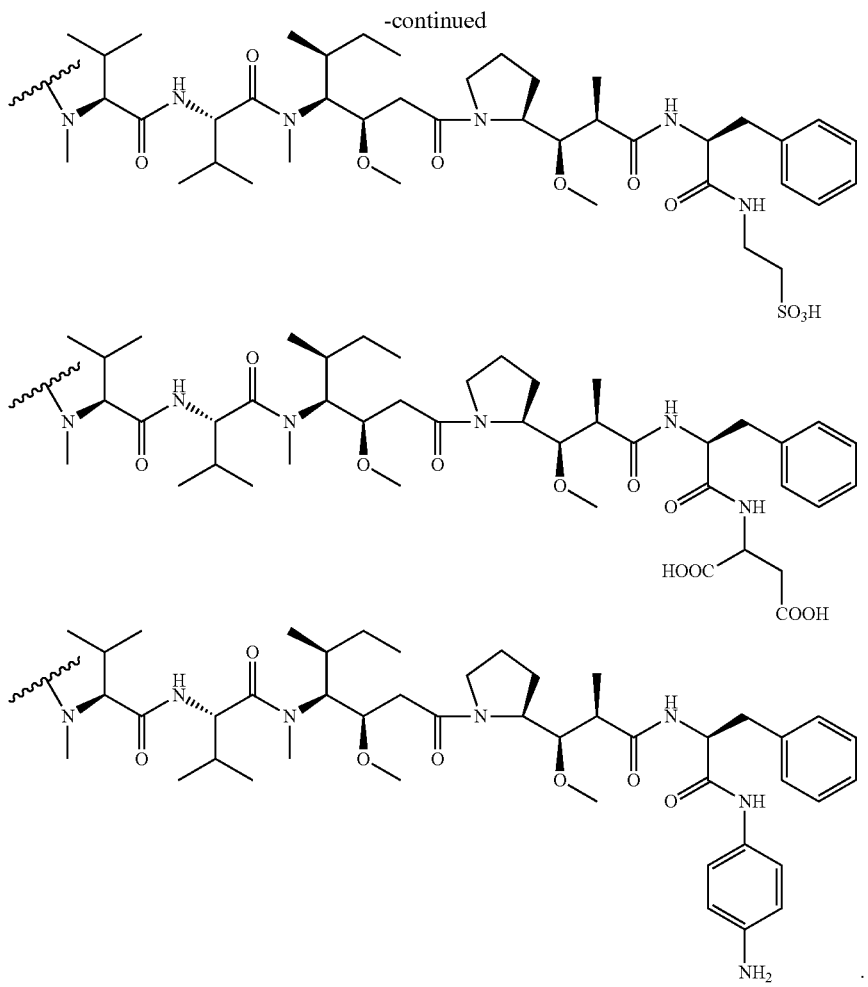

An example of a linker of the invention comprising a lysine residue as (C)$_n$ moiety, a valine-citrulline as the (V) moiety, a PAB as the (Y) moiety together with a MMAF as the (Z) moiety is shown below (corresponding to compound Ia-1):

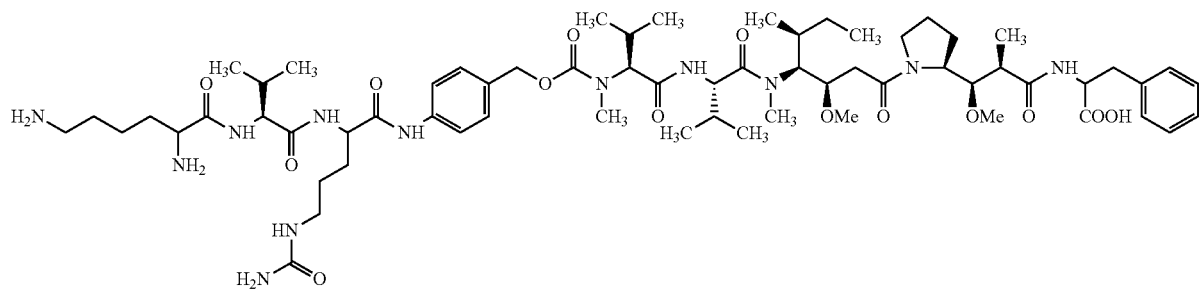 [SMILES: CC[C@H](C)[C@@H]([C@@H](CC(=O)N1CCC[C@H]1[C@H](OC)[C@@H](C)C(=O)NC(Cc1ccccc1)C(=O)O)OC)N(C)C(=O)[C@@H](NC(=O)[C@H](C(C)C)N(C)C(=O)OCc1ccc(NC(=O)C(CCCNC(N)=O)NC(=O)[C@@H](NC(=O)C(N)CCCCN)C(C)C)cc1)C(C)C]

In one embodiment, the Z moiety is an epothilone or epothilone derivative. An epothilone is a cyclic molecule with a 16-membered ring and variable substituents and pharmaceutical activity as a cytostatic agent that binds to tubulin. Various epothilone derivatives are known, including variants with 14-, 15- or 18-membered rings have also been developed (e.g. WO2011085523; WO2009105969). Examples of epothilones or epothilone analogs or derivative in the context of the present invention include epothilone A, epothilone B, epothilone C, 13-alkyl-epothilone C derivatives, epothilone D, trans-epothilone D, epothilone E, epothilone F, an effector conjugate of epothilone, Sagopilone, or any of the epothilones referred to in the literature as ixabepilone (BMS-247550), BMS-310705, EPO-906, Patupilone, Kos-862, Kos-1584, Kos-1803 and ABJ 879, and pharmaceutically active salts thereof. The production of epothilones, their precursors and derivatives is generally carried out according to the methods known to one skilled in the art. Suitable methods are, for example, described in DE 19907588, WO 98/25929, WO 99/58534, WO 99/2514, WO 99/67252, WO 99/67253, WO 99/7692, EP 99/4915, WO 00/485, WO 00/1333, WO 00/66589, WO 00/49019, WO 00/49020, WO 00/49021, WO 00/71521, WO 00/37473, WO 00/57874, WO 01/92255, WO 01/81342, WO 01/73103, WO 01/64650, WO 01/70716, U.S. Pat. Nos. 6,204,388; 6,387,927; 6,380,394, US 02/520,28, US 02/582,86, US 02/620,30, WO 02/32844, WO 02/30356, WO 02/32844, WO 02/14323, and WO 02/8440. Further epothilones are described in WO 93/10102, WO 98/25929, WO 99/02514, WO 99/07692, WO 99/02514, WO 99/67252, WO 00/49021, WO 00/66589, WO 00/71521, WO 01/027308, WO 02/080846, WO 03/074053, WO 2004/014919.

Other useful therapeutics are set forth in the Physician's Desk Reference and in the Orange Book maintained by the US Food and Drug Administration (FDA). New drugs are continually being discovered and developed, and the present invention provides that these new drugs may also be incorporated into a compound of this invention.

Chelated metals include chelates of di- or tripositive metals having a coordination number from 2 to 8 inclusive. Particular examples of such metals include technetium (Tc), rhenium (Re), cobalt (Co), copper (Cu), gold (Au), silver (Ag), lead (Pb), bismuth (Bi), indium (In), gallium (Ga), yttrium (Y), terbium (Tb), gadolinium (Gd), and scandium (Sc). In general the metal is preferably a radionuclide. Particular radionuclides include $^{99m}$Tc, $^{186}$Re, $^{188}$Re, $^{58}$Co, $^{60}$Co, $^{67}$Cu, $^{195}$Au, $^{199}$Au, $^{110}$Ag, $^{203}$Pb, $^{206}$Bi, $^{207}$Bi, $^{111}$In, $^{67}$Ga, $^{68}$Ga, $^{88}$Y, $^{90}$Y, $^{160}$Tb, $^{153}$Gd and $^{47}$Sc.

The chelated metal may be for example one of the above types of metal chelated with any suitable polydentate chelating agent, for example acyclic or cyclic polyamines, polyethers, (e.g. crown ethers and derivatives thereof); polyamides; porphyrins; and carbocyclic derivatives.

In general, the type of chelating agent will depend on the metal in use. One particularly useful group of chelating agents in conjugates according to the invention, however, are acyclic and cyclic polyamines, especially polyaminocarboxylic acids, for example diethylenetriaminepentaacetic acid and derivatives thereof, and macrocyclic amines, e.g. cyclic tri-aza and tetra-aza derivatives (for example as described in PCT publication no. WO 92/22583); and polyamides, especially desferriox-amine and derivatives thereof.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerytbrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

Synthetic or naturally occurring polymers for use as effector molecules include, for example optionally substituted straight or branched chain polyalkylene, polyalkenylene, or polyoxyalkylene polymers or branched or unbranched polysaccharides, e.g. a homo- or hetero-polysaccharide such as lactose, amylose, dextran or glycogen.

Particular optional substituents which may be present on the above-mentioned synthetic polymers include one or more hydroxy, methyl or methoxy groups. Particular examples of synthetic polymers include optionally substituted straight or branched chain poly(ethyleneglycol), poly (propyleneglycol), poly(vinylalcohol) or derivatives thereof, especially optionally substituted poly(ethyleneglycol) such as methoxypoly(ethyleneglycol) or derivatives thereof. Such compounds, when used as a moiety Z can be employed as a moiety that improves the pharmacokinetic properties of the antibody.

The size of the polymer may be varied as desired, but will generally be in an average molecular weight range from 500 Da to 50,000 Da, preferably from 5,000 to 40,000 Da and more preferably from 10,000 to 40,000 Da and 20,000 to 40,000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumor, it may be advantageous to use a small molecular weight polymer, for example with a molecular weight of around 5,000 Da. For applications where the product remains in the circulation, it may be advantageous to use a higher molecular weight polymer, for example having a molecular weight in the range from 20,000 Da to 40,000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 10,000 Da to about 40,000 Da.

In another embodiment, z' equals 1, each V, Y or V-Y (including whether any V and Y is a V' or Y') moiety contains a single attachment site for a functional group of Z.

In another embodiment, a one V (or V'), Y, (or Y') or V-Y (or V'-Y', V-Y') moiety is attached to more than one Z moiety via multiple functional groups R on the said V, Y or V-Y moiety. Optionally, the one or more V (or V') moieties comprise a polymer, optionally an oligoethylene glycol or a polyethylene glycol or a derivative thereof.

Any one of the Z moieties disclosed herein can be utilized in Formula Ia, IIII, and IVa. Any one of the Z moieties described herein can be used in combination with any of the $(C)_n$, X, L, V, R, Y, Z, M, z, q, and r groups described herein. Any one of the Z moieties described herein can be used in combination with any of the R', L', V', Y', z', q', and r' groups described herein.

Antibody-Z Conjugates

In one embodiment, a linking reagent (e.g. of Formula Ia) is directly conjugated to an antibody or antibody fragment, without requirement for a step of reaction involving reactive groups R and R'. In one aspect, an antibody or antibody fragment of the invention comprises a functionalized glutamine residue of Formula IVa, below,

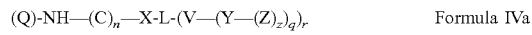  Formula IVa or a pharmaceutically acceptable salt thereof;
wherein:
Q is glutamine residue present in an antibody or antibody fragment;
$(C)_n$ is a substituted or unsubstituted alkyl or heteroalkyl chain, wherein any carbon of the chain is optionally substituted with an alkoxy, hydroxyl, alkylcarbonyloxy, alkyl-S—, thiol, alkyl-C(O)S—, amine, alkylamine, amide, or alkylamide (e.g. a O, N or S atom of an ether, ester, thioether, thioester, amine, alkylamine, amide, or alkylamide);

n is an integer selected from among the range of 2 to 20;

X is NH, O, S, or absent;

L is a bond or a carbon comprising framework, preferably of 1 to 200 atoms substituted at one or more atoms, optionally wherein the carbon comprising framework is a linear hydrocarbon, a symmetrically or asymmetrically branched hydrocarbon monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected among 1, 2, 3 or 4;

q is an integer selected among 1, 2, 3 or 4;

z is an integer selected among 1, 2, 3 or 4; and

V is independently absent, a non-cleavable moiety or a conditionally-cleavable moiety that can optionally be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";

Y is independently absent or a spacer (e.g., a self-eliminating spacer system or a non-self-elimination spacer system) which is comprised of 1 or more spacers; and Z is a moiety-of-interest, optionally a moiety that improves the pharmacokinetic properties, or a therapeutic moiety or a diagnostic moiety. Preferably, Z is a cytotoxic anti-cancer agent, e.g. a compound selected from the group consisting of taxanes, anthracyclines, camptothecins, epothilones, mytomycins, combretastatins, vinca alkaloids, nitrogen mustards, maytansinoids, calicheamycins, duocarmycins, tubulysins, amatoxins, dolastatins and auristatins, enediynes, radioisotopes, therapeutic proteins and peptides, and toxins or fragments thereof.

Generally, each Z is directly coupled to either Y or V when Y is absent, or L when both Y and V are absent.

It will be appreciated that Formula IVa can for convenience also be expressed as $(Ab)-NH-(C)_n-X-L-(V-(Y-(Z)_z)_q)_r$ (Formula IVa), where (Ab) is an immunoglobulin (Ab) is conjugated via a glutamine (Q) residue to an NH of the linking reagent (e.g the compound of Formula Ia).

Examples of antibodies or antibody fragments of Formula IVa include but are not limited to antibodies and fragments attached via an amide bond (e.g. through an acceptor glutamine residue in the primary sequence of the antibody or antibody fragment) to a compound selected from the group consisting of compounds Ia-1 to Ia-23 (wherein the terminal $NH_2$— of each of said compound Ia-1 to Ia-23 is replaced by a moiety ((Q)-NH—) when attached to the antibody or fragment, wherein Q is glutamine residue present in an antibody or antibody fragment.

The antibody conjugates resulting from the reaction of the compounds of Formula Ib or III with an antibody conjugated to a lysine-based linker will yield an antibody conjugate in which a moiety Z is connected to linker L (or L') when Y (or Y') and V (or V') are absent, to the spacer system Y (or Y') or, when Y (or Y') is absent, to V (or V). Optionally said connections are via linking group (RR') of M.

The conjugates resulting from the reaction yield an antibody (Ab) which is conjugated (i.e., covalently attached) via an acceptor glutamine residue (Q) present on the antibody to a NH group of a lysine-based linker, and one or more moieties (Z) through optional linking group (RR'), optional linker (V or V') and/or optional spacer (Y or Y').

In one embodiment, the (RR') remains present in a conjugated antibody or antibody fragment, in which case a Formula IV will comprise an (M) moiety. Such an antibody or antibody fragment of the invention comprises a functionalized glutamine residue of Formula IVb, below,

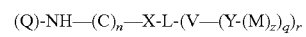

$(Q)-NH-(C)_n-X-L-(V-(Y-(M)_z)_q)_r$  Formula IVb or a pharmaceutically acceptable salt or solvate thereof; wherein:

Q is glutamine residue present in an antibody or antibody fragment;

$(C)_n$ is a substituted or unsubstituted alkyl or heteroalkyl chain, wherein any carbon of the chain is optionally substituted with an alkoxy, hydroxyl, alkylcarbonyloxy, alkyl-S—, thiol, alkyl-C(O)S—, amine, alkylamine, amide, or alkylamide;

n is an integer selected from among the range of 2 to 20;

X is NH, O, S, or absent;

L is a bond or a carbon comprising framework, preferably of 1 to 200 atoms substituted at one or more atoms, optionally wherein the carbon comprising framework is a linear hydrocarbon, a symmetrically or asymmetrically branched hydrocarbon monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymnmetrically branched or symmetrically branched) resulting from any chain-growth or step-growth polymerization process;

r is an integer selected among 1, 2, 3 or 4;

q is an integer selected among 1, 2, 3 or 4;

z is an integer selected among 1, 2, 3 or 4; and

V is independently absent, a non-cleavable moiety or a conditionally-cleavable moiety that can optionally be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";

Y is independently absent or a spacer (e.g., a self-eliminating spacer system or a non-self-elimination spacer system) which is comprised of 1 or more spacers; and M is independently: R or $(RR')-L'-(V'-(Y'-(Z)_{z'})_{q'})_{r'}$, wherein each of L', V', Y', z', q', and r' are as defined in Formula III (or are defined as L, V, Y, z, q and r, respectively, Z is a moiety-of-interest, optionally a moiety that improves the pharmacokinetic properties, or a therapeutic moiety or a diagnostic moiety, R is as defined in Formula I and wherein each (RR') is an addition product between an R of Formula I and its complementary R' of Formula III (see, for example, FIG. 1 and FIG. 2).

Thus, RR' can be for example an addition product of a thio-maleimide (or haloacetamide) addition, for example, a N,S-disubstituted-3-thio-pyrrolidine-2,5-dione; Staudinger ligation, for example, a N,3- or N,4-substituted-5-dipenyl-phosphinoxide-benzoic amide; Huisgen 1,3-cycloaddition (click reaction), for example, a N,S-disubstituted-3-thio-pyrrolidine-2,5-dione, 1,4-disubstituted-1,2,3-triazole, 3,5-disubstituted-isooxazole, or 3,5-disubstituted-tetrazole; Diels-Alder cycloaddition adduct, for example the 2,4- cycloaddition product between an O or N-substituted-5-norbornene-2-carboxylic ester or amide, N-substituted-5-norbornene-2,3-dicarboxylic imide, O or N-substituted-7-oxonorbornene-5-carboxylic ester or amide, or N-substituted-7-oxonorbornene-5,6-dicarboxylic imide and a 9-substituted anthracene or 3-substituted 1,2,4,5-tetrazine; or any high yield selective amidation or imidization reaction. Some reactions and the corresponding RR' reaction products are illustrated in FIGS. 1 and 2.

Examples of RR' include:

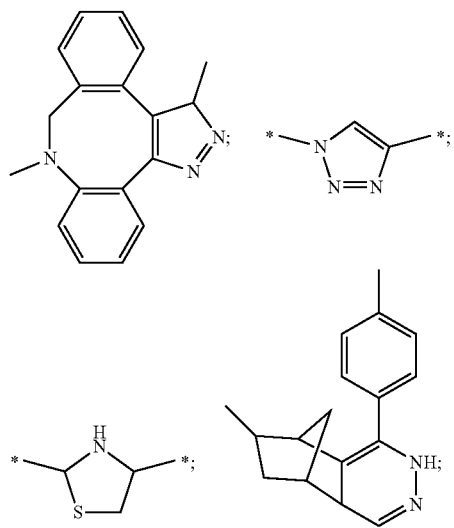

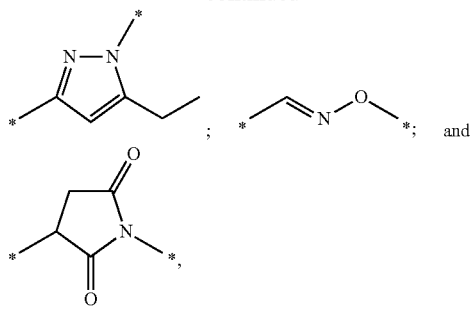

wherein (*) indicates the site of attachment of —(C)$_n$, X, L, L', V, V', Y, Y' or Z. RR' can be in either orientation with respect to their attachment to —(C)$_n$, X, L, L', V, V', Y, Y' or Z).

Optionally, the antibody conjugate comprises a group (RR') representing the remainder of a reactive moiety R when R has reacted with a reactive moiety R', wherein the group (RR') connects (a) an L to a Z, a V or a Y, (b) a V to a Z or a Y, or (c) a Y to a Z. For example, any V, Y and/or Z may be characterized as comprising a (RR') group. Any L, V, Y may be an L', V' or Y', respectively.

It will be appreciated that Formula IVb can for convenience also be expressed as (Ab)-NH—(C)$_n$—X-L-(V—(Y-(M)$_z$)$_q$)$_r$, where (Ab) is an immunoglobulin (Ab) is conjugated via a glutamine (Q) residue to an NH of the linking reagent (e.g the compound of Formula Ib).

Examples of antibodies or antibody fragments of Formula IVb include but are not limited to:

Compound IVb-1

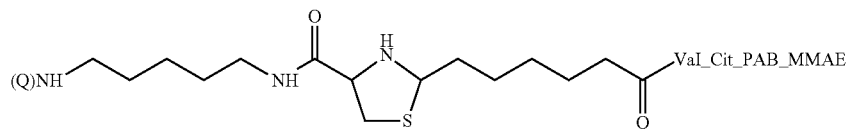

Compound IVb-2

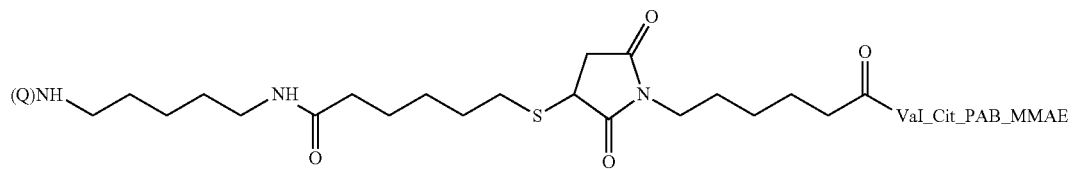

Compound IVb-3

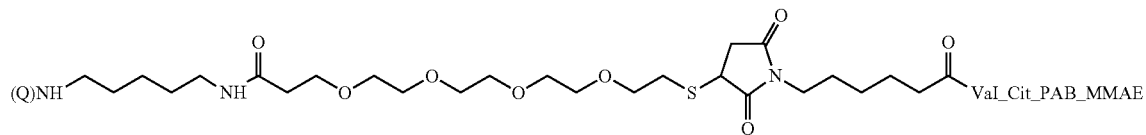

Compound IVb-4

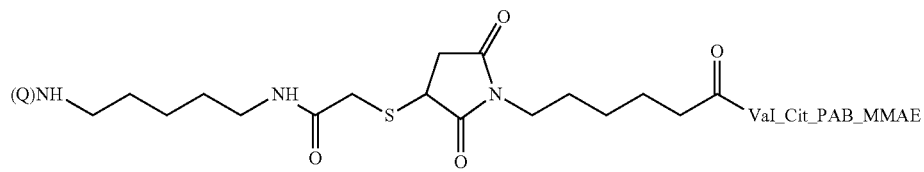

-continued

Compound IVb-5
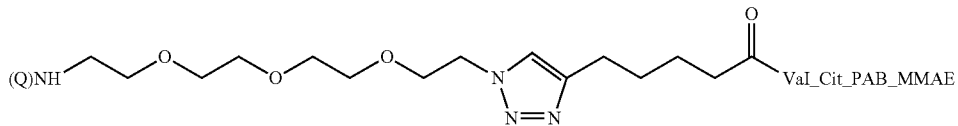

Compound IVb-6
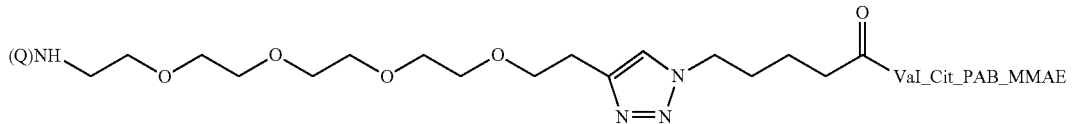

Compound IVb-7
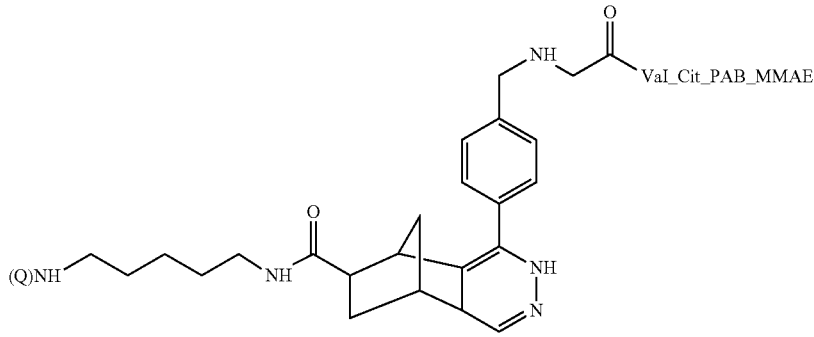

Compound IVb-8
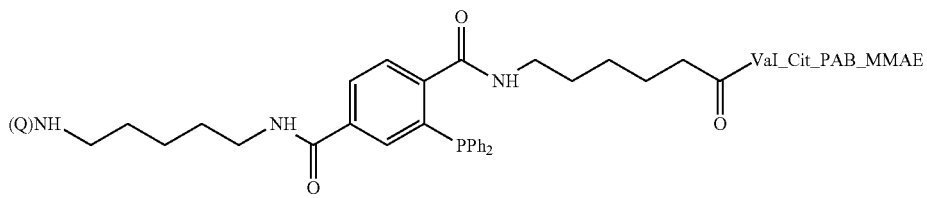

Compound IVb-8
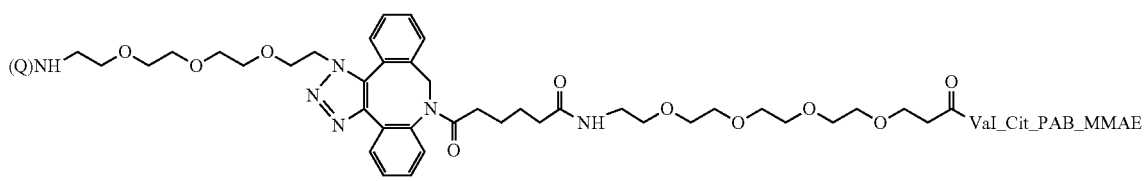

Compound IVb-9
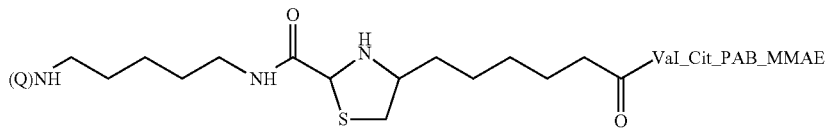

Compound IVb-9
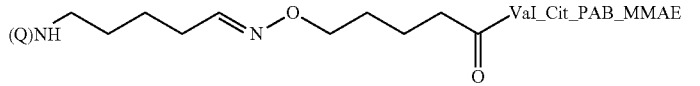

Compound IVb-9
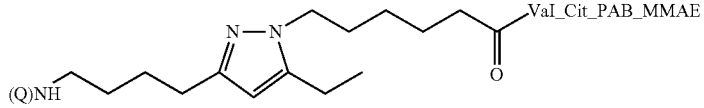

In one embodiment, the glutamine (Q) is present in the constant region of an antibody heavy chain. In one embodiment, the glutamine (Q) is at position 295. In one embodiment, an acceptor glutamine (Q) is at position 297 (e.g., a N297Q substitution). In one embodiment, the antibody comprises a substitution of an asparagine at position 297 with a non-asparagine, non-aspartic acid, non-glutamine, residue.

In one embodiment, a single surface exposed acceptor glutamine (Q) is present in the constant region of an antibody heavy chain. Optionally the antibody optionally comprises two heavy chains; such an antibody will comprise two functionalized acceptor glutamines of Formula IV per antibody molecule. Optionally said single acceptor glutamine (Q) is located at position 295. In one embodiment, the antibody comprises a N297Q substitution such that said single glutamine (Q) is located at position 295. In one embodiment, the antibody comprises a Q295 substitution (the glutamine at residue 295 is substituted by a non-glutamine residue) and a N297Q substitution, and said single glutamine (Q) is located at position 297.

In one embodiment, two surface exposed acceptor glutamines (Q) are present in the constant region of an antibody heavy chain. Optionally the antibody optionally comprises two heavy chains; such an antibody will comprise four functionalized acceptor glutamines of Formula IV per antibody molecule. Optionally the first glutamine (Q) is located at position 295 and the second glutamine (Q) is located at position 297 (e.g., a N297Q substitution).

Exemplary Methods for Preparing Compounds and Antibody-conjugates

A general scheme for preparing conjugated antibodies is shown in FIG. 10. Exemplary compounds can be prepared using known synthesis methods and starting reagents. In the examples below, all chemicals are purchased from Sigma-Aldrich, Fluka or Pierce Thermo scientific unless otherwise stated. All chemicals and solvents are used without further purification. Reactions are monitored by HPLC or by thin layer chromatography (TLC) using precoated silica gel 60 F aluminum sheets (Merck), and visualized by UV absorption or stained.

1. N-succinimidyl-S-acetylthioesters as Building Blocks

In a first step, mono-Boc-protected cadaverin is reacted with N-succinimidyl-S-acetylthioacetate (SATA) or succinimidyl acetyl(thiotetraethyleneglycol (SAT(PEG)4 or N-succinimidyl-S-acetylthiopropionate (SATP) to give the corresponding intermediates S-acetyl-cadaverin-Boc. Boc-deprotection is achieved in acidic conditions to give S-acetyl-cadaverin. Purification is achieved using reversed phase high performance liquid chromatography (RP-HPLC) to give the final product. The reaction scheme is shown in FIG. 3.

Figure 11:
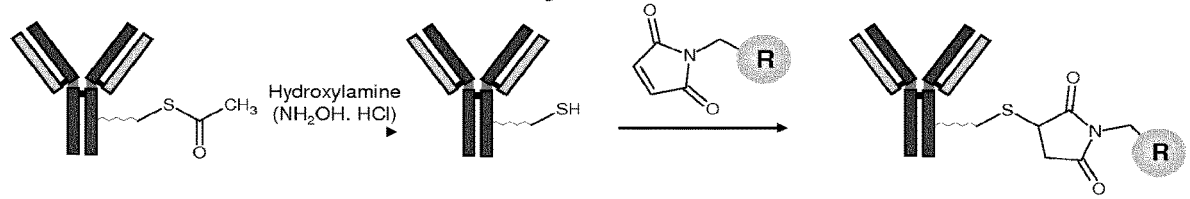
FIG. 11 shows a scheme for preparing an antibody conjugate from a S-acetyl-cadaverin linker of FIG. 3, where "R" in the figure is a moiety-of-interest Z.

The antibody conjugate is then prepared as shown in FIG. 11 ("R" is a moiety-of-interest Z). Chimeric antibody chCE7 (1 mg) in PBS buffer (0.1 mol/L NaCl and 0.05 mol/L sodium phosphate buffer, pH 7.4) are incubated with 100 units (0.2 µL) of N-glycosidase F (PNGase F) from *Flavobacterium meningosepticum* (New England BioLabs, Ipswich, UK) at 37° C. overnight to deglycosylate the antibody. The enzyme is then removed by centrifugation-dialysis (Vivaspin MWCO 50 kDa, Vivascience, Winkel, Switzerland). The product can be analyzed by LC/MS.

IgG antibody chCE7 is reacted with S-acetyl-cadaverin in the presence of recombinant BTG (EC 2.3.2.13) from *streptomyces mobaraensis* (Zedira, Darmstadt, Germany) at a concentration of 1-20 U/mL in potassium-free phosphate buffered saline (PBS; pH 8) at 37° C. After 4 h to several days (depending on the antibody and the ligand), steady-state conditions are achieved. Excess ligand and enzyme are then removed using centrifugation-dialysis (Vivaspin MWCO 50 kDa, Vivascience, Winkel, Switzerland). Reactions are monitored by LC/MS.

De-protection (deacylation) of the S-acetyl-protected IgG to generate a free sulfhydryl is accomplished using hydroxylamine-HCl. Then, the antibody-lysine-based linker conjugate is added to maleimide (or haloacetamide, e.g., bromoacetamide) containing compound at 4° C. for 1 h and the conjugation reaction is quenched by adding a 20-fold excess of cysteine. The reaction mixture is concentrated by centrifugal ultrafiltration and buffer-exchanged through Sephadex G-25 equilibrated with PBS at 4° C. The conjugate is then sterile filtered through a 0.2 µm filter.

2. Azide Moieties

Mono-Boc-protected cadaverin is reacted with N-hydroxysuccinimide ester ethane azide (NHS-azide) or N-hydroxysuccinimide ester tetraoxapentadecane azide (NHS-PEG4-Azide) or N-hydroxysuccinimide ester dodecaoxanonatriacontane azide (NHS-PEG12-Azide) to give the intermediate azide-cadaverin-Boc. Boc-deprotection is achieved the presence of trifluoroacetic acid (TFA). Purification using RP-HPLC provide azide-cadaverin. The reaction scheme is shown in FIG. 5.

Figure 12:
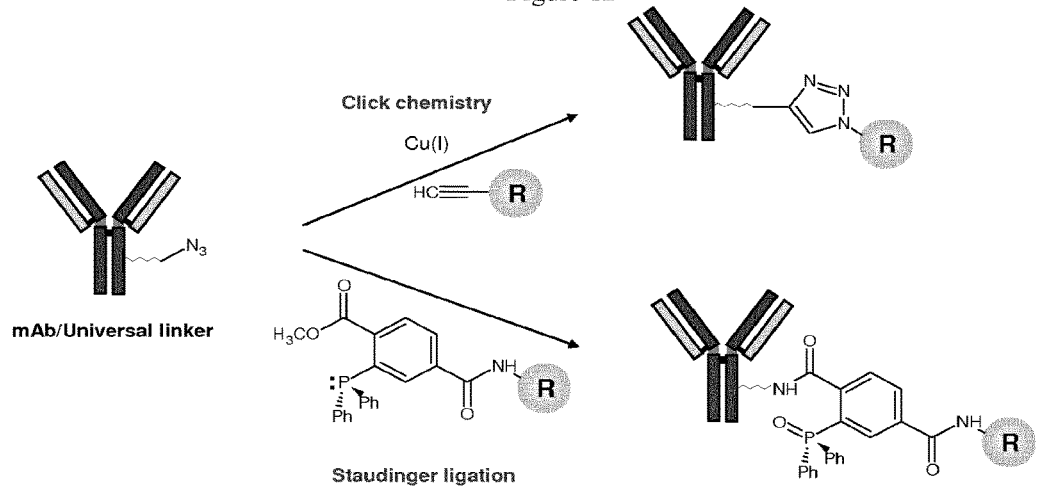
FIG. 12 shows a scheme for preparing an antibody conjugate from an azide-cadaverin linker of FIG. 5, where "R" in the figure is a moiety-of-interest Z.

The Antibody conjugate is then prepared as shown in FIG. 12 ("R" is a moiety-of-interest Z). Chimeric antibody chCE7 is deglycosylated and azide-cadaverin conjugates are prepared. The azide-modified antibody is reacted with the alkyne-reactive moiety compound using standard conditions for click chemistry.

3. Norbornene Moiety

In the first step, norbornene carboxylic acid is activated to a sulfo-NHS ester in the presence of 1-ethyl-3-(3-dimethylaminopropyl)carbodiimide (EDC). Then, mono-Boc-protected cadaverin is added and reacted with the reactive ester to give norbornyl-cadaverin-Boc. Deprotection of Boc is achieved by acidic treatment. Purification using RP-HPLC provide norbornyl-cadaverin. The reaction scheme is shown in FIG. 8.

Figure 13:
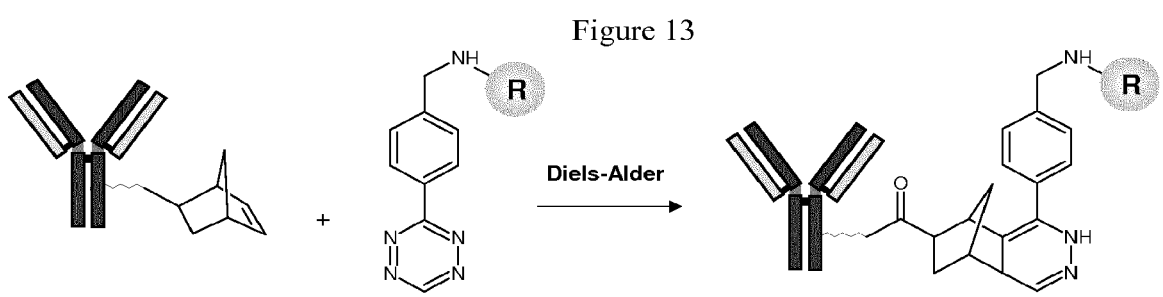
FIG. 13 shows a scheme for preparing an antibody conjugate from a norbornyl-cadaverin linker of FIG. 8, where "R" in the figure is a moiety-of-interest Z.

The Antibody conjugate is then prepared as shown in FIG. 13 ("R" is a moiety-of-interest Z). Chimeric antibody chCE7 is deglycosylated and azide-cadaverin conjugates are prepared. The norbornene-modified antibody (in PBS pH 7.4) is reacted with a molar excess of tetrazine reactive moiety compound (in DMSO or appropriate organic solvent) (molar excess is calculated based on initial norbornene reaction stoichiometry). The reaction is incubated at RT for 5 h and subsequently purified using centrifugal filtration to yield the completed antibody conjugate.

4. Alkyne Moiety

H-Lys-(Boc)-OMe is alkylated with propargyl glycine in the presence of Cs. Boc deprotection is achieved in a mixture of TFA (10%) and dichloromethane (DCM). Deprotection of the methyl ester with aqueous NaOH gives the glycan-lysine derivative in 50% yield. The reaction scheme is shown in FIG. 7.

Figure 14:
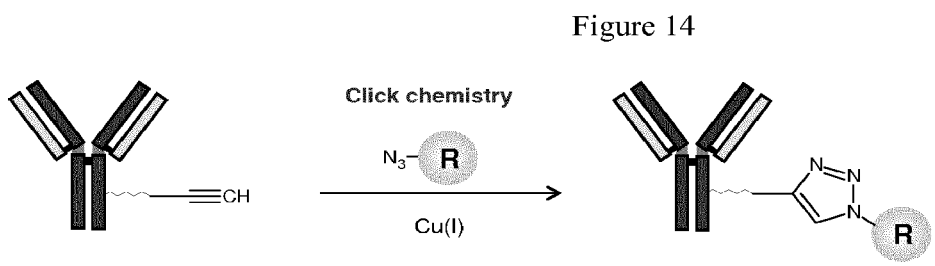
FIG. 14 shows a scheme for preparing an antibody conjugate from a glycan-lysine derivative linker of FIG. 7, where "R" in the figure is a moiety-of-interest Z.

The Antibody conjugate is then prepared as shown in FIG. 14 ("R" is a moiety-of-interest Z). Chimeric antibody chCE7 is deglycosylated and azide-cadaverin conjugates are prepared. The alkyne-modified antibody is reacted with the azide-reactive moiety compound using standard conditions for click chemistry. For conjugation by Staudinger ligation, the azido-derivated antibody is mixed with the phosphine-moiety compound and incubate at 37° C. for 2-4 hours, or at room temperature or 4° C. incubation during 16-24 hours. (final concentration of the antibody is preferably ≥2 mg/mL).

Uses of Compounds

In yet another aspect, the invention relates to the use of any of the compounds of the invention for the manufacture of a diagnostic product, a kit and/or a pharmaceutical preparation for the treatment or diagnosis of a mammal in need thereof. In one embodiment, the invention relates to the use of any of the compounds defined above for the manufacture of a pharmaceutical composition for the treatment of a tumor or infectious disease in a mammal.

Also the invention relates to any of the compounds defined above as a medicament or an active component or active substance in a medicament In a further aspect, the invention relates to a method for preparing a pharmaceutical composition containing a compound as defined above, to provide a solid or a liquid formulation for administration orally, topically, or by injection. Such a method or process at least comprises the step of mixing the compound with a pharmaceutically acceptable carrier.

In one aspect, this invention relates to a method to affect or prevent a predefined condition by exerting a certain effect, or detect a certain condition using a compound of the present invention, or a (pharmaceutical) composition comprising a compound of this invention. In one embodiment, this invention relates to a method of detecting the presence of a certain condition, e.g., the presence of an enzyme, the presence of a certain pH, the presence of a (bio)molecule, the presence of a substrate, or the presence of a certain oxygen concentration, with a compound of this invention, either in vivo or ex vivo.

In one embodiment, this invention relates to a method of determining an enzyme ex vivo, e.g., in a diagnostic assay, using a compound of this invention by incubating a sample (possibly) containing said enzyme with a compound of this invention containing one or more diagnostic moieties Z and a substrate for said (proteolytic) enzyme, and observing release of said Z moieties. The phrase "determining an enzyme" means both qualitative analysis, i.e., detecting the presence of the enzyme, determining whether it is present, and quantitative analysis, i.e., quantifying the enzyme, determining the enzyme activity present in the sample. An enzyme can also be indirectly determined via its pro-enzyme containing a recognition site, e.g., an activation site, cleavable by said enzyme to be determined. Cleavage of the pro-enzyme can in such case be detected by observing the resulting activity using a suitable compound of the present invention.

In one embodiment the invention relates to a diagnostic assay method (in vivo or ex vivo) in which a compound according to the invention is used.

In a further embodiment the invention relates to a method in which the presence or amount of an enzyme is determined by using a compound according to the invention.

In one embodiment, this invention relates to a method to affect or prevent a predefined condition, e.g., a disease such as an autoimmune disease, a microbial disease, or cancer, by exerting an effect using a compound of this invention.

In a further embodiment, the invention relates to a method of treating a mammal being in need thereof, whereby the method comprises the administration of a pharmaceutical composition to the mammal in a therapeutically effective dose.

In a further embodiment, this invention relates to a method of treating a mammal having an illness characterized by undesired (cell) proliferation with a compound of this invention. In another embodiment this invention relates to a method of treating a mammal carrying a tumor with a compound of this invention. In yet another embodiment this invention relates to a method of treating a mammal having an inflammatory disease with a compound of this invention. In yet another embodiment this invention relates to a method of treating a mammal having an autoimmune disease with a compound of this invention. In yet another embodiment this invention relates to a method of treating a mammal having a bacterial or microbial infection with a compound of this invention.

In one embodiment, the invention relates to a method of treating cancer in a mammal, whereby the method comprises the administration of a pharmaceutical composition to the mammal in a therapeutically effective dose.

In one embodiment, a compound of the invention is used to treat an illness characterized by undesired proliferation. In another embodiment, a compound of the invention is used to treat an illness characterized by undesired (cell) proliferation. In another embodiment, a compound of the invention is used to treat a tumor. In yet another embodiment, a compound of the invention is used to treat an inflammatory disease. In yet another embodiment a compound of the invention is used to treat an autoimmune disease. In yet another embodiment a compound of the invention is used to treat a bacterial or microbial infection.

In one embodiment, the compound of the invention is capable of being internalized into cells that express an antigen to which the antibody binds (e.g. a tumor or viral antigen) and/or induces internalization of the antigen on said antigen-expressing cells. In one embodiment, the compound of the invention is toxic to a cell upon internalization (i.e. the compound comprises a moiety Z that is toxic to a cell). Preferably such compounds can be used in methods of killing or eliminating cells, preferably wherein said cells are tumor cells.

The invention also relates to pharmaceutical compositions comprising the compounds of the invention as defined above a compound of the invention may be administered in purified form together with a pharmaceutical carrier as a pharmaceutical composition. The preferred form depends on the intended mode of administration and therapeutic or diagnostic application. The pharmaceutical carrier can be any compatible, nontoxic substance suitable to deliver the compounds of the invention to the patient. Pharmaceutically acceptable carriers are well known in the art and include, for example, aqueous solutions such as (sterile) water or physiologically buffered saline or other solvents or vehicles such as glycols, glycerol, oils such as olive oil or injectable organic esters, alcohol, fats, waxes, and inert solids A pharmaceutically acceptable carrier may further contain physiologically acceptable compounds that act for example to stabilize or to increase the absorption of the compounds of the invention Such physiologically acceptable compounds include, for example, carbohydrates, such as glucose, sucrose or dextrans, antioxidants, such as ascorbic acid or glutathione, chelating agents, low molecular weight proteins or other stabilizers or excipients One skilled in the art would know that the choice of a pharmaceutically acceptable carrier, including a physiologically acceptable compound, depends, for example, on the route of administration of the composition Pharmaceutically acceptable adjuvants, buffering agents, dispersing agents, and the like, may also be incorporated into the pharmaceutical compositions.

For oral administration, the active ingredient can be administered in solid dosage forms, such as capsules, tablets, and powders, or m liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours Compressed tablets can be sugar-coated or film-coated to mask any unpleasant taste and protect the tablet from the atmosphere, or enteric-coated for selective disintegration in the gastrointestinal tract Liquid dosage forms for oral administration can contain coloring and flavoring to increase patient acceptance.

The compounds of the invention are however preferably administered parenterally. Preparations of the compounds of the invention for parenteral administration must be sterile. Sterilization is readily accomplished by filtration through sterile filtration membranes, optionally prior to or following lyophilization and reconstitution. The parenteral route for administration of compounds of the invention is in accord with known methods, e.g. injection or infusion by intravenous, intraperitoneal, intramuscular, intraarterial, or intralesional routes. The compounds of the invention may be administered continuously by infusion or by bolus injection. A typical composition for intravenous infusion could be made up to contain 100 to 500 ml of sterile 0.9% NaCl or 5% glucose optionally supplemented with a 20% albumin solution and 1 mg to 10 g of the compound of the invention, depending on the particular type of compound of the invention and its required dosing regime. Methods for preparing parenterally administrable compositions are well known in the art.

EXAMPLES

Materials and Methods
Reagents

Cadaverin-dansyl, cadaverin-biotin and cadaverin-TAMRA were purchased from Zedira (Darmstadt, Germany). C2-SAc, C6-SAc, PEG-4-SAc were prepared as described in Example 1. 5-FAM cadaverin (fluorescein-5-carboxamide) was purchased from Tebu-Bio (Le Perray en Yveline, France). DBCO-amine, DBCO-PEG4-$NH_2$, Azide-PEG4-$NH_2$ and Alkyne-PEG4-$NH_2$ were purchased from Click Chemistry Tools (Scottsdale, Ariz.). C2-SH and C6-SH thiol linkers were synthesized by reduction of their corresponding disulfides as described in Example 1. PEG-4-SH was synthesized by cleavage of the acetate group of PEG-4-SAc with sodium methoxide. MMAF linkers were prepared by reacting C6-SH with maleimide-valine-citrullin-PAB-MMAF and subsequent Boc-deprotetion. C2-DOTA and C6-DOTA linkers (thiol linkers coupled to maleimide-DOTA) were prepared by reacting C2-SH or C6-SH with DOTA-maleimide followed by Boc deprotection. C2-fluorescein (C2-thiol linker coupled to fluorescein maleimide) was prepared with a similar procedure. C2-$N_3$ and C6-$N_3$ linkers were synthesized as mentioned in Example 1. chADC1 (or chimADC1) is an antibody specific for a human tumor antigen, chimADC1 (or chADC1), generated in mice and converted to human IgG isotype.
Deglycosylation of Antibodies To antibody in PBS buffer (PBS (10×): Weight 2.1 g $KH_2PO_4$, 90 g NaCl, 4.8 g $Na_2HPO_4 \times 2 H_2O$ and transferred to a 1 L glass bottle, was added water to a volume of 1 L. To get PBS 1×, use 100 mL PBS (10×) and add water to a volume of 900 mL. pH was adjusted to 7.2 and filled to 1 L with water), and was incubated with 6 Units/mg protein of N-glycosidase F (PNGase F) from *Flavobacterium meningosepticum* (Roche, Switzerland) overnight at 37° C. The enzyme was then removed by centrifugation-dialysis (Vivaspin MWCO 50 kDa, Vivascience, Winkel, Switzerland).
Enzymatic Modification of Antibodies 1 mg/mL deglycosylated antibody in PBS was incubated with 80 equivalents of ligand and 1 U/mL or >1 U/mL bacterial transglutaminase (BTGase, Zedira, Darmstadt, Germany) overnight at 37° C. Excess of ligand and the BTGase were removed by centrifugation-dialysis (Vivaspin MWCO 50 kDa, Vivascience, Winkel, Switzerland).
Deprotection of Protected Thiol Linkers The method for deacetylation of the protected thiol linker is adapted from published procedures (Thermo Scientific). 0.5M hydroxylamine, 25 mM EDTA is prepared in phosphate buffered saline (PBS), pH 7.2-8.5. 1 mL of antibody-linker conjugate is combined with 100-200 µL of prepared 0.5M hydroxylamine. The mixture is incubated for 2 h at room temperature. The reaction mixture is then be purified into PBS containing 10 mM EDTA by using a desalting column (HiTrap Desalting column, 5 mL, GE Healthcare).
Coupling Deprotected Antibody-linker Conjugate with Maleimide Functionalized Moiety of Interest (Z)

Coupling of deprotected antibody-linker conjugate with maleimide functionalized toxin is carried out as in J. R. Junutula et al., (2008) Nat Biotechnol 26, 925. 5 equivalents per SH group of the maleimide functionalized ligand is combined with the deprotected antibody-linker conjugate. The reaction is incubated at RT for 1.5 h before desalting into PBS.
LC-MS Analysis LC-MS analysis was performed on a Waters LCT Premier mass spectrometer. Samples were chromatographed on an Aeris WIDEPORE XB-C18 column (3.6 µm, 100 mm×2.1 mm; Phenomenex) heated to 65° C. using a linear gradient from 22 to 55% A in 15 min plus 5% solvent C (solvent A: acetonitrile+0.1% formic acid, solvent B: water+0.1% formic acid, solvent C: 2-propanol) at a flow rate of 0.5 mL/min. The eluent was ionized using an electrospray source. Data were collected with MassLynx 4.1 and deconvolution was performed using MaxEnt1. Before the LC-MS analysis, 10 µg of antibody were mixed with DTT (final concentration should be 20 mM). Guan-buffer (7.5M Guan-HCl, 0.1M Tris-HCl, 1 mM EDTA buffer pH 8.5 (adjusted by addition of concentrated $NH_4OH$ (28% aqueous solution) was added to a final volume of 50 µL. Finally, 5 µL of the mixture were injected.

Example 1

Synthesis of New Lysine-based Linkers with and without Spacer Groups

Materials and Methods

All solvents used for reactions were purchased as anhydrous grade from Acros Organics (puriss., dried over molecular sieves, $H_2O$<0.005%) and were used without further purification unless otherwise stated. Solvents for extractions, column chromatography and thin layer chromatography (TLC) were purchased as commercial grade. All non-aqueous reactions were performed under an argon atmosphere using flame-dried glassware and standard syringe/septa techniques. Commercially available reagents were used without further purification. In general, reactions were magnetically stirred and monitored by TLC performed on Merck TLC glass sheets (silica gel 60 $F_{254}$). Spots were visualized with UV light (λ=254 nm) or by staining with anisaldehyde solution or $KMnO_4$ solution and subsequent heating. Chromatographic purification of products was performed using Fluka silica gel 60 for preparative column chromatography.

Nuclear magnetic resonance (NMR) spectra were recorded in $CDCl_3$, $CD_3OD$ or $D_2O$ either on a Bruker Av-400 or a Bruker Av-500 spectrometer at room temperature. The measured chemical shifts are reported in δ (ppm) and the residual signal of the solvent was used as the internal standard (CDCl$_3$ $^1$H: δ=7.26 ppm, $^{13}$C: δ=77.0 ppm, CD$_3$OD $^1$H: δ=3.31 ppm, $^{13}$C: δ=49.1 ppm, D$_2$O $^1$H: δ=4.81 ppm). All $^{13}$C NMR spectra were measured with complete proton decoupling. Data of NMR spectra are reported as follows: s=singlet, d=doublet, t=triplet, m=multiplet, dd=doublet of doublets, dt=doublet of triplets, br=broad signal. The coupling constant J is reported in Hertz (Hz). High resolution mass spectrometry (HRMS) was performed on a Bruker Daltonics maxis ESI-QTOF or a Varian HiResMALDI instrument.

The analytical and preparative HPLC system used was a Merck-Hitachi D-7000 system. The columns used for chromatography were either an Ultimate XB-C18 (4.6×150 mm, 3 μm) or an Xbridge C18 (4.6×150 mm, 5 μm) for analytical separations operated with a flow of 1 ml/min. For preparative purifications, either an Ultimate XB-C18 (21.2×150 mm, 5 μm) or an Xbridge C18 (10×150 mm, 5 μm) column was used operated with a flow of 15 ml/min and 4 ml/min respectively.

Figure 15:
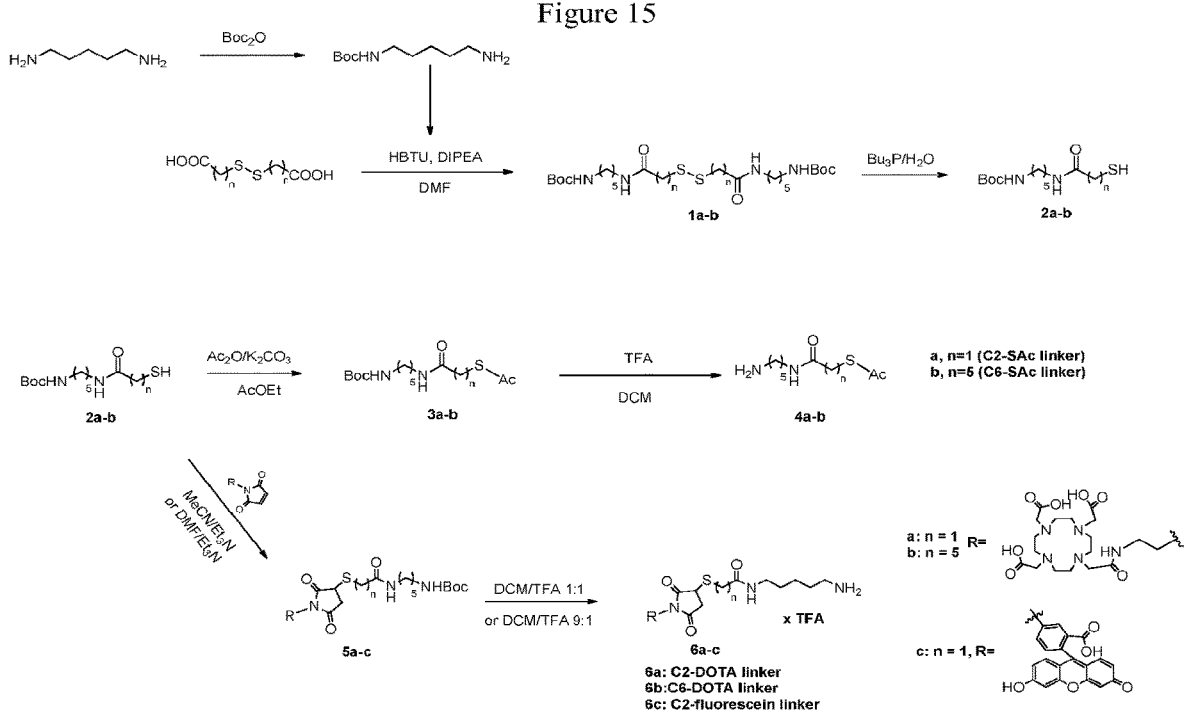
FIG. 15 shows a scheme for preparing S-acetyl-protected cadaverin linkers of different lengths (either n=1 or 5 carbons) as well as a short thiol linker coupled to maleimide-DOTA.
Figure 16A:
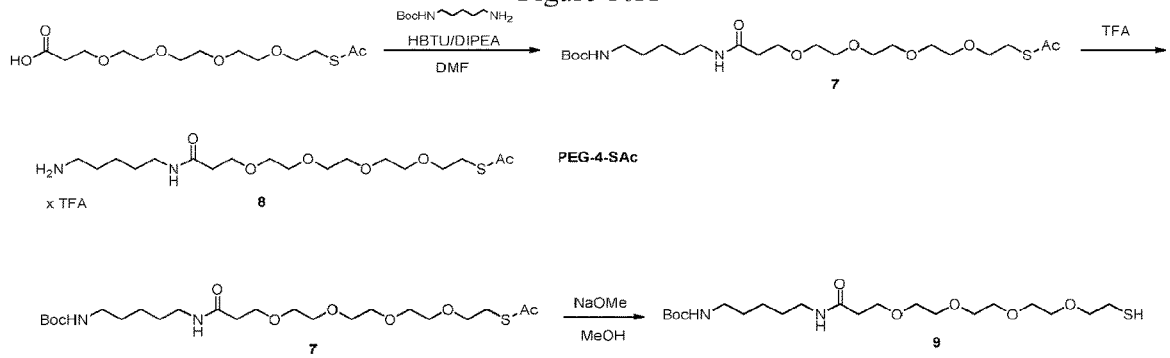
FIGS. 16A, 16B and 16C show schemes for preparing linkers of the invention.

Compounds 1-6 and reaction schemes are shown in FIG. 15. Compounds 7-9 and reaction schemes are shown in FIG. 16A. For Compounds 10-13 and reaction schemes, see FIG. 16B.

di-tert-butyl (((2,2'-disulfanediylbis(acetyl))bis(azanediyl))bis(pentane-5,1-diyl))dicarbamate (1a)

In a solution of 2,2'-disulfanediyldiacetic acid (160 mg, 0.878 mmol), tert-butyl (5-amino-pentyl)carbamate (391 mg, 1.932 mmol) and DIPEA (920 μl, 5.27 mmol) in DMF (4.9 ml), HBTU (1.33 g, 3.51 mmol) was added portionwise at room temperature. After stirring for 5 hours, the brownish solution was diluted with ethyl acetate (80 ml) and washed with water (3×30 ml) and brine (1×30 ml). The organic layer was dried under sodium sulfate, filtered and evaporated to dryness. The crude was purified by flash column chromatography on silica using CHCl$_3$/EtOH 95:5 to yield 420 mg (87%) of a yellow oil which solidified upon standing at room temperature. $^1$H NMR (400 MHz, CDCl$_3$): δ 6.91 (br, 2 H), 4.68 (br, 2 H), 3.44 (s, 4 H), 3.29 (dt, J$_1$=7.2 Hz, J$_2$=6.8 Hz, 4H), 3.10 (dt, J$_1$=7.7 Hz, J$_2$=6.3 Hz, 4H), 1.64-1.31 (m, 30H). $^{13}$C NMR (100 MHz, CDCl$_3$): δ 168.5, 156.1, 79.1, 42.6, 40.2, 39.8, 29.7, 28.8, 28.4, 23.9. ESI-QTOF MS m/z calculated for C$_{24}$H$_{46}$N$_4$O$_6$S$_2$ [M+H]$^+$ 551.2932, measured 551.2921.

di-tert-butyl(((6,6'-disulfanediylbis(hexanoyl))bis(azanediyl))bis(pentane-5,1-diyl))dicarbamate (1b)

In a solution of 6,6'-disulfanediyldihexanoic acid (250 mg, 0.849 mmol), tert-butyl (5-amino-pentyl)carbamate (412 mg, 2.038 mmol) and DIPEA (0.890 ml, 5.09 mmol) in DMF (4.7 ml), HBTU (1.29 g, 3.40 mmol) was added portionwise at room temperature. After stirring for 20 hours, the yellowish reaction mixture was diluted with ethyl acetate (70 ml) and washed with cold HCl 0.1N (3×50 ml), NaHCO$_3$ (sat) (1×50 ml) water (1×50 ml) and brine (1×50 ml). The organic layer was dried under sodium sulfate, filtered and evaporated to dryness. The crude was purified by flash column chromatography on silica using CHCl$_3$/EtOH 95:5 to yield 525 mg (93%) of compound as a yellow sticky solid. $^1$H NMR (400 MHz, CDCl$_3$): δ 5.87 (br, 2 H), 4.64 (br, 2 H), 3.22 (dt, J$_1$=7.3 Hz, J$_2$=6.8 Hz, 4H), 3.09 (dt, J$_1$=8.1 Hz, J$_2$=6.7 Hz, 4H), 2.65 (t, J=7.2 Hz, 4H), 2.16 (t, J=7.2 Hz, 4H), 1.73-1.59 (m, 8H), 1.55-1.45 (m, 8H), 1.42 (s, 18H), 1.37-1.28 (m, 4H). $^{13}$C NMR (100 MHz, CDCl$_3$): δ 172.9, 156.1, 79.0, 40.2, 39.2, 38.8, 36.5, 29.7, 29.1, 28.8, 28.4, 28.0, 25.3, 23.9. ESI-QTOF MS m/z calculated for C$_{32}$H$_{62}$N$_4$O$_6$S$_2$ [M+H]$^+$ 663.4184, measured 663.4185.

tert-butyl (5-(2-mercaptoacetamido)pentyl)carbamate (2a)

To a solution of Di-tert-butyl((((2,2'-disulfanediylbis(acetyl))bis(azanediyl))bis(pentane-5,1-diyl))di-carbamate (390 mg, 0.478 mmol) in a mixture of tetrahydrofuran (7 ml) and water (0.74 ml), tributylphosphine (528 mg, 2.48 mmol) was added dropwise at room temperature, within 1 min. The reaction mixture was stirred for 1 h and then the volatiles were removed under reduced pressure at 33° C. The crude was azeotroped once with 50 ml benzene to remove traces of water and the residue was purified with flash column chromatography on silica with CHCl$_3$/EtOH 95:5 to yield a slightly yellow clear oil. The product was re-purified with flash column chromatography with hexane/ethyl acetate 2:8 to remove oxidized tributylphosphine byproducts. Final yield was 180 mg (91%) of product as a colorless oil which solidified to a white solid after storage at −25° C. $^1$H NMR (400 MHz, CDCl$_3$): δ 6.73 (br, 1 H), 4.57 (br, 1 H), 3.28 (dt, J$_1$=7.6 Hz, J$_2$=6.9 Hz, 2H), 3.23 (d, J=9.0 Hz, 2H), 3.11 (dt, J$_1$=8.1 Hz, J$_2$=6.6 Hz, 2H), 1.87 (t, $^3$J=9.0 Hz, 1H), 1.61-1.47 (m, 4 H), 1.43 (s, 9H), 1.40-1.30 (m, 2H). $^{13}$C NMR (100 MHz, CDCl$_3$): δ 169.1, 156.1, 79.1, 40.2, 39.7, 29.7, 29.0, 28.4, 28.3, 23.9. EST-QTOF MS m/z calculated for C$_{12}$H$_{24}$N$_2$O$_3$S [M+Na]$^+$ 299.1400, measured 299.1408.

tert-butyl (5-(6-mercaptohexanamido)pentyl)carbamate (2b)

To a solution of di-tert-butyl((((6,6'-disulfanediylbis(hexanoyl))bis(azanediyl))bis(pentane-5,1-diyl))di-carbamate (196 mg, 0.296 mmol) in a mixture of tetrahydrofuran (3 ml) and water (0.31 ml, 17.21 mmol), tributylphosphine (272 μl, 1.035 mmol) was added dropwise at room temperature, within 1 min. The reaction mixture was stirred for 1 h and then the volatiles were removed under reduced pressure at 33° C. The crude was azeotroped once with 50 ml benzene to remove traces of water and the residue was purified with flash column chromatography on silica with chloroform/ethanol 95:5 to yield a slightly yellow clear oil. NMR revealed that the compound was contaminated with tributylphosphine oxidized byproducts so the crude was purified again with flash column chromatography with hexane/ethyl acetate 2:8 to yield 180 mg (91%) of product as a colorless oil which solidified after storage at −25° C. $^1$H NMR (400 MHz, CDCl$_3$): δ 5.88 (br, 1 H), 4.57 (br, 1 H), 3.23 (dt, J$_1$=7.3 Hz, J$_2$=6.9 Hz, 2H), 3.09 (dt, J$_1$=7.8 Hz, J$_2$=6.5 Hz, 2H), 2.52 (dt, J=8.0 Hz, J$_2$=7.6 Hz, 2H), 2.16 (t, J=7.5 Hz, 4H), 1.69-1.57 (m, 4H), 1.56-1.46 (m, 4H), 1.43 (s, 9H), 1.36-1.28 (m, 3H). $^{13}$C NMR (100 MHz, CDCl$_3$): δ 172.8, 156.1, 79.1, 40.2, 39.2, 36.5, 33.6, 29.7, 29.1, 28.4, 27.9, 25.1, 24.4, 23.9. ESI-QTOF MS m/z calculated for C$_{16}$H$_{32}$N$_2$O$_3$S [M+H]$^+$ 333.2206, measured 333.2198.

S-(2-((5-((tert-butoxycarbonyl)amino)pentyl)amino)-2-oxoethyl) ethanethioate (3a)

To a mixture of tert-butyl (5-(2-mercaptoacetamido)pentyl)carbamate (189 mg, 0.684 mmol) and dry potassium carbonate (189 mg, 1.368 mmol) in degassed (freeze-pump-thaw) ethyl acetate (2.7 ml), acetic anhydride (77 mg, 0.821 mmol) was added and the reaction was stirred for 16 h. The reaction was then diluted with ethyl acetate (30 ml), filtered and washed with cold water (1×15 ml) and brine (1×15 ml), dried under sodium sulfate and evaporated to dryness. The crude was purified by flash column chromatography on silica with CHC$_3$/EtOH 96:4 to yield 192 mg (88%) of product as a white solid. $^1$H NMR (400 MHz, CDCl$_3$): δ 6.22 (br, 1 H), 4.56 (br, 1 H), 3.51 (s, 2H), 3.21 (dt, J$_1$=7.1 Hz, J$_2$=6.9 Hz, 2H), 3.09 (dt, J$_1$=7.6 Hz, J$_2$=6.6 Hz, 2H), 2.40 (s, 3H), 1.54-1.45 (m, 4H), 1.43 (s, 9H), 1.35-1.26 (m, 2H). $^{13}$C NMR (100 MHz, CDCl$_3$): δ 190.5, 168.0, 156.0, 79.1, 40.3, 39.6, 33.1, 30.3, 29.6, 29.0, 28.4, 23.8. ESI-QTOF MS m/z calculated for C$_{14}$H$_{26}$N$_2$O$_4$S [M+Na]$^+$ 341.1505, measured 341.1506.

S-(6-((5-((tert-butoxycarbonyl)amino)pentyl)amino)-6-oxohexyl) ethanethioate (3b)

To a solution of tert-butyl (5-(6-mercaptohexanamido)pentyl)carbamate (180 mg, 0.541 mmol) and dry potassium carbonate (150 mg, 1.083 mmol) in degassed (freeze-pump-thaw) ethyl acetate (2.2 ml), acetic anhydride (61 µl, 0.650 mmol) was added and the reaction was stirred for 16 h. The reaction was then diluted with ethyl acetate (20 ml), filtered and washed with cold water (1 x 10 ml) and brine (1×10 ml), dried under sodium sulfate and evaporated to dryness. The crude was purified by flash column chromatography using chloroform/ethanol 96:4 to yield 182 mg (90%) of a white solid. $^1$H NMR (400 MHz, CDCl$_3$): δ 5.68 (br, 1 H), 4.61 (br, 1 H), 3.21 (dt, J$_1$=7.3 Hz, J$_2$=6.9 Hz, 2H), 3.09 (dt, J$_1$=7.7 Hz, J$_2$=6.4 Hz, 2H), 2.83 (t, J=7.2 Hz, 2H), 2.30 (s, 1H), 2.14 (t, J=7.2 Hz, 2H), 1.67-1.44 (m, 8H), 1.42 (s, 9H), 1.40-1.27 (m, 4H). $^{13}$C NMR (100 MHz, CDCl$_3$): δ 196.0, 172.8, 156.1, 79.3, 40.2, 39.2, 36.4, 30.6, 29.7, 29.2, 29.1, 28.8, 28.4, 28.3, 25.1, 23.9. ESI-QTOF MS m/z calculated for C$_{18}$H$_{34}$N$_2$O$_4$S [M+H]$^+$ 375.2312, measured 375.2312

S-(2-((5-aminopentyl)amino)-2-oxoethyl) ethanethioate (4a) (C2-SAc linker)

To a solution of S-(2-((5-((tert-butoxycarbonyl)amino)pentyl)amino)-2-oxoethyl)ethanethioate (189 mg, 0.594 mmol) in dichloromethane (7.9 ml), trifluoroacetic acid (0.92 ml, 11.87 mmol) was added dropwise at 0° C. After stirring for 10 min, the reaction mixture was allowed to reach room temperature where it was stirred for 1 h. Toluene was then added (20 ml), volatiles were removed under reduced pressure and the residue was dried under high vacuum for 30 min to yield quantitatively a slightly yellow oil which was sufficiently pure when analyzed by NMR. The oil was dissolved in water and lyophilized to give a white solid. $^1$H NMR (400 MHz, CD3OD): 3.60 (s, 2H), 3.20 (t, J=6.9 Hz, 2H), 2.91 (t, J=7.6 Hz, 2H), 2.37 (s, 3H), 1.72-1.61 (m, 2H), 1.59-1.50 (m, 2H), 1.45-1.35 (m, 2H). $^{13}$C NMR (100 MHz, CDCl$_3$): δ 196.3, 170.8, 40.7, 40.4, 33.9, 30.1, 29.9, 28.2, 24.6. ESI-QTOF MS m/z calculated for C$_9$H$_{18}$N$_2$O$_2$S [M+H]$^+$ 219.1162, measured 219.1171.

S-(6-((5-aminopentyl)amino)-6-oxohexyl) ethanethioate (4b) (C6-SAc Linker)

To a solution of S-(6-((5-((tert-butoxycarbonyl)amino)pentyl)amino)-6-oxohexyl) ethanethioate (187 mg, 0.5 mmol) in dichloromethane (6.6 ml), trifluoroacetic acid (0.77 ml, 5.34 mmol) was added dropwise at 0° C. After stirring for 10 min, the reaction mixture was allowed to reach room temperature where it was stirred for 1 h. The volatiles were removed under reduced pressure at 30° C. and the residue was azeotroped with toluene and dried under high vacuum for 30 min. Lyophilization yielded a white solid (185 mg) which was sufficiently pure by NMR. $^1$H NMR (400 MHz, CD$_3$OD): δ 3.18 (t, J=7.0 Hz, 2H), 2.92 (t, J=7.8 Hz, 2H), 2.86 (t, J=7.3 Hz, 2H), 2.30 (s, 3H), 2.17 (t, J=7.3 Hz, 2H), 1.72-1.50 (m, 8H), 1.45-1.33 (m, 4H). $^{13}$C NMR (100 MHz, CD$_3$OD): 197.7, 176.2, 40.7, 40.0, 37.0, 30.64, 30.61, 30.0, 29.8, 29.4, 28.3, 26.6, 24.8. ESI-QTOF MS m/z calculated for C$_{13}$H$_{26}$N$_2$O$_2$S [M+H]$^+$ 275.1788, measured 275.1785.

2,2',2''-(10-(2-((2-(3-((2-((5-((tert-butoxycarbonyl)amino)pentyl)amino)-2-oxoethyl)thio)-2,5-dioxopyrrolidin-1-yl)ethyl)amino)-2-oxoethyl)-1,4,7,10-tetraazacyclododecane-1,4,7-triyl)triacetic acid (5a)

DOTA-maleimide (25 mg, 0.032 mmol) was suspended in acetonitrile (1 ml) and triethylamine was added (22.59 µl, 0.162 mmol) and after 5 min of stirring, a clear colorless solution was formed. A solution of tert-butyl (5-(2-mercaptoacetamido)pentyl)-carbamate (10.54 mg, 0.038 mmol) in 0.5 ml acetonitrile was then added and the reaction was stirred for 1 h at which point HPLC confirmed complete consumption of starting material. The solvent system used for reaction monitoring is as follows: water/0.1% TFA (solvent A), acetonitrile (solvent B); 0-5 min: 0% B, 5-20 min: 0-50% B, 20-25 min: 50% B, 25-30 min 50-0% B; UV=214 nm; t$_R$=18.3 min. The reaction was then diluted with 3 ml water and was purified by preparative HPLC with the following solvent system: water/0.1% TFA (solvent A), acetonitrile (solvent B); 0-5 min: 0% B, 5-20 min: 0-50% B. The product eluted approximately at 17 min; XB-C18 column; UV=214 nm. The product was obtained as a white solid after lyophilization (19.7 mg, 77% yield). ESI-MS m/z calculated for C$_{34}$H$_{58}$N$_8$O$_{12}$S [M+H]$^+$ 803.39, measured 803.40.

2,2',2''-(10-(2-((2-(3-((6-((5-((tert-butoxycarbonyl)amino)pentyl)amino)-6-oxohexyl)thio)-2,5-dioxopyrrolidin-1-yl)ethyl)amino)-2-oxoethyl)-1,4,7,10-tetraazacyclododecane-1,4,7-triyl)triacetic acid (5b)

To a solution of DOTA-maleimide (80 mg, 0.102 mmol) and triethylamine (52.5 mg, 0.519 mmol) in acetonitrile (3.5 ml) was added a solution of tert-butyl(5-(6-nmercaptohexanamido)pentyl)carbamate (40.6 mg, 0.122 mmol) in acetonitrile (1.5 ml) and the reaction mixture was stirred for 6 h at room temperature. Approximately half of the solvent was then removed under reduced pressure, water was added (3 ml) and the mixture was purified with preparative RP HPLC with the following solvent system: water/0.1% TFA (solvent A), acetonitrile (solvent B); 0-5 min: 0% B, 5-20 min: 0-50% B; t$_R$=17.4 min; UV=214 nm; XB-C18 column. The product was obtained as a white solid after lyophilization (58 mg, 57% yield). ESI-MS m/z calculated for C$_{38}$H$_{66}$N$_8$O$_{12}$S [M+H]$^+$ 859.46, measured 859.39.

5-(3-((2-((5-((tert-butoxycarbonyl)amino)pentyl)amino)-2-oxoethyl)thio)-2,5-dioxopyrrolidin-1-yl)-2-(6-hydroxy-3-oxo-3H-xanthen-9-yl)benzoic acid (5c)

A solution of tert-butyl(5-(2-mercaptoacetamido)pentyl)carbamate (14.22 mg, 0.051 mmol) in DMF (0.3 ml) was added to a solution of 5-(2,5-dioxo-2,5-dihydro-1H-pyrrol-1-yl)-2-(6-hydroxy-3-oxo-3H-xanthen-9-yl)benzoic acid (18.32 mg, 0.043 mmol) and triethylamine (4.29 µmol) and the clear yellow solution was stirred for 3 h at room temperature. After this time, the reaction was diluted with water (3 ml) and purified with preparative RP HPLC with the following solvent system: water/0.1% HCOOH (solvent A), acetonitrile (solvent B); 0-5 min: 30% B, 5-20 min: 30-80% B; UV=254 nm; $t_R$=15.4 min; XB-C18 column. The product was obtained as a bright yellow solid after lyophilization (22 mg, 73% yield). ESI-MS m/z calculated for $C_{36}H_{37}N_3O_{10}S$ [M+H]$^+$ 704.23, measured 704.05.

2,2',2''-(10-(2-((2-(3-((2-((5-aminopentyl)amino)-2-oxoethyl)thio)-2,5-dioxopyrrolidin-1-yl)ethyl)-amino)-2-oxoethyl)-1,4,7,10-tetraazacyclododecane-1,4,7-triyl)triacetic acid (6a) (C2-DOTA Linker)

2,2',2''-(10-(2-((2-(3-((2-((5-((tert-butoxycarbonyl) amino)pentyl)amino)-2-oxoethyl)thio)-2,5-dioxo-pyrrolidin-1-yl)ethyl)amino)-2-oxoethyl)-1,4,7,10-tetraazacyclododecane-1,4,7-triyl)triaceticacid (18 mg, 0.022 mmol) was dissolved in a mixture of dichloromethane/TFA 1:1 (2.7 ml) at 0° C. The reaction mixture was stirred for 10 min at this temperature and was then allowed to reach room temperature where it was stirred for 1 h at which point HPLC confirmed complete consumption of the starting material. The volatiles were removed under reduced pressure at 20° C. and the crude was dried under high vacuum for 30 min. The residue was dissolved in 1 ml water and was purified with preparative HPLC to provide 12.7 mg (81%) of a white solid after lyophilization. The solvent systems that were used were the same as in the case of 5a ($t_R$=12.8 min and $t_R$=11.6 min for analytical and preparative HPLC respectively). $^1$H NMR (500 MHz, D$_2$O): δ 4.26-2.89 (br, 28 H), 4.07 (dd, $J_1$=9.1 Hz, $J_2$=4.1 Hz, 1 H), 3.58 (d, J=15.3 Hz, 1 H), 3.42 (d, J=15.3 Hz, 1 H), 3.31 (dd, $J_1$=19.1 Hz, $J_2$=9.1 Hz, 1H), 3.22, (t, J=7.1 Hz, 2 H), 2.99 (t, J=7.5 Hz, 2H), 2.74 (dd, $J_1$=19.1 Hz, $J_2$=4.1 Hz, 1 H), 1.72-1.64 (m, 2 H), 1.60-1.52 (m, 2 H), 1.44-1.36 (m, 2 H). $^{13}$C NMR (100 MHz, D$_2$O): δ 178.8, 178.1, 171.3, 163.0, 162.7, 117.4, 115.1, 54.7, 40.3, 39.4, 39.3, 38.3, 37.1, 35.5, 34.5, 27.7, 27.6, 26.3, 22.9 ESI-MS m/z calculated for $C_{29}H_{51}N_8O_{10}S$ [M+H]$^+$ 703.34, measured 703.32.

2,2',2''-(10-(2-((2-(3-((6-((5-aminopentyl)amino)-6-oxohexyl)thio)-2,5-dioxopyrrolidin-1-yl)ethyl)-amino)-2-oxoethyl)-1,4,7,10-tetraazacyclododecane-1,4,7-triyl)triacetic acid (6b) (C6-DOTA Linker)

Compound 5b (45 mg, 0.045 mmol) was dissolved in a mixture of dichloromethane/TFA 1:1 (5.4 ml) at 0° C. and after stirring for 10 min at this temperature, the reaction mixture was allowed to reach room temperature where it was stirred for 2 h. The volatiles when then removed under reduced pressure at 30° C. and traces of TFA were removed with drying under high vacuum for 30 min. The residue was dissolved in water (4 ml) and was purified with preparative RP HPLC using the method described for 5b; $t_R$=13.5 min. ESI-MS m/z calculated for $C_{33}H_{58}N_8O_{10}S$ [M+H]$^+$ 759.41, measured 759.40.

5-(3-((2-((5-aminopentyl)amino)-2-oxoethyl)thio)-2, 5-dioxopyrrolidin-1-yl)-2-(6-hydroxy-3-oxo-3H-xanthen-9-yl)benzoic acid (6c) (C2-Fluorescein Linker)

To an ice cold suspension of 5c (10 mg, 0.014 mmol) in dichloromethane (2 ml), TFA (200 μl, 2.60 mmol) was added dropwise and the clear bright yellow solution was stirred for 10 min at 0° C. for 10 min before allowing it to reach room temperature where it was stirred for 40 min. Toluene was then added and the volatiles were removed under reduced pressure. The crude was purified with semi-preparative RP HPLC with the following system: water/0.1% TFA (solvent A), acetonitrile (solvent B); 0-3 min: 5% B, 3-10 min: 5-25% B, 10-20 min: 25% B; UV=254 nm; $t_R$=15.3 min; Xbridge column. The product was obtained as a bright yellow solid after lyophilization (6.7 mg, 78% yield). ESI-MS m/z calculated for $C_{31}H_{29}N_3O_8S$ [M+H]$^+$ 604.18, measured 604.04.

Synthesis of PEG Linkers

For Compounds 7-9 and reaction schemes, see FIG. 16A.

S-(2,2-dimethyl-4,12-dioxo-3,15,18,21,24-pentaoxa-5,11-diazahexacosan-26-yl) ethanethioate (7)

HBTU (421 mg, 1.11 mmol) was slowly added to a solution of 2-oxo-6,9,12,15-tetraoxa-3-thiaocta-decan-18-oic acid (300 mg, 0.925 mmol) and DIPEA (0.32 ml, 1.85 mmol) in DMF (4.5 ml) and the resulting solution was stirred for 15 min. A solution of tert-butyl (5-aminopentyl) carbamate (225 mg, 1.11 mmol) in DMF (0.6 ml) was then added dropwise and the reaction was stirred for 14 h. The reaction was then diluted with 60 ml ethyl acetate and was washed with water (2×25 ml) and brine (1×25 ml). The organic layer was dried under sodium sulfate, filtered and evaporated under reduced pressure. The crude was purified by flash column chromatography on silica using chloroform/ethanol 95:5 to afford 380 mg (81%) of product as a slight yellow oil. $^1$H NMR (400 MHz, CDCl$_3$): δ 6.51 (br, 1 H), 4.66 (br, 1 H), 3.70 (t, J=5.8 Hz, 2H), 3.65-3.59 (m, 12H), 3.57 (t, J=6.6 Hz, 2H), 3.21 (dt, $J_1$=7.3 Hz, $J_2$=6.9 Hz, 2H), 3.12-3.02 (m, 4H), 2.44 (t, J=5.8, 2H), 2.31 (s, 3H), 1.53-1.43 (m, 4H), 1.41 (s, 9H), 1.36-1.27 (m, 2H). $^{13}$C NMR (100 MHz, CDCl$_3$): δ 195.4, 171.5, 156.0, 78.9, 70.6, 70.5, 70.3, 70.2, 70.1, 69.7, 67.3, 40.3, 39.0, 36.9, 30.5, 29.6, 29.2, 28.7, 28.4, 24.0. ESI-QTOF MS m/z calculated for $C_{23}H_{44}N_2O_8S$ [M+H]$^+$ 509.2891, measured 509.2884.

S-(21-amino-15-oxo-3,6,9,12-tetraoxa-16-azahenicosyl) ethanethioate (8) (PEG-4-SAc Linker)

To an ice cold solution of S-(2,2-dimethyl-4,12-dioxo-3, 15,18,21,24-pentaoxa-5,11-diazahexacosan-26-yl) ethanethioate (370 mg, 0.73 mmol) in dichloromethane (9.7 ml) was added trifluoroacetic acid (1.1 ml, 14.55 mmol). After stirring for 10 min, the reaction mixture was allowed to reach room temperature and stirred for 2 h. The volatiles were then removed under reduced pressure, followed by drying under high vacuum. A light yellow oil resulted which was sufficiently pure as revealed by NMR (quantitative yield). $^1$H NMR (400 MHz, CDCl$_3$): δ 7.79 (br, 1 H), 7.23 (br, 3H), 2.33 (t, J=5.3 Hz, 2 H), 3.69-3.56 (m, 14 H), 3.31 (dt, $J_1$=7.5 Hz, $J_2$=6.1 Hz, 2 H), 3.06 (t, J=6.7 Hz, 2 H), 3.03-2.92 (m, 2 H), 2.58 (t, J=5.3 Hz, 2 H), 2.32 (s, 3 H), 1.77-1.65 (m, 2H), 1.64-1.51 (m, 2 H), 1.49-1.38 (m, 2 H). $^{13}$C NMR (100 MHz, CDCl$_3$): δ 195.7, 174.0, 70.2, 69.99, 69.97, 69.9, 69.8, 69.6, 67.2, 40.0, 38.8, 35.8, 30.4, 28.1, 27.2, 26.0, 22.5. ESI-QTOF MS m/z calculated for $C_{18}H_{36}N_2O_6S$ [M+H]$^+$ 409.2367, measured 409.2381.

Tert-butyl (1-mercapto-15-oxo-3,6,9,12-tetraoxa-16-azahenicosan-21-yl)carbamate (9)

A solution of sodium methoxide 0.5 M in methanol (1.8 ml, 0.904 mmol) was added dropwise to a solution of 7 (92 mg, 0.181 mmol) in degassed (freeze-pump-thaw) methanol and the reaction was stirred at room temperature for 3 h.

After neutralization with Amberlite 120, the solution was filtered and evaporated to dryness. The crude was purified by flash column chromatography on silica using chloroform/ethanol 95:5 to yield a clear colorless oil (75 mg, 89%). $^1$H NMR (400 MHz, CDCl$_3$): δ 6.48 (br, 1 H), 4.64 (br, 1 H), 3.71 (t, J=5.7 Hz, 2H), 3.66-3.61 (m, 12H), 3.60 (t, J=6.4 Hz, 2H, partially overlapped by the previous multiplet), 3.22 (q, J$_1$≈J$_2$=7.0, 2H), 3.09 (dt, J$_1$=6.4 Hz, J$_2$=7.8 Hz, 2H), 2.68 (td, J$_1$=6.4 Hz, J$_2$=8.2 Hz, 2H), 2.45 (t, J=5.7 Hz, 2H), 1.59 (t, J=8.2 Hz, 1H), 1.55-1.46 (m, 4H), 1.43 (s, 9H), 1.37-1.30 (m, 2H). $^{13}$C NMR (100 MHz, CDCl$_3$): δ 171.5, 156.0, 79.0, 72.8, 70.6, 70.5, 70.3, 70.2, 67.3, 40.3, 39.1, 37.0, 29.6, 29.2, 28.4, 24.2, 24.0

Synthesis of Azide Linkers

Figure 16B:
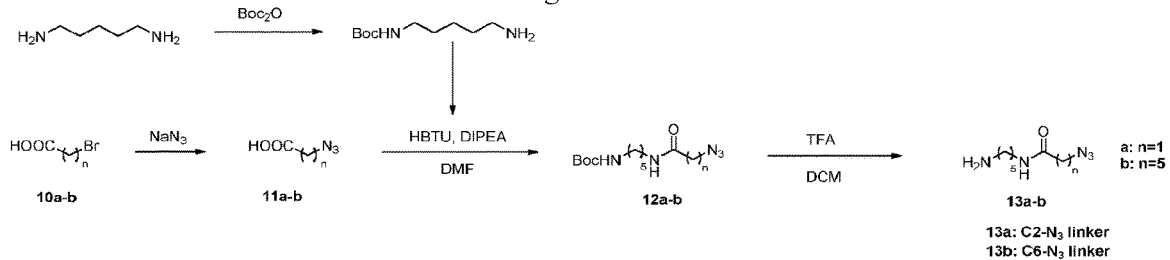

For Compounds 10-13 and reaction schemes, see FIG. 16B.

Compounds 11a and 11b were synthesized by following procedures already published in the literature (Brabez N. et al, Journal of Medicinal Chemistry, 2011, 54(20), 7375-7384 for 11a and Kuil J. et al, Organic and Biomolecular Chemistry, 2009, 7, 4088-4094 for 11b)

tert-butyl (5-(2-azidoacetamido)pentyl)carbamate (12a)

In a solution of 2-azidoacetic acid (50 mg, 0.495 mmol), tert-butyl (5-amino-pentyl)carbamate (120 mg, 0.594 mmol) and DIPEA (128 mg, 0.989 mmol) in DMF (2.7 ml), HBTU (225 mg, 0.594 mmol) was added slowly at room temperature. After stirring for 3 hours, the slight yellow solution was diluted with ethyl acetate (30 ml) and was washed with HCl 0.5 M (3×15 ml) and sat. NaHCO$_3$ (1×15 ml) solutions, water (1×15 ml) and brine (1×15 ml). The organic layer was dried under sodium sulfate, filtered and evaporated to dryness. The crude was purified by flash column chromatography on silica using chloroform/EtOH 95:5 to yield a clear colorless oil (128 mg, 91%). $^1$H NMR (400 MHz, CDCl$_3$): δ 6.35 (br, 1 H), 4.55 (br, 1 H), 3.97 (s, 2 H), 3.28 (dt, J$_1$=7.2 Hz, J$_2$=6.9 Hz, 2H), 3.11 (dt, J$_1$=7.8 Hz, J$_2$=6.5 Hz, 2H), 1.61-1.47 (m, 4 H), 1.43 (s, 9H), 1.40-1.31 (m, 2H). $^{13}$C NMR (100 MHz, CDCl$_3$): δ 166.5, 156.0, 79.1, 52.7, 40.2, 39.2, 29.7, 29.0, 28.4, 23.9.

Tert-butyl (5-(6-azidohexanamido)pentyl)carbamate (12b)

HBTU (290 mg, 0.764 mmol) was slowly added to a solution of 6-azidohexanoic acid (100 mg, 0.636 mmol) and DIPEA (164 mg, 1.273 mmol) in DMF (3 ml) and the resulting solution was stirred for 15 min. A solution of tert-butyl (5-aminopentyl)carbamate (154 mg, 0.764 mmol) in DMF (0.5 ml) was then added dropwise and the reaction was stirred for 3 h. After this time, the reaction mixture was diluted with ethyl acetate (40 ml) and washed with HCl 0.5 M (3×20 ml) and sat. NaHCO$_3$ (1×20 ml) solutions, water (1×20 ml) and brine (1×20 ml). The organic layer was dried under sodium sulfate, filtered and evaporated to dryness. The crude was purified by flash column chromatography on silica using chloroform/EtOH 95:5 to yield a clear colorless oil (189 mg, 87%). $^1$H NMR (400 MHz, CDCl$_3$): δ 5.61 (br, 1 H), 4.58 (br, 1 H), 3.30-3.20 (m, 4 H), 3.10 (dt, J$_1$=8.0 Hz, J$_2$=6.8 Hz, 2H), 2.16 (t, J=7.4 Hz, 2H), 1.56-1.45 (m, 4 H), 1.56-1.45 (m, 4H), 1.43 (s, 9H), 1.41-1.29 (m, 4H). $^{13}$C NMR (100 MHz, CDCl$_3$): δ 172.7, 156.1, 79.1, 51.3, 40.2, 39.3, 36.5, 29.8, 29.2, 28.6, 28.4, 26.4, 25.2, 23.9.

N-(5-aminopentyl)-2-azidoacetamide (13a) (C2-N$_3$ linker)

To an ice cold solution of 12a (19.2 mg, 0.067 mmol) in dichloromethane (0.9 ml) was added trifluoroacetic acid (153 mg, 1.346 mmol). After stirring for 10 min, the reaction mixture was allowed to reach room temperature and stirred for 2 h. Toluene (4 ml) was then added and the volatiles were removed under reduced pressure. The crude was azeotroped again with toluene to remove traces of TFA and was then dried under HVP for 3 hours to yield a light yellow oil (quantitative yield) which was sufficiently pure for further use, as revealed by NMR. $^1$H NMR (400 MHz, CD$_3$OD): δ 3.87 (s, 2H), 3.24 (t, J=7.1 Hz, 2H), 2.92 (t, J=7.5 Hz, 2H), 1.72-1.63 (m, 2H), 1.62-1.53 (m, 2H), 1.46-1.36 (m, 2H). $^{13}$C NMR (100 MHz, CD$_3$OD): δ 170.3, 53.1, 40.7, 40.1, 30.0, 28.3, 24.7.

N-(5-aminopentyl)-6-azidohexanamide (13b) (C6-N$_3$ Linker)

Compound 13b was synthesized by following a similar procedure as described above for 13a (starting with 22.8 mg, 0.067 mmol of 12b). $^1$H NMR (400 MHz, CD$_3$OD): δ 3.29 (t, J=6.8 Hz, 2H), 3.19 (t, J=7 Hz, 2H), 2.92 (t, J=7.7 Hz, 2H), 2.20 (t, J=7.3 Hz, 2H), 1.73-1.51 (m, 8H), 1.46-1.35 (m, 4H). $^{13}$C NMR (100 MHz, CD$_3$OD): δ 176.2, 52.5, 40.7, 40.0, 37.0, 30.1, 29.8, 28.3, 27.5, 26.7, 24.8.

MMAF-6Cthiol Linker Synthesis

Figure 16C:
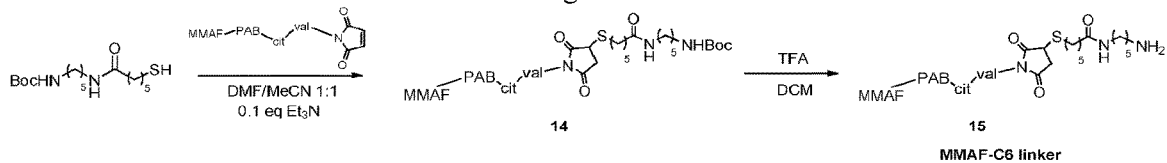

Compounds 14-15 and reaction schemes are shown in FIG. 16C.

maleimide-valine-citrullin-PAB-MMAF+6C Thiol Linker (Boc Protected) (14)

To a solution of maleimide-valine-citrullin-PAB-MMAF (8.8 mg, 6.61 µmol) in DMF (0.6 ml) was added 6.6 µl of a 0.1 M solution of triethylamine in DMF (0.66 µmol Et$_3$N), followed by the dropwise addition of a solution of tert-butyl (5-(6-mercaptohexanamido)pentyl)carbamate (3 mg, 9.02 µmol) in acetonitrile (0.3 ml). The reaction was stirred for 3 h, diluted with water (2 ml) and purified with semi-preparative RP HPLC with the following system: water/50 mM NH$_4$HCO$_3$ (solvent A), acetonitrile (solvent B); 0-5 min: 40% B, 5-20 min: 40-80% B; UV=254 nm; t$_R$=10.3 min; Xbridge column. The product was obtained as a white solid after lyophilization (8.7 mg, 79% yield).

maleimide-valine-citrullin-PAB-MMAF+6C Thiol Linker (MMAF-6C Linker) (15)

Compound 14 (8 mg, 4.81 µm) was dissolved in an ice cold solution of dichloromethane/TFA 95:5 (8 ml). The reaction mixture was allowed to reach room temperature and stirred for 40 min after which time the volatiles were removed under reduced pressure with the addition of toluene. Traces of solvents were removed under high vacuum and the residue was purified by semi-preparative HPLC with the following system: water/50 mM NH$_4$HCO$_3$ (solvent A), acetonitrile (solvent B); 0-5 min: 30% B, 5-20 min: 30-70% B; UV=254 nm; t$_R$=11.7 min; Xbridge column. The product was obtained as a white solid after lyophilization (4.86 mg, 65% yield). ESI-QTOF MS m/z calculated for C$_{79}$H$_{127}$N$_{13}$O$_{17}$S [M+2H]$^{2+}$ 781.9670, measured 781.9667.

Example 2
BTG is Unable to Couple Linkers with Large, Hydrophobic and/or Charged Payloads in Quantitative Fashion to Antibodies 1. Coupling of Dansyl and Biotin Linkers The structures of biotin-cadaverin and dansyl cadaverin are shown below.

2. Coupling of Linkers with DOTA Payload is Unsuccessful

The chemical structure of a thiol linker coupled to maleimide-DOTA (1,4,7,10-tetraazacyclododecane-1,4,7,10-tetraacetic acid) is shown below (for preparation see Example 1). The molecular weight is indicated below the structure.

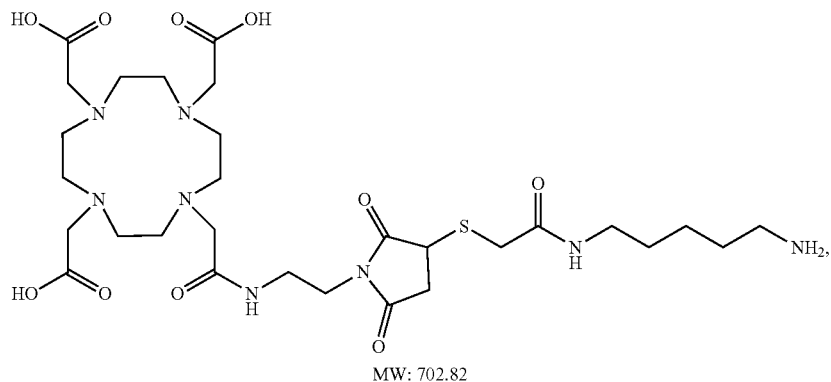

MW: 702.82

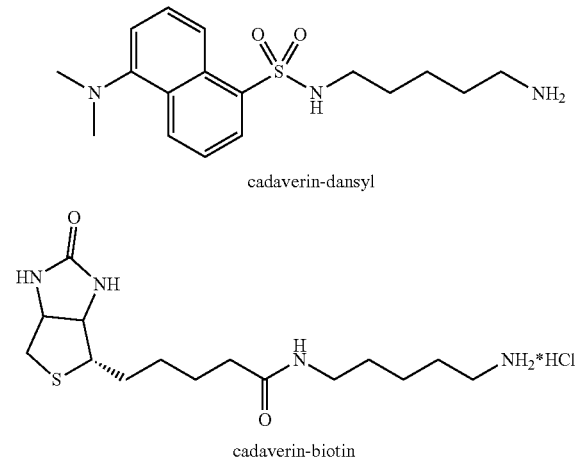

cadaverin-dansyl cadaverin-biotin

Antibody chADC1 having one potential acceptor glutamine on each heavy chain was degycolsylated by PNGaseF treatment and a mass of 48945 Da for unmodified, deglycosylated heavy chain was determined. The light chain remained unaffected (23341 Da found). The coupling reaction (using standard conditions with 1 U/mL BTG) for biotin-cadaverin and dansyl cadaverin was successful however it did not go to completion In view of the only partial coupling of biotin-cadaverin and dansyl cadaverin, reaction conditions were explored in an initial step of testing factors influencing reaction conditions. It was found that using 6 U/mL BTG permitted the modification of all heavy chains of PNGaseF-deglycosylated antibody chADC1 was achieved with either exactly one biotin-cadaverin (MW: 328 g/mol; 328−17=311 Da; 48945+311=49256 Da, 49257 Da found) or one dansyl-cadaverin (MW: 335 g/mol; 335−17=318 Da; 48945+318=49263 Da, 49264 Da found) per heavy chain.

Figure 17A:
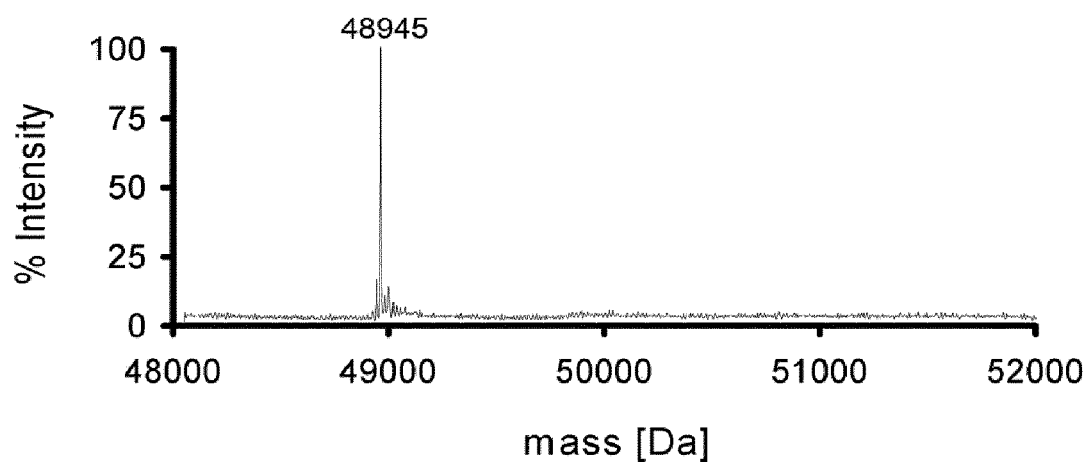
FIGS. 17A and 17B show the deconvoluted mass spectra of chADC1 heavy chain coupled to DOTA thiol linker 5 using either 1 U/mL (left) or 6 U/mL BTG.
Figure 17B:
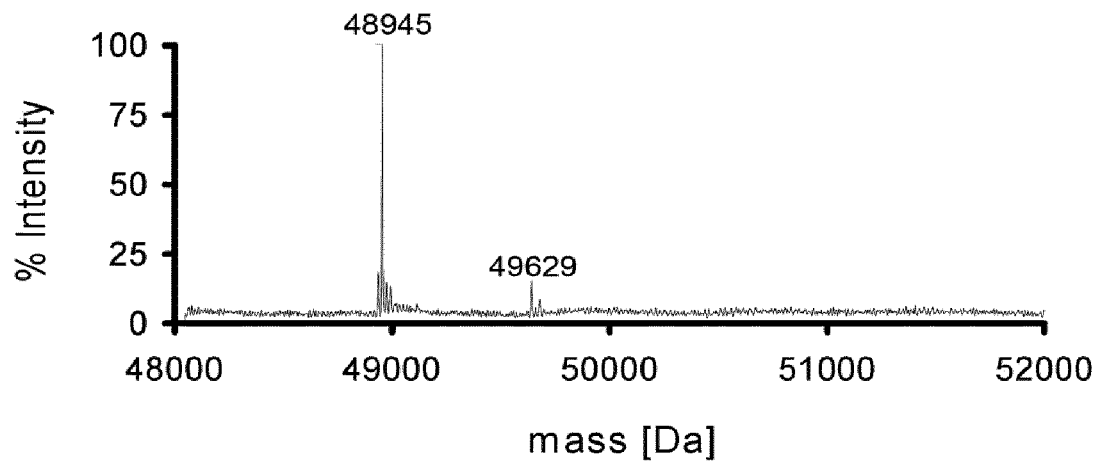

ChADC1 antibodies and DOTA linker were reacted in the presence of BTG to modify antibodies. Quantitative enzymatic modification of chimADC1 heavy chain with short DOTA thiol linker (compound 5) by BTG could not be accomplished (see FIG. 17A: 1 U/mL BTG, only unmodified chADC1 heavy chain, 48945 Da, was found. FIG. 17B: 6 U/mL BTG, minor peak modified chADC1 heavy chain with one DOTA thiol linker per heavy chain, MW 702 g/mol, 702−17=685 Da, 48945+685=49630 Da, 49629 Da found). Reaction conditions were explored but neither by using 1 U/mL (expected) nor by using 6 U/mL BTG could significantly complete coupling be achieved. Prolonged incubation time could not influence the efficiency or completion of coupling. Compared to biotin and dansyl, DOTA has a higher molecular weight, has a more rigid structure (containing a macrocycle), and in particular is electronically negatively charged that may interfere with BTG activity.

3. Coupling of Linker with Fluorescein Payload is Unsuccessful

The chemical structure of lysine-based linker (cadaverin) coupled to fluorescein is shown below.

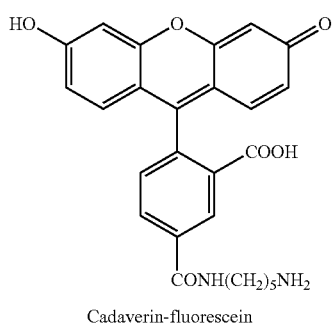

Cadaverin-fluorescein

ChADC1 antibodies and cadaverin-fluorescein linker were reacted in the presence of BTG to modify antibodies. The light chain remained unaffected. Quantitative enzymatic modification of chADC1 heavy chain with short fluorescein-containing linker by BTG could not be accomplished, only unmodified chADC1 heavy chain was found. Following exploration of reaction conditions (see Example 3), optimized conditions were tested (80 eq ligand, 6 U/ml BTG, 1 mg/ml mAb, 18H at 37° C.) but coupling could not be achieved. Compared to biotin and dansyl, fluorescein has a higher molecular weight, has a possibly more rigid and hydrophobic structure, notably containing a polycycle, notably a tri-cycle and a further cyclic group in proximity to the site of BTG activity.

4. Coupling of Linker withDBCO Payload is Unsuccessful

The chemical structure of the dibenzylcyclooctyne (DBCO) lysine-based linker (DBCO-amine) used is shown below.

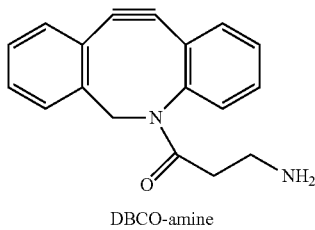 [SMILES: NCCC(=O)N1Cc2ccccc2C#Cc2ccccc21]

DBCO-amine

ChADC1 antibodies and the DBCO lysine-based linker were reacted in the presence of BTG to modify antibodies. The light chain remained unaffected. Quantitative enzymatic modification of chADC1 heavy chain with short DBCO lysine-based linker by BTG could not be accomplished, only unmodified chADC1 heavy chain was found. Following exploration of reaction conditions (see Example 3), optimized conditions were tested (80 eq ligand, 6 U/ml BTG, 1 mg/ml mAb, 37° C.) but coupling could not be achieved. Compared to biotin and dansyl linkers, the DBCO has a possibly more rigid structure, notably containing a polycycle, notably a tri-cycle group in proximity to the site of BTG activity.

5. Coupling of Linker with TAMRA Payload is Unsuccessful

The chemical structure of a TAMRA lysine-based linker is shown below.

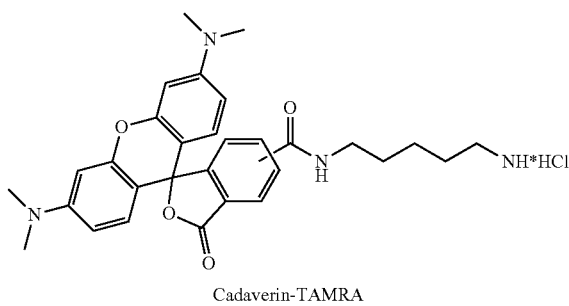

Cadaverin-TAMRA

ChADC1 antibodies and TAMRA lysine-based linker were reacted in the presence of BTG to modify antibodies. The light chain remained unaffected. Quantitative enzymatic modification of chimADC1 heavy chain with short TAMRA lysine-based linker by BTG could not be accomplished, only unmodified chADC1 heavy chain was found. Following exploration of reaction conditions (see Example 3), optimized conditions were tested (80 eq ligand, 6 U/ml BTG, 1 mg/ml mAb, 18 h at 37° C.) but at best only partial coupling could be achieved, with about 50% of all heavy chains having a linker coupled thereto. Compared to biotin and dansyl, TAMRA has a higher molecular weight, has a possibly more rigid and hydrophobic structure, notably containing a polycycle, notable a tri-cycle and a cyclic group in proximity to the site of BTG activity.

Example 3

Discovery of Optimized Reaction Conditions for BTG

Despite improvement with spacers, large and/or hydrophobic organic molecules representative of cytotoxic drugs are not able to be coupled by BTG onto acceptor glutamines quantitatively (complete coupling). To explore the possibility that optimized reactions might permit quantitative coupling reaction parameters were explored.

All the experiments were performed on chADC1 deglycosylated with PNGase F. Antibody concentration was to 1 mg/mL for all experiments. All the experiments were performed using 6 U/mL of BTG. All reactions were monitored by HIC analysis and LC-MS. Samples for HIC analysis were taken after time periods and directly injected in HIC. Samples for MS analysis were frozen to stop the reaction.

Figure 18A:
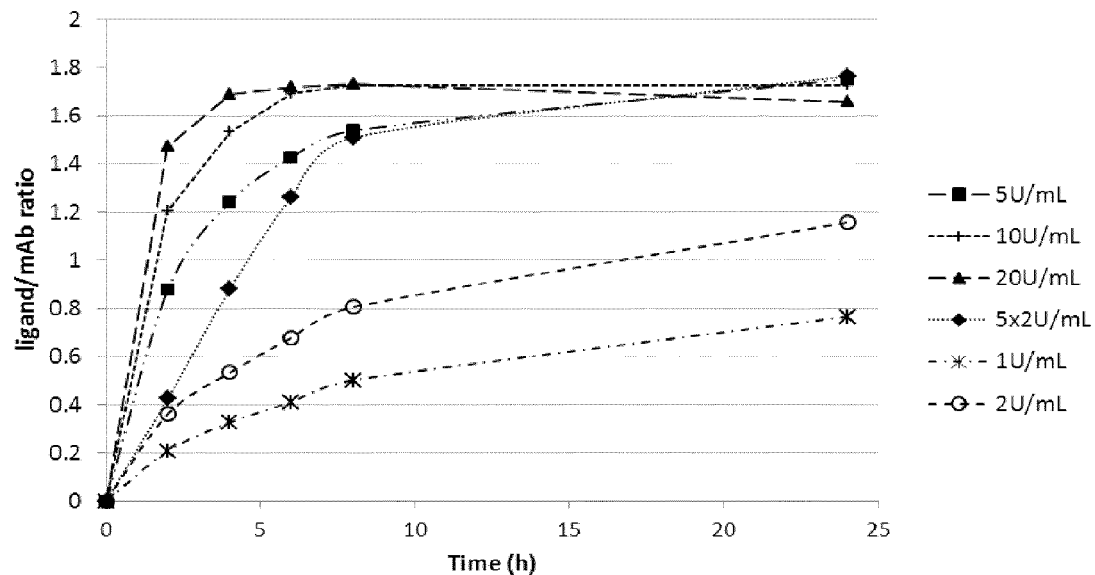
FIGS. 18A-18G shows optimized conditions for BTG coupling, including BTG concentrations (18A), pH (18B and 18C), temperature (18D and 18E), and substrate stoichiometry (18F and 18G).

First, the effect of enzyme concentrations was investigated. FIG. 18A depicts the labeling of chADC1 at different concentrations of BTGase. Higher labeling yields were achieved with increasing enzyme concentrations for BTGase. The following exploration of reaction conditions then used optimized conditions (6 U/ml BTG, 1 mg/ml mAb, 18 h) at which a plateau was reached for conjugation.

Figure 18B:
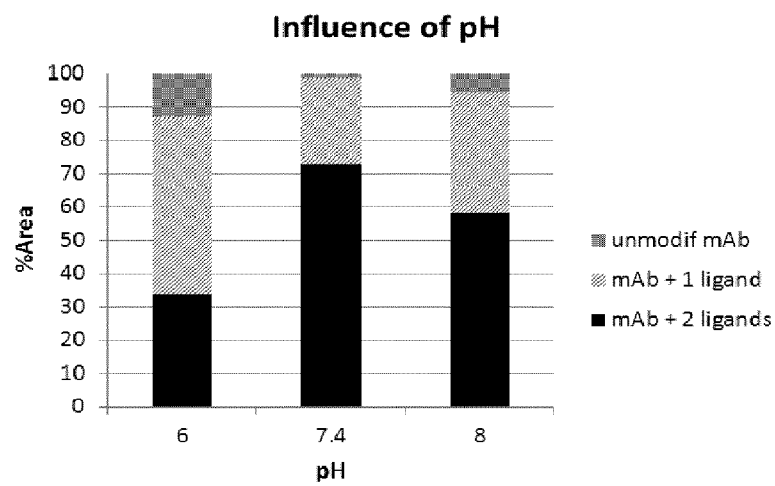
Figure 18C:
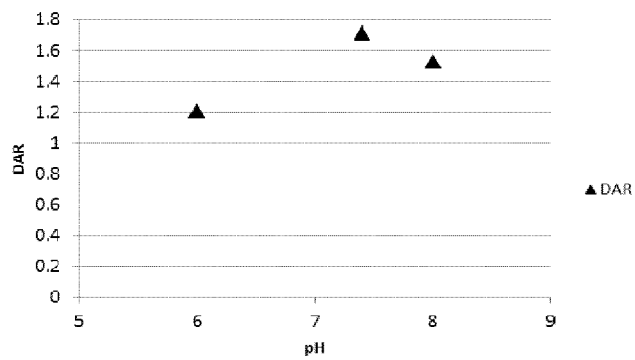

We then investigated the effect of the pH of the reaction media on the enzymatic labeling. FIGS. 18B and 18C show the labeling degrees achieved at different pH values by the BTG-mediated modification of the antibody. The most efficient labeling was detected at neutral reaction conditions (pH 7.4).

Figure 18D:
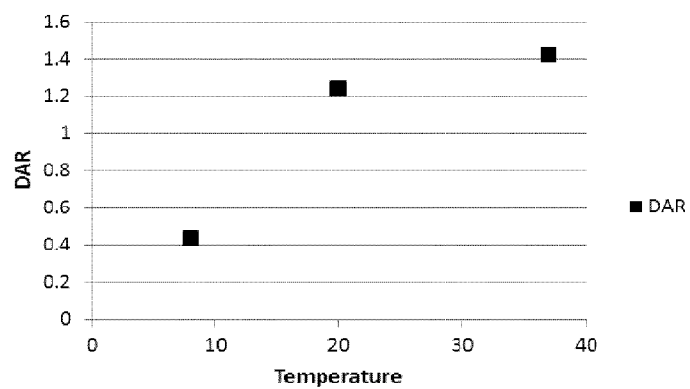
Figure 18E:
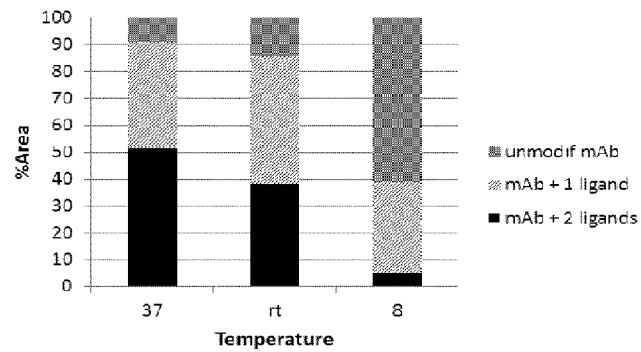

Next, the effect of temperature was investigated. FIGS. 18D and 18E depict the labeling of chADC1 at different temperatures. Higher labeling yields were achieved at 37° C.

Figure 18F:
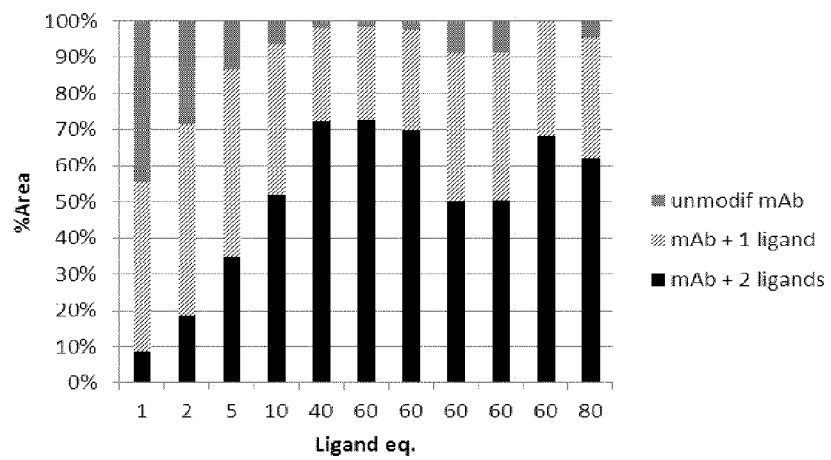
Figure 18G:
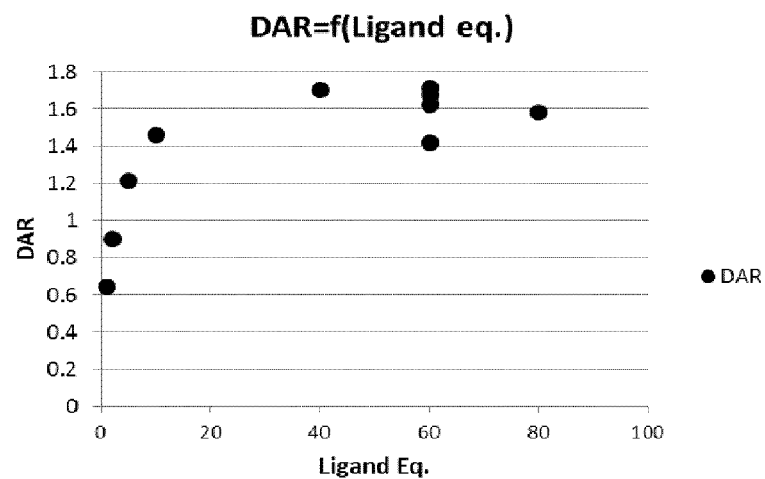

As a further parameter for optimization, we examined the effect of the substrate stoechiometry. FIGS. 18F and 18G show the labeling of chADC1 with BTG employing varying amount of dansyl-cadaverin substrate. Increasing amount of the substrate resulted in a higher labeling yield. The best labeling of the antibody was achieved with dansyl-cadaverin substrate above 40 eq/mAb. Because of the limited solubility of the dansyl-cadaverin in aqueous buffer (containing a maximum of 10% DMSO), higher concentrations could not be investigated.

Example 4

Improved Lysine-based Linkers for BTG-mediated Direct Coupling

To explore the possibility that large, charged or hydrophobic groups close to the site of BTG coupling (i.e. the primary amine) influences and inhibits BTG coupling efficiency, linkers having linear carbon-containing frameworks acting as spacers were tested.

1. Coupling of DOTA Linkers with Spacer Group

The chemical structure of a spacer-containing thiol linker coupled to maleimide-DOTA (1,4,7,10-tetraazacyclododecane-1,4,7,10-tetraacetic acid) and a short linker were compared (for preparation see Example 1). The molecular weights are indicated below the structures.

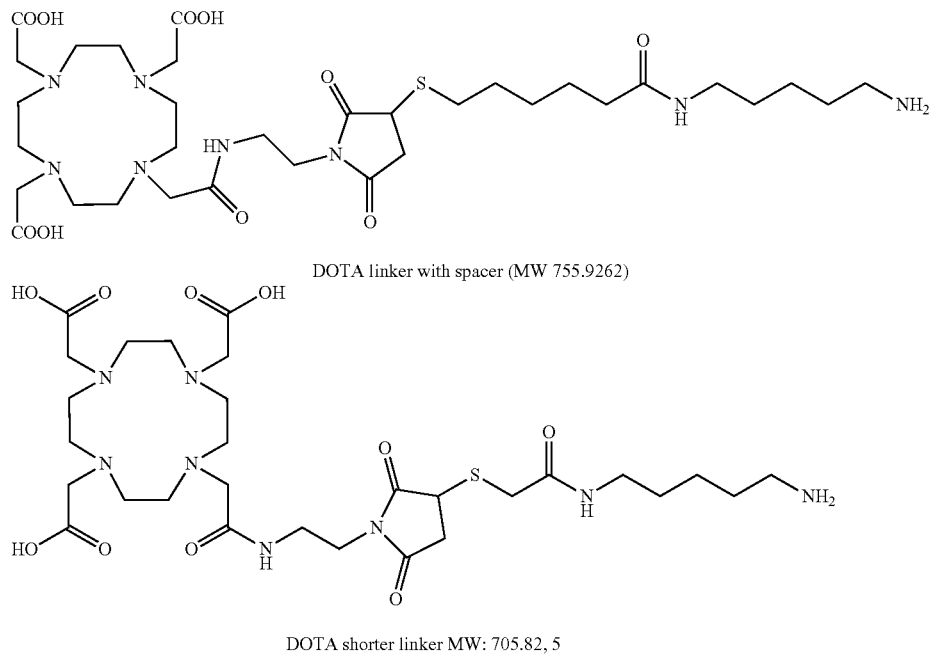

DOTA linker with spacer (MW 755.9262)

DOTA shorter linker MW: 705.82, 5

ChADC1 antibodies and short DOTA linker (see Example 2, part 3, referred to as C2-DOTA) or DOTA linker comprising a 6-carbon spacer (referred to as C6-DOTA) were reacted in the presence of BTG to modify antibodies. Following exploration of reaction conditions (see Example 3), optimized conditions were used (80 eq ligand, 6 U/ml BTG, 1 mg/ml mAb, 18 h at 37° C.).

Figure 19:
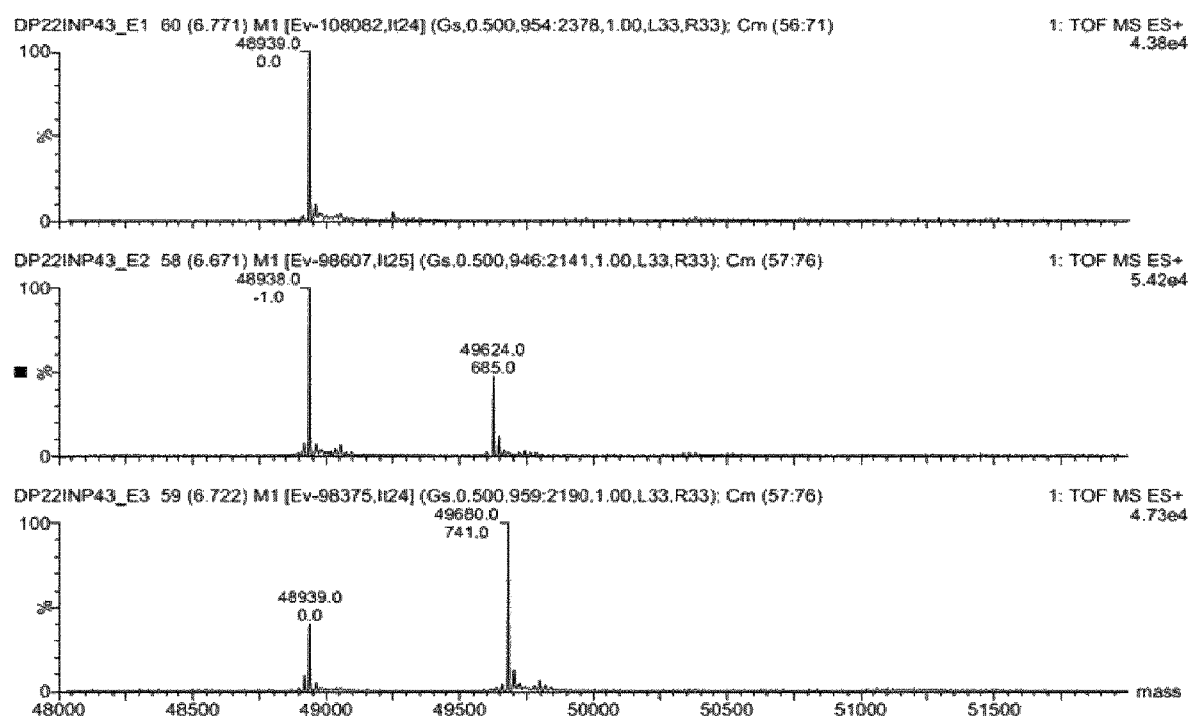
FIG. 19 shows improved enzymatic modification of deglycosylated chimeric antibody heavy chain C6-DOTA linker by BTG, compared to C2-DOTA linker.

Quantitative enzymatic modification of chADC1 heavy chain with C2-DOTA linker by BTG could not be accomplished and primarily unmodified chADC1 heavy chain was found, with a major peak corresponding to unmodified heavy chain (70%) and a minor peak to heavy chain with one C2-DOTA (30%). C6-DOTA linker comprising a 6-carbon spacer however achieved significantly improved coupling, with a major peak corresponding to heavy chain with one C6-DOTA (70%) and a minor peak corresponding to unmodified heavy chain (30%). Results are shown in FIG. 19.

Example 5

The Environment of the Acceptor Glutamine in the Heavy Chain Influences BTG Coupling Despite improvement with spacers, large and/or hydrophobic organic molecules representative of cytotoxic drugs could not be coupled by BTG onto acceptor glutamines of deglycosylated chADC1 quantitatively (complete coupling). To explore the possibility that the environment, in terms of amino acids of the antibody, at the site of BTG-mediated coupling influences and inhibits BTG coupling efficiency, modified antibodies having amino acid substitutions were tested.

Antibodies treated with PNGaseF to remove N297-linked glcoyslation will have an aspartic acid at residue 297 as a result of PNGaseF-induced deamidation at the asparagine. Three antibodies having N297S substitutions were generated which avoided N297-linked glycosylation and avoided an aspartic acid or other negatively charged residue: chADC1, SGN-35 (anti-CD30) and chCE7. The modified antibodies comprise a single acceptor glutamine at position Q295 on each heavy chain and do not require PNGaseF treatment to remove N297-linked glycans prior to coupling with BTG (the presence of N-linked glycosylation on antibodies interferes with BTG coupling).

Unmodified (N297), PNGaseF-deglycosylated chADC1 antibodies were reacted with the cadaverin-fluorescein linker in the presence of BTG to modify antibodies using optimized reaction conditions (80 eq ligand, 6 U/ml BTG, 1 mg/ml mAb, 37° C.). Quantitative enzymatic modification of chADC1 heavy chain with cadaverin-fluorescein linker by BTG could not be accomplished. Only partial modification of chADC1 heavy chains was found, with a substantial peak corresponding to unmodified heavy chains. However, when N297S chADC1 mutant antibodies were reacted with the cadaverin-fluorescein linker in the presence of BTG, high levels of coupling was observed, with a major peak corresponding to heavy chain with one cadaverin-fluorescein linker (80%) and a minor peak to unmodified heavy chains (20%).

In another experiment, unmodified (N297), PNGaseF-deglycosylated chADC1 antibodies were reacted with the cadaverin-TAMRA linker in the presence of BTG to modify antibodies using optimized reaction conditions (80 eq ligand, 6 U/ml BTG, 1 mg/ml mAb, 37° C.). Quantitative enzymatic modification of chADC1 heavy chain with cadaverin-TAMRA linker by BTG could not be accomplished. Partly modified chADC1 heavy chain was found, with a substantial peak corresponding to unmodified heavy chain. However, when modified N297S chADC1 antibodies were reacted with the cadaverin-TAMRA linker in the presence of BTG, quantitative coupling was achieved, with a peak corresponding to heavy chains with one cadaverin-TAMRA linker and no uncoupled heavy chains.

In another experiment, the chemical structure of a spacer-containing linker having a representative large cytotoxic drug used in antibody drug conjugates was tested. The linker comprises the monomethyl auristatin F (MMAF), as well as a valine-citrulline dipeptide spacer, a 6-carbon spacer and a PAB self-elimination spacer. The structure is shown below. The molecular weight is indicated below the structure.

the Fc domain of the antibody. The findings therefore open the possibility to use modified antibodies where aspartic acids are no longer present at the +2 position for the coupling of large and/or hydrophobic molecules to antibodies, or more generally to modify antibodies to avoid negative electrical charges adjacent to the acceptor glutamine, notably at the +2 position.

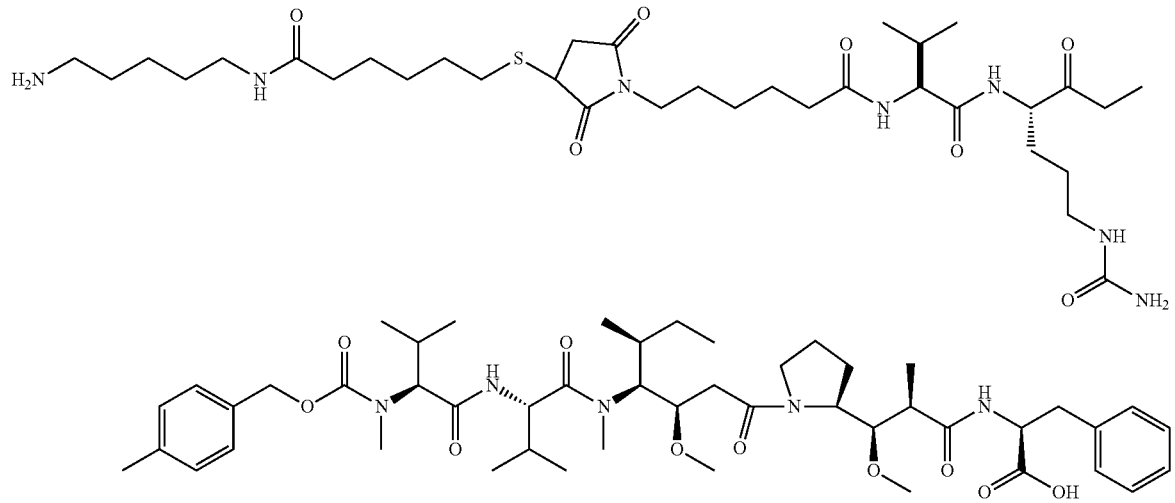

Chemical formula: $C_{192}H_{128}N_{12}O_{17}S$
Exact mass: 1560.9241
Molecular weight: 1562.0375

Unmodified (N297), PNGaseF deglycosylated chADC1 and chCE7 antibodies were reacted with the MMAF linker in the presence of BTG to modify antibodies using optimized reaction conditions (80 eq ligand, 6 U/ml BTG, 1 mg/ml mAb, 37° C.). Quantitative enzymatic modification of chADC1 heavy chain with MMAF linker by BTG could not be accomplished. Primarily unmodified chADC1 or chCE7 heavy chain was found, with a major peak corresponding to unmodified heavy chain (70%) and a minor peak to heavy chain with one MMAF linker (30%) for chADC1 and a major peak corresponding to unmodified heavy chain (81%) and a minor peak to heavy chain with one MMAF linker (19%) for chCE7.

Figure 20A:
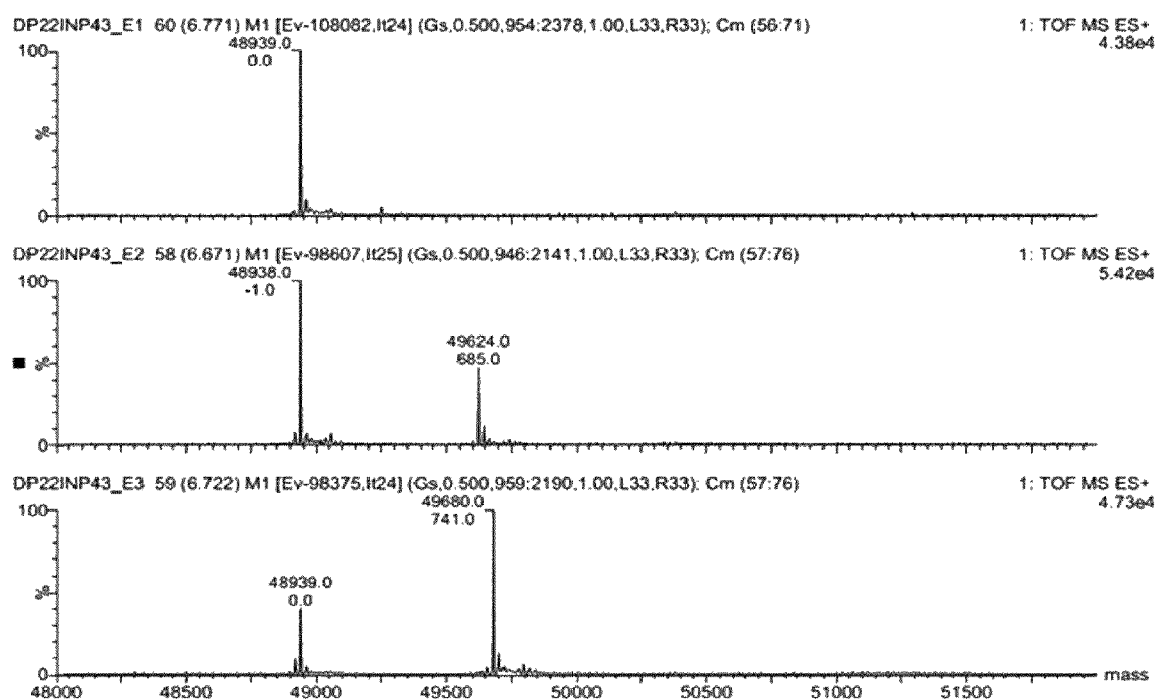
FIG. 20A shows the MS spectrum of chADC1dgl coupled to C6-Maleimide-vc-PAB-MMAF.
Figure 20B:
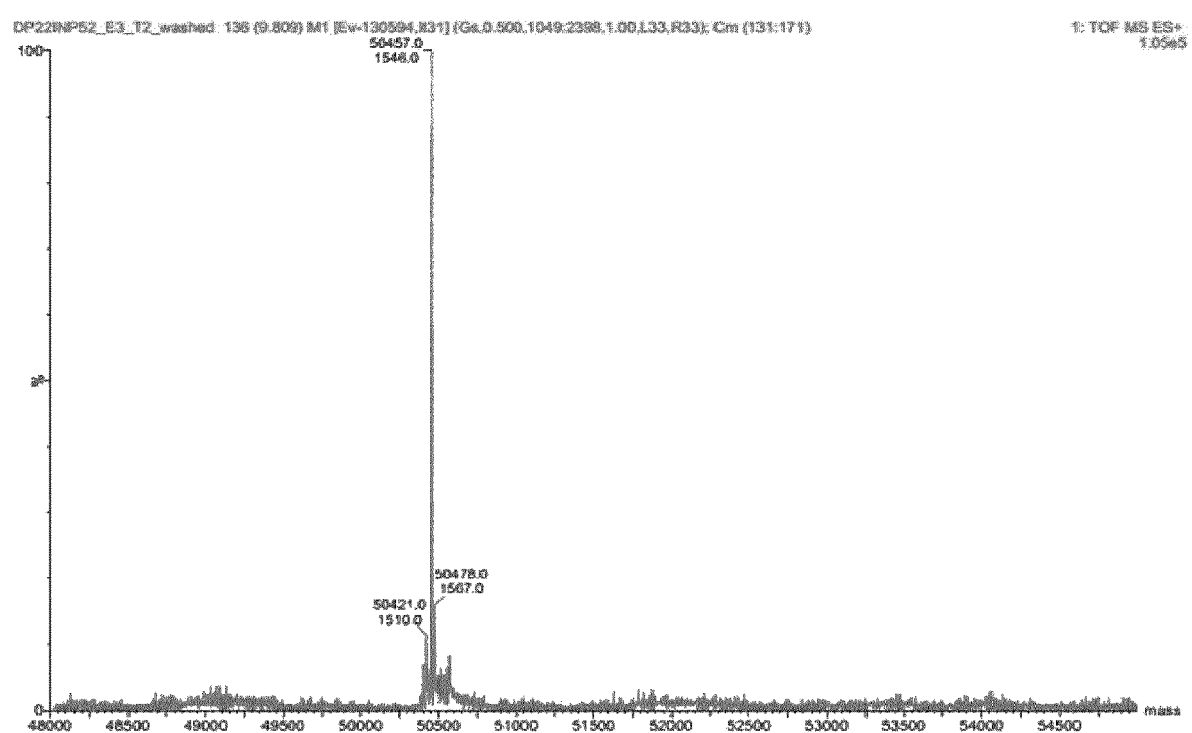
FIG. 20B shows the MS spectrum of chADC1N297S coupled to C6-Maleimide-vc-PAB-MMAF.

However, when modified N297S chADC1 antibodies were reacted with the MMAF linker in the presence of BTG achieved, quantitative coupling was achieved, with a major peak corresponding to heavy chains with one MMAF linker (greater than 90%). The MS spectrum of chADC1 coupled to C6-Maleimide-vc-PAB-MMAF is shown in FIG. 20A and the MS spectrum of chADC1 N297S coupled to C6-Maleimide-vc-PAB-MMAF is shown in FIG. 20B.

PNGaseF treatment modifies the side chain of the asparagine at position 297 such that an aspartic acid is present at position 297 following PNGaseF treatment. It is believed that BTG activity is inhibited by negative electrical charges. One possible explanation is therefore that a negative electrical charge at the amino acid residue at the +2 position relative to the acceptor glutamine inhibits BTG's ability to couple onto the glutamine within the particular context of Example 6

Analysis of Variable Region Glutamines

Figure 21A:
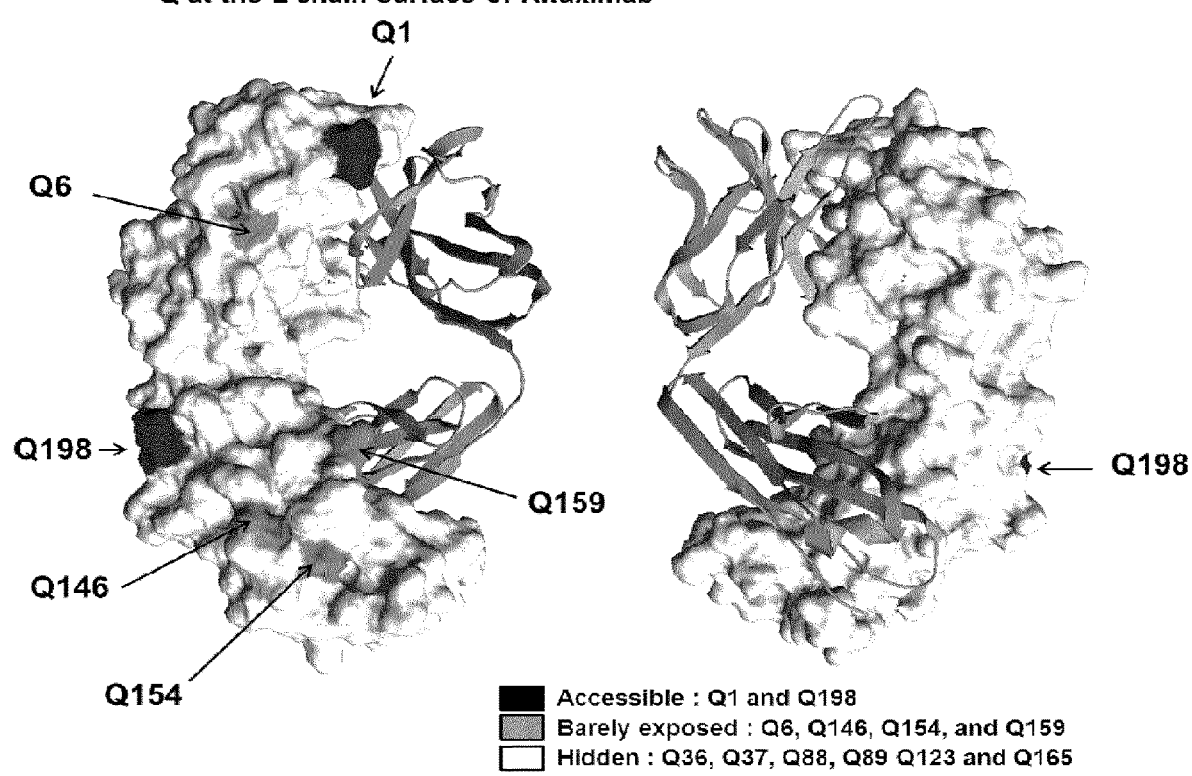
FIG. 21A shows a surface map showing the light chain surface of rituximab (anti-CD20) as a Fab.
Figure 21B:
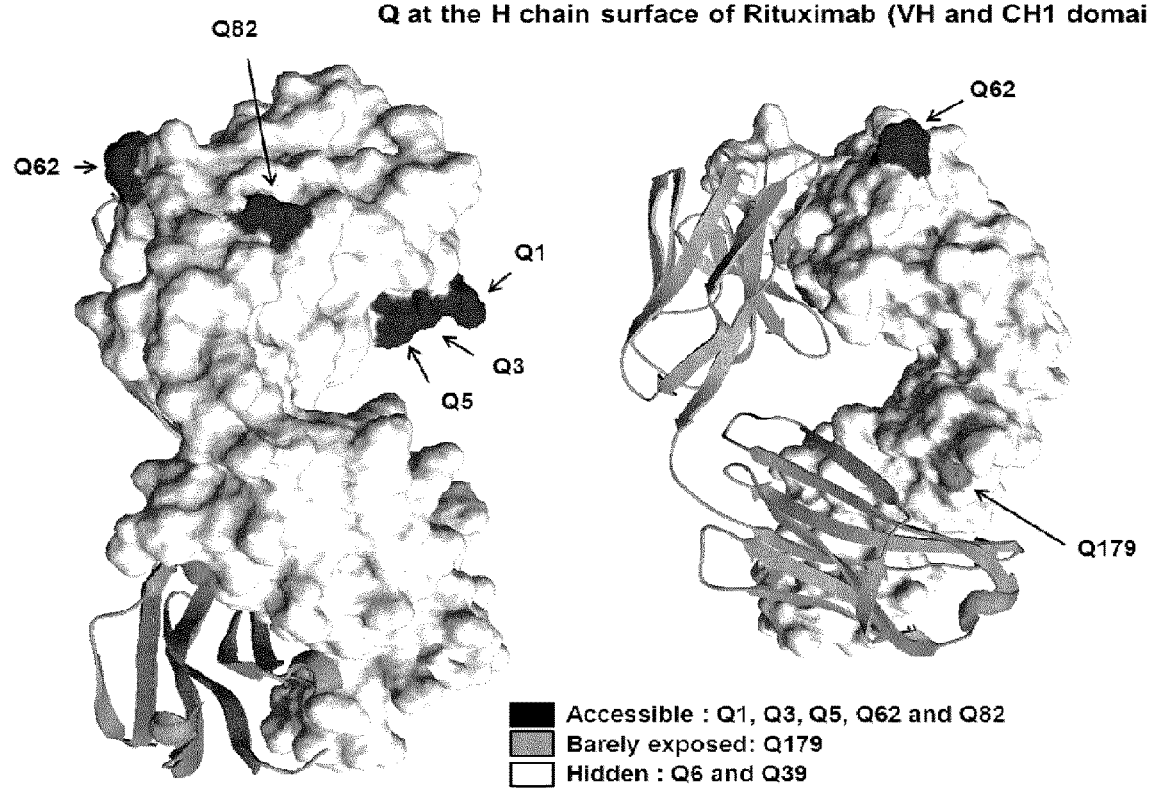
FIG. 21B shows a surface map showing the heavy chain surface of rituximab (anti-CD20) as a Fab.
Figure 22A:
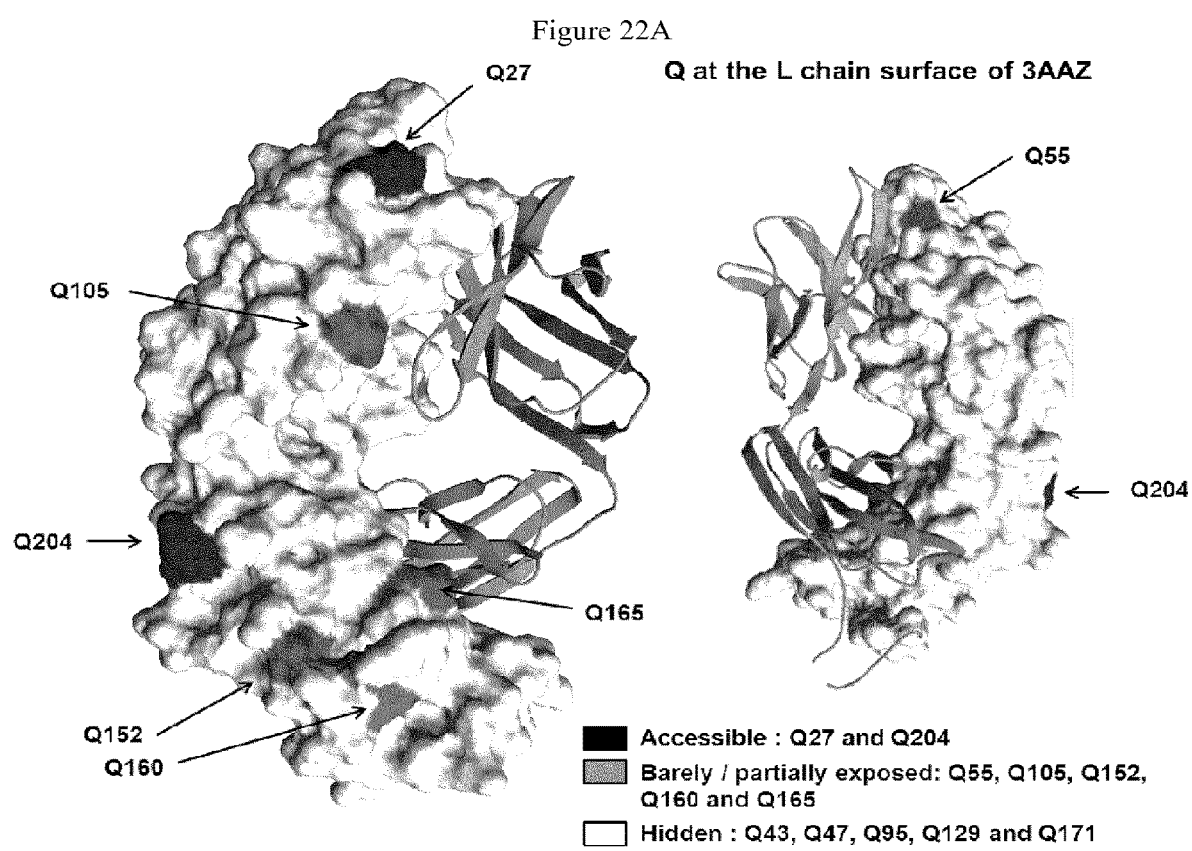
FIG. 22A shows a surface map showing the light chain surface of a human antibody as a Fab.
Figure 22B:
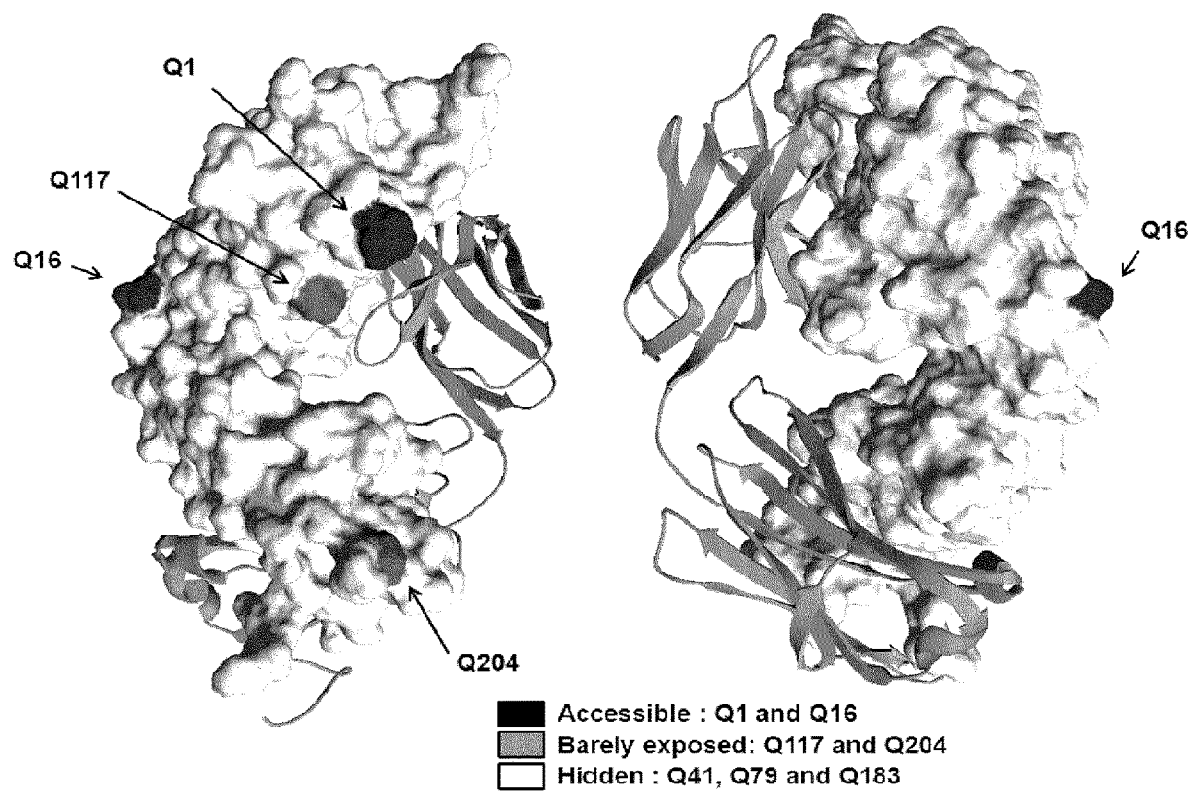
FIG. 22B shows a surface map showing the heavy chain surface of a human antibody as a Fab.

Antibodies rituximab (anti-CD20) and chCE7 had been previously conjugated at the Paul Scherrer Institute (Villigen, Switzerland) to a cadaverin linker via BTG. However, these antibodies appear relatively devoid of solvent-exposed glutamines in various variable regions. chCE7 does not have any glutamines at all in CDRs (see SEQ ID NOS: 1 and 2 for chCE7 heavy and light chain variable regions). For rituximab, crystal structures are available, and while rituximab has glutamines in its CDR at positions 88 and 89 of the CK chain, these positions correspond to the VL-VH interface are buried and therefore not accessible for conjugation with BTG. Other than N terminal glutamines at positions 1-6, rituximab has no accessible glutamines in the VL and has glutamine at positions 62 and 82 in the VH. FIG. 21A shows a surface map of rituximab Fab, with the L chain surface map shown; FIG. 21B shows a surface map of rituximab Fab, with the H chain surface map shown.

All human variable region light chain V segment genes, including known alleles, were analyzed revealing that human antibodies can (depending on the V segment used, alleles and potential somatic mutation) present surface glutamines that are solvent exposed at Kabat positions 27, 47, 55 and 105. Glutamines are additionally present in human light chain V genes giving rise to glutamines in the variable region at Kabat positions 3, 6, 11, 17, 18, 37, 38, 42, 45, 49, 50, 53, 79, 89, 90 and 93. All human variable region heavy chain V segment genes, including known alleles, were analyzed revealing that human antibodies can (depending on the V segment used, alleles and potential somatic mutation)

present surface glutamines that are solvent exposed at positions 1, 16 and 204. Glutamines are additionally present in human light chain V genes giving rise to glutamines in the variable regions at Kabat residues 3, 5, 6, 10, 11, 12, 13, 16, 19, 35, 38, 39, 43, 35, 36, 50, 61, 64, 66, 73, 75, 77, 83, 85 and 94.

Analysis of chADC1 showed at least one glutamine residue in each CDR of the light chain, at Kabat positions 27 (CDR-L1), 55 (CDR-L2) and 90 (CDR-L3), thus including in particular residues 27 and 55 corresponding to accessible solvent exposed glutamines present at high frequencies in humans. chADC1 also showed heavy chain glutamines, including in the heavy chain at Kabat residues 13, 39 (39 is in the VH-VL and thus hidden) and 109. However, only constant region glutamine at position 295 was conjugated in chADC1. FIG. 21 shows a surface map of a public domain 3AAZ Fab to show amino acid positions of residues in chADC1, with the L chain surface map shown in FIG. 21A and the H chain surface map in FIG. 21B (note that for the H chain, residues 16 and 41 are shown in 3AAZ, which are similar in position in the molecule to 13 and 39 in chADC1; alternative models with glutamine positions at 13 and 39 can be visualized using PDB reference antibody 1AD0).

At conditions were BTG-mediated coupling is partial (when non-optimal conditions are used such as 1 unit of BTG/ml), TGase will not couple accessible surface and solvent-exposed glutamines present in variable regions, including in CDRs and including surface-accessible present in human antibodies, yet will couple acceptor glutamines in the constant regions. At conditions where complete coupling of the acceptor glutamine at residue 295 is achieved (80 eq ligand, 6 U/ml BTG, 1 mg/ml mAb, 18 h at 37° C.) TGase will achieve complete coupling on an acceptor glutamine in the constant regions yet will not couple accessible surface and solvent-exposed glutamines present across human variable regions, including when CDRs with surface-accessible are present.

Example 7

BTG-mediated Coupling of Substrates to Human Antibodies

Materials and Methods

Dansyl-cadaverin, biotin-cadaverin and bacterial TGase (recombinant bacterial transglutaminase, gene derived from *streptomyces mobaraensis*, BTG) were purchased from Zedira, Darmstadt, Germany. Polyclonal antibody (from serum Human AB Male) was purchased from Biowest.

Deglycosylation of Antibody

Antibody in PBS buffer (1 mg/mL) was incubated with 100 Units/mg protein of N-glycosidase F (PNGase F) from *Elizabethkingia meningosepticum* (Sigma) overnight at 37° C. The enzyme was then removed by centrifugation-dialysis (Vivaspin MWCO 50 kDa, Sigma).

General Coupling Reaction Conditions

Antibody (1 mg/mL), substrate (dansyl-cadaverin 400 µM or biotin-cadaverin 530 µM) and bacterial transglutaminase (6 U/mL; Zedira, Darmstadt, Germany) were mixed in PBS buffer (pH 7.4). The reaction was heated at 37° C. until steady-state conditions were achieved. Excess ligand and enzyme were then removed using centrifugation-dialysis (Vivaspin MWCO 50 kDa, Sigma-Aldrich). Reactions are monitored by HIC or LC/MS.

Western Blot Analysis

Western blot analysis: Enzymatically modified antibodies were subjected to SDS-PAGE and were tansferred to poly-vinylidene difluoride (PVDF) membranes (Immobilon P, Millipore). After blocking with 2% bovine serum albumine (BSA) in TBST (20 mM Tris-HCl, pH 7.5, 140 mM NaCl, 0.05% Tween-20) for 2 hour at room temperature (RT), membrane was incubated with Strepavidin-horseradish peroxidase conjugate (High Sensitivity Strepavidin-HRP diluted 1:20000; Beclkmnan Coulter) for 30 min. Membrane was washed three times with TBST for 15 min and antibodies were detected with Immune-Star Western C Kit chemiluminescence substrate from Biorad.

Results

The selectivity of BTG coupling with respect to labeling of the heavy and light chain of a diverse range of human antibodies of various isotypes was studied by reacting human polyclonal antibodies with biotin-cadaverin as substrate in the presence of BTG. All human gamma isotypes have a glutamine at residue 295 (Kabat EU Index) of the heavy chain constant region and thus can potentially have an acceptor glutamine in each heavy chain.

In order to assess unwanted labeling onto variable regions of antibodies, including at higher concentrations of BTGase that permit complete functionalization of acceptor glutamines (6 U/mL BTGase), polyclonal human antibody was reacted without prior PNGaseF deglycosylation which will serve to mask conjugation onto acceptor glutamines located in CH2 domains but not variable regions, and results were observed on SDS-PAGE. SDS-PAGE analysis of the conjugates revealed lack of substantial labeling of the heavy chain of the antibodies. Thus, BTG does not functionalize glutamines present within the variable regions of the antibodies.

In order to assess labeling onto constant region acceptor glutamines of antibodies, polyclonal human antibody was deglycosylated using PNGaseF deglycosylation, and results were observed on SDS-PAGE. SDS-PAGE analysis of the conjugates revealed that the enzymatic reaction resulted in an substantially exclusive labeling of the heavy chain of the antibodies. Taken together with results observed with antibody chADC1, BTG functionalizes glutamines present within the constant regions of the human antibodies throughout the mixture of different antibodies and gamma isotypes (i.e. IgG1, IgG2, IgG3 and IgG4).

All headings and sub-headings are used herein for convenience only and should not be construed as limiting the invention in any way. Any combination of the above-described elements in all possible variations thereof is encompassed by the invention unless otherwise indicated herein or otherwise clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e. g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as reference to an element or elements is intended to provide support for a similar aspect or embodiment of the invention that "consists of," "consists essentially of" or "substantially comprises" that particular element or elements, unless otherwise stated or clearly contradicted by context (e. g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

---

The invention claimed is:

1. A human or humanized antibody comprising one or more solvent-exposed glutamine residues in a variable region and at least one acceptor glutamine residue in its constant region or in a sequence fused to a variable or constant region, wherein said one or more solvent-exposed glutamine residues are present in a light chain variable domain (VL) CDR at a Kabat position selected from the group consisting of 27, 55, and a combination thereof,
wherein said antibody is conjugated via said acceptor glutamine residue to one or more moieties-of-interest (Z) through a linker that comprises a NH—$(C)_n$— moiety,
wherein
$(C)_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide, and n is an integer selected from among the range of 2 to 20;
Z is a reactive moiety or a moiety that improves the pharmacokinetic properties, a therapeutic moiety or a diagnostic moiety, and
wherein the antibody comprises heavy chain variable region sequence selected from the group consisting of SEQ ID NOs: 3-239 and light chain variable region sequence selected from group consisting of SEQ ID NO: 240-299.

2. The antibody of claim 1, wherein the antibody is a tetrameric antibody and said constant region is a heavy chain constant region.

3. The antibody of claim 1, wherein the antibody comprises:
a heavy chain framework region 1 (FR-H1) comprising a glutamine residue at Kabat position 1, 3, 5, 6, 10, 11, 12, 13 and/or 16;
a heavy chain framework region 2 (FR-H2) comprising a glutamine residue at Kabat position 38, 39, 43 and/or 45;
a heavy chain framework region 3 (FR-H3) comprising a glutamine residue at Kabat position 66, 75, 77, 81 and/or 85;
a heavy chain framework region 1 (CDR-H1) comprising a glutamine residue at Kabat position 26 and/or 35; and/or
a heavy chain framework region 2 (CDR-H2) comprising a glutamine residue at Kabat position 50, 52, 56, 61 and/or 64, wherein said glutamine residue is not an acceptor glutamine.

4. A composition comprising a plurality of human or humanized antibodies of claim 1, wherein each of said human or humanized antibodies comprises one acceptor glutamine on each heavy chain, wherein at least 80% of the antibodies in the composition comprise on each heavy chain one functionalized acceptor glutamine residue (Q) having Formula IVa, (Q)-NH—$(C)_n$—X-L- (V—$(Y—(Z)_z)_q)_r$    Formula IVa, or a pharmaceutically acceptable salt or solvate thereof, wherein:
Q is a glutamine residue present in the human or humanized antibody;
$(C)_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;
n is an integer selected from among the range of 2 to 20;
X is NH, O, S, absent, or a bond;
L is independently absent, a bond or a continuation of a bond, or a carbon comprising framework of 5 to 200 atoms substituted at one or more atoms;
r is an integer selected from among 1, 2, 3 or 4;
q is an integer selected from among 1 , 2, 3 or 4;
z is an integer selected from among 1, 2, 3 or 4; and
V is independently absent, a bond or a continuation of a bond, a non-cleavable moiety or a conditionally-cleavable moiety;
Y is independently absent, a bond or a continuation of a bond, or a spacer system which is comprised of 1 or more spacers; and
Z is a moiety that improves pharmacokinetic properties, a therapeutic moiety or a diagnostic moiety.

5. A composition comprising a plurality of human or humanized antibodies of claim 1, wherein each of said human or humanized antibodies comprises one acceptor glutamine on each heavy chain, wherein at least 80% of the antibodies in the composition comprise on each heavy chain two functionalized acceptor glutamine residues (Q) having Formula IVb, (Q)-NH—$(C)_n$—X-L-(V—$(Y-(M)_z)_q)_r$    Formula IVb or a pharmaceutically acceptable salt or solvate thereof, wherein:
Q is a glutamine residue present in the human or humanized antibody;
$(C)_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;
n is an integer selected from among the range of 2 to 20;
X is NH, O, S, absent, or a bond;
L is independently absent, a bond or a continuation of a bond, or a carbon comprising framework of 5 to 200 atoms substituted at one or more atoms;
r is an integer selected from among 1, 2, 3 or 4;
q is an integer selected from among 1 , 2, 3 or 4;

z is an integer selected from among 1, 2, 3 or 4; and
V is independently absent, a bond or a continuation of a bond, a non-cleavable moiety or a conditionally-cleavable moiety;
Y is independently absent, a bond or a continuation of a bond, or a spacer system which is comprised of 1 or more spacers; and
M is independently: R or (RR') -L'-(V'—(Y'—(Z)z')q')r'), wherein R is a reactive moiety, wherein each of L', V', Y', z', q', and r' are as defined for L, V, Y, z, q, and r, wherein RR' is an addition product between a reactive moiety R and a complementary reactive moiety R', and wherein Z is a moiety that improves pharmacokinetic properties, a therapeutic moiety or a diagnostic moiety.

6. The composition of claim 5, wherein the composition has a mean Z:antibody ratio of at least 1.5, wherein less than 10% of the antibodies comprise more than two moieties of interest (Z) per antibody and less than 25% comprise less than two moieties of interest (Z) per antibody.

7. A composition comprising a plurality of human or humanized antibodies of claim 1, wherein each of said human or humanized antibodies is linked to a moiety of interest (Z), wherein the composition has a mean Z: antibody ratio of at least 1.5 wherein less than 10% of the antibodies comprise more than two moieties of interest (Z) per antibody.

8. The composition of claim 7, wherein less than 25% comprise less than two moieties of interest (Z) per antibody.

9. The composition of claim 7, wherein the antibodies are linked to said moiety of interest (Z) via one functionalized acceptor glutamine on each heavy chain of the antibody.

10. A composition comprising a plurality of human or humanized antibodies of claim 1, wherein at least 80% of the antibodies in the composition comprise on each heavy chain one functionalized acceptor glutamine residue (Q) having Formula IVa or Formula IVb,

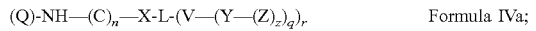   Formula IVa;

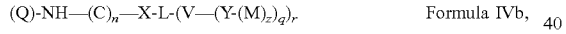   Formula IVb, or a pharmaceutically acceptable salt or solvate thereof, wherein:
Q is a glutamine residue present in the human or humanized antibody;
$(C)_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;
n is an integer selected from among the range of 2 to 20;
X is NH, O, S, absent, or a bond;
L is independently absent, a bond or a continuation of a bond, or a carbon comprising framework of 5 to 200 atoms substituted at one or more atoms;
r is an integer selected from among 1, 2, 3 or 4;
q is an integer selected from among 1 , 2, 3 or 4;
z is an integer selected from among 1, 2, 3 or 4; and
V is independently absent, a bond or a continuation of a bond, a non-cleavable moiety or a conditionally-cleavable moiety;
Y is independently absent, a bond or a continuation of a bond, or a spacer system which is comprised of 1 or more spacers;
Z is a moiety that improves pharmacokinetic properties, a therapeutic moiety or a diagnostic moiety; and
M is independently: R or (RR')-L'-(V'—(Y'—(Z)z')q')r'), wherein R is a reactive moiety, wherein each of L', V', Y', z', q', and r' are as defined for L, V, Y, z, q, and r, and wherein RR' is an addition product between a reactive moiety R and a complementary reactive moiety R'.

11. A composition comprising a plurality of human or humanized antibodies of claim 1, wherein each of the human or humanized antibodies comprises in a constant region or in a sequence fused to a variable region a functionalized acceptor glutamine linked to a moiety of interest (Z), wherein the composition is characterized by a mean Z: antibody ratio of at least 3.2, wherein less than 10% of the antibodies comprise more than two moieties of interest (Z) per antibody.

12. The composition of claim 11, wherein the antibodies are linked to said moiety of interest (Z) via two functionalized acceptor glutamines on each heavy chain of the antibody.

13. A composition comprising a plurality of human or humanized antibodies of claim 1, wherein at least 80% of the antibodies in the composition comprise on each heavy chain two functionalized acceptor glutamine residues (Q) having Formula IVa or Formula IVb,

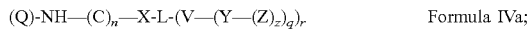   Formula IVa;

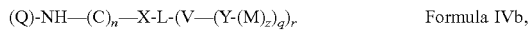   Formula IVb, or a pharmaceutically acceptable salt or solvate thereof, wherein:
Q is a glutamine residue present in the human or humanized antibody;
$(C)_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;
n is an integer selected from among the range of 2 to 20;
X is NH, O, S, absent, or a bond;
L is independently absent, a bond or a continuation of a bond, or a carbon comprising framework of 5 to 200 atoms substituted at one or more atoms;
r is an integer selected from among 1, 2, 3 or 4;
q is an integer selected from among 1 , 2, 3 or 4;
z is an integer selected from among 1, 2, 3 or 4; and
V is independently absent, a bond or a continuation of a bond, a non-cleavable moiety or a conditionally-cleavable moiety;
Y is independently absent, a bond or a continuation of a bond, or a spacer system which is comprised of 1 or more spacers;
Z is a moiety that improves pharmacokinetic properties, a therapeutic moiety or a diagnostic moiety; and
M is independently: R or (RR')-L'-(V'—(Y'—(Z)z')q')r'), wherein R is a reactive moiety, wherein each of L', V', Y', z', q', and r' are as defined for L, V, Y, z, q, and r, and wherein RR' is an addition product between a reactive moiety R and a complementary reactive moiety R'.

14. The antibody of claim 1, wherein Z is a hydrophobic compound.

15. The antibody of claim 1, wherein Z is an organic compound having a molecular weight of at least 400 g/mol.

16. The antibody of claim 1, wherein Z is an organic compound having a molecular weight of at least 500 g/mol.

17. The antibody of claim 1, wherein Z is a negatively charged compound.

18. The antibody of claim 1, wherein said constant region is a human constant region.

19. The antibody of claim 1, wherein said functionalized or conjugated acceptor glutamine residue(s) (Q) has a structure of Formula IVa,

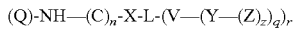   Formula IVa or a pharmaceutically acceptable salt or solvate thereof, wherein:
Q is a glutamine residue present in the human or humanized antibody;
$(C)_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;
n is an integer selected from among the range of 2 to 20;
X is NH, O, S, absent, or a bond;
L is independently absent, a bond or a continuation of a bond, or a carbon comprising framework of 5 to 200 atoms substituted at one or more atoms;
r is an integer selected from among 1, 2, 3 or 4;
q is an integer selected from among 1, 2, 3 or 4;
z is an integer selected from among 1, 2, 3 or 4; and
V is independently absent, a bond or a continuation of a bond, a non-cleavable moiety or a conditionally-cleavable moiety;
Y is independently absent, a bond or a continuation of a bond, or a spacer system which is comprised of 1 or more spacers; and
Z is a moiety that improves pharmacokinetic properties, a therapeutic moiety or a diagnostic moiety.

20. The antibody of claim 1, wherein said functionalized or conjugated acceptor glutamine residue(s) (Q) has a structure of Formula II:

   Formula II or a pharmaceutically acceptable salt or solvate thereof, wherein:
Q is a glutamine residue present in the human or humanized antibody;
$(C)_n$ is a substituted or unsubstituted alkyl or heteroalkyl chain, optionally wherein any carbon of the chain is optionally substituted with alkoxy, hydroxyl, alkylcarbonyloxy, alkyl-S—, thiol, alkyl- C(O)S—, amine, alkylamine, amide, or alkylamide;
n is an integer from among the range of 2 to 20;
X is NH, O, S, absent or a bond;
L is independently absent, a bond or a continuation of a bond, or a carbon comprising framework of 1 to 200 atoms substituted at one or more atoms, optionally wherein the carbon comprising framework comprises a linear framework of 3 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;
r is an integer selected from among 1, 2, 3 or 4;
q is an integer selected from among 1, 2, 3 or 4;
z is an integer selected from among 1, 2, 3 or 4; and
V is independently absent, a bond or a continuation of a bond, a non-cleavable moiety or a conditionally-cleavable moiety;
Y is independently absent, a bond or a continuation of a bond, or a spacer system which is comprised of 1 or more spacers; and
R is a reactive moiety.

21. The antibody of claim 1, wherein V is a conditionally-cleavable moiety following prior conditional transformation, which can be cleaved or transformed by a chemical, photochemical, physical, biological, or enzymatic process, such as a di-, tri-, tetra-, or oligopeptide.

22. The antibody of claim 1, wherein Z is a cytotoxic anti-cancer agent.

23. The antibody of claim 22, wherein Z is selected from the group consisting of taxanes, anthracyclines, camptothecins, epothilones, mytomycins, combretastatins, vinca alkaloids, nitrogen mustards, maytansinoids, calicheamycins, duocarmycins, tubulysins, amatoxins, dolastatins and auristatins, enediynes, radioisotopes, therapeutic proteins and peptides, and toxins or fragments thereof.

24. A pharmaceutical composition comprising an antibody of claim 1, and a pharmaceutically acceptable carrier.

* * * * *

SEQUENCE LISTING

```
<160> NUMBER OF SEQ ID NOS: 299

<210> SEQ ID NO 1
<211> LENGTH: 450
<212> TYPE: PRT
<213> ORGANISM: Artificial
<220> FEATURE:
<223> OTHER INFORMATION: Murine VH fused to human CH

<400> SEQUENCE: 1

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Gly Tyr
                20                  25                  30

Trp Met His Trp Val Lys Gln Arg Pro Gly His Gly Leu Glu Trp Ile
            35                  40                  45

Gly Glu Ile Asn Pro Ser Asn Gly Arg Thr Asn Tyr Asn Glu Arg Phe
        50                  55                  60

Lys Ser Lys Ala Thr Leu Thr Val Asp Lys Ser Ser Thr Thr Ala Phe
65                  70                  75                  80

Met Gln Leu Ser Gly Leu Thr Ser Glu Asp Ser Ala Val Tyr Phe Cys
                85                  90                  95

Ala Arg Asp Tyr Tyr Gly Thr Ser Tyr Asn Phe Asp Tyr Trp Gly Gln
                100                 105                 110

Gly Thr Thr Leu Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
```

```
                        245                 250                 255
Ser Arg Thr Pro Glu Val Thr Cys Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 2
<211> LENGTH: 214
<212> TYPE: PRT
<213> ORGANISM: Artificial
<220> FEATURE:
<223> OTHER INFORMATION: Murine VL fused to human VK

<400> SEQUENCE: 2

Asp Ile Gln Met Thr Gln Ser Ser Ser Phe Ser Val Ser Leu Gly
1               5                   10                  15

Asp Arg Val Thr Ile Thr Cys Lys Ala Asn Glu Asp Ile Asn Asn Arg
                20                  25                  30

Leu Ala Thr Tyr Gln Gln Thr Pro Gly Asn Ser Pro Arg Leu Leu Ile
            35                  40                  45

Ser Gly Ala Thr Asn Leu Val Thr Gly Val Pro Ser Arg Phe Ser Gly
        50                  55                  60

Ser Gly Ser Gly Lys Asp Tyr Thr Leu Thr Ile Thr Ser Leu Gln Ala
65                  70                  75                  80

Glu Asp Phe Ala Thr Tyr Tyr Cys Gln Gln Tyr Trp Ser Thr Pro Phe
                85                  90                  95

Thr Phe Gly Ser Gly Thr Glu Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
```

```
                145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                    195                 200                 205

Phe Asn Arg Gly Glu Cys
        210

<210> SEQ ID NO 3
<211> LENGTH: 98
<212> TYPE: PRT
<213> ORGANISM: Homo sapiens

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 4
<211> LENGTH: 92
<212> TYPE: PRT
<213> ORGANISM: Homo sapiens

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala
                85                  90

<210> SEQ ID NO 5
<211> LENGTH: 98
<212> TYPE: PRT
<213> ORGANISM: Homo sapiens

<400> SEQUENCE: 5

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Met Ala Val Tyr Tyr Cys
                85                  90                  95

Ala Arg

<210> SEQ ID NO 6
<211> LENGTH: 98
<212> TYPE: PRT
<213> ORGANISM: Homo sapiens

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg

<210> SEQ ID NO 7
<211> LENGTH: 98
<212> TYPE: PRT
<213> ORGANISM: Homo sapiens

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 8
<211> LENGTH: 98
<212> TYPE: PRT
<213> ORGANISM: Homo sapiens
<220> FEATURE:

-continued

```
<221> NAME/KEY: misc_feature
<222> LOCATION: (38)..(38)
<223> OTHER INFORMATION: Xaa can be any naturally occurring amino acid

<400> SEQUENCE: 8
```

Gln Val Gln Leu Val Gln Ser Gly Ala Glu Val Lys Lys Leu Gly Ala
1               5                   10                  15

Ser Val Lys Val Ser Cys Lys Ala Ser Gly Tyr Thr Phe Thr Gly Tyr
                20                  25                  30

Tyr Met His Trp Val Xaa Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

```
<210> SEQ ID NO 9
<211> LENGTH: 98
<212> TYPE: PRT
<213> ORGANISM: Homo sapiens

<400> SEQUENCE: 9
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Trp Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

```
<210> SEQ ID NO 10
<211> LENGTH: 98
<212> TYPE: PRT
<213> ORGANISM: Homo sapiens

<400> SEQUENCE: 10
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg

<210> SEQ ID NO 11
<211> LENGTH: 98
<212> TYPE: PRT
<213> ORGANISM: Homo sapiens

<400> SEQUENCE: 11

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr
```

<210> SEQ ID NO 12
<211> LENGTH: 98
<212> TYPE: PRT
<213> ORGANISM: Homo sapiens

<400> SEQUENCE: 12

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

<210> SEQ ID NO 13
<211> LENGTH: 98
<212> TYPE: PRT
<213> ORGANISM: Homo sapiens

<400> SEQUENCE: 13

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ser Asn Ala Gly Asn Gly Asn Thr Lys Tyr Ser Gln Glu Phe
    50                  55                  60
```

-continued

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
                85                  90                  95

Ala Arg

<210> SEQ ID NO 14
<211> LENGTH: 98
<212> TYPE: PRT
<213> ORGANISM: Homo sapiens

<400> SEQUENCE: 14

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Tyr Arg
                20                  25                  30

Tyr Leu His Trp Val Arg Gln Ala Pro Gly Gln Ala Leu Glu Trp Met
            35                  40                  45

Gly Trp Ile Thr Pro Phe Asn Gly Asn Thr Asn Tyr Ala Gln Lys Phe
        50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg

<210> SEQ ID NO 15
<211> LENGTH: 98
<212> TYPE: PRT
<213> ORGANISM: Homo sapiens

<400> SEQUENCE: 15

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Tyr Arg
                20                  25                  30

Tyr Leu His Trp Val Arg Gln Ala Pro Gly Gln Ala Leu Glu Trp Met
            35                  40                  45

Gly Trp Ile Thr Pro Phe Asn Gly Asn Thr Asn Tyr Ala Gln Lys Phe
        50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg

<210> SEQ ID NO 16
<211> LENGTH: 86
<212> TYPE: PRT
<213> ORGANISM: Homo sapiens

<400> SEQUENCE: 16

Lys Thr Gly Ser Ser Val Lys Val Ser Cys Lys Ala Ser Gly Tyr Thr
1               5                   10                  15

Phe Thr Tyr Arg Tyr Leu His Trp Val Arg Gln Ala Pro Arg Gln Ala
                20                  25                  30

Leu Glu Trp Met Gly Trp Ile Thr Pro Phe Asn Gly Asn Thr Asn Tyr

```
                35                  40                  45
Ala Gln Lys Phe Gln Asp Arg Val Thr Ile Thr Arg Asp Arg Ser Met
             50                  55                  60

Ser Thr Ala Tyr Met Glu Leu Ser Ser Leu Arg Ser Glu Asp Thr Ala
 65                  70                  75                  80

Met Tyr Tyr Cys Ala Arg
                 85

<210> SEQ ID NO 17
<211> LENGTH: 98
<212> TYPE: PRT
<213> ORGANISM: Homo sapiens

<400> SEQUENCE: 17

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Tyr Met His Trp Val Arg Gln Ala Pro Gly Gln Gly Leu Glu Trp Met
             35                  40                  45

Gly Ile Ile Asn Pro Ser Gly Gly Ser Thr Ser Tyr Ala Gln Lys Phe
         50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 18
<211> LENGTH: 98
<212> TYPE: PRT
<213> ORGANISM: Homo sapiens

<400> SEQUENCE: 18

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Asn Ser Tyr
             20                  25                  30

Tyr Met His Trp Val Arg Gln Ala Pro Gly Gln Gly Leu Glu Trp Met
             35                  40                  45

Gly Ile Ile Asn Pro Ser Gly Gly Ser Thr Ser Tyr Ala Gln Lys Phe
         50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 19
<211> LENGTH: 98
<212> TYPE: PRT
<213> ORGANISM: Homo sapiens

<400> SEQUENCE: 19

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
```

```
            20                  25                  30
Tyr Met His Trp Val Arg Gln Ala Pro Gly Gln Gly Leu Glu Trp Met
        35                  40                  45
Gly Ile Ile Asn Pro Ser Gly Gly Ser Thr Ser Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg

<210> SEQ ID NO 20
<211> LENGTH: 98
<212> TYPE: PRT
<213> ORGANISM: Homo sapiens

<400> SEQUENCE: 20

Gln Met Gln Leu Val Gln Ser Gly Pro Glu Val Lys Lys Pro Gly Thr
1               5                   10                  15
Ser Val Lys Val Ser Cys Lys Ala Ser Gly Phe Thr Phe Thr Ser Ser
            20                  25                  30
Ala Val Gln Trp Val Arg Gln Ala Arg Gly Gln Arg Leu Glu Trp Ile
        35                  40                  45
Gly Trp Ile Val Val Gly Ser Gly Asn Thr Asn Tyr Ala Gln Lys Phe
    50                  55                  60
Gln Glu Arg Val Thr Ile Thr Arg Asp Met Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Ala

<210> SEQ ID NO 21
<211> LENGTH: 98
<212> TYPE: PRT
<213> ORGANISM: Homo sapiens

<400> SEQUENCE: 21

Gln Met Gln Leu Val Gln Ser Gly Pro Glu Val Lys Lys Pro Gly Thr
1               5                   10                  15
Ser Val Lys Val Ser Cys Lys Ala Ser Gly Phe Thr Phe Thr Ser Ser
            20                  25                  30
Ala Met Gln Trp Val Arg Gln Ala Arg Gly Gln Arg Leu Glu Trp Ile
        35                  40                  45
Gly Trp Ile Val Val Gly Ser Gly Asn Thr Asn Tyr Ala Gln Lys Phe
    50                  55                  60
Gln Glu Arg Val Thr Ile Thr Arg Asp Met Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Ala

<210> SEQ ID NO 22
<211> LENGTH: 98
<212> TYPE: PRT
<213> ORGANISM: Homo sapiens

<400> SEQUENCE: 22
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 23
<211> LENGTH: 98
<212> TYPE: PRT
<213> ORGANISM: Homo sapiens

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 24
<211> LENGTH: 91
<212> TYPE: PRT
<213> ORGANISM: Homo sapiens

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr
                85                  90

<210> SEQ ID NO 25
<211> LENGTH: 98
<212> TYPE: PRT
```

<213> ORGANISM: Homo sapiens

<400> SEQUENCE: 25

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 26
<211> LENGTH: 98
<212> TYPE: PRT
<213> ORGANISM: Homo sapiens

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 27
<211> LENGTH: 98
<212> TYPE: PRT
<213> ORGANISM: Homo sapiens

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

```
<210> SEQ ID NO 28
<211> LENGTH: 77
<212> TYPE: PRT
<213> ORGANISM: Homo sapiens

<400> SEQUENCE: 28

Lys Pro Gly Ser Ser Val Lys Val Ser Cys Lys Ala Ser Gly Gly Thr
1               5                   10                  15

Phe Ser Ser Tyr Ala Ile Ser Trp Val Arg Gln Ala Pro Gly Gln Gly
            20                  25                  30

Leu Glu Trp Met Gly Arg Ile Ile Pro Ile Phe Gly Thr Ala Asn Tyr
        35                  40                  45

Ala Gln Lys Phe Gln Gly Arg Val Thr Ile Thr Ala Asp Glu Ser Thr
    50                  55                  60

Ser Thr Ala Tyr Met Glu Leu Ser Ser Leu Arg Ser Glu
65                  70                  75

<210> SEQ ID NO 29
<211> LENGTH: 98
<212> TYPE: PRT
<213> ORGANISM: Homo sapiens

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Ile Leu Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 30
<211> LENGTH: 98
<212> TYPE: PRT
<213> ORGANISM: Homo sapiens

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

<210> SEQ ID NO 31
<211> LENGTH: 98
<212> TYPE: PRT
<213> ORGANISM: Homo sapiens

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 32
<211> LENGTH: 98
<212> TYPE: PRT
<213> ORGANISM: Homo sapiens

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 33
<211> LENGTH: 98
<212> TYPE: PRT
<213> ORGANISM: Homo sapiens

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 34
<211> LENGTH: 98
<212> TYPE: PRT
<213> ORGANISM: Homo sapiens

<400> SEQUENCE: 34

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 35
<211> LENGTH: 98
<212> TYPE: PRT
<213> ORGANISM: Homo sapiens

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 36
<211> LENGTH: 98
<212> TYPE: PRT
<213> ORGANISM: Homo sapiens

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
            50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 37
<211> LENGTH: 98
<212> TYPE: PRT
<213> ORGANISM: Homo sapiens

<400> SEQUENCE: 37

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
                20                  25                  30

Tyr Met His Trp Val Gln Gln Ala Pro Gly Lys Gly Leu Glu Trp Met
            35                  40                  45

Gly Leu Val Asp Pro Glu Asp Gly Glu Thr Ile Tyr Ala Glu Lys Phe
        50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 38
<211> LENGTH: 77
<212> TYPE: PRT
<213> ORGANISM: Homo sapiens

<400> SEQUENCE: 38

Lys Pro Gly Ala Thr Val Lys Ile Ser Cys Lys Val Ser Gly Tyr Thr
1               5                   10                  15

Phe Thr Asp Tyr Tyr Met His Trp Val Gln Gln Ala Pro Gly Lys Gly
                20                  25                  30

Leu Glu Trp Met Gly Leu Val Asp Pro Glu Asp Gly Glu Thr Ile Tyr
            35                  40                  45

Ala Glu Lys Phe Gln Gly Arg Val Thr Ile Thr Ala Asp Thr Ser Thr
        50                  55                  60

Asp Thr Ala Tyr Met Glu Leu Ser Ser Leu Arg Ser Glu
65                  70                  75

<210> SEQ ID NO 39
<211> LENGTH: 100
<212> TYPE: PRT
<213> ORGANISM: Homo sapiens

<400> SEQUENCE: 39

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
                20                  25                  30

Arg Met Gly Val Ser Trp Ile Arg Gln Pro Pro Gly Lys Ala Leu Glu
            35                  40                  45

Trp Leu Ala His Ile Phe Ser Asn Asp Glu Lys Ser Tyr Ser Thr Ser
            50                  55                  60

Leu Lys Ser Arg Leu Thr Ile Ser Lys Asp Thr Ser Lys Ser Gln Val
 65                  70                  75                  80

Val Leu Thr Met Thr Asn Met Asp Pro Val Asp Thr Ala Thr Tyr Tyr
                 85                  90                  95

Cys Ala Arg Ile
            100

<210> SEQ ID NO 40
<211> LENGTH: 100
<212> TYPE: PRT
<213> ORGANISM: Homo sapiens

<400> SEQUENCE: 40

Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ser Thr Ser
                 20                  25                  30

Gly Val Gly Val Gly Trp Ile Arg Gln Pro Pro Gly Lys Ala Leu Glu
             35                  40                  45

Trp Leu Ala Leu Ile Tyr Trp Asn Asp Asp Lys Arg Tyr Ser Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala His Arg
            100

<210> SEQ ID NO 41
<211> LENGTH: 41
<212> TYPE: PRT
<213> ORGANISM: Homo sapiens

<400> SEQUENCE: 41

Thr Ser Gly Val Gly Val Gly Trp Ile Arg Gln Pro Pro Gly Lys Ala
 1               5                  10                  15

Leu Glu Trp Leu Ala Leu Ile Tyr Trp Asp Asp Asp Lys Arg Tyr Ser
                 20                  25                  30

Pro Ser Leu Lys Ser Arg Leu Thr Ile
             35                  40

<210> SEQ ID NO 42
<211> LENGTH: 69
<212> TYPE: PRT
<213> ORGANISM: Homo sapiens

<400> SEQUENCE: 42

Leu Val Lys Pro Thr Gln Thr Leu Thr Leu Thr Cys Thr Phe Ser Gly
 1               5                  10                  15

Phe Ser Leu Ser Thr Ser Gly Val Gly Val Gly Trp Ile Arg Gln Pro
                 20                  25                  30

Pro Gly Lys Ala Leu Glu Trp Leu Ala Leu Ile Tyr Trp Asp Asp Asp
             35                  40                  45

Lys Arg Tyr Ser Pro Ser Leu Lys Ser Arg Leu Thr Ile Thr Lys Asp
 50                  55                  60

Thr Ser Lys Asn Gln

<210> SEQ ID NO 43
<211> LENGTH: 99
<212> TYPE: PRT
<213> ORGANISM: Homo sapiens

<400> SEQUENCE: 43

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Gly Thr Tyr Tyr
                85                  90                  95

Cys Val Arg

<210> SEQ ID NO 44
<211> LENGTH: 100
<212> TYPE: PRT
<213> ORGANISM: Homo sapiens

<400> SEQUENCE: 44

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Asp Lys Arg Tyr Gly Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg
            100

<210> SEQ ID NO 45
<211> LENGTH: 100
<212> TYPE: PRT
<213> ORGANISM: Homo sapiens

<400> SEQUENCE: 45

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Asp Lys Arg Tyr Gly Pro Ser
    50                  55                  60

```
Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala His Arg
            100

<210> SEQ ID NO 46
<211> LENGTH: 98
<212> TYPE: PRT
<213> ORGANISM: Homo sapiens

<400> SEQUENCE: 46

Gln Ile Thr Leu Lys Glu Ser Gly Pro Thr Leu Val Lys Pro Thr Gln
  1               5                  10                  15

Thr Leu Thr Leu Thr Cys Thr Phe Ser Gly Phe Ser Leu Ser Thr Ser
                 20                  25                  30

Gly Val Gly Val Gly Trp Ile Arg Gln Pro Pro Gly Lys Ala Leu Glu
             35                  40                  45

Trp Leu Ala Leu Ile Tyr Trp Asn Asp Asp Lys Arg Tyr Ser Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Gly Thr Tyr Tyr
                 85                  90                  95

Cys Val

<210> SEQ ID NO 47
<211> LENGTH: 100
<212> TYPE: PRT
<213> ORGANISM: Homo sapiens

<400> SEQUENCE: 47

Gln Val Thr Leu Lys Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
                 20                  25                  30

Gly Met Arg Val Ser Trp Ile Arg Gln Pro Pro Gly Lys Ala Leu Glu
             35                  40                  45

Trp Leu Ala Leu Ile Tyr Trp Asp Asp Asp Lys Arg Tyr Ser Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala His Arg
            100

<210> SEQ ID NO 48
<211> LENGTH: 100
<212> TYPE: PRT
<213> ORGANISM: Homo sapiens

<400> SEQUENCE: 48

Gln Val Thr Leu Lys Glu Ser Gly Pro Thr Leu Val Lys Pro Thr Gln
  1               5                  10                  15

Thr Leu Thr Leu Thr Cys Thr Phe Ser Gly Phe Ser Leu Ser Thr Ser
                 20                  25                  30
```

Gly Val Gly Val Gly Trp Ile Arg Gln Pro Pro Gly Lys Ala Leu Glu
            35                  40                  45

Trp Leu Ala Leu Ile Tyr Trp Asp Asp Lys Arg Tyr Gly Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala His Arg
            100

<210> SEQ ID NO 49
<211> LENGTH: 99
<212> TYPE: PRT
<213> ORGANISM: Homo sapiens

<400> SEQUENCE: 49

Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ser Thr Ser
                 20                  25                  30

Gly Val Gly Val Gly Trp Ile Arg Gln Pro Pro Gly Lys Ala Leu Glu
            35                  40                  45

Trp Leu Ala Leu Ile Tyr Trp Asp Asp Lys Arg Tyr Ser Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg

<210> SEQ ID NO 50
<211> LENGTH: 100
<212> TYPE: PRT
<213> ORGANISM: Homo sapiens

<400> SEQUENCE: 50

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
                 20                  25                  30

Gly Met Cys Val Ser Trp Ile Arg Gln Pro Pro Gly Lys Ala Leu Glu
            35                  40                  45

Trp Leu Ala Leu Ile Asp Trp Asp Asp Lys Tyr Tyr Ser Thr Ser
 50                  55                  60

Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile
            100

<210> SEQ ID NO 51
<211> LENGTH: 96
<212> TYPE: PRT
<213> ORGANISM: Homo sapiens

<400> SEQUENCE: 51

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Cys Val Ser Trp Ile Arg Gln Pro Pro Gly Lys Ala Leu Glu
        35                  40                  45

Trp Leu Ala Leu Ile Asp Trp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Val Tyr Tyr
                85                  90                  95

<210> SEQ ID NO 52
<211> LENGTH: 96
<212> TYPE: PRT
<213> ORGANISM: Homo sapiens

<400> SEQUENCE: 52

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Arg Val Ser Trp Ile Arg Gln Pro Pro Gly Lys Ala Leu Glu
        35                  40                  45

Trp Leu Ala Arg Ile Asp Trp Asp Asp Lys Phe Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Val Tyr Tyr
                85                  90                  95

<210> SEQ ID NO 53
<211> LENGTH: 96
<212> TYPE: PRT
<213> ORGANISM: Homo sapiens

<400> SEQUENCE: 53

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Arg Val Ser Trp Ile Arg Gln Pro Pro Gly Lys Ala Leu Glu
        35                  40                  45

Trp Leu Ala Arg Ile Asp Trp Asp Asp Lys Phe Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

<210> SEQ ID NO 54
<211> LENGTH: 78
<212> TYPE: PRT
<213> ORGANISM: Homo sapiens

<400> SEQUENCE: 54

```
Ala Leu Val Lys Pro Thr Gln Thr Leu Thr Leu Thr Cys Thr Phe Ser
1               5                   10                  15

Gly Phe Ser Leu Ser Thr Ser Gly Met Arg Ala Ser Trp Ile Arg Gln
            20                  25                  30

Pro Pro Gly Lys Ala Leu Glu Trp Leu Ala Arg Ile Asp Trp Asp Asp
        35                  40                  45

Asp Lys Phe Tyr Ser Thr Ser Leu Lys Thr Arg Leu Thr Ile Ser Lys
    50                  55                  60

Asp Thr Ser Lys Asn Gln Val Val Leu Thr Met Thr Asn Met
65                  70                  75
```

<210> SEQ ID NO 55
<211> LENGTH: 96
<212> TYPE: PRT
<213> ORGANISM: Homo sapiens

<400> SEQUENCE: 55

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Arg Val Ser Trp Ile Arg Gln Pro Pro Gly Lys Ala Leu Glu
        35                  40                  45

Trp Leu Ala Arg Ile Asp Trp Asp Asp Asp Lys Phe Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Val Tyr Tyr
                85                  90                  95
```

<210> SEQ ID NO 56
<211> LENGTH: 96
<212> TYPE: PRT
<213> ORGANISM: Homo sapiens

<400> SEQUENCE: 56

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Cys Val Ser Trp Ile Arg Gln Pro Pro Gly Lys Ala Leu Glu
        35                  40                  45

Trp Leu Ala Leu Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Val Tyr Tyr
                85                  90                  95
```

<210> SEQ ID NO 57
<211> LENGTH: 96
<212> TYPE: PRT
<213> ORGANISM: Homo sapiens

<400> SEQUENCE: 57

```
Gln Val Thr Leu Arg Glu Ser Gly Pro Ala Leu Val Lys Pro Thr Gln
1               5                   10                  15
```

```
Thr Leu Thr Leu Thr Cys Ala Phe Ser Gly Phe Ser Leu Ser Thr Ser
            20                  25                  30

Gly Met Cys Val Ser Trp Ile Arg Gln Pro Pro Gly Lys Ala Leu Glu
        35                  40                  45

Trp Leu Ala Arg Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Val Tyr Tyr
                85                  90                  95
```

<210> SEQ ID NO 58
<211> LENGTH: 99
<212> TYPE: PRT
<213> ORGANISM: Homo sapiens

<400> SEQUENCE: 58

```
Gln Ile Thr Leu Lys Glu Ser Gly Pro Thr Leu Val Lys Pro Thr Gln
1               5                   10                  15

Thr Leu Thr Leu Thr Arg Thr Phe Ser Gly Phe Ser Leu Ser Thr Ser
            20                  25                  30

Gly Met Cys Val Ser Trp Ile Arg Gln Pro Pro Gly Lys Ala Leu Glu
        35                  40                  45

Trp Leu Ala Leu Ile Asp Trp Asp Asp Asp Lys Tyr Tyr Ser Thr Ser
    50                  55                  60

Leu Asn Thr Arg Leu Thr Ile Ser Lys Asp Thr Ser Lys Asn Gln Val
65                  70                  75                  80

Val Leu Thr Met Thr Asn Met Asp Pro Val Asp Thr Gly Thr Tyr Tyr
                85                  90                  95

Cys Val Arg
```

<210> SEQ ID NO 59
<211> LENGTH: 100
<212> TYPE: PRT
<213> ORGANISM: Homo sapiens

<400> SEQUENCE: 59

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Arg Val Ser Trp Ile Arg Gln Pro Pro Gly Lys Ala Leu Glu
        35                  40                  45

Trp Ile Ala Arg Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile
            100
```

<210> SEQ ID NO 60
<211> LENGTH: 100
<212> TYPE: PRT
<213> ORGANISM: Homo sapiens

<400> SEQUENCE: 60

```
Arg Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Cys Val Ser Trp Ile Arg Gln Pro Pro Gly Lys Ala Leu Glu
            35                  40                  45

Trp Leu Ala Arg Ile Asp Trp Asp Asp Asp Lys Tyr Tyr Ser Thr Ser
        50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile
            100

<210> SEQ ID NO 61
<211> LENGTH: 100
<212> TYPE: PRT
<213> ORGANISM: Homo sapiens

<400> SEQUENCE: 61

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Cys Val Ser Trp Ile Arg Gln Pro Pro Gly Lys Ala Leu Glu
            35                  40                  45

Trp Leu Ala Leu Ile Asp Trp Asp Asp Asp Lys Tyr Tyr Ser Thr Ser
        50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg
            100

<210> SEQ ID NO 62
<211> LENGTH: 100
<212> TYPE: PRT
<213> ORGANISM: Homo sapiens

<400> SEQUENCE: 62

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Cys Val Ser Trp Ile Arg Gln Pro Pro Gly Lys Ala Leu Glu
            35                  40                  45

Trp Leu Ala Leu Ile Asp Trp Asp Asp Asp Lys Tyr Tyr Ser Thr Ser
        50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile
            100
```

<210> SEQ ID NO 63
<211> LENGTH: 98
<212> TYPE: PRT
<213> ORGANISM: Homo sapiens

<400> SEQUENCE: 63

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 64
<211> LENGTH: 98
<212> TYPE: PRT
<213> ORGANISM: Homo sapiens

<400> SEQUENCE: 64

Gln Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Ser Tyr Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 65
<211> LENGTH: 98
<212> TYPE: PRT
<213> ORGANISM: Homo sapiens

<400> SEQUENCE: 65

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Val Tyr Tyr Cys
                85                  90                  95

Ala Arg

<210> SEQ ID NO 66
<211> LENGTH: 97
<212> TYPE: PRT
<213> ORGANISM: Homo sapiens

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg

<210> SEQ ID NO 67
<211> LENGTH: 97
<212> TYPE: PRT
<213> ORGANISM: Homo sapiens

<400> SEQUENCE: 67

Glu Val His Leu Val Glu Ser Gly Gly Gly Leu Val Gln Pro Gly Gly
1               5                   10                  15

Ala Leu Arg Leu Ser Cys Ala Ala Ser Gly Phe Thr Phe Ser Asn Tyr
            20                  25                  30

Asp Met His Trp Val Arg Gln Ala Thr Gly Lys Gly Leu Glu Trp Val
        35                  40                  45

Ser Ala Asn Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg

<210> SEQ ID NO 68
<211> LENGTH: 97
<212> TYPE: PRT
<213> ORGANISM: Homo sapiens

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Cys Gly Phe Thr Phe Ser Ser Tyr
            20                  25                  30

Asp Met His Trp Val Arg Gln Ala Thr Gly Lys Gly Leu Glu Trp Val
        35                  40                  45
```

```
Ser Ala Ile Gly Thr Ala Gly Asp Thr Tyr Tyr Pro Gly Ser Val Lys
    50                  55                  60

Gly Gln Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg

<210> SEQ ID NO 69
<211> LENGTH: 97
<212> TYPE: PRT
<213> ORGANISM: Homo sapiens

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Asp Met His Trp Val Arg Gln Ala Thr Gly Lys Gly Leu Glu Trp Val
            35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg

<210> SEQ ID NO 70
<211> LENGTH: 100
<212> TYPE: PRT
<213> ORGANISM: Homo sapiens

<400> SEQUENCE: 70

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 71
<211> LENGTH: 100
<212> TYPE: PRT
<213> ORGANISM: Homo sapiens

<400> SEQUENCE: 71

Glu Val Gln Leu Val Glu Ser Gly Gly Ala Leu Val Lys Pro Gly Gly
1               5                   10                  15
```

-continued

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 72
<211> LENGTH: 100
<212> TYPE: PRT
<213> ORGANISM: Homo sapiens

<400> SEQUENCE: 72

Glu Val Gln Leu Val Glu Ser Ala Gly Ala Leu Val Gln Pro Gly Gly
1               5                   10                  15

Ser Leu Arg Leu Ser Cys Ala Ala Ser Gly Phe Thr Cys Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Ala Asn Gly Gly Thr Thr Asp Tyr Ala Ala
    50                  55                  60

Pro Val Lys Gly Arg Phe Thr Ile Ser Arg Val Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 73
<211> LENGTH: 100
<212> TYPE: PRT
<213> ORGANISM: Homo sapiens

<400> SEQUENCE: 73

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Glu Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 74
<211> LENGTH: 100

<212> TYPE: PRT
<213> ORGANISM: Homo sapiens

<400> SEQUENCE: 74

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 75
<211> LENGTH: 100
<212> TYPE: PRT
<213> ORGANISM: Homo sapiens

<400> SEQUENCE: 75

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asn Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 76
<211> LENGTH: 100
<212> TYPE: PRT
<213> ORGANISM: Homo sapiens

<400> SEQUENCE: 76

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr

-continued

```
                85                  90                  95

Tyr Cys Thr Thr
            100

<210> SEQ ID NO 77
<211> LENGTH: 100
<212> TYPE: PRT
<213> ORGANISM: Homo sapiens

<400> SEQUENCE: 77

Glu Val Gln Leu Val Glu Ser Ala Gly Gly Leu Val Gln Pro Gly Gly
1               5                   10                  15

Ser Leu Arg Leu Ser Cys Ala Ala Ser Gly Phe Thr Cys Ser Asn Ala
            20                  25                  30

Trp Met Ser Trp Val Arg Gln Ala Pro Gly Lys Gly Leu Glu Trp Val
        35                  40                  45

Gly Cys Ile Lys Ser Lys Ala Asn Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Ile Ser Leu Lys Thr Glu Asp Thr Ala Val Tyr
                85                  90                  95

Tyr Cys Thr Thr
            100

<210> SEQ ID NO 78
<211> LENGTH: 98
<212> TYPE: PRT
<213> ORGANISM: Homo sapiens

<400> SEQUENCE: 78

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg

<210> SEQ ID NO 79
<211> LENGTH: 98
<212> TYPE: PRT
<213> ORGANISM: Homo sapiens

<400> SEQUENCE: 79

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45
```

```
Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 80
<211> LENGTH: 98
<212> TYPE: PRT
<213> ORGANISM: Homo sapiens

<400> SEQUENCE: 80

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 81
<211> LENGTH: 98
<212> TYPE: PRT
<213> ORGANISM: Homo sapiens

<400> SEQUENCE: 81

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 82
<211> LENGTH: 98
<212> TYPE: PRT
<213> ORGANISM: Homo sapiens

<400> SEQUENCE: 82

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
```

```
                    20                  25                  30
Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 83
<211> LENGTH: 98
<212> TYPE: PRT
<213> ORGANISM: Homo sapiens

<400> SEQUENCE: 83

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys
```

<210> SEQ ID NO 84
<211> LENGTH: 98
<212> TYPE: PRT
<213> ORGANISM: Homo sapiens

<400> SEQUENCE: 84

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Ser Thr Tyr Tyr Gly Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys
```

<210> SEQ ID NO 85
<211> LENGTH: 98
<212> TYPE: PRT
<213> ORGANISM: Homo sapiens

<400> SEQUENCE: 85

-continued

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys

<210> SEQ ID NO 86
<211> LENGTH: 98
<212> TYPE: PRT
<213> ORGANISM: Homo sapiens

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys

<210> SEQ ID NO 87
<211> LENGTH: 98
<212> TYPE: PRT
<213> ORGANISM: Homo sapiens

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Tyr Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys

<210> SEQ ID NO 88

```
<211> LENGTH: 98
<212> TYPE: PRT
<213> ORGANISM: Homo sapiens

<400> SEQUENCE: 88

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 89
<211> LENGTH: 98
<212> TYPE: PRT
<213> ORGANISM: Homo sapiens

<400> SEQUENCE: 89

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 90
<211> LENGTH: 98
<212> TYPE: PRT
<213> ORGANISM: Homo sapiens

<400> SEQUENCE: 90

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg

<210> SEQ ID NO 91
<211> LENGTH: 98
<212> TYPE: PRT
<213> ORGANISM: Homo sapiens

<400> SEQUENCE: 91

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 92
<211> LENGTH: 98
<212> TYPE: PRT
<213> ORGANISM: Homo sapiens

<400> SEQUENCE: 92

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Leu Arg Ala Arg Leu Cys Ile Thr Val
                85                  90                  95

Arg Glu

<210> SEQ ID NO 93
<211> LENGTH: 98
<212> TYPE: PRT
<213> ORGANISM: Homo sapiens

<400> SEQUENCE: 93

Gln Val Gln Leu Val Glu Ser Gly Gly Gly Val Val Gln Pro Gly Arg
1               5                   10                  15

Ser Leu Arg Leu Ser Cys Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 94
<211> LENGTH: 98
<212> TYPE: PRT
<213> ORGANISM: Homo sapiens

<400> SEQUENCE: 94

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Ala Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 95
<211> LENGTH: 98
<212> TYPE: PRT
<213> ORGANISM: Homo sapiens

<400> SEQUENCE: 95

Gln Val Gln Leu Val Asp Ser Gly Gly Gly Val Val Gln Pro Gly Arg
  1               5                  10                  15

Ser Leu Arg Leu Ser Cys Ala Ala Ser Ala Phe Thr Phe Ser Ser Tyr
                 20                  25                  30

Ala Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 96
<211> LENGTH: 98
<212> TYPE: PRT
<213> ORGANISM: Homo sapiens

<400> SEQUENCE: 96

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Ala Met His Trp Val Arg Gln Ala Pro Gly Lys Gly Leu Glu Trp Val
```

```
                    35                  40                  45
Ala Val Ile Ser Tyr Asp Gly Ser Asn Lys Tyr Tyr Ala Asp Ser Val
     50                  55                  60

Lys Gly Arg Phe Ala Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 97
<211> LENGTH: 98
<212> TYPE: PRT
<213> ORGANISM: Homo sapiens

<400> SEQUENCE: 97

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Ala Met His Trp Val Arg Gln Ala Pro Gly Lys Gly Leu Glu Trp Val
         35                  40                  45

Ala Val Ile Ser Tyr Asp Gly Ser Asn Lys Tyr Tyr Thr Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 98
<211> LENGTH: 98
<212> TYPE: PRT
<213> ORGANISM: Homo sapiens

<400> SEQUENCE: 98

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Ala Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 99
<211> LENGTH: 98
<212> TYPE: PRT
<213> ORGANISM: Homo sapiens

<400> SEQUENCE: 99

Gln Val Gln Leu Val Glu Ser Gly Gly Gly Val Val Gln Pro Gly Arg
 1               5                  10                  15
```

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 100
<211> LENGTH: 98
<212> TYPE: PRT
<213> ORGANISM: Homo sapiens

<400> SEQUENCE: 100

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Arg Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 101
<211> LENGTH: 98
<212> TYPE: PRT
<213> ORGANISM: Homo sapiens

<400> SEQUENCE: 101

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 102
<211> LENGTH: 98
<212> TYPE: PRT
<213> ORGANISM: Homo sapiens

<400> SEQUENCE: 102

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg

<210> SEQ ID NO 103
<211> LENGTH: 98
<212> TYPE: PRT
<213> ORGANISM: Homo sapiens

<400> SEQUENCE: 103

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 104
<211> LENGTH: 98
<212> TYPE: PRT
<213> ORGANISM: Homo sapiens

<400> SEQUENCE: 104

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 105
<211> LENGTH: 98
<212> TYPE: PRT
<213> ORGANISM: Homo sapiens

<400> SEQUENCE: 105

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys
```

<210> SEQ ID NO 106
<211> LENGTH: 98
<212> TYPE: PRT
<213> ORGANISM: Homo sapiens

<400> SEQUENCE: 106

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg
```

<210> SEQ ID NO 107
<211> LENGTH: 98
<212> TYPE: PRT
<213> ORGANISM: Homo sapiens

<400> SEQUENCE: 107

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Ala Met His Trp Val Arg Gln Ala Pro Gly Lys Gly Leu Glu Trp Val
        35                  40                  45
Ala Val Ile Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg

<210> SEQ ID NO 108
<211> LENGTH: 98
<212> TYPE: PRT
<213> ORGANISM: Homo sapiens

<400> SEQUENCE: 108

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 109
<211> LENGTH: 98
<212> TYPE: PRT
<213> ORGANISM: Homo sapiens

<400> SEQUENCE: 109

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 110
<211> LENGTH: 98
<212> TYPE: PRT
<213> ORGANISM: Homo sapiens

<400> SEQUENCE: 110

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Ala
```

```
            50                  55                  60
Lys Gly Arg Phe Thr Ile Ser Arg Asp Asn Ser Thr Asn Thr Leu Phe
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 111
<211> LENGTH: 98
<212> TYPE: PRT
<213> ORGANISM: Homo sapiens

<400> SEQUENCE: 111

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys

<210> SEQ ID NO 112
<211> LENGTH: 98
<212> TYPE: PRT
<213> ORGANISM: Homo sapiens

<400> SEQUENCE: 112

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 113
<211> LENGTH: 98
<212> TYPE: PRT
<213> ORGANISM: Homo sapiens

<400> SEQUENCE: 113

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30
```

```
Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 114
<211> LENGTH: 98
<212> TYPE: PRT
<213> ORGANISM: Homo sapiens

<400> SEQUENCE: 114

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 115
<211> LENGTH: 99
<212> TYPE: PRT
<213> ORGANISM: Homo sapiens

<400> SEQUENCE: 115

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Leu Ile Ser Trp Asp Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp

<210> SEQ ID NO 116
<211> LENGTH: 98
<212> TYPE: PRT
<213> ORGANISM: Homo sapiens

<400> SEQUENCE: 116
```

Glu Val Gln Leu Val Glu Ser Gly Gly Gly Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Leu Ile Ser Gly Asp Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys

<210> SEQ ID NO 117
<211> LENGTH: 98
<212> TYPE: PRT
<213> ORGANISM: Homo sapiens

<400> SEQUENCE: 117

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 118
<211> LENGTH: 98
<212> TYPE: PRT
<213> ORGANISM: Homo sapiens

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg

<210> SEQ ID NO 119
<211> LENGTH: 98

```
<212> TYPE: PRT
<213> ORGANISM: Homo sapiens

<400> SEQUENCE: 119

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 120
<211> LENGTH: 98
<212> TYPE: PRT
<213> ORGANISM: Homo sapiens

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 121
<211> LENGTH: 100
<212> TYPE: PRT
<213> ORGANISM: Homo sapiens

<400> SEQUENCE: 121

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Thr Ala
    50                  55                  60

Ser Val Lys Gly Arg Phe Thr Ile Ser Arg Asp Gly Ser Lys Ser Ile
65                  70                  75                  80

Ala Tyr Leu Gln Met Asn Ser Leu Lys Thr Glu Asp Thr Ala Val Tyr
                85                  90                  95
```

Tyr Cys Thr Arg
            100

<210> SEQ ID NO 122
<211> LENGTH: 100
<212> TYPE: PRT
<213> ORGANISM: Homo sapiens

<400> SEQUENCE: 122

Glu Val Gln Leu Val Glu Ser Gly Gly Gly Leu Val Gln Pro Gly Pro
1               5                   10                  15

Ser Leu Arg Leu Ser Cys Thr Ala Ser Gly Phe Thr Phe Gly Tyr Tyr
            20                  25                  30

Pro Met Ser Trp Val Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 123
<211> LENGTH: 100
<212> TYPE: PRT
<213> ORGANISM: Homo sapiens

<400> SEQUENCE: 123

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Val Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 124
<211> LENGTH: 100
<212> TYPE: PRT
<213> ORGANISM: Homo sapiens

<400> SEQUENCE: 124

Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala

```
                        50                  55                  60
Ser Val Lys Gly Arg Phe Thr Ile Ser Arg Asp Asp Ser Lys Ser Ile
 65                  70                  75                  80

Ala Tyr Leu Gln Met Asn Ser Leu Lys Thr Glu Asp Thr Ala Val Tyr
                 85                  90                  95

Tyr Cys Thr Arg
            100

<210> SEQ ID NO 125
<211> LENGTH: 97
<212> TYPE: PRT
<213> ORGANISM: Homo sapiens

<400> SEQUENCE: 125

Glu Val Gln Leu Val Glu Ser Gly Gly Gly Leu Ile Gln Pro Gly Gly
  1               5                  10                  15

Ser Leu Arg Leu Ser Cys Ala Ala Ser Gly Phe Thr Val Ser Ser Asn
                 20                  25                  30

Tyr Met Ser Trp Val Arg Gln Ala Pro Gly Lys Gly Leu Glu Trp Val
             35                  40                  45

Ser Val Ile Tyr Ser Gly Gly Ser Thr Tyr Tyr Ala Asp Ser Val Lys
         50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg

<210> SEQ ID NO 126
<211> LENGTH: 97
<212> TYPE: PRT
<213> ORGANISM: Homo sapiens

<400> SEQUENCE: 126

Glu Val Gln Leu Val Glu Thr Gly Gly Gly Leu Ile Gln Pro Gly Gly
  1               5                  10                  15

Ser Leu Arg Leu Ser Cys Ala Ala Ser Gly Phe Thr Val Ser Ser Asn
                 20                  25                  30

Tyr Met Ser Trp Val Arg Gln Ala Pro Gly Lys Gly Leu Glu Trp Val
             35                  40                  45

Ser Val Ile Tyr Ser Gly Gly Ser Thr Tyr Tyr Ala Asp Ser Val Lys
         50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg

<210> SEQ ID NO 127
<211> LENGTH: 97
<212> TYPE: PRT
<213> ORGANISM: Homo sapiens

<400> SEQUENCE: 127

Glu Val Gln Leu Val Glu Ser Gly Gly Gly Leu Ile Gln Pro Gly Gly
  1               5                  10                  15

Ser Leu Arg Leu Ser Cys Ala Ala Ser Gly Phe Thr Val Ser Ser Asn
```

```
                    20                  25                  30

Tyr Met Ser Trp Val Arg Gln Pro Pro Gly Lys Gly Leu Glu Trp Val
            35                  40                  45

Ser Val Ile Tyr Ser Gly Gly Ser Thr Tyr Tyr Ala Asp Ser Val Lys
        50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg

<210> SEQ ID NO 128
<211> LENGTH: 97
<212> TYPE: PRT
<213> ORGANISM: Homo sapiens

<400> SEQUENCE: 128

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Val Ser Ser Asn
                20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
        50                  55                  60

Gly Arg Phe Thr Ile Ser Arg His Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg

<210> SEQ ID NO 129
<211> LENGTH: 98
<212> TYPE: PRT
<213> ORGANISM: Homo sapiens

<400> SEQUENCE: 129

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Tyr Val
            35                  40                  45

Ser Ala Ile Ser Ser Asn Gly Gly Ser Thr Tyr Tyr Ala Asn Ser Val
        50                  55                  60

Lys Gly Arg Phe Thr Ile Ser Arg Asp Asn Ser Lys Asn Thr Leu Tyr
 65                  70                  75                  80

Leu Gln Met Gly Ser Leu Arg Ala Glu Asp Met Ala Val Tyr Tyr Cys
                85                  90                  95

Ala Arg

<210> SEQ ID NO 130
<211> LENGTH: 98
<212> TYPE: PRT
<213> ORGANISM: Homo sapiens

<400> SEQUENCE: 130
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
            35                  40                  45

Ser Ala Ile Ser Ser Asn Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg

<210> SEQ ID NO 131
<211> LENGTH: 98
<212> TYPE: PRT
<213> ORGANISM: Homo sapiens

<400> SEQUENCE: 131

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
            35                  40                  45

Ser Ala Ile Ser Ser Asn Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Val Gln Met Ser Ser Leu Arg Ala Glu Asp Thr Ala Val Tyr Tyr Cys
                85                  90                  95

Val Lys

<210> SEQ ID NO 132
<211> LENGTH: 98
<212> TYPE: PRT
<213> ORGANISM: Homo sapiens

<400> SEQUENCE: 132

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
            35                  40                  45

Ser Ala Ile Ser Ser Asn Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 133
```

<211> LENGTH: 98
<212> TYPE: PRT
<213> ORGANISM: Homo sapiens

<400> SEQUENCE: 133

```
Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Val Gln Met Ser Ser Leu Arg Ala Glu Asp Thr Ala Val Tyr Tyr Cys
                85                  90                  95

Val Lys
```

<210> SEQ ID NO 134
<211> LENGTH: 97
<212> TYPE: PRT
<213> ORGANISM: Homo sapiens

<400> SEQUENCE: 134

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg
```

<210> SEQ ID NO 135
<211> LENGTH: 97
<212> TYPE: PRT
<213> ORGANISM: Homo sapiens

<400> SEQUENCE: 135

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

-continued

Arg

<210> SEQ ID NO 136
<211> LENGTH: 97
<212> TYPE: PRT
<213> ORGANISM: Homo sapiens

<400> SEQUENCE: 136

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Cys Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 137
<211> LENGTH: 97
<212> TYPE: PRT
<213> ORGANISM: Homo sapiens

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 138
<211> LENGTH: 98
<212> TYPE: PRT
<213> ORGANISM: Homo sapiens

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 139
<211> LENGTH: 98
<212> TYPE: PRT
<213> ORGANISM: Homo sapiens

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 140
<211> LENGTH: 98
<212> TYPE: PRT
<213> ORGANISM: Homo sapiens

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 141
<211> LENGTH: 100
<212> TYPE: PRT
<213> ORGANISM: Homo sapiens

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val

```
                35                  40                  45
Gly Arg Thr Arg Asn Lys Ala Asn Ser Tyr Thr Thr Glu Tyr Ala Ala
 50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Ala Arg
            100

<210> SEQ ID NO 142
<211> LENGTH: 55
<212> TYPE: PRT
<213> ORGANISM: Homo sapiens

<400> SEQUENCE: 142

Thr Phe Ser Asp His Tyr Met Asp Trp Val Arg Gln Ala Pro Gly Lys
 1               5                  10                  15

Gly Leu Glu Trp Val Gly Arg Thr Arg Asn Lys Ala Asn Ser Tyr Thr
                20                  25                  30

Thr Glu Tyr Ala Ala Ser Val Lys Gly Arg Phe Thr Ile Ser Arg Asp
             35                  40                  45

Asp Ser Lys Asn Ser Leu Tyr
         50                  55

<210> SEQ ID NO 143
<211> LENGTH: 100
<212> TYPE: PRT
<213> ORGANISM: Homo sapiens

<400> SEQUENCE: 143

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Gly Ser
                20                  25                  30

Ala Met His Trp Val Arg Gln Ala Ser Gly Lys Gly Leu Glu Trp Val
             35                  40                  45

Gly Arg Ile Arg Ser Lys Ala Asn Ser Tyr Ala Thr Ala Tyr Ala Ala
 50                  55                  60

Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Thr Arg
            100

<210> SEQ ID NO 144
<211> LENGTH: 100
<212> TYPE: PRT
<213> ORGANISM: Homo sapiens

<400> SEQUENCE: 144

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Gly Ser
                20                  25                  30

Ala Met His Trp Val Arg Gln Ala Ser Gly Lys Gly Leu Glu Trp Val
             35                  40                  45
```

Gly Arg Ile Arg Ser Lys Ala Asn Ser Tyr Ala Thr Ala Tyr Ala Ala
            50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 145
<211> LENGTH: 98
<212> TYPE: PRT
<213> ORGANISM: Homo sapiens

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 146
<211> LENGTH: 98
<212> TYPE: PRT
<213> ORGANISM: Homo sapiens

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 147
<211> LENGTH: 98
<212> TYPE: PRT
<213> ORGANISM: Homo sapiens

<400> SEQUENCE: 147

Glu Val Gln Leu Val Glu Ser Gly Gly Gly Leu Val Gln Pro Gly Gly
1               5                   10                  15

-continued

```
Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Thr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 148
<211> LENGTH: 99
<212> TYPE: PRT
<213> ORGANISM: Homo sapiens

<400> SEQUENCE: 148

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp

<210> SEQ ID NO 149
<211> LENGTH: 99
<212> TYPE: PRT
<213> ORGANISM: Homo sapiens

<400> SEQUENCE: 149

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Ser Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp

<210> SEQ ID NO 150
<211> LENGTH: 98
<212> TYPE: PRT
<213> ORGANISM: Homo sapiens
```

<400> SEQUENCE: 150

Gln Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Val Ile Tyr Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 151
<211> LENGTH: 96
<212> TYPE: PRT
<213> ORGANISM: Homo sapiens

<400> SEQUENCE: 151

Glu Val Gln Leu Val Glu Ser Arg Gly Val Leu Val Gln Pro Gly Gly
1               5                   10                  15

Ser Leu Arg Leu Ser Cys Ala Ala Ser Gly Phe Thr Val Ser Ser Asn
            20                  25                  30

Glu Met Ser Trp Val Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Asn Thr Leu His Leu Gln
65                  70                  75                  80

Met Asn Ser Leu Arg Ala Glu Asp Thr Ala Val Tyr Tyr Cys Lys Lys
                85                  90                  95

<210> SEQ ID NO 152
<211> LENGTH: 98
<212> TYPE: PRT
<213> ORGANISM: Homo sapiens

<400> SEQUENCE: 152

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Ser
            20                  25                  30

Asn Trp Trp Gly Trp Ile Arg Gln Pro Pro Gly Lys Gly Leu Glu Trp
        35                  40                  45

Ile Gly Tyr Ile Tyr Tyr Ser Gly Ser Thr Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg

<210> SEQ ID NO 153

```
<211> LENGTH: 98
<212> TYPE: PRT
<213> ORGANISM: Homo sapiens

<400> SEQUENCE: 153
```

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Ser Ser
            20                  25                  30

Asn Trp Trp Gly Trp Ile Arg Gln Pro Pro Gly Lys Gly Leu Glu Trp
        35                  40                  45

Ile Gly Tyr Ile Tyr Tyr Ser Gly Ser Ile Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg

```
<210> SEQ ID NO 154
<211> LENGTH: 98
<212> TYPE: PRT
<213> ORGANISM: Homo sapiens

<400> SEQUENCE: 154
```

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Ser
            20                  25                  30

Asn Trp Trp Gly Trp Ile Arg Gln Pro Pro Gly Lys Gly Leu Glu Trp
        35                  40                  45

Ile Gly Tyr Ile Tyr Tyr Ser Gly Ser Thr Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg

```
<210> SEQ ID NO 155
<211> LENGTH: 98
<212> TYPE: PRT
<213> ORGANISM: Homo sapiens

<400> SEQUENCE: 155
```

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Ser
            20                  25                  30

Asn Trp Trp Gly Trp Ile Arg Gln Pro Pro Gly Lys Gly Leu Glu Trp
        35                  40                  45

Ile Gly Tyr Ile Tyr Tyr Ser Gly Ser Thr Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Gly Val Tyr Tyr Cys
                85                  90                  95

Ala Arg

<210> SEQ ID NO 156
<211> LENGTH: 95
<212> TYPE: PRT
<213> ORGANISM: Homo sapiens

<400> SEQUENCE: 156

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Ser
            20                  25                  30

Asn Trp Trp Gly Trp Ile Arg Gln Pro Pro Gly Lys Gly Leu Glu Trp
        35                  40                  45

Ile Gly Tyr Ile Tyr Tyr Ser Gly Ser Ile Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr
                85                  90                  95

<210> SEQ ID NO 157
<211> LENGTH: 98
<212> TYPE: PRT
<213> ORGANISM: Homo sapiens

<400> SEQUENCE: 157

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Ser
            20                  25                  30

Asn Trp Trp Gly Trp Ile Arg Gln Pro Pro Gly Lys Gly Leu Glu Trp
        35                  40                  45

Ile Gly Tyr Ile Tyr Tyr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Leu Asp Thr Ala Val Tyr Tyr Cys
                85                  90                  95

Ala Arg

<210> SEQ ID NO 158
<211> LENGTH: 99
<212> TYPE: PRT
<213> ORGANISM: Homo sapiens

<400> SEQUENCE: 158

Gln Leu Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly Tyr Ser Trp Ser Trp Ile Arg Gln Pro Pro Gly Lys Gly Leu Glu
        35                  40                  45

Trp Ile Gly Tyr Ile Tyr His Ser Gly Ser Thr Tyr Tyr Asn Pro Ser
    50                  55                  60

Leu Lys Ser Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 159
<211> LENGTH: 98
<212> TYPE: PRT
<213> ORGANISM: Homo sapiens

<400> SEQUENCE: 159

Gln Leu Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly Tyr Ser Trp Ser Trp Ile Arg Gln Pro Pro Gly Lys Gly Leu Glu
        35                  40                  45

Trp Ile Gly Tyr Ile Tyr His Ser Gly Ser Thr Tyr Tyr Asn Pro Ser
    50                  55                  60

Leu Lys Ser Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala

<210> SEQ ID NO 160
<211> LENGTH: 99
<212> TYPE: PRT
<213> ORGANISM: Homo sapiens

<400> SEQUENCE: 160

Gln Leu Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly Tyr Ser Trp Ser Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 161
<211> LENGTH: 75
<212> TYPE: PRT
<213> ORGANISM: Homo sapiens

<400> SEQUENCE: 161

Ser Gly Gly Ser Ile Ser Ser Gly Gly Tyr Ser Trp Ser Trp Ile Arg
1               5                   10                  15

Gln Pro Pro Gly Lys Gly Leu Glu Trp Ile Gly Tyr Ile Tyr His Ser
            20                  25                  30

Gly Ser Thr Tyr Tyr Asn Pro Ser Leu Lys Ser Arg Val Thr Ile Ser
        35                  40                  45

-continued

Val Asp Thr Ser Lys Asn Gln Phe Ser Leu Lys Leu Ser Ser Val Thr
 50                  55                  60

Ala Ala Asp Thr Ala Val Tyr Tyr Cys Ala Arg
 65                  70                  75

<210> SEQ ID NO 162
<211> LENGTH: 99
<212> TYPE: PRT
<213> ORGANISM: Homo sapiens

<400> SEQUENCE: 162

Gln Leu Gln Leu Gln Glu Ser Gly Ser Gly Leu Val Lys Pro Ser Gln
 1               5                  10                  15

Thr Leu Ser Leu Thr Cys Ala Val Ser Gly Gly Ser Ile Ser Ser Gly
             20                  25                  30

Gly Tyr Ser Trp Ser Trp Ile Arg Gln Pro Pro Gly Lys Gly Leu Glu
         35                  40                  45

Trp Ile Gly Tyr Ile Tyr His Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg

<210> SEQ ID NO 163
<211> LENGTH: 99
<212> TYPE: PRT
<213> ORGANISM: Homo sapiens

<400> SEQUENCE: 163

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Asp Tyr Tyr Trp Ser Trp Ile Arg Gln Pro Pro Gly Lys Gly Leu Glu
         35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg

<210> SEQ ID NO 164
<211> LENGTH: 99
<212> TYPE: PRT
<213> ORGANISM: Homo sapiens

<400> SEQUENCE: 164

Gln Val Gln Leu Gln Glu Ser Gly Pro Gly Leu Val Lys Pro Ser Asp
 1               5                  10                  15

Thr Leu Ser Leu Thr Cys Thr Val Ser Gly Gly Ser Ile Ser Ser Gly
             20                  25                  30

Asp Tyr Tyr Trp Ser Trp Ile Arg Gln Pro Pro Gly Lys Gly Leu Glu
         35                  40                  45

```
Trp Ile Gly Tyr Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 165
<211> LENGTH: 96
<212> TYPE: PRT
<213> ORGANISM: Homo sapiens

<400> SEQUENCE: 165

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

Asp Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

<210> SEQ ID NO 166
<211> LENGTH: 96
<212> TYPE: PRT
<213> ORGANISM: Homo sapiens

<400> SEQUENCE: 166

Gln Val Gln Leu Gln Asp Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

Asp Tyr Tyr Trp Ser Trp Ile Arg Gln Pro Pro Gly Lys Gly Leu Glu
            35                  40                  45

Trp Ile Gly Tyr Phe Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

<210> SEQ ID NO 167
<211> LENGTH: 75
<212> TYPE: PRT
<213> ORGANISM: Homo sapiens
<220> FEATURE:
<221> NAME/KEY: misc_feature
<222> LOCATION: (18)..(18)
<223> OTHER INFORMATION: Xaa can be any naturally occurring amino acid

<400> SEQUENCE: 167

Ser Gly Gly Ser Ile Ser Ser Gly Asp Tyr Tyr Trp Ser Trp Ile Arg
1               5                   10                  15

Gln Xaa Pro Gly Lys Gly Leu Glu Trp Ile Gly Tyr Ile Tyr Tyr Ser
```

```
                20                  25                  30

Gly Ser Thr Tyr Tyr Asn Pro Ser Leu Lys Ser Arg Val Thr Ile Ser
            35                  40                  45

Val Asp Thr Ser Lys Asn Gln Phe Ser Leu Lys Leu Ser Ser Val Thr
 50                  55                  60

Ala Ala Asp Thr Ala Val Tyr Tyr Cys Ala Arg
 65                  70                  75

<210> SEQ ID NO 168
<211> LENGTH: 75
<212> TYPE: PRT
<213> ORGANISM: Homo sapiens

<400> SEQUENCE: 168

Ser Gly Gly Ser Ile Ser Ser Gly Asp Tyr Tyr Trp Ser Trp Ile Arg
 1               5                  10                  15

Gln His Pro Gly Lys Gly Leu Glu Trp Ile Gly Tyr Ile Tyr Tyr Ser
                20                  25                  30

Gly Ser Thr Tyr Tyr Asn Pro Ser Leu Lys Ser Arg Val Thr Ile Ser
            35                  40                  45

Val Asp Thr Ser Lys Asn Gln Phe Ser Leu Lys Leu Ser Ser Val Thr
 50                  55                  60

Ala Ala Asp Thr Ala Val Tyr Tyr Cys Ala Arg
 65                  70                  75

<210> SEQ ID NO 169
<211> LENGTH: 99
<212> TYPE: PRT
<213> ORGANISM: Homo sapiens

<400> SEQUENCE: 169

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
 50                  55                  60

Leu Lys Ser Leu Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 170
<211> LENGTH: 99
<212> TYPE: PRT
<213> ORGANISM: Homo sapiens

<400> SEQUENCE: 170

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                20                  25                  30

Gly Tyr Tyr Trp Ser Trp Ile Arg Gln His Pro Gly Lys Gly Leu Glu
            35                  40                  45
```

```
Trp Ile Gly Tyr Ile Tyr Tyr Ser Gly Ser Thr Tyr Tyr Asn Pro Ser
            50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                    85                  90                  95

Cys Ala Arg

<210> SEQ ID NO 171
<211> LENGTH: 99
<212> TYPE: PRT
<213> ORGANISM: Homo sapiens

<400> SEQUENCE: 171

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
            50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                    85                  90                  95

Cys Ala Arg

<210> SEQ ID NO 172
<211> LENGTH: 98
<212> TYPE: PRT
<213> ORGANISM: Homo sapiens

<400> SEQUENCE: 172

Gln Val Arg Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
            50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                    85                  90                  95

Cys Ala

<210> SEQ ID NO 173
<211> LENGTH: 97
<212> TYPE: PRT
<213> ORGANISM: Homo sapiens

<400> SEQUENCE: 173

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
```

20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Asp Ala Ala Val Tyr Tyr Cys
                85                  90                  95

Ala

<210> SEQ ID NO 174
<211> LENGTH: 96
<212> TYPE: PRT
<213> ORGANISM: Homo sapiens

<400> SEQUENCE: 174

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ser Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

<210> SEQ ID NO 175
<211> LENGTH: 96
<212> TYPE: PRT
<213> ORGANISM: Homo sapiens

<400> SEQUENCE: 175

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

<210> SEQ ID NO 176
<211> LENGTH: 96
<212> TYPE: PRT
<213> ORGANISM: Homo sapiens

<400> SEQUENCE: 176

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

<210> SEQ ID NO 177
<211> LENGTH: 96
<212> TYPE: PRT
<213> ORGANISM: Homo sapiens

<400> SEQUENCE: 177

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Lys Ser Lys Asn Gln Phe
65                  70                  75                  80

Ser Leu Lys Leu Ser Ser Val Thr Ala Ala Asp Thr Ala Val Tyr Tyr
                85                  90                  95

<210> SEQ ID NO 178
<211> LENGTH: 99
<212> TYPE: PRT
<213> ORGANISM: Homo sapiens

<400> SEQUENCE: 178

Gln Val Gln Leu Gln Glu Ser Gly Pro Gly Leu Leu Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Cys Ile Tyr Tyr Ser Gly Ser Thr Tyr Tyr Asn Pro Ser
50                  55                  60

Leu Lys Ser Arg Val Thr Ile Ser Val Asp Pro Ser Lys Asn Gln Phe
65                  70                  75                  80

Ser Leu Lys Pro Ser Ser Val Thr Ala Ala Asp Thr Ala Val Asp Tyr
                85                  90                  95

Cys Ala Arg

<210> SEQ ID NO 179
<211> LENGTH: 97
<212> TYPE: PRT
<213> ORGANISM: Homo sapiens

<400> SEQUENCE: 179

Gln Val Gln Leu Gln Gln Trp Gly Ala Gly Leu Leu Lys Pro Ser Glu
1               5                   10                  15

-continued

```
Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 180
<211> LENGTH: 97
<212> TYPE: PRT
<213> ORGANISM: Homo sapiens

<400> SEQUENCE: 180

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 181
<211> LENGTH: 94
<212> TYPE: PRT
<213> ORGANISM: Homo sapiens

<400> SEQUENCE: 181

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr
                85                  90

<210> SEQ ID NO 182
<211> LENGTH: 97
<212> TYPE: PRT
<213> ORGANISM: Homo sapiens

<400> SEQUENCE: 182
```

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg
```

```
<210> SEQ ID NO 183
<211> LENGTH: 97
<212> TYPE: PRT
<213> ORGANISM: Homo sapiens

<400> SEQUENCE: 183

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Cys Trp Ile Arg Gln Pro Leu Gly Lys Gly Leu Glu Trp Ile
        35                  40                  45

Gly Glu Ile Asn His Ser Gly Ser Thr Asn Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg
```

```
<210> SEQ ID NO 184
<211> LENGTH: 94
<212> TYPE: PRT
<213> ORGANISM: Homo sapiens

<400> SEQUENCE: 184

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Gly Ser Val Thr Ala Ala Asp Thr Ala Val Tyr Tyr
            85                  90
```

```
<210> SEQ ID NO 185
<211> LENGTH: 94
<212> TYPE: PRT
```

<213> ORGANISM: Homo sapiens

<400> SEQUENCE: 185

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr
                85                  90

<210> SEQ ID NO 186
<211> LENGTH: 96
<212> TYPE: PRT
<213> ORGANISM: Homo sapiens

<400> SEQUENCE: 186

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Thr Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

<210> SEQ ID NO 187
<211> LENGTH: 97
<212> TYPE: PRT
<213> ORGANISM: Homo sapiens

<400> SEQUENCE: 187

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 188
<211> LENGTH: 97

<212> TYPE: PRT
<213> ORGANISM: Homo sapiens

<400> SEQUENCE: 188

```
Gln Val Gln Leu Gln Glu Ser Gly Pro Gly Leu Val Lys Pro Ser Glu
1               5                   10                  15
Thr Leu Ser Leu Thr Cys Ala Val Tyr Gly Gly Ser Phe Ser Gly Tyr
            20                  25                  30
Tyr Trp Ser Trp Ile Arg Gln Pro Pro Gly Lys Gly Leu Glu Trp Ile
        35                  40                  45
Gly Glu Ile Asn His Ser Gly Ser Thr Asn Tyr Asn Pro Ser Leu Lys
    50                  55                  60
Ser Arg Ile Thr Met Ser Val Asp Thr Ser Lys Asn Gln Phe Tyr Leu
65                  70                  75                  80
Lys Leu Ser Ser Val Thr Ala Ala Asp Thr Ala Val Tyr Tyr Cys Ala
                85                  90                  95
Arg
```

<210> SEQ ID NO 189
<211> LENGTH: 97
<212> TYPE: PRT
<213> ORGANISM: Homo sapiens

<400> SEQUENCE: 189

```
Gln Val Gln Leu Gln Gln Trp Gly Ala Gly Leu Leu Lys Pro Ser Glu
1               5                   10                  15
Thr Leu Ser Leu Thr Cys Ala Val Tyr Gly Gly Ser Val Ser Gly Tyr
            20                  25                  30
Tyr Trp Ser Trp Ile Arg Gln Pro Pro Gly Lys Gly Leu Glu Trp Ile
        35                  40                  45
Gly Tyr Ile Tyr Tyr Ser Gly Ser Thr Asn Asn Pro Ser Leu Lys
    50                  55                  60
Ser Arg Ala Thr Ile Ser Val Asp Thr Ser Lys Asn Gln Phe Ser Leu
65                  70                  75                  80
Asn Leu Ser Ser Val Thr Ala Ala Asp Thr Ala Val Tyr Cys Cys Ala
                85                  90                  95
Arg
```

<210> SEQ ID NO 190
<211> LENGTH: 97
<212> TYPE: PRT
<213> ORGANISM: Homo sapiens

<400> SEQUENCE: 190

```
Gln Val Gln Leu Gln Gln Trp Gly Ala Gly Leu Leu Lys Pro Ser Glu
1               5                   10                  15
Thr Leu Ser Leu Thr Cys Ala Val Tyr Gly Gly Ser Phe Ser Gly Tyr
            20                  25                  30
Tyr Trp Ser Trp Ile Arg Gln Pro Pro Gly Lys Gly Leu Glu Trp Ile
        35                  40                  45
Gly Glu Ile Ile His Ser Gly Ser Thr Asn Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
```

Arg

<210> SEQ ID NO 191
<211> LENGTH: 73
<212> TYPE: PRT
<213> ORGANISM: Homo sapiens

<400> SEQUENCE: 191

Tyr Gly Gly Ser Phe Ser Gly Tyr Tyr Trp Ser Trp Ile Arg Gln Pro
1               5                   10                  15

Pro Gly Lys Gly Leu Glu Trp Ile Gly Glu Ile Asn His Ser Gly Ser
            20                  25                  30

Thr Asn Tyr Asn Pro Ser Leu Lys Ser Arg Val Thr Ile Ser Val Asp
        35                  40                  45

Thr Ser Lys Asn Gln Phe Ser Leu Lys Leu Ser Val Thr Ala Ala
    50                  55                  60

Asp Thr Ala Val Tyr Tyr Cys Ala Arg
65                  70

<210> SEQ ID NO 192
<211> LENGTH: 99
<212> TYPE: PRT
<213> ORGANISM: Homo sapiens

<400> SEQUENCE: 192

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 193
<211> LENGTH: 99
<212> TYPE: PRT
<213> ORGANISM: Homo sapiens

<400> SEQUENCE: 193

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn His Phe
65                  70                  75                  80

Ser Leu Lys Leu Ser Ser Val Thr Ala Ala Asp Thr Ala Val Tyr Tyr
                85                  90                  95

-continued

Cys Ala Arg

<210> SEQ ID NO 194
<211> LENGTH: 96
<212> TYPE: PRT
<213> ORGANISM: Homo sapiens

<400> SEQUENCE: 194

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

<210> SEQ ID NO 195
<211> LENGTH: 64
<212> TYPE: PRT
<213> ORGANISM: Homo sapiens

<400> SEQUENCE: 195

Ser Ile Ser Ser Ser Ser Tyr Tyr Trp Gly Trp Ile Arg Gln Pro Pro
1               5                   10                  15

Gly Lys Gly Leu Glu Trp Ile Gly Ser Ile Tyr Tyr Ser Gly Ser Thr
            20                  25                  30

Tyr Tyr Asn Pro Ser Leu Lys Ser Arg Val Thr Ile Ser Val Asp Thr
        35                  40                  45

Ser Lys Asn Gln Phe Ser Leu Lys Leu Ser Ser Val Thr Ala Ala Asp
    50                  55                  60

<210> SEQ ID NO 196
<211> LENGTH: 98
<212> TYPE: PRT
<213> ORGANISM: Homo sapiens

<400> SEQUENCE: 196

Gln Leu Gln Leu Gln Glu Ser Gly Pro Gly Leu Val Lys Pro Ser Glu
1               5                   10                  15

Thr Pro Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala

<210> SEQ ID NO 197
<211> LENGTH: 99

```
<212> TYPE: PRT
<213> ORGANISM: Homo sapiens

<400> SEQUENCE: 197

Arg Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Pro Leu Lys Leu Ser Ser Val Thr Ala Ala Asp Thr Ala Val Tyr Tyr
                85                  90                  95

Cys Ala Arg

<210> SEQ ID NO 198
<211> LENGTH: 99
<212> TYPE: PRT
<213> ORGANISM: Homo sapiens

<400> SEQUENCE: 198

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 199
<211> LENGTH: 98
<212> TYPE: PRT
<213> ORGANISM: Homo sapiens

<400> SEQUENCE: 199

Gln Val Gln Leu Gln Glu Ser Gly Pro Gly Leu Val Lys Pro Pro Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Cys Cys
                85                  90                  95
```

-continued

Ala Arg

<210> SEQ ID NO 200
<211> LENGTH: 98
<212> TYPE: PRT
<213> ORGANISM: Homo sapiens

<400> SEQUENCE: 200

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg

<210> SEQ ID NO 201
<211> LENGTH: 95
<212> TYPE: PRT
<213> ORGANISM: Homo sapiens

<400> SEQUENCE: 201

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr
                85                  90                  95

<210> SEQ ID NO 202
<211> LENGTH: 95
<212> TYPE: PRT
<213> ORGANISM: Homo sapiens

<400> SEQUENCE: 202

Gln Val Gln Leu Gln Glu Ser Gly Pro Gly Leu Val Lys Pro Ser Gly
1               5                   10                  15

Thr Leu Ser Leu Thr Cys Ala Ile Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

```
Leu Lys Leu Ser Ser Val Thr Ala Ala Asp Thr Ala Val Tyr Tyr
                85                  90                  95

<210> SEQ ID NO 203
<211> LENGTH: 95
<212> TYPE: PRT
<213> ORGANISM: Homo sapiens

<400> SEQUENCE: 203

Gln Val Gln Leu Gln Glu Leu Gly Pro Gly Leu Val Lys Pro Pro Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr
                85                  90                  95

<210> SEQ ID NO 204
<211> LENGTH: 74
<212> TYPE: PRT
<213> ORGANISM: Homo sapiens
<220> FEATURE:
<221> NAME/KEY: misc_feature
<222> LOCATION: (20)..(21)
<223> OTHER INFORMATION: Xaa can be any naturally occurring amino acid

<400> SEQUENCE: 204

Ser Gly Gly Ser Ile Ser Ser Asn Trp Trp Ser Trp Val Arg Gln
1               5                   10                  15

Pro Pro Gly Xaa Xaa Leu Glu Trp Ile Gly Glu Ile Tyr His Ser Gly
            20                  25                  30

Ser Thr Asn Tyr Asn Pro Ser Leu Lys Ser Arg Val Thr Met Ser Val
        35                  40                  45

Asp Thr Ser Lys Asn Gln Phe Ser Leu Lys Leu Ser Ser Val Thr Ala
    50                  55                  60

Ala Asp Thr Ala Val Tyr Tyr Cys Ala Arg
65                  70

<210> SEQ ID NO 205
<211> LENGTH: 97
<212> TYPE: PRT
<213> ORGANISM: Homo sapiens

<400> SEQUENCE: 205

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80
```

```
Lys Leu Ser Ser Val Thr Ala Ala Asp Thr Ala Val Tyr Tyr Cys Ala
                85                  90                  95

Arg

<210> SEQ ID NO 206
<211> LENGTH: 97
<212> TYPE: PRT
<213> ORGANISM: Homo sapiens

<400> SEQUENCE: 206

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 207
<211> LENGTH: 96
<212> TYPE: PRT
<213> ORGANISM: Homo sapiens

<400> SEQUENCE: 207

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

<210> SEQ ID NO 208
<211> LENGTH: 96
<212> TYPE: PRT
<213> ORGANISM: Homo sapiens

<400> SEQUENCE: 208

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Tyr Tyr Asn Pro Ser Leu Lys
    50                  55                  60
```

```
Ser Arg Val Thr Met Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95
```

<210> SEQ ID NO 209
<211> LENGTH: 96
<212> TYPE: PRT
<213> ORGANISM: Homo sapiens

<400> SEQUENCE: 209

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
                 20                  25                  30

Tyr Trp Ser Trp Ile Arg Gln Pro Pro Gly Lys Gly Leu Glu Trp Ile
             35                  40                  45

Gly Arg Ile Tyr Tyr Ser Gly Ser Thr Tyr Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95
```

<210> SEQ ID NO 210
<211> LENGTH: 96
<212> TYPE: PRT
<213> ORGANISM: Homo sapiens

<400> SEQUENCE: 210

```
Gln Val Gln Leu Gln Glu Ser Gly Pro Gly Leu Val Lys Pro Ser Glu
  1               5                  10                  15

Thr Leu Ser Leu Thr Cys Thr Val Thr Gly Gly Ser Ile Ser Ser Tyr
                 20                  25                  30

Tyr Trp Ser Trp Ile Arg Gln Pro Ala Gly Lys Gly Leu Glu Trp Ile
             35                  40                  45

Gly Tyr Ile Tyr Tyr Ser Gly Ser Thr Tyr Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95
```

<210> SEQ ID NO 211
<211> LENGTH: 97
<212> TYPE: PRT
<213> ORGANISM: Homo sapiens

<400> SEQUENCE: 211

```
Gln Val Gln Leu Gln Glu Ser Gly Pro Gly Leu Val Lys Pro Ser Asp
  1               5                  10                  15

Thr Leu Ser Leu Thr Cys Thr Val Ser Gly Gly Ser Ile Ser Ser Tyr
                 20                  25                  30

Tyr Trp Ser Trp Ile Arg Gln Pro Pro Gly Lys Gly Leu Glu Trp Ile
             35                  40                  45

Gly Tyr Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
```

```
                65                  70                  75                  80
Lys Leu Ser Ser Val Thr Ala Ala Asp Thr Ala Val Tyr Tyr Cys Ala
                    85                  90                  95

Arg

<210> SEQ ID NO 212
<211> LENGTH: 97
<212> TYPE: PRT
<213> ORGANISM: Homo sapiens

<400> SEQUENCE: 212

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 213
<211> LENGTH: 73
<212> TYPE: PRT
<213> ORGANISM: Homo sapiens
<220> FEATURE:
<221> NAME/KEY: misc_feature
<222> LOCATION: (19)..(20)
<223> OTHER INFORMATION: Xaa can be any naturally occurring amino acid

<400> SEQUENCE: 213

Ser Gly Gly Ser Ile Ser Ser Tyr Tyr Trp Ser Trp Ile Arg Gln Pro
1               5                   10                  15

Pro Gly Xaa Xaa Leu Glu Trp Ile Gly Tyr Ile Tyr Tyr Ser Gly Ser
                20                  25                  30

Thr Asn Tyr Asn Pro Ser Leu Lys Ser Arg Val Thr Ile Ser Val Asp
            35                  40                  45

Thr Ser Lys Asn Gln Phe Ser Leu Lys Leu Ser Ser Val Thr Ala Ala
        50                  55                  60

Asp Thr Ala Val Tyr Tyr Cys Ala Arg
65                  70

<210> SEQ ID NO 214
<211> LENGTH: 97
<212> TYPE: PRT
<213> ORGANISM: Homo sapiens

<400> SEQUENCE: 214

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Ile Ser Ser Tyr
                20                  25                  30

Tyr Trp Ser Trp Ile Arg Gln Pro Ala Gly Lys Gly Leu Glu Trp Ile
            35                  40                  45
```

```
Gly Arg Ile Tyr Thr Ser Gly Ser Thr Asn Tyr Asn Pro Ser Leu Lys
        50                  55                  60

Ser Arg Val Thr Met Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg
```

<210> SEQ ID NO 215
<211> LENGTH: 99
<212> TYPE: PRT
<213> ORGANISM: Homo sapiens

<400> SEQUENCE: 215

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Val Ser Ser Gly
                 20                  25                  30

Ser Tyr Tyr Trp Ser Trp Ile Arg Gln Pro Pro Gly Lys Gly Leu Glu
             35                  40                  45

Trp Ile Gly Tyr Ile Tyr Tyr Ser Gly Ser Thr Asn Tyr Asn Pro Ser
         50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg
```

<210> SEQ ID NO 216
<211> LENGTH: 99
<212> TYPE: PRT
<213> ORGANISM: Homo sapiens

<400> SEQUENCE: 216

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                 20                  25                  30

Ser Tyr Tyr Trp Ser Trp Ile Arg Gln Pro Ala Gly Lys Gly Leu Glu
             35                  40                  45

Trp Ile Gly Arg Ile Tyr Thr Ser Gly Ser Thr Asn Tyr Asn Pro Ser
         50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg
```

<210> SEQ ID NO 217
<211> LENGTH: 99
<212> TYPE: PRT
<213> ORGANISM: Homo sapiens

<400> SEQUENCE: 217

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Val Ser Ser Gly
```

```
                    20                  25                  30

Ser Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn His Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 218
<211> LENGTH: 95
<212> TYPE: PRT
<213> ORGANISM: Homo sapiens

<400> SEQUENCE: 218

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
                20                  25                  30

Ser Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Asp Thr Ala Val Tyr Tyr
                85                  90                  95

<210> SEQ ID NO 219
<211> LENGTH: 99
<212> TYPE: PRT
<213> ORGANISM: Homo sapiens

<400> SEQUENCE: 219

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser
                20                  25                  30

Ser Tyr Tyr Trp Gly Trp Ile Arg Gln Pro Pro Gly Lys Gly Leu Glu
            35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Lys Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 220
<211> LENGTH: 75
<212> TYPE: PRT
<213> ORGANISM: Homo sapiens

<400> SEQUENCE: 220

Ser Gly Gly Ser Val Ser Ser Gly Ser Tyr Tyr Trp Ser Trp Ile Arg
```

```
                1               5                  10                 15
Gln Pro Pro Gly Lys Gly Leu Glu Trp Ile Gly Tyr Ile Tyr Tyr Ser
                               20                  25                 30

Gly Ser Thr Asn Tyr Asn Pro Ser Leu Lys Ser Arg Val Thr Ile Ser
            35                  40                  45

Val Asp Thr Ser Lys Asn Gln Phe Ser Leu Lys Leu Ser Ser Val Thr
        50                  55                  60

Ala Ala Asp Thr Ala Val Tyr Tyr Cys Ala Arg
65                  70                  75

<210> SEQ ID NO 221
<211> LENGTH: 75
<212> TYPE: PRT
<213> ORGANISM: Homo sapiens

<400> SEQUENCE: 221

Ser Gly Gly Ser Val Ser Ser Gly Ser Tyr Tyr Trp Ser Trp Ile Arg
1               5                  10                  15

Gln Pro Pro Gly Lys Gly Leu Glu Trp Ile Gly Tyr Ile Tyr Tyr Ser
                        20                  25                  30

Gly Ser Thr Asn Tyr Asn Pro Ser Leu Lys Ser Arg Val Thr Ile Ser
            35                  40                  45

Val Asp Thr Ser Lys Asn Gln Phe Ser Leu Lys Leu Ser Ser Val Thr
        50                  55                  60

Ala Ala Asp Thr Ala Val Tyr Tyr Cys Ala Arg
65                  70                  75

<210> SEQ ID NO 222
<211> LENGTH: 98
<212> TYPE: PRT
<213> ORGANISM: Homo sapiens

<400> SEQUENCE: 222

Gln Val Gln Leu Gln Glu Ser Gly Pro Gly Leu Val Lys Pro Ser Glu
1               5                  10                  15

Thr Leu Ser Leu Thr Cys Ala Val Ser Gly Tyr Ser Ile Ser Ser Gly
                20                  25                  30

Tyr Tyr Trp Gly Trp Ile Arg Gln Pro Pro Gly Lys Gly Leu Glu Trp
            35                  40                  45

Ile Gly Ser Ile Tyr His Ser Gly Ser Thr Tyr Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg

<210> SEQ ID NO 223
<211> LENGTH: 98
<212> TYPE: PRT
<213> ORGANISM: Homo sapiens

<400> SEQUENCE: 223

Gln Val Gln Leu Gln Glu Ser Gly Pro Gly Leu Val Lys Pro Ser Glu
1               5                  10                  15

Thr Leu Ser Leu Thr Cys Thr Val Ser Gly Tyr Ser Ile Ser Ser Gly
                20                  25                  30
```

Tyr Tyr Trp Gly Trp Ile Arg Gln Pro Pro Gly Lys Gly Leu Glu Trp
            35                  40                  45

Ile Gly Ser Ile Tyr His Ser Gly Ser Thr Tyr Tyr Asn Pro Ser Leu
50                      55                  60

Lys Ser Arg Val Thr Ile Ser Val Asp Thr Ser Lys Asn Gln Phe Ser
65                      70                  75                  80

Leu Lys Leu Ser Ser Val Thr Ala Ala Asp Thr Ala Val Tyr Tyr Cys
                    85                  90                  95

Ala Arg

<210> SEQ ID NO 224
<211> LENGTH: 98
<212> TYPE: PRT
<213> ORGANISM: Homo sapiens

<400> SEQUENCE: 224

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 225
<211> LENGTH: 98
<212> TYPE: PRT
<213> ORGANISM: Homo sapiens

<400> SEQUENCE: 225

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Thr Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 226
<211> LENGTH: 98
<212> TYPE: PRT
<213> ORGANISM: Homo sapiens

<400> SEQUENCE: 226

Glu Val Gln Leu Val Gln Ser Gly Ala Glu Val Lys Lys Pro Gly Glu

```
                1               5                  10                 15
Ser Leu Lys Ile Ser Cys Lys Gly Ser Gly Tyr Ser Phe Thr Ser Tyr
            20                  25                 30

Trp Ile Gly Trp Val Arg Gln Met Pro Gly Lys Gly Leu Glu Trp Met
            35                  40                 45

Gly Ile Ile Tyr Pro Gly Asp Ser Asp Thr Arg Tyr Ser Pro Ser Phe
        50                  55                 60

Gln Gly Gln Val Thr Ile Ser Ala Asp Lys Ser Ile Ser Thr Ala Tyr
65                  70                  75                      80

Leu Gln Trp Ser Ser Leu Lys Ala Ser Asp Thr Ala Met Tyr Tyr Cys
                85                  90                  95

Ala Arg

<210> SEQ ID NO 227
<211> LENGTH: 98
<212> TYPE: PRT
<213> ORGANISM: Homo sapiens

<400> SEQUENCE: 227

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Pro Ile Ser Thr Ala Tyr
65                  70                  75                      80

Leu Gln Trp Ser Ser Leu Lys Ala Ser Asp Thr Ala Met Tyr Tyr Cys
                85                  90                  95

Ala Arg

<210> SEQ ID NO 228
<211> LENGTH: 81
<212> TYPE: PRT
<213> ORGANISM: Homo sapiens

<400> SEQUENCE: 228

Lys Pro Gly Glu Ser Leu Lys Ile Ser Cys Lys Gly Ser Gly Tyr Ser
1               5                   10                  15

Phe Thr Ser Tyr Trp Ile Gly Trp Val Arg Gln Met Pro Arg Lys Gly
            20                  25                  30

Leu Glu Trp Met Gly Ile Ile Tyr Pro Gly Asp Ser Asp Thr Arg Tyr
            35                  40                  45

Ser Pro Ser Phe Gln Gly Gln Val Thr Ile Ser Ala Asp Lys Ser Ile
        50                  55                  60

Ser Thr Ala Tyr Leu Gln Trp Ser Ser Leu Lys Ala Ser Asp Thr Ala
65                  70                  75                      80

Met

<210> SEQ ID NO 229
<211> LENGTH: 98
<212> TYPE: PRT
<213> ORGANISM: Homo sapiens

<400> SEQUENCE: 229
```

-continued

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
                20                  25                  30

Trp Ile Ser Trp Val Arg Gln Met Pro Gly Lys Gly Leu Glu Trp Met
            35                  40                  45

Gly Arg Ile Asp Pro Ser Asp Ser Tyr Thr Asn Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 230
<211> LENGTH: 98
<212> TYPE: PRT
<213> ORGANISM: Homo sapiens

<400> SEQUENCE: 230

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
                20                  25                  30

Trp Ile Ser Trp Val Arg Gln Met Pro Gly Lys Gly Leu Glu Trp Met
            35                  40                  45

Gly Arg Ile Asp Pro Ser Asp Ser Tyr Thr Asn Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Arg Thr Pro Pro Cys Ile Thr Val
                85                  90                  95

Arg Asp

<210> SEQ ID NO 231
<211> LENGTH: 98
<212> TYPE: PRT
<213> ORGANISM: Homo sapiens

<400> SEQUENCE: 231

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
                20                  25                  30

Trp Ile Ser Trp Val Arg Gln Met Pro Gly Lys Gly Leu Glu Trp Met
            35                  40                  45

Gly Arg Ile Asp Pro Ser Asp Ser Tyr Thr Asn Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 232

<211> LENGTH: 98
<212> TYPE: PRT
<213> ORGANISM: Homo sapiens

<400> SEQUENCE: 232

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 233
<211> LENGTH: 101
<212> TYPE: PRT
<213> ORGANISM: Homo sapiens

<400> SEQUENCE: 233

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg
            100

<210> SEQ ID NO 234
<211> LENGTH: 101
<212> TYPE: PRT
<213> ORGANISM: Homo sapiens

<400> SEQUENCE: 234

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val

```
                            85                  90                  95

Tyr Tyr Cys Ala Arg
            100

<210> SEQ ID NO 235
<211> LENGTH: 98
<212> TYPE: PRT
<213> ORGANISM: Homo sapiens

<400> SEQUENCE: 235

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg

<210> SEQ ID NO 236
<211> LENGTH: 98
<212> TYPE: PRT
<213> ORGANISM: Homo sapiens

<400> SEQUENCE: 236

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg

<210> SEQ ID NO 237
<211> LENGTH: 91
<212> TYPE: PRT
<213> ORGANISM: Homo sapiens

<400> SEQUENCE: 237

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
```

```
                    50                  55                  60
Thr Gly Arg Phe Val Phe Ser Leu Asp Thr Ser Val Ser Thr Ala Tyr
 65                  70                  75                  80
Leu Gln Ile Ser Thr Leu Lys Ala Glu Asp Thr
                 85                  90
```

<210> SEQ ID NO 238
<211> LENGTH: 98
<212> TYPE: PRT
<213> ORGANISM: Homo sapiens

<400> SEQUENCE: 238

```
Gln Val Gln Leu Val Gln Ser Gly Ser Glu Leu Lys Lys Pro Gly Ala
  1               5                  10                  15
Ser Val Lys Val Ser Cys Lys Ala Ser Gly Tyr Thr Phe Thr Ser Tyr
                 20                  25                  30
Ala Met Asn Trp Val Arg Gln Ala Pro Gly Gln Gly Leu Glu Trp Met
                 35                  40                  45
Gly Trp Ile Asn Thr Asn Thr Gly Asn Pro Thr Tyr Ala Gln Gly Phe
             50                  55                  60
Thr Gly Arg Phe Val Phe Ser Leu Asp Thr Ser Val Ser Met Ala Tyr
 65                  70                  75                  80
Leu Gln Ile Ser Ser Leu Lys Ala Glu Asp Thr Ala Val Tyr Tyr Cys
                 85                  90                  95
Ala Arg
```

<210> SEQ ID NO 239
<211> LENGTH: 98
<212> TYPE: PRT
<213> ORGANISM: Homo sapiens

<400> SEQUENCE: 239

```
Gln Val Gln Leu Val Gln Ser Gly Ser Glu Leu Lys Lys Pro Gly Ala
  1               5                  10                  15
Ser Val Lys Val Ser Cys Lys Ala Ser Gly Tyr Thr Phe Thr Ser Tyr
                 20                  25                  30
Ala Met Asn Trp Val Arg Gln Ala Pro Gly Gln Gly Leu Glu Trp Met
                 35                  40                  45
Gly Trp Ile Asn Thr Asn Thr Gly Asn Pro Thr Tyr Ala Gln Gly Phe
             50                  55                  60
Thr Gly Arg Phe Val Phe Ser Leu Asp Thr Ser Val Ser Met Ala Tyr
 65                  70                  75                  80
Leu Gln Ile Ser Ser Leu Lys Ala Glu Asp Thr Ala Val Cys Tyr Cys
                 85                  90                  95
Ala Arg
```

<210> SEQ ID NO 240
<211> LENGTH: 95
<212> TYPE: PRT
<213> ORGANISM: Homo sapiens

<400> SEQUENCE: 240

```
Asp Ile Gln Met Thr Gln Ser Pro Ser Ser Val Ser Ala Ser Val Gly
  1               5                  10                  15
Asp Arg Val Thr Ile Thr Cys Arg Ala Ser Gln Gly Ile Ser Ser Trp
                 20                  25                  30
Leu Ala Trp Tyr Gln Gln Lys Pro Gly Lys Ala Pro Lys Leu Leu Ile
```

```
            35                  40                  45

Tyr Ala Ala Ser Ser Leu Gln Ser Gly Val Pro Ser Arg Phe Ser Gly
             50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro
                 85                  90                  95
```

<210> SEQ ID NO 241
<211> LENGTH: 94
<212> TYPE: PRT
<213> ORGANISM: Homo sapiens

<400> SEQUENCE: 241

```
Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
             20                  25                  30

Leu Ala Tyr Gln Gln Lys Pro Gly Lys Ala Pro Lys Leu Leu Ile Tyr
         35                  40                  45

Asp Ala Ser Ser Leu Glu Ser Gly Val Pro Ser Arg Phe Ser Gly Ser
     50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Phe Asn Asn Tyr Pro
             85                  90
```

<210> SEQ ID NO 242
<211> LENGTH: 95
<212> TYPE: PRT
<213> ORGANISM: Homo sapiens

<400> SEQUENCE: 242

```
Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
             20                  25                  30

Leu Ala Trp Tyr Gln Gln Lys Pro Gly Lys Ala Pro Lys Leu Leu Ile
         35                  40                  45

Tyr Asp Ala Ser Ser Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro
                 85                  90                  95
```

<210> SEQ ID NO 243
<211> LENGTH: 95
<212> TYPE: PRT
<213> ORGANISM: Homo sapiens

<400> SEQUENCE: 243

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
             20                  25                  30

Leu Ala Trp Phe Gln Gln Lys Pro Gly Lys Ala Pro Lys Ser Leu Ile
         35                  40                  45
```

```
Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                 85                  90                  95

<210> SEQ ID NO 244
<211> LENGTH: 95
<212> TYPE: PRT
<213> ORGANISM: Homo sapiens

<400> SEQUENCE: 244

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
                 20                  25                  30

Leu Ala Trp Phe Gln Gln Lys Pro Gly Lys Ala Pro Lys Ser Leu Ile
             35                  40                  45

Tyr Ala Ala Ser Ser Leu Gln Ser Gly Val Pro Ser Lys Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                 85                  90                  95

<210> SEQ ID NO 245
<211> LENGTH: 95
<212> TYPE: PRT
<213> ORGANISM: Homo sapiens

<400> SEQUENCE: 245

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro
                 85                  90                  95

<210> SEQ ID NO 246
<211> LENGTH: 95
<212> TYPE: PRT
<213> ORGANISM: Homo sapiens

<400> SEQUENCE: 246

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Lys Ala Pro Lys Arg Leu Ile
             35                  40                  45
```

```
Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Asn Ser Tyr Pro
                85                  90                  95
```

<210> SEQ ID NO 247
<211> LENGTH: 95
<212> TYPE: PRT
<213> ORGANISM: Homo sapiens

<400> SEQUENCE: 247

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro
                85                  90                  95
```

<210> SEQ ID NO 248
<211> LENGTH: 95
<212> TYPE: PRT
<213> ORGANISM: Homo sapiens

<400> SEQUENCE: 248

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95
```

<210> SEQ ID NO 249
<211> LENGTH: 95
<212> TYPE: PRT
<213> ORGANISM: Homo sapiens

<400> SEQUENCE: 249

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95
```

<210> SEQ ID NO 250
<211> LENGTH: 95
<212> TYPE: PRT
<213> ORGANISM: Homo sapiens

<400> SEQUENCE: 250

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Gly Tyr Ser Thr Pro
                85                  90                  95
```

<210> SEQ ID NO 251
<211> LENGTH: 95
<212> TYPE: PRT
<213> ORGANISM: Homo sapiens

<400> SEQUENCE: 251

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95
```

<210> SEQ ID NO 252
<211> LENGTH: 95
<212> TYPE: PRT
<213> ORGANISM: Homo sapiens

<400> SEQUENCE: 252

```
Asp Ile Gln Met Thr Gln Ser Pro Ser Thr Leu Ser Ala Ser Val Gly
1               5                   10                  15

Asp Arg Val Thr Ile Ile Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60
```

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 253
<211> LENGTH: 95
<212> TYPE: PRT
<213> ORGANISM: Homo sapiens

<400> SEQUENCE: 253

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 254
<211> LENGTH: 95
<212> TYPE: PRT
<213> ORGANISM: Homo sapiens

<400> SEQUENCE: 254

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro
                85                  90                  95

<210> SEQ ID NO 255
<211> LENGTH: 95
<212> TYPE: PRT
<213> ORGANISM: Homo sapiens

<400> SEQUENCE: 255

Ala Ile Arg Met Thr Gln Ser Pro Ser Phe Ser Ala Ser Thr Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Tyr Pro
                85                  90                  95

<210> SEQ ID NO 256
<211> LENGTH: 95
<212> TYPE: PRT
<213> ORGANISM: Homo sapiens

<400> SEQUENCE: 256

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro
                85                  90                  95

<210> SEQ ID NO 257
<211> LENGTH: 95
<212> TYPE: PRT
<213> ORGANISM: Homo sapiens

<400> SEQUENCE: 257

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Ser
            20                  25                  30

Leu Ala Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro
                85                  90                  95

<210> SEQ ID NO 258
<211> LENGTH: 95
<212> TYPE: PRT
<213> ORGANISM: Homo sapiens

<400> SEQUENCE: 258

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Gln Ala Asn Ser Phe Pro
                85                  90                  95

<210> SEQ ID NO 259
<211> LENGTH: 95
<212> TYPE: PRT
<213> ORGANISM: Homo sapiens

<400> SEQUENCE: 259

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asn Tyr Pro
                85                  90                  95

<210> SEQ ID NO 260
<211> LENGTH: 95
<212> TYPE: PRT
<213> ORGANISM: Homo sapiens

<400> SEQUENCE: 260

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 261
<211> LENGTH: 95
<212> TYPE: PRT
<213> ORGANISM: Homo sapiens

<400> SEQUENCE: 261

Asp Ile Gln Met Thr Gln Ser Pro Ser Ser Leu Ser Ala Ser Val Gly
1               5                   10                  15

Asp Arg Val Thr Ile Thr Cys Arg Ala Arg Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Tyr Asn Ser Tyr Pro
                85                  90                  95

<210> SEQ ID NO 262
<211> LENGTH: 95
<212> TYPE: PRT
<213> ORGANISM: Homo sapiens

<400> SEQUENCE: 262

Asn Ile Gln Met Thr Gln Ser Pro Ser Ala Met Ser Ala Ser Val Gly
1               5                   10                  15

Asp Arg Val Thr Ile Thr Cys Arg Ala Arg Gln Gly Ile Ser Asn Tyr
            20                  25                  30

Leu Ala Trp Phe Gln Gln Lys Pro Gly Lys Val Pro Lys His Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 263
<211> LENGTH: 95
<212> TYPE: PRT
<213> ORGANISM: Homo sapiens

<400> SEQUENCE: 263

Asp Ile Gln Met Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Val Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 264
<211> LENGTH: 95
<212> TYPE: PRT
<213> ORGANISM: Homo sapiens

<400> SEQUENCE: 264

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95

<210> SEQ ID NO 265
<211> LENGTH: 95
<212> TYPE: PRT
<213> ORGANISM: Homo sapiens

<400> SEQUENCE: 265

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 266
<211> LENGTH: 95
<212> TYPE: PRT
<213> ORGANISM: Homo sapiens

<400> SEQUENCE: 266

Ala Ile Arg Met Thr Gln Ser Pro Phe Ser Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Ala Lys Ala Pro Lys Leu Phe Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro
                85                  90                  95

<210> SEQ ID NO 267
<211> LENGTH: 95
<212> TYPE: PRT
<213> ORGANISM: Homo sapiens

<400> SEQUENCE: 267

Val Ile Trp Met Thr Gln Ser Pro Ser Leu Leu Ser Ala Ser Thr Gly
1               5                   10                  15

Asp Arg Val Thr Ile Ser Cys Arg Met Ser Gln Gly Ile Ser Ser Tyr
            20                  25                  30

Leu Ala Trp Tyr Gln Gln Lys Pro Gly Lys Ala Pro Glu Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Phe Pro 85                  90                  95

<210> SEQ ID NO 268
<211> LENGTH: 100
<212> TYPE: PRT
<213> ORGANISM: Homo sapiens

<400> SEQUENCE: 268

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro
            100

<210> SEQ ID NO 269
<211> LENGTH: 100
<212> TYPE: PRT
<213> ORGANISM: Homo sapiens

<400> SEQUENCE: 269

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 270
<211> LENGTH: 99
<212> TYPE: PRT
<213> ORGANISM: Homo sapiens

<400> SEQUENCE: 270

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Met Gln Gly Ile
                85                  90                  95

His Leu Pro

<210> SEQ ID NO 271
<211> LENGTH: 100
<212> TYPE: PRT
<213> ORGANISM: Homo sapiens

<400> SEQUENCE: 271

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
                20                  25                  30

Asp Gly Lys Thr Tyr Leu Tyr Trp Tyr Leu Gln Lys Pro Gly Gln Ser
            35                  40                  45

Pro Gln Leu Leu Ile Tyr Glu Val Ser Ser Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro
            100

<210> SEQ ID NO 272
<211> LENGTH: 100
<212> TYPE: PRT
<213> ORGANISM: Homo sapiens

<400> SEQUENCE: 272

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
                20                  25                  30

Asp Gly Lys Thr Tyr Leu Tyr Trp Tyr Leu Gln Lys Pro Gly Gln Ser
            35                  40                  45

Pro Gln Leu Leu Ile Tyr Glu Val Ser Ser Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro
            100

<210> SEQ ID NO 273
<211> LENGTH: 100
<212> TYPE: PRT
<213> ORGANISM: Homo sapiens

<400> SEQUENCE: 273

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser 20                  25                  30

Asp Gly Asn Thr Tyr Leu Asn Trp Phe Gln Gln Arg Pro Gly Gln Ser
            35                  40                  45

Pro Arg Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                85                  90                  95

Thr His Trp Pro
            100

<210> SEQ ID NO 274
<211> LENGTH: 100
<212> TYPE: PRT
<213> ORGANISM: Homo sapiens

<400> SEQUENCE: 274

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                85                  90                  95

Thr His Trp Pro
            100

<210> SEQ ID NO 275
<211> LENGTH: 101
<212> TYPE: PRT
<213> ORGANISM: Homo sapiens

<400> SEQUENCE: 275

Asp Ile Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
            35                  40                  45

Ser Pro Gln Leu Leu Ile Tyr Thr Leu Ser Tyr Arg Ala Ser Gly Val
        50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                85                  90                  95

Arg Ile Glu Phe Pro
            100

<210> SEQ ID NO 276
<211> LENGTH: 83
<212> TYPE: PRT

<213> ORGANISM: Homo sapiens

<400> SEQUENCE: 276

Ala Ser Ile Ser Cys Arg Ser Gln Ser Leu Leu Asp Ser Asp
1               5                   10                  15
Gly Asn Thr Tyr Leu Asp Cys Tyr Leu Gln Lys Pro Gly Gln Ser Pro
            20                  25                  30
Gln Leu Leu Ile Tyr Thr Leu Ser Tyr Arg Ala Ser Gly Val Pro Asp
        35                  40                  45
Arg Phe Ser Asp Ser Gly Ser Gly Thr Asp Phe Thr Leu Lys Ile Ser
    50                  55                  60
Arg Val Glu Ala Glu Asp Val Gly Val Tyr Tyr Cys Met Gln Arg Ile
65                  70                  75                  80
Glu Phe Pro

<210> SEQ ID NO 277
<211> LENGTH: 100
<212> TYPE: PRT
<213> ORGANISM: Homo sapiens

<400> SEQUENCE: 277

Glu Ile Val Met Thr Gln Thr Pro Leu Ser Leu Ser Ile Thr Pro Gly
1               5                   10                  15
Glu Gln Ala Ser Ile Ser Cys Arg Ser Ser Gln Ser Leu Leu His Ser
            20                  25                  30
Asp Gly Tyr Thr Tyr Leu Tyr Trp Phe Leu Gln Lys Ala Arg Pro Val
        35                  40                  45
Ser Thr Leu Leu Ile Tyr Glu Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Phe Gly Val Tyr Tyr Cys Met Gln Asp
                85                  90                  95
Ala Gln Asp Pro
            100

<210> SEQ ID NO 278
<211> LENGTH: 100
<212> TYPE: PRT
<213> ORGANISM: Homo sapiens

<400> SEQUENCE: 278

Glu Ile Val Met Thr Gln Thr Pro Leu Ser Leu Ser Ile Thr Pro Gly
1               5                   10                  15
Glu Gln Ala Ser Met Ser Cys Arg Ser Ser Gln Ser Leu Leu His Ser
            20                  25                  30
Asp Gly Tyr Thr Tyr Leu Tyr Trp Phe Leu Gln Lys Ala Arg Pro Val
        35                  40                  45
Ser Thr Leu Leu Ile Cys Glu Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Phe Gly Val Tyr Tyr Cys Met Gln Asp
                85                  90                  95
Ala Gln Asp Pro
            100

<210> SEQ ID NO 279
<211> LENGTH: 100
<212> TYPE: PRT
<213> ORGANISM: Homo sapiens

<400> SEQUENCE: 279

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 280
<211> LENGTH: 100
<212> TYPE: PRT
<213> ORGANISM: Homo sapiens

<400> SEQUENCE: 280

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro
            100

<210> SEQ ID NO 281
<211> LENGTH: 100
<212> TYPE: PRT
<213> ORGANISM: Homo sapiens

<400> SEQUENCE: 281

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile

```
                 65                  70                  75                  80
Ser Arg Val Glu Ala Glu Asp Val Gly Val Tyr Tyr Cys Met Gln Ser
                 85                  90                  95

Ile Gln Leu Pro
            100

<210> SEQ ID NO 282
<211> LENGTH: 100
<212> TYPE: PRT
<213> ORGANISM: Homo sapiens

<400> SEQUENCE: 282

Asp Val Val Met Thr Gln Ser Pro Leu Ser Leu Pro Val Thr Leu Gly
1               5                  10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100

<210> SEQ ID NO 283
<211> LENGTH: 101
<212> TYPE: PRT
<213> ORGANISM: Homo sapiens

<400> SEQUENCE: 283

Asp Ile Val Met Thr Gln Thr Pro Leu Ser Leu Pro Val Thr Pro Gly
1               5                  10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro
            100

<210> SEQ ID NO 284
<211> LENGTH: 95
<212> TYPE: PRT
<213> ORGANISM: Homo sapiens

<400> SEQUENCE: 284

Glu Ile Val Leu Thr Gln Ser Pro Ala Thr Leu Ser Leu Ser Pro Gly
1               5                  10                  15

Glu Arg Ala Thr Leu Ser Cys Arg Ala Ser Gln Ser Val Ser Ser Tyr
            20                  25                  30
```

-continued

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 285
<211> LENGTH: 95
<212> TYPE: PRT
<213> ORGANISM: Homo sapiens

<400> SEQUENCE: 285

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Arg Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 286
<211> LENGTH: 96
<212> TYPE: PRT
<213> ORGANISM: Homo sapiens

<400> SEQUENCE: 286

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 287
<211> LENGTH: 90
<212> TYPE: PRT
<213> ORGANISM: Homo sapiens

<400> SEQUENCE: 287

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

```
Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Ala Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln
                 85                  90

<210> SEQ ID NO 288
<211> LENGTH: 89
<212> TYPE: PRT
<213> ORGANISM: Homo sapiens

<400> SEQUENCE: 288

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln
                 85

<210> SEQ ID NO 289
<211> LENGTH: 89
<212> TYPE: PRT
<213> ORGANISM: Homo sapiens

<400> SEQUENCE: 289

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Gly Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Ser Arg Ala Thr Gly Ile Pro Ala Arg Phe Ser Gly
 50                  55                  60

Ser Gly Pro Gly Thr Asp Phe Thr Leu Thr Ile Ser Ser Leu Glu Pro
 65                  70                  75                  80

Glu Asp Phe Ala Val Tyr Tyr Cys Gln
                 85

<210> SEQ ID NO 290
<211> LENGTH: 90
<212> TYPE: PRT
<213> ORGANISM: Homo sapiens

<400> SEQUENCE: 290

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Leu Ala Pro Arg Leu Leu
```

```
            35                  40                  45
Ile Tyr Gly Ala Ser Thr Arg Ala Thr Gly Ile Pro Ala Arg Phe Ser
 50                  55                  60
Gly Ser Gly Ser Gly Thr Glu Phe Thr Leu Thr Ile Ser Arg Leu Gln
65                  70                  75                  80
Ser Glu Asp Phe Ala Val Tyr Tyr Cys Gln
                85                  90
```

<210> SEQ ID NO 291
<211> LENGTH: 95
<212> TYPE: PRT
<213> ORGANISM: Homo sapiens

<400> SEQUENCE: 291

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Gly Val Ser Ser Asn
                20                  25                  30
Leu Ala Trp Tyr Gln Gln Lys Pro Gly Gln Ala Pro Arg Leu Leu Ile
            35                  40                  45
Tyr Asp Ala Ser Asn Arg Ala Thr Gly Ile Pro Ala Arg Phe Ser Gly
 50                  55                  60
Ser Gly Pro Gly Thr Asp Phe Thr Leu Thr Ile Ser Ser Leu Glu Pro
65                  70                  75                  80
Glu Asp Phe Ala Val Tyr Tyr Cys Gln Gln Arg Ser Asn Trp His
                85                  90                  95
```

<210> SEQ ID NO 292
<211> LENGTH: 96
<212> TYPE: PRT
<213> ORGANISM: Homo sapiens

<400> SEQUENCE: 292

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Ser
                20                  25                  30
Tyr Leu Ala Trp Tyr Gln Gln Lys Pro Gly Gln Ala Pro Arg Leu Leu
            35                  40                  45
Ile Tyr Asp Ala Ser Ser Arg Ala Thr Gly Ile Pro Asp Arg Phe Ser
 50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Arg Ser Asn Trp His
                85                  90                  95
```

<210> SEQ ID NO 293
<211> LENGTH: 95
<212> TYPE: PRT
<213> ORGANISM: Homo sapiens

<400> SEQUENCE: 293

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Gly Val Ser Ser Tyr
                20                  25                  30
Leu Ala Trp Tyr Gln Gln Lys Pro Gly Gln Ala Pro Arg Leu Leu Ile
            35                  40                  45
```

```
Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His
                85                  90                  95
```

<210> SEQ ID NO 294
<211> LENGTH: 95
<212> TYPE: PRT
<213> ORGANISM: Homo sapiens

<400> SEQUENCE: 294

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95
```

<210> SEQ ID NO 295
<211> LENGTH: 93
<212> TYPE: PRT
<213> ORGANISM: Homo sapiens

<400> SEQUENCE: 295

```
Glu Ile Val Met Met Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn
                85                  90
```

<210> SEQ ID NO 296
<211> LENGTH: 96
<212> TYPE: PRT
<213> ORGANISM: Homo sapiens

<400> SEQUENCE: 296

```
Glu Ile Val Leu Thr Gln Ser Pro Ala Thr Leu Ser Leu Ser Pro Gly
1               5                   10                  15

Glu Arg Ala Thr Leu Ser Cys Gly Ala Ser Gln Ser Val Ser Ser Ser
                20                  25                  30

Tyr Leu Ala Trp Tyr Gln Gln Lys Pro Gly Leu Ala Pro Arg Leu Leu
            35                  40                  45
```

```
Ile Tyr Asp Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
```

<210> SEQ ID NO 297
<211> LENGTH: 96
<212> TYPE: PRT
<213> ORGANISM: Homo sapiens

<400> SEQUENCE: 297

```
Glu Ile Val Met Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Ser
                20                  25                  30
Tyr Leu Ser Trp Tyr Gln Gln Lys Pro Gly Gln Ala Pro Arg Leu Leu
            35                  40                  45
Ile Tyr Gly Ala Ser Thr Arg Ala Thr Gly Ile Pro Ala Arg Phe Ser
    50                  55                  60
Gly Ser Gly Ser Gly Thr Asp Phe Thr Leu Thr Ile Ser Ser Leu Gln
65                  70                  75                  80
Pro Glu Asp Phe Ala Val Tyr Tyr Cys Gln Gln Asp Tyr Asn Leu Pro
                85                  90                  95
```

<210> SEQ ID NO 298
<211> LENGTH: 101
<212> TYPE: PRT
<213> ORGANISM: Homo sapiens

<400> SEQUENCE: 298

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
                20                  25                  30
Ser Asn Asn Lys Asn Tyr Leu Ala Trp Tyr Gln Gln Lys Pro Gly Gln
            35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Tyr Ser Thr Pro
                100
```

<210> SEQ ID NO 299
<211> LENGTH: 95
<212> TYPE: PRT
<213> ORGANISM: Homo sapiens

<400> SEQUENCE: 299

```
Glu Thr Thr Leu Thr Gln Ser Pro Ala Phe Met Ser Ala Thr Pro Gly
1               5                   10                  15
Asp Lys Val Asn Ile Ser Cys Lys Ala Ser Gln Asp Ile Asp Asp Asp
                20                  25                  30
Met Asn Trp Tyr Gln Gln Lys Pro Gly Glu Ala Ala Ile Phe Ile Ile
```

-continued

```
            35                  40                  45
Gln Glu Ala Thr Thr Leu Val Pro Gly Ile Pro Pro Arg Phe Ser Gly
                50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro
                85                  90                  95
```